US012297250B2

(12) United States Patent
Sparre-Ulrich et al.

(10) Patent No.: US 12,297,250 B2
(45) Date of Patent: May 13, 2025

(54) MODIFIED GIP PEPTIDE ANALOGUES

(71) Applicant: Antag Therapeutics ApS, Copenhagen N (DK)

(72) Inventors: Alexander Hovard Sparre-Ulrich, Copenhagen N (DK); Bjørn Behrens Sivertsen, Copenhagen S (DK); Ditte Riber, Brønshøj (DK); Mette Marie Rosenkilde, Hellerup (DK)

(73) Assignee: ANTAG THERAPEUTICS APS, Copenhagen N (DK)

( * ) Notice: Subject to any disclaimer, the term of this patent is extended or adjusted under 35 U.S.C. 154(b) by 939 days.

(21) Appl. No.: 17/298,512

(22) PCT Filed: Dec. 3, 2019

(86) PCT No.: PCT/EP2019/083506
§ 371 (c)(1),
(2) Date: May 28, 2021

(87) PCT Pub. No.: WO2020/115048
PCT Pub. Date: Jun. 11, 2020

(65) Prior Publication Data
US 2022/0298218 A1    Sep. 22, 2022

(30) Foreign Application Priority Data

Dec. 3, 2018   (EP) .................................. 18209896
May 27, 2019   (EP) .................................. 19176739

(51) Int. Cl.
*C07K 14/605*    (2006.01)
*A61K 38/00*     (2006.01)
*A61K 38/22*     (2006.01)
*C07K 14/645*    (2006.01)

(52) U.S. Cl.
CPC ............ *C07K 14/605* (2013.01); *A61K 38/22* (2013.01); *C07K 14/645* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 6,004,297 A   | 12/1999 | Steenfeldt-Jensen et al. | |
| 6,268,343 B1  | 7/2001  | Knudsen et al. | |
| 6,384,016 B1  | 5/2002  | Kaarsholm | |
| 6,410,508 B1  | 6/2002  | Isales et al. | |
| 6,458,924 B2  | 10/2002 | Knudsen et al. | |
| 7,326,688 B2  | 2/2008  | O'Harte et al. | |
| 7,875,587 B2  | 1/2011  | Gault et al. | |
| 8,450,266 B2  | 5/2013  | Dong et al. | |
| 9,072,703 B2  | 7/2015  | Dong | |
| 10,774,127 B2 | 9/2020  | Hartmann et al. | |
| 11,572,399 B2 * | 2/2023 | Rosenkilde .......... | C07K 14/605 |
| 2001/0011071 A1 | 8/2001 | Knudsen et al. | |
| 2005/0272652 A1 | 12/2005 | Gault et al. | |
| 2007/0167370 A1 | 7/2007 | Gault et al. | |
| 2008/0009603 A1 | 1/2008 | Gault et al. | |
| 2008/0312157 A1 | 12/2008 | Levy et al. | |
| 2019/0330332 A1 | 10/2019 | Okahara et al. | |
| 2019/0330333 A1 | 10/2019 | Okahara et al. | |
| 2019/0330334 A1 | 10/2019 | Okahara et al. | |

FOREIGN PATENT DOCUMENTS

| | | |
|---|---|---|
| EP | 3560514 A1 | 10/2019 |
| EP | 3560515 A1 | 10/2019 |
| EP | 3569248 A1 | 11/2019 |
| WO | WO 1996/29342 A1 | 9/1996 |
| WO | WO 1998/08871 A1 | 3/1998 |
| WO | WO 1998/24464 A1 | 6/1998 |
| WO | WO 99/43708 A1 | 9/1999 |
| WO | WO 2000/34331 A2 | 6/2000 |
| WO | WO 2000/58360 A2 | 10/2000 |
| WO | WO 2002/46227 A2 | 6/2002 |
| WO | WO 2003/082898 A2 | 10/2003 |
| WO | WO 2004/067548 A2 | 8/2004 |
| WO | WO 2005/082928 A2 | 9/2005 |
| WO | WO 2006/086769 A2 | 8/2006 |
| WO | WO 2006/097537 A2 | 9/2006 |
| WO | WO 2007/109354 A2 | 9/2007 |
| WO | WO 2010/016935 A2 | 2/2010 |
| WO | WO 2010/016936 A1 | 2/2010 |
| WO | WO 2010/016938 A2 | 2/2010 |
| WO | WO 2010/016940 A2 | 2/2010 |
| WO | WO 2010/016944 A2 | 2/2010 |
| WO | WO 2012/055770 A1 | 5/2012 |
| WO | WO 2012/088379 A2 | 6/2012 |

(Continued)

OTHER PUBLICATIONS

Bech, et al., ACS Med. Chem. Lett. 9:577-580 (first published online Jun. 2018) (Year: 2018).*
Coskun T. et al.: "LY3298176, a novel dual GIP and GLP-1 receptor agonist for the treatment of type 2 diabetes mellitus: From discovery to clinical proof of concept"; Mol. Metab., 2018 (OT 03.10.2018), v. 18: 3-14; doi: 10.1016/j.molmet. 2018.09.009.
Frias J.P. et al., "Efficacy and safety of LY3298176, a novel dual GIP and GLP-1 receptor agonist, inpa tients with type 2 diabetes: a randomised, placebo- controlled and active comparator-controlled phase2 trial", Lancet, 2018, v. 392: 2180-93, doi: 10.1016/S0140-6736(18)32260-8.

(Continued)

*Primary Examiner* — Thea D' Ambrosio
(74) *Attorney, Agent, or Firm* — Mintz, Levin, Cohn, Ferris, Glovsky and Popeo, P.C.

(57) ABSTRACT

Disclosed are glucose-dependent insulinotropic peptide (GIP)-derived peptide analogues which are antagonists of the GIP receptor. These GIP peptide analogues are modified by comprising one or more individual amino acid substitutions and are fatty acid conjugated with/without a linker, so to have improved antagonistic activity and improved pharmacokinetic profile.

17 Claims, 1 Drawing Sheet
Specification includes a Sequence Listing.

(56) References Cited

FOREIGN PATENT DOCUMENTS

| WO | WO 2012/167744 A1 | 12/2012 |
|---|---|---|
| WO | WO 2016/034186 A1 | 3/2016 |
| WO | WO 2016/066744 | 5/2016 |
| WO | WO 2016/066744 A2 | 5/2016 |
| WO | WO 2016/205488 A1 | 12/2016 |
| WO | WO 2018/220123 A1 | 12/2018 |
| WO | WO 2000/20592 A1 | 4/2020 |

OTHER PUBLICATIONS

Green B. D. & Flatt P.R.: "Incretin hormone mimetics and analogues in diabetes therapeutics", Best Practice & Research Clinical Endocrinology & Metabolism, 2007, v. 21 (4): 497-516, doi: 10.1016/j.beem.2007.09.003, abstract, table 4.
Knudsen L.B. et al.: "Small-molecule agonists for the glucagon-likepeptide 1 receptor", PNAS, 2007, v. 104(3): 937-942, doi: 10.1073/pnas.0605701104, abstract, cpd1-2.
Sha Y. et al.: "Cochinchinenin C, a potential nonpolypeptide antidiabetic drug, targets a glucagon-like peptide-1 receptor", RSC Adv., 2017, v. 7: 49015-49023, DOI: 10.1039/c7ra09470a, abstract, fig. 1.
Seino Y. et al.: "Glucose-dependent insulinotropic polypeptide and glucagon-like peptide-1: Incretin actions beyond the pancreas"—Journal of Diabetes Investigation, 2013, v. 4(2): 108-130.
Adrian TE, Bloom SR, Hermansen K, Iversen J. Pancreatic polypeptide, glucagon and insulin secretion from the isolated perfused canine pancreas. Diabetologia;14(6):413-417, 1978.
Ahlqvist E, Osmark P, Kuulasmaa T et al. Link Between GIP and Osteopontin in Adipose Tissue and Insulin Resistance. Diabetes;62(6):2088-2094, 2013.
Asmar M, Simonsen L, Madsbad S, Stallknecht B, Holst JJ, B++low J. Glucose-Dependent Insulinotropic Polypeptide May Enhance Fatty Acid Re-esterification in Subcutaneous Abdominal Adipose Tissue in Lean Humans. Diabetes;59(9):2160-2163, 2010.
Baggio LL, Drucker DJ. Biology of Incretins: GLP-1 and GIP. Gastroenterology;132(6):2131-2157, 2007.
Brunicardi FC, Druck P, Seymour NE, Sun YS, Elahi D, Andersen DK. Selective neurohormonal interactions in islet cell secretion in the isolated perfused human pancreas. Journal of Surgical Research;48(4):273-278, 1990.
Brons C, Jensen CB, Storgaard H et al. Impact of short-term high-fat feeding on glucose and insulin metabolism in young healthy men. The Journal of Physiology; 587(10):2387-2397, 2009.
Calanna S, Christensen M, Holst JJ et al. Secretion of Glucose-Dependent Insulinotropic Polypeptide in Patients With Type 2 Diabetes: Systematic review and meta-analysis of clinical studies. Diabetes Care; 36(10):3346-3352, 2013.
Christensen M, Calanna S, Sparre-Ulrich AH et al. Glucose-Dependent Insulinotropic Polypeptide Augments Glucagon Responses to Hypoglycemia in Type 1 Diabetes. Diabetes 64(1):72-78 ( Jan. 2015, e-published Jul. 22, 2014).
Christensen M, Vedtofte L, Holst JJ, Vilsboell T, Knop FK. Glucose-Dependent Insulinotropic Polypeptide: A Bifunctional Glucose-Dependent Regulator of Glucagon and Insulin Secretion in Humans. Diabetes; 60(12):3103-3109 (Dec. 2011, e-published Oct. 7, 2011).
Christensen MB, Calanna S, Holst JJ, Vilsboell T, Knop FK. Glucose-dependent Insulinotropic Polypeptide: Blood Glucose Stabilizing Effects in Patients With Type 2 Diabetes. The Journal of Clinical Endocrinology & Metabolism; 99(3):E418-E426, 2013.
Deacon CFP. GIP-(3-42) does not antagonize insulinotropic effects of GIP at physiological concentrations. American Journal of Physiology—Endocrinology and Metabolism;291(3):E468-E475, 2006.
DeBlasi A, O'Reilly K, Motulsky HJ. Calculating receptor No. from binding experiments using same compound as radioligand and competitor. Trends in pharmacological sciences.;10(6):227-9, 1989.
Deschamps I, Heptner W, Desjeux JF, Baltakse V, Machinot S, Lestradet H. Effects of diet on insulin and gastric inhibitory polypeptide levels in obese children. Pediatr Res; 14(4 Pt 1):300-303, 1980.
Ding WG, Renstrom E, Rorsman P, Buschard K, Gromada J. Glucagon-like peptide I and glucose-dependent insulinotropic polypeptide stimulate Ca2+-induced secretion in rat alpha-cells by a protein kinase A—mediated mechanism. Diabetes; 46(5):792-800, 1997.
Dupre J, Caussignac Y, McDonald TJ, Van Vliet S. Stimulation of Glucagon Secretion by Gastric Inhibitory Polypeptide in Patients with Hepatic Cirrhosis and Hyperglucagonemia. The Journal of Clinical Endocrinology & Metabolism; 72(1):125-129, 1991.
Ebert R, Illmer K, Creutzfeldt W. Release of gastric inhibitory polypeptide (GIP) by intraduodenal acidification in rats and humans and abolishment of the incretin effect of acid by GIP-antiserum in rats. Gastroenterology;76(3):515-523, 1979.
Fujita Y, Asadi A, Yang GK, Kwok YN, Kieffer TJ. Differential processing of pro-glucose-dependent insulinotropic polypeptide in gut. American Journal of Physiology—Gastrointestinal and Liver Physiology.;298(5):G608-G614, 2010.
Fulurija A, Lutz TA, Sladko K et al. Vaccination against GIP for the Treatment of Obesity. PLoS ONE; 3(9):e3163, 2008.
Gault et al: Evidence that the major degradation product of glucose-dependent insulinotropic polypeptide, GIP (3-42) . . . ; J. Endocrinology; 175; 525-533, 2002.
Gault VA, Hunter K, Irwin N, Green BD, Harriott P, O'Harte FPM, Flatt PR. Characterization and biological activity of Glu3 amino acid substituted GIP receptor antagonists. Archives of Biochemistry and Biophysics 2007:461:263-274.
Gault VA, O'Harte FPM, Harriott P, Flatt PR. Characterization of the Cellular and Metabolic Effects of a Novel Enzyme-Resistant Antagonist of Glucose-Dependent Insulinotropic Polypeptide. Biochemical and Biophysical Research Communications;290(5):1420-1426, 2002.
Gelling RW, Coy DH, Pederson RA et al. GIP(6-30amide) contains the high affinity binding region of GIP and is a potent inhibitor of GIP1-42 action in vitro. Regulatory Peptides; 69(3):151-154, 1997.
Getty-Kaushik L, Song DH, Boylan MO, Corkey BE, Wolfe MM. Glucose-Dependent Insulinotropic Polypeptide Modulates Adipocyte Lipolysis and Reesterification. Obesity;14(7):1124-1131, 2006.
Goetze JP, Hunter I, Lippert SK, Bardram L, Rehfeld JF. Processing-independent analysis of peptide hormones and prohormones in plasma. Front Biosci; 17:1804-15, 2012.
Goetze JP, Rehfeld JF. Peptide hormones and their prohormones as biomarkers. Biomarkers in Medicine; Aug. 1, 2009: Future Medicine; p. 335-8, 2009.
Graham FL, van der Eb AJ. A new technique for the assay of infectivity of human adenovirus 5 DNA. Virology;52(2):456-467, 1973.
Gutniak M, Orkov C, Holst JJ, Ahrén B, Efendi-ç S. Antidiabetogenic Effect of Glucagon-like Peptide-1 (7-36)amide in Normal Subjects and Patients with Diabetes Mellitus. N Engl J Med;326(20):1316-1322, 1992.
Hansen et al; "N-terminally and C-terminally truncated forms . . . "; British J.of Pharmacology; vol. 173; pp. 826-838, 2016.
Hauner H, Glatting G, Kaminska D, Pfeiffer EF. Effects of gastric inhibitory polypeptide on glucose and lipid metabolism of isolated rat adipocytes. Ann Nutr Metab;32(5-6):282-288, 1988.
Heer J, Rasmussen C, Coy DH, Holst JJ. Glucagon-like peptide-1, but not glucose-dependent insulinotropic peptide, inhibits glucagon secretion via somatostatin (receptor subtype 2) in the perfused rat pancreas. Diabetologia; 51(12):2263-2270, 2008.
Hinke SA, Gelling R, Manhart S, Lynn F, Pederson RA, Kühn-Wache K, et al. Structure-Activity Relationships of Glucose-Dependent Insulinotropic Polypeptide (GIP). bchm Biological Chemistry, p. 403, 2003.
Hinke SA, Manhart S, Pamir N et al. Identification of a bioactive domain in the amino-terminus of glucose-dependent insulinotropic polypeptide (GIP) . Biochimica et Biophysica Acta (BBA)—Protein Structure and Molecular Enzymology;1547(1):143-155, 2001.
Hinke SA, Manhart S, Speck M, Pederson RA, Demuth HU, McIntosh CHS. In depth analysis of the N-terminal bioactive domain of gastric inhibitory polypeptide. Life Sciences; 75(15):1857-70, 2004.
Hoejberg PV, Vilsboell T, Raboel R, Knop FK, Bache M, Krarup T, et al. Four weeks of near-normalisation of blood glucose improves

(56) References Cited

OTHER PUBLICATIONS the insulin response to glucagon-like peptide-1 and glucose-dependent insulinotropic polypeptide in patients with type 2 diabetes. Diabetologia; 2009: Springer-Verlag; p. 199-207, 2009.
Holst JJ, Bersani M. 1—Assays for Peptide Products of Somatostatin Gene Expression. In: Conn PM, editor. Methods in Neurosciences. vol. 5: Academic Press; . p. 3-22, 1991.
Holst JJ. On the Physiology of GIP and GLP-1. Horm Metab Res;36(11/12):747-754, 2004.
Irwin N, Green BD, Parker JC, Gault VA, O'Harte FPM, Flatt PR. Biological activity and antidiabetic potential of synthetic fragment peptides of glucose-dependent insulinotropic polypeptide, GIP (1-16) and (Pro3) GIP(1-16). Regulatory Peptides;135(1GÇô2):45-53, 2006.
Irwin N, McClean PL, Patterson S, Hunter K, Flatt PR. Active immunisation against gastric inhibitory polypeptide (GIP) improves blood glucose control in an animal model of obesity-diabetes. Biological Chemistry. bchm 390, 75. 2009. Jul. 16, 2014.
Irwin, N. et al.: "GIP (Lys 16PAL) and GIP (Lys 37 PAL) : Novel Long-Acting Acylated Analogues of Glucose-Dependent Insulinotropic Polypeptide with Improved Antidiabetic Potential", Journal of Medicinal Chemistry, vol. 49, No. 3, pp. 1047-1054, 2006.
Jørgensen NB, Dirksen C, Bojsen-Møller KN et al. Exaggerated Glucagon-Like Peptide 1 Response is Important for Improved β-Cell Function and Glucose Tolerance After Roux-en-Y Gastric Bypass in Patients With Type 2 Diabetes. Diabetes; 62(9):3044-3052, 2013.
Kerr, B.D. et al. (Jan. 21, 2011, e-published Dec. 22, 2010). "Characterization and biological actions of N-terminal truncated forms of glucose-dependent insulinotropic polypeptide," Biochem Biophys Res Commun vol. 404, No. 3; pp. 870-876.
Kim SJ, Nian C, Karunakaran S, Clee SM, Isales CM, McIntosh CHS. GIP-Overexpressing Mice Demonstrate Reduced Diet-Induced Obesity and Steatosis, and Improved Glucose Homeostasis. PLoS ONE; 7(7):e40156, 2012.
Kissow H, Hartmann B, Holst JJ et al. Glucagon-like peptide-1 (GLP-1) receptor agonism or DPP-4 inhibition does not accelerate neoplasia in carcinogen treated mice. Regulatory Peptides;179(1-3):91 -100, 2012.
Lazareno S, Birdsall NJ. Estimation of competitive antagonist affinity from functional inhibition curves using the Gaddum, Schild and Cheng-Prusoff equations. British journal of pharmacology; 109(4):1110-9, 1993.
Martin CM, Irwin N, Flatt PR, Gault Va. A novel acylated form of (d-Ala(2))GIP with improved antidiabetic potential, lacking effect on body fat stores. Biochimica et biophysica acta.; 1830(6):3407-13, 2013.
Meier JJ, Gallwitz B, Siepmann N et al. Gastric inhibitory polypeptide (GIP) dose-dependently stimulates glucagon secretion in healthy human subjects at euglycaemia. Diabetologia;46(6):798-801, 2003.
Miyawaki K, Yamada Y, Ban N et al. Inhibition of gastric inhibitory polypeptide signaling prevents obesity. Nat Med;8(7):738-742, 2002.
Miyawaki K, Yamada Y, Yano H et al. Glucose intolerance caused by a defect in the entero-insular axis: A study in gastric inhibitory polypeptide receptor knockout mice. Proceedings of the National Academy of Sciences;96(26):14843-14847, 1999.
Nakamura T, Tanimoto H, Mizuno Y, Tsubamoto Y, Noda H. Biological and functional characteristics of a novel low-molecular weight antagonist of glucose-dependent insulinotropic polypeptide receptor, SKL-14959, in vitro and in vivo. Diabetes, Obesity and Metabolism; 14(6):511-517, 2012.

Nasteska D, Harada N, Suzuki K et al. Chronic Reduction of GIP Secretion Alleviates Obesity and Insulin Resistance Under High-Fat Diet Conditions. Diabetes; 63(7):2332-2343, 2014.
Pathak V, Gault VA, Flatt PR, Irwin N. Antagonism of gastric inhibitory polypeptide (GIP) by palmitoylation of GIP analogues with N- and C-terminal modifications improves obesity and metabolic control in high fat fed mice. Molecular and Cellular Endocrinology; 401(0):120-9, 2015.
Pathak, V. et al.: "Sequential induction of beta cell rest and stimulation using stable GIP inhibitor and GLP-1 mimetic peptides improves metabolic control in C57BL/KsJdb/dbmice", Diabetologica, vol. 58, No. 9, 2015.
Pederson R, Brown J. Interaction of Gastric Inhibitory Polypeptide, Glucose, and Arginine on Insulin and Glucagon Secretion from the Perfused Rat Pancreas. Endocrinology; 103(2):610-615, 1978.
Perryra, Craig SL, Ng MT, Gault VA, Flatt PR, Irwin N. Characterization of glucose-dependent insulinotropic polypeptide receptor antagonists in rodent pancreatic beta cells and mice. Clinical Medicine Insights: Endocrinology and Diabetes 2019(12):1-9.
Raufman JP, Singh L, Eng J. Exendin-3, a novel peptide from Heloderma horridum venom, interacts with vasoactive intestinal peptide receptors and a newly described receptor on dispersed acini from guinea pig pancreas. Description of exendin-3(9-39) amide, a specific exendin receptor antagonist. Journal of Biological Chemistry; 266(5):2897-2902, 1991.
Ravn P, Madhurantakam C, Kunze S et al. Structural and Pharmacological Characterization of Novel Potent and Selective Monoclonal Antibody Antagonists of Glucose-dependent Insulinotropic Polypeptide Receptor. Journal of Biological Chemistry; 288(27):19760-19772, 2013.
Rosenkilde MM, Cahir M, Gether U, Hjorth SA, Schwartz TW. Mutations along transmembrane segment II of the NK-1 receptor affect substance P competition with non-peptide antagonists but not substance P binding. Journal of Biological Chemistry.; 269(45):28160-4, 1994.
Sauber J, Grothe J, Behm M, Scherag A, Grallert H, Illig T, et al. Association of variants in gastric inhibitory polypeptide receptor gene with impaired glucose homeostasis in obese children and adolescents from Berlin. European journal of endocrinology; 163(2):259-64, 2010.
Song DH, Getty-Kaushik L, Tseng E, Simon J, Corkey BE, Wolfe MM. Glucose-Dependent Insulinotropic Polypeptide Enhances Adipocyte Development and Glucose Uptake in Part Through Akt Activation. Gastroenterology;133(6):1796-1805, 2007.
Sparre-Ulrich, A.H. et al. (May 1, 2017, e-published Feb. 22, 2017). "GIP (3-30) NH2 is a potent competitive antagonist of the GIP receptor and effectively inhibits GIP-mediated insulin, glucagon, and somatostatin release," Biochemical Pharmacology; vol. 131; pp. 78-88.
Starich GH, Bar RS, Mazzaferri El. Gip increases insulin receptor affinity and cellular sensitivity in adipocytes. Am J Physiol; 249(6 Pt 1):E603-E607, 1985.
Tseng CC, Kieffer TJ, Jarboe LA, Usdin TB, Wolfe MM. Postprandial stimulation of insulin release by glucose-dependent insulinotropic polypeptide (GIP). Effect of a specific glucose-dependent insulinotropic polypeptide receptor antagonist in the rat. J Clin Invest; 98(11):2440-2445, 1996.
Widenmaier SB, Kim SJ, Yang GK, De Los Reyes T, Nian C, Asadi A, et al. A GIP Receptor Agonist Exhibits beta-Cell Anti-Apoptotic Actions in Rat Models of Diabetes Resulting in Improved beta-Cell Function and Glycemic Control. PLoS One; 5(3):e9590, 2010.

\* cited by examiner

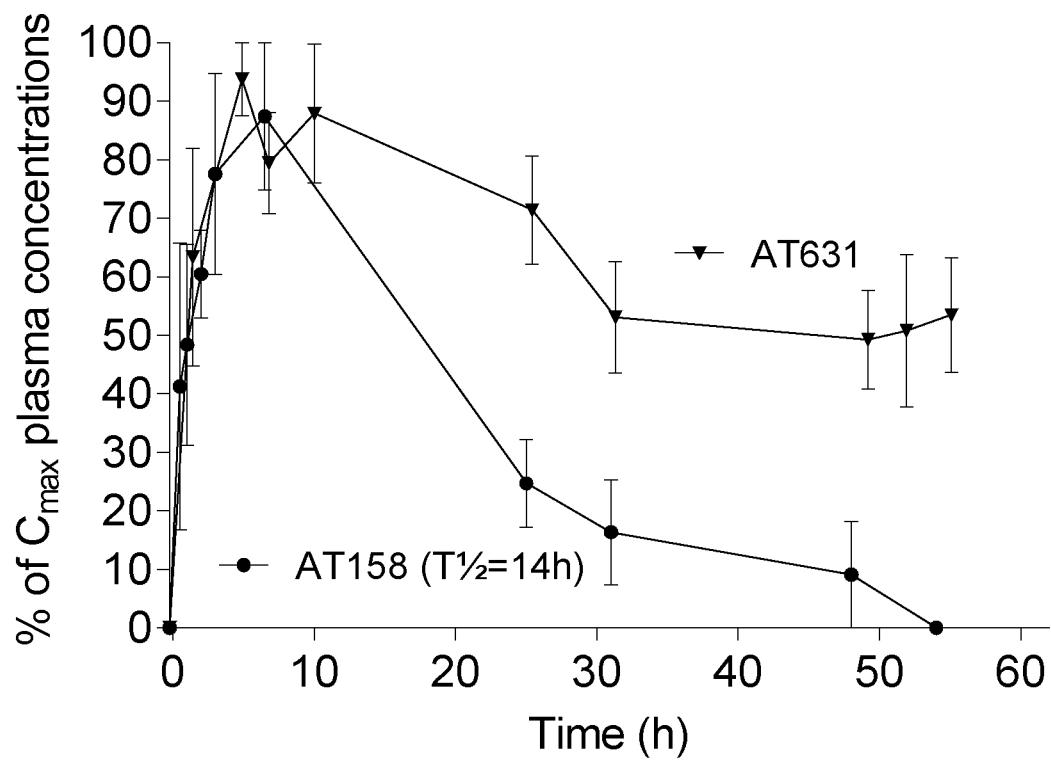

MODIFIED GIP PEPTIDE ANALOGUES

CROSS-REFERENCED TO RELATED APPLICATIONS

This application is a U.S. National Phase Application of PCT International Application No. PCT/EP2019/083506, filed on Dec. 3, 2019, designating the United States of America, which is an International Application of and claims the benefit of priority to European Patent Application No. 18209896.2, filed on Dec. 3, 2018 and European Patent Application No. 19176739.1, filed on May 27, 2019. The disclosures of the above-referenced applications are herein expressly incorporated by reference in their entireties, including any drawing.

TECHNICAL FIELD

The present invention relates to glucose-dependent insulinotropic peptide (GIP)-derived peptide analogues which are antagonists of the GIP receptor. These GIP peptide analogues are modified by comprising one or more individual amino acid substitutions and are fatty acid conjugated with/without a linker, so to have improved antagonistic activity and improved pharmacokinetic profile.

INCORPORATION OF THE SEQUENCE LISTING

This application contains a Sequence Listing which is hereby incorporated by reference in its entirety. The accompanying Sequence Listing text file, named "2022-02-28_Substitute_Sequence_Listing_059433-503N01US.txt, was created on Jun. 23, 2021 and is 93 KB

BACKGROUND

Glucose-dependent insulinotropic peptide (GIP) is a hormone secreted from the K cells of the gut following a meal[1]. Like its sister hormone glucagon-like peptide 1 (GLP-1), GIP is a potent insulin secretagogue[2]. In contrast to the glucagonostatic effect of GLP-1[3, 4], GIP has been shown to display glucagon-releasing properties under certain conditions ([3, 5-13]). The interest in understanding the biology of GIP was intensified by the association between rodent GIPR (GIP receptor) and adiposity[14-21] In humans, although less clear, there is likewise evidence for a role of GIP in fat metabolism with the demonstration of the GIPR expression in adipose tissue[22], an association between high BMI and increased GIP levels[22, 23], increased adipose tissue blood flow and TAG (triacylglycerol) deposition following GIP administration in a state of high insulin and high glucose[24], decreased basal and postprandial GIP levels observed in obese children put on a diet[25], and increased fasting GIP levels observed in healthy young men put on a high fat diet[26].

Thus, in addition to the general demand from researchers who witnessed the advances in the understanding of GLP-1 following the discovery of the GLP-1 receptor antagonist, exendin(9-39)[27, 28], the potential as an anti-obesity agent has attracted additional attention for the development of potent GIPR antagonists. Many different strategies have been undertaken in order to antagonize GIP's function, e.g. a small molecule receptor antagonist[29], immunization against GIP[30-32], various truncations and mutations of the GIP molecule with antagonistic properties[33-39], and recently a potent antagonist antibody against the GIPR[40].

Under physiological conditions the 42 amino acid hormone, GIP, is degraded by the enzyme dipeptidylpeptidase 4 (DPP-4), which cleaves at the third position of the GIP molecule to yield GIP3-42. Synthetic porcine GIP3-42 displayed no antagonist properties in pigs or perfused rat pancreata in physiological concentrations while in vitro it antagonized the human GIPR[41]. Many peptide hormones are post-translationally modified resulting in various biological forms with different lengths and amino acid modifications[42, 43]. Thus, it has been shown that GIP1-30 is produced as a result of post-translational processing 44 and that it is an agonist on the GIPR[33, 45]. If GIP1-30 is secreted into the circulation in humans, the cleavage catalyzed by DPP-4 would result in GIP3-30.

U.S. Pat. No. 7,875,587 discloses GIP receptor antagonists derived from GIP(1-42) having enhanced resistance to degradation by DPP-4, and their use for treatment of insulin resistance and obesity. In WO2004/067548 DPP-4 metabolites are modified by covalent coupling of a pharmacophore to achieve the longer half-life associated with the peptide metabolites and to retain the biological activity of the cleaved peptides similar to the native peptides, including GIP. WO2012/055770 discloses GIP(3-42) as an endogenous metabolite that is readily cleared and with GIPR antagonist effects, and GIP(2-30) as an example of a truncated GIP analogue with GIPR agonist activity. WO1998/24464 discloses the antagonist GIP(7-30).

WO 2016/034186 and Hansen et al. 2016 discloses the antagonists GIP(3-30) and GIP(5-30). Pathak et al. 2015 discloses GIP(3-30) which is C-terminally modified with the 9-amino acid Cex from exendin(1-39) and a lysine-residue modified with palmitoyl.

A range of different approaches have been used for modifying the structure of GLP-1 compounds in order to provide a longer duration of action in vivo. These include introduction of a lipophilic substituent to an amino acid residue (WO 96/29342 and WO 98/08871) and acylated GLP-1 analogues (WO 00/34331). WO 02/46227 discloses GLP-1 and exendin-4 analogues fused to human serum albumin in order to extend in vivo half-life.

SUMMARY

The present inventors have identified GIP peptides which are antagonists of the GIPR, which comprise one or more individual substitutions which result in GIP peptides with improved antagonistic properties. The GIP peptides of the present disclosure are acylated herewith to increase half-life and in vivo stability. The GIP peptides of the present disclosure are also N-terminal truncated compared to native GIP(1-42) and do at least not comprise the first two amino acids in position 1 and 2 of GIP(1-42). The inventors have further surprisingly found that longer GIP peptides, such as peptides comprising one or more of GIP(31-42) residues or peptides comprising one or more residues of Exendin-4 attached to the C-terminus of any one of GIP3-30, GIP5-30 and GIP6-30, and which are acylated, retain or even show improved GIPR antagonistic properties and/or extraordinarily long in vivo half-life's and/or increased selectivity. This makes them potentially useful in a range of therapeutic applications.

In one aspect, the present disclosure relates to a glucose-dependent insulinotropic peptide (GIP) analogue consisting of amino acid sequence SEQ ID NO:1:

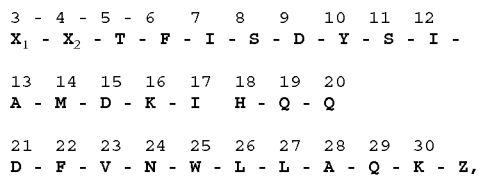

wherein X₁ and X₂ are individually any amino acid or omitted;
or a functional variant thereof, wherein said variant has 1 to 8, such as 1 to 4 individual amino acid substitutions at any amino acid of SEQ ID NO:1,
wherein said peptide is modified by attaching at least one fatty acid molecule at one or more amino acid residues at positions 3 to 29 of SEQ ID NO: 1, or said functional variant thereof,
wherein Z is a peptide comprising one or more amino acid residues of GIP(31-42) (GKKNDWKHNITQ; SEQ ID NO: 2) or one or more amino acid residues of Exendin-4 (HGEGTFTSDLSKQMEEEAVRLFIEWLKNGGPSSGAPPPS; SEQ ID NO: 3).

An important advantage of the above aspect, where GIP (3-30)/GIP(5-30)/GIP(6-30) and analogues thereof are extended with amino acid residues from the C-terminal part of Exendin-4 or GIP(1-42), such as e.g. GPSSGAPPPS (SEQ ID NO: 5), PSSGAPPPS (SEQ ID NO: 4) or GKKNDW (SEQ ID NO: 19), is that the in vivo half-life is extended to a surprisingly high degree compared to corresponding non-extended analogues. This may in particular be the case, when the extended GIP analogues are lipidated in specific positions, such as e.g. in position 18 for the extended GIP(3-30) analogues and in position 11 for the extended GIP(5-30) analogues.

Another important advantage of the above aspect, where GIP(3-30)/GIP(5-30)/GIP(6-30) and analogues thereof are extended with amino acid residues from the C-terminal part of Exendin-4 or GIP(1-42), such as e.g. GPSSGAPPPS (SEQ ID NO: 5), PSSGAPPPS (SEQ ID NO: 4) or GKKNDW (SEQ ID NO: 19), is that the antagonistic properties may be increased and/or the selectivity with respect to GIP receptor agonism is increased. Thus, when the extended GIP analogues are lipidated in specific positions, such as e.g. in position 18 for the extended GIP(3-30) analogues and in position 11 for the extended GIP(5-30) analogues, improved antagonistic effect may be obtained while also increasing the half-life to a surprising extent.

A further important advantage of the above aspect, where GIP(3-30)/GIP(5-30)/GIP(6-30) and analogues thereof are extended with amino acid residues from the C-terminal part of Exendin-4 or GIP(1-42), such as e.g. GPSSGAPPPS (SEQ ID NO: 5), PSSGAPPPS (SEQ ID NO: 4) or GKKNDW (SEQ ID NO: 19), is that the selectivity is increased with respect to activation or inhibition of other receptor members of family B GPCRs, such as e.g. GLP-1R and Glucagon-R.

DESCRIPTION OF THE DRAWINGS

FIG. 1. GIP(3-30) antagonists with C-terminal extensions, such as e.g. AT631, show extraordinarily long $T_{1/2}$ of more than 30 hours compared to non-C-terminal extended GIP(3-30) antagonists such as analogue AT158. Subcutaneously administration of the lipidated GIP(3-30)NH₂ analogue AT158 and the lipidated GIP(3-30)Cex(31-39) analogue AT631 in pigs and blood samples were collected at the indicated time points from a central venous catheter. The half-life of AT631 is determined based on RIA (see "Materials and methods"), and the percentage of Cmax plotted against time in hours. AT631 shows a surprisingly longer half-life than AT158.

DEFINITIONS

The term "affinity" refers to the strength of binding between a receptor and its ligand(s). In the present context, affinity of a peptide antagonist for its binding site (Ki) will determine the duration of inhibition of agonist activity. The affinity of an antagonist can be determined experimentally using Schild regression on functional studies or by radioligand binding studies like 1) competitive binding experiments using the Cheng-Prusoff equation, 2) saturation binding experiments using the Scatchard equation or 3) kinetic studies with determination of on- and off rates ($K_{on}$ and $K_{off}$, respectively).

The term "IC50" represents the half maximal inhibitory concentration (IC50), which is a measure of the effectiveness of a substance in inhibiting a specific biological or biochemical function. This quantitative measure indicates how much of a particular drug or other substance (e.g. antagonist) is needed to inhibit a given biological process (or component of a process, i.e. an enzyme, cell, cell receptor or microorganism) by half. It is commonly used as a measure of antagonist drug potency in pharmacological research. IC50 represents the concentration of a drug that is required for 50% inhibition in vitro. In the present context, the IC50 value can also refer to the concentration of a drug at which 50% of a radio labelled ligand is displaced from the receptor, which is a characterization of drug affinity done in competition binding experiments.

The term "agonist" in the present context refers to a peptide, or analogue thereof, capable of binding to and activating downstream signalling cascades from a receptor.

The term "antagonist" in the present context refers to a GIP peptide analogue as defined herein, capable of binding to and blocking or reducing agonist-mediated responses of a receptor. Antagonists usually do not provoke a biological response themselves upon binding to a receptor. Antagonists have affinity but no efficacy for their cognate receptors, and binding of an antagonist to its receptor will inhibit the function of an agonist or inverse agonist at receptors. Antagonists mediate their effects by binding to the active (orthosteric) site or to allosteric sites on receptors, or they may interact at unique binding sites not normally involved in the biological regulation of the receptor's activity. Antagonist activity may be reversible or irreversible depending on the longevity of the antagonist-receptor complex, which, in turn, depends on the nature of antagonist-receptor binding. The majority of drug antagonists typically achieve their potency by competing with endogenous ligands or substrates at structurally defined binding sites on receptors. Antagonists may be competitive, non-competitive, uncompetitive, silent antagonists, partial agonists or inverse agonists.

A competitive antagonist (also known as surmountable antagonist) reversibly binds to receptors at the same binding site (i.e. at the active site) as the endogenous ligand or agonist, but without activating the receptor. Agonists and antagonists thus "compete" for the same binding site on the receptor. Once bound, an antagonist blocks agonist binding. The level of activity of the receptor is determined by the relative affinity of each molecule for the site and their relative concentrations. High concentrations of a competitive antagonist will increase the proportion of receptors that the antagonist occupies.

The term "non-competitive antagonism" (also called non-surmountable or insurmountable antagonism) describes two distinct phenomena with functionally similar results: one in which the antagonist binds to the active site of the receptor, and one in which the antagonist binds to an allosteric site of the receptor. Unlike competitive antagonists, which affect the amount of agonist necessary to achieve a maximal response but do not affect the magnitude of that maximal response, non-competitive antagonists reduce the magnitude of the maximum response that can be attained by any amount of agonist.

The term "silent antagonist" refers to a competitive receptor antagonist that has absolutely no intrinsic activity for activating a receptor.

The term "partial agonist" refers to an agonist that, at a given receptor, might differ in the amplitude of the functional response that it elicits after maximal receptor occupancy. Partial agonists can act as a competitive antagonist in the presence of a full agonist (or a more efficacious agonist), as it competes with the full agonist for receptor occupancy, thereby producing a net decrease in the receptor activation as compared to that observed with the full agonist alone.

The term "inverse agonist" refers to a ligand, such as a GIP peptide analogue, that is capable of binding to the same receptor binding site as an agonist and antagonize its effects. Furthermore, an inverse agonist can also inhibit the basal activity of constitutively active receptors.

The term "glucose-dependent insulinotropic polypeptide receptor (GIPR) antagonists" as used herein refers to a compound, such as a peptide, capable of binding to and blocking or reducing agonist-mediated responses of GIPR.

The term "Individual" refers to vertebrates, particular members of the mammalian species, preferably primates including humans. As used herein, 'subject' and 'individual' may be used interchangeably.

An "isolated peptide" is a peptide separated and/or recovered from a component of their natural, typically cellular, environment, that is essentially free from contaminating cellular components, such as carbohydrate, lipid, or other proteinaceous impurities associated with the polypeptide in nature. Typically, a preparation of isolated peptide comprises the peptide in a highly purified form, i.e., at least about 80% pure, at least about 90% pure, at least about 95% pure, greater than 95% pure, or greater than 99% pure. The term "isolated" does not exclude the presence of the same peptide in alternative physical forms, such as dimers, tetramers or alternatively glycosylated or derived forms.

An "amino acid residue" can be a natural or non-natural amino acid residue linked by peptide bonds or bonds different from peptide bonds. The amino acid residues can be in D-configuration or L-configuration. An amino acid residue comprises an amino terminal part ($NH_2$) and a carboxy terminal part (COOH) separated by a central part comprising a carbon atom, or a chain of carbon atoms, at least one of which comprises at least one side chain or functional group. $NH_2$ refers to the amino group present at the amino terminal end of an amino acid or peptide, and COOH refers to the carboxy group present at the carboxy terminal end of an amino acid or peptide. The generic term amino acid comprises both natural and non-natural amino acids. Natural amino acids of standard nomenclature as listed in J. Biol. Chem., 243:3552-59 (1969) and adopted in 37 C.F.R., section 1.822(b)(2) belong to the group of amino acids listed herewith: Y,G,F,M,A,S,I,L,T,V,P,K,H,Q,E,W,R,D,N and C.

Non-natural amino acids are those not listed immediately above. Also, non-natural amino acid residues include, but are not limited to, modified amino acid residues, L-amino acid residues, and stereoisomers of D-amino acid residues.

An "equivalent amino acid residue" refers to an amino acid residue capable of replacing another amino acid residue in a polypeptide without substantially altering the structure and/or functionality of the polypeptide. Equivalent amino acids thus have similar properties such as bulkiness of the side-chain, side chain polarity (polar or non-polar), hydrophobicity (hydrophobic or hydrophilic), pH (acidic, neutral or basic) and side chain organization of carbon molecules (aromatic/aliphatic). As such, "equivalent amino acid residues" can be regarded as "conservative amino acid substitutions", and it is the substitution of amino acids whose side chains have similar biochemical properties and thus do not affect the function of the peptide.

Among the common amino acids, for example, a "conservative amino acid substitution" can also be illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine.

Within the meaning of the term "equivalent amino acid substitution" as applied herein, one amino acid may be substituted for another, in one embodiment, within the groups of amino acids indicated herein below:
i) Amino acids having polar side chains (Asp, Glu, Lys, Arg, His, Asn, Gln, Ser, Thr, Tyr, and Cys,)
ii) Amino acids having non-polar side chains (Gly, Ala, Val, Leu, Ile, Phe, Trp, Pro, and Met)
iii) Amino acids having aliphatic side chains (Gly, Ala Val, Leu, Iie)
iv) Amino acids having cyclic side chains (Phe, Tyr, Trp, His, Pro)
v) Amino acids having aromatic side chains (Phe, Tyr, Trp)
vi) Amino acids having acidic side chains (Asp, Glu)
vii) Amino acids having basic side chains (Lys, Arg, His)
viii) Amino acids having amide side chains (Asn, Gln)
ix) Amino acids having hydroxy side chains (Ser, Thr, Tyr)
x) Amino acids having sulphur-containing side chains (Cys, Met),
xi) Neutral, weakly hydrophobic amino acids (Pro, Ala, Gly, Ser, Thr)
xii) Hydrophilic, acidic amino acids (Gln, Asn, Glu, Asp), and
xiii) Hydrophobic amino acids (Leu, Iie, Val)

In addition, a serine residue of a peptide of the present disclosure may be substituted with an amino acid selected from the group consisting of Gln, Asn and Thr (all amino acids with polar uncharged side chains); and independently thereof, a glycine residue (Gly) is substituted with an amino acid selected from the group consisting of Ala, Val, Leu, and Iie; and independently thereof, an arginine residue (Arg) is substituted with an amino acid selected from the group consisting of Lys and His (all have positively charged side chains); and independently thereof, a lysine residue (Lys) may be substituted with an amino acid selected from the group consisting of Arg and His; and independently thereof, a methionine residue (Met) may be substituted with an amino acid selected from the group consisting of Leu, Pro, Iie, Val, Phe, Tyr and Trp (all have hydrophobic side chains); and independently thereof, a glutamine residue (Gln) may be substituted with an amino acid selected from the group consisting of Asp, Glu, and Asn; and independently thereof, an alanine residue (Ala) may be substituted with an amino acid selected from the group consisting of Gly, Val, Leu, and Ile.

Where the L or D form (optical isomers) has not been specified it is to be understood that the amino acid in question has the natural L form, cf. Pure & Appl. Chem. Vol. (56(5) pp 595-624 (1984) or the D form, so that the peptides formed may be constituted of amino acids of L form, D form, or a sequence of mixed L forms and D forms.

As used herein, a Glutamic acid (Glu) mimetic is a moiety, with two carboxy functional groups separated by three carbon atoms. Examples are beta-Glu, gamma-Glu or glutaric acid.

A "functional variant" of a peptide is a peptide capable of performing essentially the same functions as the peptide it is a functional variant of. In particular, a functional variant can essentially bind the same molecules, such as receptors, or perform the same receptor mediated responses as the peptide it is a functional variant of. A functional variant of a "glucose-dependent insulinotropic peptide (GIP) analogue" is a peptide, that can bind to the GIPR and either activate or inhibit GIPR downstream signalling, such as cAMP generation. A functional variant of a glucose-dependent insulinotropic peptide receptor (GIPR) antagonist is a peptide, that can bind to the GIPR and inhibit or reduce agonist-mediated GIPR signalling, such as cAMP generation.

A "bioactive agent" (i.e. a biologically active substance/agent) is any agent, drug, compound, composition of matter or mixture which provides some pharmacologic, often beneficial, effect that can be demonstrated in vivo or in vitro. It refers to the GIP peptide analogues as defined herein and compounds or compositions comprising these. As used herein, this term further includes any physiologically or pharmacologically active substance that produces a localized or systemic effect in an individual.

The terms "drug" and "medicament" as used herein include biologically, physiologically, or pharmacologically active substances that act locally or systemically in the human or animal body.

The terms "treatment" and "treating" as used herein refer to the management and care of a patient for the purpose of combating a condition, disease or disorder. The term is intended to include the full spectrum of treatments for a given condition from which the patient is suffering, and refer equally to curative therapy, prophylactic or preventative therapy and ameliorating or palliative therapy, such as administration of the peptide or composition for the purpose of: alleviating or relieving symptoms or complications; delaying the progression of the condition, partially arresting the clinical manifestations, disease or disorder; curing or eliminating the condition, disease or disorder; amelioration or palliation of the condition or symptoms, and remission (whether partial or total), whether detectable or undetectable; and/or preventing or reducing the risk of acquiring the condition, disease or disorder, wherein "preventing" or "prevention" is to be understood to refer to the management and care of a patient for the purpose of hindering the development of the condition, disease or disorder, and includes the administration of the active compounds to prevent or reduce the risk of the onset of symptoms or complications. The term "palliation", and variations thereof, as used herein, means that the extent and/or undesirable manifestations of a physiological condition or symptom are lessened and/or time course of the progression is slowed or lengthened, as compared to not administering compositions of the present invention.

The individual to be treated is preferably a mammal, in particular a human being. Treatment of animals, such as mice, rats, dogs, cats, cows, horses, sheep and pigs, is, however, also encompassed herewith.

An "individual in need thereof" refers to an individual who may benefit from the present disclosure. In one embodiment, said individual in need thereof is a diseased individual, wherein said disease may be a metabolic disease or disorder such as obesity or diabetes, a bone density disorder or a cancer.

A treatment according to the invention can be prophylactic, ameliorating and/or curative.

"Pharmacologically effective amount", "pharmaceutically effective amount" or "physiologically effective amount" of a bioactive agent is the amount of a bioactive agent present in a pharmaceutical composition as described herein that is needed to provide a desired level of active agent in the bloodstream or at the site of action in an individual (e.g. the lungs, the gastric system, the colorectal system, prostate, etc.) to be treated to give an anticipated physiological response when such composition is administered. A bioactive agent in the present context refers to a GIP peptide analogue as disclosed herein.

"Co-administering" or "co-administration" as used herein refers to the administration of one or more GIP peptide analogues of the present invention and a state-of-the-art pharmaceutical composition. The at least two components can be administered separately, sequentially or simultaneously.

DETAILED DESCRIPTION

GIP refers to glucose-dependent insulinotropic polypeptide, also known as Gastric Inhibitory Peptide (or polypeptide). As used herein the abbreviation GIP or hGIP is human GIP (Uniprot accession number P09681). GIP is derived from a 153-amino acid proprotein and circulates as a biologically active 42-amino acid peptide. It is synthesized by K cells of the mucosa of the duodenum and the jejunum of the gastrointestinal tract.

GIPR (or GIP receptor) refers to gastric inhibitory polypeptide receptors. These seven-transmembrane proteins are found at least on beta-cells in the pancreas. As used herein the abbreviation GIPR or hGIPR is human GIPR (Uniprot accession number P48546).

The present inventors have identified GIP peptides which are antagonists of the GIPR, which comprise one or more individual substitutions which result in GIP peptides with improved antagonistic properties. The GIP peptides of the present disclosure are acylated herewith to increase half-life and in vivo stability. The inventors have further surprisingly found that longer GIP peptides, such as peptides comprising one or more of GIP(31-42) residues or peptides comprising one or more of residue of Exendin-4 attached to the C-terminus of any one of GIP3-30, GIP5-30 and GIP6-30, and which are acylated, retain GIPR antagonistic properties. This makes them potentially useful in a range of therapeutic applications.

In one embodiment, Exendin-4 is a peptide having amino acid sequence HGEGTFTSDLSKQMEEEAVRLFIEW-LKNGGPSSGAPPPS (SEQ ID NO:3).

GIP Peptides

The present invention is directed to GIP peptide analogues which comprise a peptide fragment of GIP comprising one or more individual substitutions, having unprecedented GIPR antagonistic properties, and one or more fatty acids attached thereto to increase the half-life of said peptide while retaining the GIPR antagonistic properties.

Elongated GIP Peptide Analogues

It is an aspect of the present disclosure to provide a glucose-dependent insulinotropic peptide (GIP) analogue consisting of amino acid sequence SEQ ID NO:1:

```
 3 - 4 - 5 - 6   7   8   9  10  11  12
X₁ - X₂ - T - F - I - S - D - Y - S - I -

13  14  15  16  17  18  19  20
A - M - D - K - I   H - Q - Q 21  22  23  24  25  26  27  28  29  30
D - F - V - N - W - L - L - A - Q - K - Z,
``` wherein X₁ and X₂ are individually any amino acid or omitted;
or a functional variant thereof, wherein said variant has 1 to 8 individual amino acid substitutions at any amino acid of SEQ ID NO:1,
wherein said peptide is modified by attaching at least one fatty acid molecule at one or more amino acid residues at positions 3 to 29 of SEQ ID NO: 1, or said functional variant thereof,
wherein Z is a peptide comprising one or more amino acid residues of GIP(31-42) (GKKNDWKHNITQ; SEQ ID NO: 2) or one or more amino acid residues of Exendin-4 (HGEGTFTSDLSKQMEEEAVRLFIEW-LKNGGPSSGAPPPS; SEQ ID NO: 3).

It is also an aspect of the present disclosure to provide a glucose-dependent insulinotropic peptide (GIP) analogue consisting of amino acid sequence SEQ ID NO:1:

```
 3 - 4 - 5 - 6   7   8   9  10  11  12
X₁ - X₂ - T - F - I - S - D - Y - S - I -

13  14  15  16  17  18  19  20
A - M - D - K - I   H - Q - Q 21  22  23  24  25  26  27  28  29  30
D - F - V - N - W - L - L - A - Q - K - Z,
``` wherein X₁ and X₂ are individually any amino acid or omitted;
or a functional variant thereof, wherein said variant has 1 to 4 individual amino acid substitutions at any amino acid of SEQ ID NO:1,
wherein said peptide is modified by attaching at least one fatty acid molecule at one or more amino acid residues at positions 3 to 29 of SEQ ID NO:1, or said functional variant thereof,
wherein Z is a peptide comprising one or more amino acid residues of GIP(31-42) (GKKNDWKHNITQ; SEQ ID NO: 2) or one or more amino acid residues of Exendin-4 (HGEGTFTSDLSKQMEEEAVRLFIEW-LKNGGPSSGAPPPS; SEQ ID NO: 3).

In one embodiment, the present disclosure provides a glucose-dependent insulinotropic peptide (GIP) analogue selected from the group consisting of:
a peptide having an amino acid sequence consisting of SEQ ID NO:32 hGIP(3-30):

```
 3 - 4 - 5 - 6   7   8   9  10  11  12  13
E - G - T - F - I - S - D - Y - S - I - A -

14  15  16  17  18  19  20  21  22
M - D - K - I   H - Q - Q - D - F -
```

```
23  24  25  26  27  28  29  30
V - N - W - L - L - A - Q - K - Z,
``` a peptide having an amino acid sequence consisting of SEQ ID NO:35 hGIP(5-30):

```
 5 - 6   7   8   9  10  11  12  13  14  15  16  17
 T - F - I - S - D - Y - S - I - A - M - D - K - I 18  19  20  21  22  23  24  25  26  27  28  29  30
 H - Q - Q - D - F - V - N - W - L - L - A - Q - K
- Z
``` and
a peptide having an amino acid sequence consisting of SEQ ID NO:36 hGIP(6-30):

```
 6   7   8   9  10  11  12  13  14  15  16  17
 F - I - S - D - Y - S - I - A - M - D - K - I 18  19  20  21  22  23  24  25  26  27  28  29  30
 H - Q - Q - D - F - V - N - W - L - L - A - Q - K
- Z
``` or a functional variant thereof, wherein said variant has 1 to 4 individual amino acid substitutions at any one of SEQ ID NO; and SEQ ID NO:
wherein said peptide is modified by attaching at least one fatty acid molecule at one or more amino acid residues at positions 4 to 29 of any one of SEQ ID NO; and SEQ ID NO: or a functional variant thereof comprising between 1 and 4 amino acid substitutions at any one of SEQ ID NO; and SEQ ID NO: with or without a linker
wherein Z is:
a glycine or a proline,
a fragment selected from the group consisting of:
GP, GPS, GPSS (SEQ ID NO: 6), GPSSG (SEQ ID NO: 7), GPSSGA (SEQ ID NO: 8), GPSSGAP (SEQ ID NO: 9), GPSSGAPP (SEQ ID NO: 10), GPSSGAPPP (SEQ ID NO: 11) and GPSSGAPPPS (SEQ ID NO: 5),
a fragment selected from the group consisting of:
PS, PSS, PSSG (SEQ ID NO: 12), PSSGA (SEQ ID NO: 13), PSSGAP (SEQ ID NO: 14), PSSGAPP (SEQ ID NO: 15), PSSGAPPP (SEQ ID NO: 16) and PSSGAPPPS (SEQ ID NO: 4),
a fragment selected from the group consisting of:
GK, GKK, GKKN (SEQ ID NO: 17), GKKND (SEQ ID NO: 18), GKKNDW (SEQ ID NO: 19), GRKNDW (SEQ ID NO: 20), GKRNDW (SEQ ID NO: 21), GRRNDW (SEQ ID NO: 22), GKKNDWK (SEQ ID NO: 23), GKKNDWKH (SEQ ID NO: 24), GKKNDWKHN (SEQ ID NO: 25), GKKNDWKHNI (SEQ ID NO: 26), GKKNDWKHNIT (SEQ ID NO: 27) and GKKNDWKHNITQ (SEQ ID NO: 2), or
a fragment selected from the group consisting of:
GPSSGA (SEQ ID NO: 8), GPSSGAP (SEQ ID NO: 9), GPSSGAPP (SEQ ID NO: 10), GPSSGAPPP (SEQ ID NO: 11), GPSSGAPPPS (SEQ ID NO: 5), GKKNDW (SEQ ID NO: 19), GRKNDW (SEQ ID NO: 20), GKRNDW (SEQ ID NO: 21), GRRNDW (SEQ ID NO: 22), GKKNDWK (SEQ ID NO: 23), GKKNDWKH (SEQ ID NO: 24), GKKNDWKHN (SEQ ID NO: 25), GKKNDWKHNI (SEQ ID NO: 26), GKKNDWKHNIT (SEQ ID NO: 27) and GKKNDWKHNITQ (SEQ ID NO: 2), or a variant thereof comprising 1 or 2 individual amino acid substitutions at any one of the amino acid residues, or a fragment selected from the group consisting of:
PSSG (SEQ ID NO: 12), PSSGA (SEQ ID NO: 13), PSSGAP (SEQ ID NO: 14),
PSSGAPP (SEQ ID NO: 15), PSSGAPPP (SEQ ID NO: 16), PSSGAPPPS (SEQ ID NO: 4),
or a variant thereof comprising 1 or 2 individual amino acid substitutions at any one of the amino acid residues.

An important advantage of the above aspects, where GIP antagonists GIP(3-30)/GIP(4-30)/GIP(5-30)/GIP(6-30) and analogues thereof are extended with amino acid residues from the C-terminal part of Exendin-4 or GIP(1-42), such as e.g. GPSSGAPPPS (SEQ ID NO: 5), PSSGAPPPS (SEQ ID NO: 4) or GKKNDW (SEQ ID NO: 19), is that the in vivo half-life is extended to a surprisingly high degree compared to corresponding non-extended analogues. This may in particular be the case, when the extended GIP(3-30) analogues are lipidated in specific positions, such as e.g. positions 11, 12, 17 and 18 for the extended GIP(3-30), GIP(4-30) GIP(5-30) and GIP(6-30) analogues. Thus, a C-terminal extension of e.g. GPSSGAPPPS (SEQ ID NO: 5), PSSGAPPPS (SEQ ID NO: 4), GKKNDW (SEQ ID NO: 19), or fragments thereof, and lipidation in specific positions may result in both improved antagonistic effect and at the same time improved half-life to a surprisingly large extent of more than 5 or 10 hours or even more than 15 or 20 hours compared to the corresponding sequence without C-terminal extension.

As used herein "GIP(3-30)" refers to a GIP peptide analogue consisting residues 3 to 30 of GIP, or a functional variant thereof, for example SEQ ID NO:1 GIP(3-30)$X_1$-$X_2$, SEQ ID NO:30 GIP(3-30)$X_2$, SEQ ID NO:31 GIP(3-30)$X_1$, SEQ ID NO:32 GIP(3-30),and their functional variants. As used herein "GIP(4-30)" refers to a GIP peptide analogue consisting residues 4 to 30 of GIP, or a functional variant thereof, for example SEQ ID NO:33 GIP(4-30) $X_2$, SEQ ID NO: 34 GIP(4-30) and their functional variants. As used herein "GIP(5-30)" refers to a GIP peptide analogue consisting residues 5 to 30 of GIP, such as SEQ ID NO:35 GIP(5-30), or a functional variant thereof. As used herein "GIP(6-30)" refers to a GIP peptide analogue consisting residues 6 to 30 of GIP, such as SEQ ID NO: GIP(6-30), or a functional variant thereof.

In one embodiment said peptide is C-terminally carboxylated (—COOH).

Without being bound to any theory, a free C-terminal carboxylic acid may be able to assist in an increased binding to albumin and thus unexpectedly extend in vivo half-life further.

Another important advantage of the above aspect, where GIP antagonists of SEQ ID NO:1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36 GIP(6-30) and analogues thereof are extended with amino acid residues from the C-terminal part of Exendin-4 or GIP(1-42), such as e.g. GPSSGAPPPS (SEQ ID NO: 5), PSSGAPPPS (SEQ ID NO: 4) or GKKNDW (SEQ ID NO: 19), is that the antagonistic properties may be increased and/or the selectivity with respect to GIP receptor agonism is increased. As GIP(3-42) is a worse antagonist than GIP (3-30) [Hansen et al 2016 Br J Pharmacol] it is unexpected that the antagonism of AT631 with a C-terminal extension originating from Exendin-4, -PSSGAPPPS, is improved. Furthermore, Exendin-4 is a GLP-1 agonist, thus improving GIP antagonistic effects by extending of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36 GIP(6-30) analogues with amino acid residues from the C-terminal part of Exendin-4 is very unexpected.

A further important advantage of the above aspect, where GIP antagonists of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36 GIP(6-30) and analogues thereof are extended with amino acid residues from the C-terminal part of Exendin-4 or GIP(1-42), such as e.g. GPSSGAPPPS (SEQ ID NO: 5), PSSGAPPPS (SEQ ID NO: 4) or GKKNDW (SEQ ID NO: 19), is that the selectivity is increased with respect to activation or inhibition of other receptor members of GPCR family B, such as e.g. GLP-1R and Glucagon-R.

In one embodiment, it is provided a GIP antagonists of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36 GIP(6-30) and analogues thereof extended with amino acid residues from the C-terminal part of Exendin-4 or GIP(1-42), such as e.g. GPSSGAPPPS (SEQ ID NO: 5), PSSGAPPPS (SEQ ID NO: 4) or GKKNDW (SEQ ID NO: 19), and being C-terminal carboxylated.

In one embodiment it is provided a GIP peptide analogue or a functional variant thereof is an isolated peptide.

In one embodiment it is provided a GIP peptide analogue or a functional variant thereof as disclosed herein, wherein
the amino acid at position 5 is T or omitted;
the amino acid at position 9 is selected from D, E and T;
the amino acid at position 11 is selected from S, K and A;
the amino acid at position 12 is selected from I, K and 2-Aminoisobutyric acid (Aib);
the amino acid at position 13 is selected from A and Aib;
the amino acid at position 14 is selected from M, K, E, S, L and Nle;
the amino acid at position 15 is selected from D and E;
the amino acid at position 16 is selected from K and R;
the amino acid at position 17 is selected from I and K;
the amino acid at position 18 is selected from H and K;
the amino acid at position 20 is selected from Q and K;
the amino acid at position 21 is selected from D and E;
the amino acid at position 24 is selected from N, K, Q and E;
the amino acid at position 28 is selected from A and E;
the amino acid at position 29 is selected from Q and G; and/or
the amino acid at position 30 is selected from K, R, G and A.

In one embodiment it is provided a GIP peptide analogue or a functional variant thereof as disclosed herein, wherein said functional variant has 1 individual amino acid substitution, such as 2 individual amino acid substitutions, for example 3 individual amino acid substitutions, such as 4 individual amino acid substitutions at any amino acid residue of SEQ ID NO:1.

In one embodiment it is provided a GIP peptide analogue or a functional variant thereof as disclosed herein, wherein said functional variant has 1 individual amino acid substitution, such as 2 individual amino acid substitutions, for example 3 individual amino acid substitutions, such as 4 individual amino acid substitutions at any amino acid residue of SEQ ID NO:1, wherein said substitutions are conservative amino acid substitutions.

In one embodiment it is provided a GIP peptide analogue or a functional variant thereof as disclosed herein, wherein said functional variant has 1 to 2 individual amino acid substitutions, such as 2 to 3 individual amino acid substitutions, such as 3 to 4 individual amino acid substitutions, such as 4 to 5 individual amino acid substitutions, such as 5 to 6 individual amino acid substitutions, such as 6 to 7 individual amino acid substitutions, such as 7 to 8 individual amino acid substitutions at any amino acid residue of SEQ ID NO:1.

In one embodiment it is provided a GIP peptide analogue or a functional variant thereof as disclosed herein, wherein said GIP peptide analogue consists of amino acid sequence SEQ ID NO:1, and wherein $X_1$ and $X_2$ are omitted.

In one embodiment it is provided a GIP peptide analogue or a functional variant thereof as disclosed herein, wherein said GIP peptide analogue consists of amino acid sequence SEQ ID NO:1, and $X_1$, $X_2$ and the amino acid residue at position 5 are omitted. In one embodiment it is provided a GIP peptide analogue or a functional variant thereof as disclosed herein, wherein said functional variant has 1 to 7 individual amino acid substitutions, such as 1 individual amino acid substitutions, such as 2 individual amino acid substitutions, such as 3 individual amino acid substitutions, such as 4 individual amino acid substitutions, such as 5 individual amino acid substitutions, such as 6 individual amino acid substitutions, such as 7 individual amino acid substitutions at any one of amino acid residues 3 to 30 of SEQ ID NO:1.

In one embodiment it is provided a GIP peptide analogue or a functional variant thereof as disclosed herein, wherein said functional variant has 1 to 2 individual amino acid substitutions, such as 2 to 3 individual amino acid substitutions, such as 3 to 4 individual amino acid substitutions, such as 4 to 5 individual amino acid substitutions, such as 5 to 6 individual amino acid substitutions, such as 6 to 7 individual amino acid substitutions, such as 7 to 8 individual amino acid substitutions at any one of amino acid residues 3 to 30 of SEQ ID NO:1.

In one embodiment it is provided a GIP peptide analogue or a functional variant thereof as disclosed herein, wherein said functional variant has 1 to 2 individual amino acid substitutions, such as 2 to 3 individual amino acid substitutions, such as 3 to 4 individual amino acid substitutions, such as 4 to 5 individual amino acid substitutions, such as 5 to 6 individual amino acid substitutions, such as 6 to 7 individual amino acid substitutions, such as 7 to 8 individual amino acid substitutions at any one of amino acid residues 3, 4, 7, 8, 9, 11, 12, 13, 14, 15, 16, 17, 18, 19, 20, 21, 24, 28, 29 and 30 of SEQ ID NO:1.

In one embodiment it is provided a GIP peptide analogue or a functional variant thereof as disclosed herein, wherein said functional variant has 1 to 2 individual amino acid substitutions at any one of amino acid residues 4 to 10 of SEQ ID NO:1 GIP(3-30)$X_1$-$X_2$, SEQ ID NO: 30 GIP(3-30) $X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36 GIP(6-30).

In one embodiment it is provided a GIP peptide analogue or a functional variant thereof as disclosed herein, wherein said functional variant has 1 to 2, such as 1 to 3, such as 2 to 3 individual amino acid substitutions at any one of amino acid residues 19 to 27 of SEQ ID NO:1, such as of any one of SEQ ID NO:1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36 GIP(6-30).

In one embodiment it is provided a GIP peptide analogue or a functional variant thereof as disclosed herein, wherein at least one amino acid residue of the GIP peptide analogue of SEQ ID NO:1 is substituted with E.

In one embodiment it is provided a GIP peptide analogue or a functional variant thereof as disclosed herein, wherein at least one amino acid residue at any one of positions 9, 14, 15, 21, 24 and 28 is substituted with E, preferably at least one amino acid residue at any one of positions 9, 15, 21 and 24 of SEQ ID NO:1 is substituted with E.

Substitution of one or more amino acid residues of the peptide of SEQ ID NO:1 with E as defined herein is particularly advantageous as it may result in increased antagonistic effect, increased solubility, and/or increased stability of the substituted peptide.

In one embodiment it is provided a GIP peptide analogue or a functional variant thereof as disclosed herein, wherein $X_1$ is an amino acid residue selected from the group consisting of E, S, G, V, 2-Aminoisobutyric acid (Aib), P, D, γ-glutamic acid (γGlu), D-γ-glutamic acid (D-γGlu), β-Glutamic acid (βGlu), pyroE (pyroglutamic acid), glutaric acid.

In one embodiment it is provided a GIP peptide analogue or a functional variant thereof as disclosed herein, wherein $x_1$ is E.

In one embodiment it is provided a GIP peptide analogue or a functional variant thereof as disclosed herein, wherein $x_1$ is pyroE (pyroglutamic acid).

In one embodiment it is provided a GIP peptide analogue or a functional variant thereof as disclosed herein, wherein the E (Glu) at position 3 of (hGIP3-30, SEQ ID NO:32), such as of SEQ ID NO:1, is substituted with any amino acid, such with an amino acid residue selected from the group consisting of S, G, V, 2-Aminoisobutyric acid (Aib), P, D, γ-glutamic acid (γGlu), D-γ-glutamic acid (D-γGlu), β-Glutamic acid (βGlu), pyroE (pyroglutamic acid), glutaric acid. Glutaric acid, which may also be referred to as pentanedioic acid, is desamino glutamic acid i.e. glutamic acid where the amino group is lacking. Glutaric acid may also be referred to as a glutamic acid mimetic.

In one embodiment it is provided a GIP peptide analogue or a functional variant thereof as disclosed herein, wherein $X_1$ is E or glutaric acid.

GIP peptide analogues according to the present disclosure having E at position 3 may be very potent antagonists at the GIPR. However, having E in position 3 may lead to compounds which are unstable. Without wishing to be bound by theory, E at position 3 may form a pyroGlu by cyclization between the amino group at the N-terminus and the side chain carboxylic acid of E. It may therefore be an advantage to substitute the E at position 3. The present inventors have found that the amino group at the N-terminus may not be necessary for obtaining potent antagonists.

It may be advantageous to substitute E in position 3 (i.e. the first amino acid from the N-terminus) with glutaric acid, since glutaric acid has no amino group and therefore the N-terminal pyroGlu formation is not possible. PyroGlu formation may be an unwanted side reaction for glutamic acid. Substitution with glutaric acid in position 3 may also increase the potency. Glutaric acid is naturally produced in the body during the metabolism of some amino acids, including lysine and tryptophan.

In one embodiment it is provided a GIP peptide analogue or a functional variant thereof as disclosed herein, wherein the E (Glu) at position 3 of (hGIP3-30, SEQ ID NO:32), such as of any one of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO: 32 GIP(3-30) is substituted with a S (Ser).

In one embodiment it is provided a GIP peptide analogue or a functional variant thereof as disclosed herein, wherein the E (Glu) at position 3 of (hGIP3-30, SEQ ID NO:32), such as of any one of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO: 32 GIP(3-30) is substituted with a pyroE (pyroglutamate).

In one embodiment it is provided a GIP peptide analogue or a functional variant thereof as disclosed herein, wherein the E (Glu) at position 3 of (hGIP3-30, SEQ ID NO:32), such as of any one of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO: 32 GIP(3-30) is substituted with a P (Pro).

In one embodiment it is provided a GIP peptide analogue or a functional variant thereof as disclosed herein, wherein the E (Glu) at position 3 of (hGIP3-30, SEQ ID NO:32), such as of any one of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO: 32 GIP(3-30) is substituted with a G (Gly).

In one embodiment it is provided a GIP peptide analogue or a functional variant thereof as disclosed herein, wherein the E (Glu) at position 3 of (hGIP3-30, SEQ ID NO:32), such as of any one of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO: 32 GIP(3-30) is substituted with a A (Ala).

In one embodiment it is provided a GIP peptide analogue or a functional variant thereof, wherein $X_2$ is an amino acid residue selected from the group consisting of G and E.

In one embodiment it is provided a GIP peptide analogue or a functional variant thereof, wherein the D at position 9 of any one of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36, GIP(6-30), or a functional variant thereof, is substituted with any amino acid.

In one embodiment it is provided a GIP peptide analogue or a functional variant thereof, wherein the D at position 9 of any one of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36, GIP(6-30), or a functional variant thereof, is substituted with a conservative amino acid.

In one embodiment it is provided a GIP peptide analogue or a functional variant thereof, wherein the D at position 9 of any one of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36, GIP(6-30), or a functional variant thereof, is substituted with an amino acid residue selected from the group consisting of E and T. An advantage of having E at position 9 is that the potency and/or physical stability, such as solubility, may be increased. E in position 9 may also prevent agonistic activity.

In one embodiment it is provided a GIP peptide analogue or a functional variant thereof, wherein the S at position 11 of any one of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36 GIP(6-30), or of the functional variant thereof, is substituted with any amino acid.

In one embodiment it is provided a GIP peptide analogue or a functional variant thereof, wherein the S at position 11 of any one of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36 GIP(6-30), or a functional variant thereof, is substituted with a conservative amino acid.

In one embodiment it is provided a GIP peptide analogue or a functional variant thereof, wherein the S at position 11 of any one of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36 GIP(6-30), or a functional variant thereof, is substituted with an amino acid residue selected from the group consisting of A, K and Orn.

In one embodiment it is provided a GIP peptide analogue or a functional variant thereof, wherein the S at position 11 of any one of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36 GIP(6-30), or of the functional variant thereof, is substituted with an amino acid selected from the group consisting of A, R, K and Orn.

In one embodiment it is provided a GIP peptide analogue or a functional variant thereof, wherein the S at position 11 of any one of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36 GIP(6-30), or of the functional variant thereof, is substituted with a K or a Orn.

In one embodiment it is provided a GIP peptide analogue or a functional variant thereof, wherein the I at position 12 of any one of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36 GIP(6-30), or a functional variant thereof, is substituted with any amino acid.

In one embodiment it is provided a GIP peptide analogue or a functional variant thereof, wherein the I at position 12 of any one of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36 GIP(6-30), or a functional variant thereof, is substituted with a conservative amino acid.

In one embodiment it is provided a GIP peptide analogue or a functional variant thereof, wherein the I at position 12 of any one of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36 GIP(6-30), or a functional variant thereof, is substituted with an amino acid residue selected from the group consisting of K, Orn and 2-Aminoisobutyric acid (Aib).

In one embodiment it is provided a GIP peptide analogue or a functional variant thereof, wherein the A at position 13 of any one of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36 GIP(6-30), or a functional variant thereof, is substituted with any amino acid.

In one embodiment it is provided a GIP peptide analogue or a functional variant thereof, wherein the A at position 13 of any one of SEQ ID NO: 1 GIP(3-30)X$_1$-X$_2$, SEQ ID NO: 30 GIP(3-30)X$_2$, SEQ ID NO: 31 GIP(3-30)X$_1$, SEQ ID NO:32 GIP(3-30), SEQ ID NO:33 GIP(4-30)X$_2$, SEQ ID NO: 34 GIP(4-30), SEQ ID NO: 35 GIP(5-30), SEQ ID NO: 36 GIP(6-30), or a functional variant thereof, is substituted with a conservative amino acid.

In one embodiment it is provided a GIP peptide analogue or a functional variant thereof, wherein the A at position 13 of any one of SEQ ID NO: 1 GIP(3-30)X$_1$-X$_2$, SEQ ID NO: 30 GIP(3-30)X$_2$, SEQ ID NO: 31 GIP(3-30)X$_1$, SEQ ID NO:32 GIP(3-30), SEQ ID NO:33 GIP(4-30)X$_2$, SEQ ID NO: 34 GIP(4-30), SEQ ID NO: 35 GIP(5-30), SEQ ID NO: 36 GIP(6-30), or a functional variant thereof, is substituted with 2-Aminoisobutyric acid (Aib). An advantage of having Aib at position 13 is that the potency may be considerably increased. In addition, Aib in position 13 may also increase the stability of the peptide, such as the in vivo stability or physical stability.

It has been observed that substitutions of any one of the amino acid residues at positions 12 and 13 of any one of SEQ ID NO: 1 GIP(3-30)X$_1$-X$_2$, SEQ ID NO: 30 GIP(3-30)X$_2$, SEQ ID NO: 31 GIP(3-30)X$_1$, SEQ ID NO:32 GIP(3-30), SEQ ID NO:33 GIP(4-30)X$_2$, SEQ ID NO: 34 GIP(4-30), SEQ ID NO: 35 GIP(5-30), SEQ ID NO: 36 GIP(6-30), or a functional variant thereof, may further increases stability and half-life of the GIP peptide analogue.

In one embodiment it is provided a GIP peptide analogue or a functional variant thereof, wherein the M at position 14 of any one of SEQ ID NO: 1 GIP(3-30)X$_1$-X$_2$, SEQ ID NO: 30 GIP(3-30)X$_2$, SEQ ID NO: 31 GIP(3-30)X$_1$, SEQ ID NO:32 GIP(3-30), SEQ ID NO:33 GIP(4-30)X$_2$, SEQ ID NO: 34 GIP(4-30), SEQ ID NO: 35 GIP(5-30), SEQ ID NO: 36 GIP(6-30), or a functional variant thereof, is substituted with any amino acid.

In one embodiment it is provided a GIP peptide analogue or a functional variant thereof, wherein the M at position 14 of any one of SEQ ID NO: 1 GIP(3-30)X$_1$-X$_2$, SEQ ID NO: 30 GIP(3-30)X$_2$, SEQ ID NO: 31 GIP(3-30)X$_1$, SEQ ID NO:32 GIP(3-30), SEQ ID NO:33 GIP(4-30)X$_2$, SEQ ID NO: 34 GIP(4-30), SEQ ID NO: 35 GIP(5-30), SEQ ID NO: 36 GIP(6-30), or a functional variant thereof, is substituted with a conservative amino acid.

In one embodiment it is provided a GIP peptide analogue or a functional variant thereof, wherein the M at position 14 of any one of SEQ ID NO: 1 GIP(3-30)X$_1$-X$_2$, SEQ ID NO: 30 GIP(3-30)X$_2$, SEQ ID NO: 31 GIP(3-30)X$_1$, SEQ ID NO:32 GIP(3-30), SEQ ID NO:33 GIP(4-30)X$_2$, SEQ ID NO: 34 GIP(4-30), SEQ ID NO: 35 GIP(5-30), SEQ ID NO: 36 GIP(6-30), or a functional variant thereof, is substituted with an amino acid residue selected from the group consisting of L, Norleucine (Nle), E, S, K and Orn.

In one embodiment it is provided a GIP peptide analogue or a functional variant thereof, wherein the M at position 14 of any one of SEQ ID NO: 1 GIP(3-30)X$_1$-X$_2$, SEQ ID NO: 30 GIP(3-30)X$_2$, SEQ ID NO: 31 GIP(3-30)X$_1$, SEQ ID NO:32 GIP(3-30), SEQ ID NO:33 GIP(4-30)X$_2$, SEQ ID NO: 34 GIP(4-30), SEQ ID NO: 35 GIP(5-30), SEQ ID NO: 36 GIP(6-30), or a functional variant thereof, is substituted with an amino acid residue selected from the group consisting of L, Norleucine (Nle) and K. In some embodiments, the amino acid at position 14 is L or Nle. Since, M is prone to oxidation it may be an advantage to substitute it with another amino acid such as L, Nle or K, for example L or Nle.

In some embodiments, the amino acid at position 14 is L.

In one embodiment it is provided a GIP peptide analogue or a functional variant thereof, wherein the D at position 15 of any one of SEQ ID NO: 1 GIP(3-30)X$_1$-X$_2$, SEQ ID NO: 30 GIP(3-30)X$_2$, SEQ ID NO: 31 GIP(3-30)X$_1$, SEQ ID NO:32 GIP(3-30), SEQ ID NO:33 GIP(4-30)X$_2$, SEQ ID NO: 34 GIP(4-30), SEQ ID NO: 35 GIP(5-30), SEQ ID NO: 36 GIP(6-30), or a functional variant thereof, is substituted with any amino acid.

In one embodiment it is provided a GIP peptide analogue or a functional variant thereof, wherein the D at position 15 of any one of SEQ ID NO: 1 GIP(3-30)X$_1$-X$_2$, SEQ ID NO: 30 GIP(3-30)X$_2$, SEQ ID NO: 31 GIP(3-30)X$_1$, SEQ ID NO:32 GIP(3-30), SEQ ID NO:33 GIP(4-30)X$_2$, SEQ ID NO: 34 GIP(4-30), SEQ ID NO: 35 GIP(5-30), SEQ ID NO: 36 GIP(6-30), or a functional variant thereof, is substituted with a conservative amino acid.

In one embodiment it is provided a GIP peptide analogue or a functional variant thereof, wherein the D at position 15 of any one of SEQ ID NO: 1 GIP(3-30)X$_1$-X$_2$, SEQ ID NO: 30 GIP(3-30)X$_2$, SEQ ID NO: 31 GIP(3-30)X$_1$, SEQ ID NO:32 GIP(3-30), SEQ ID NO:33 GIP(4-30)X$_2$, SEQ ID NO: 34 GIP(4-30), SEQ ID NO: 35 GIP(5-30), SEQ ID NO: 36 GIP(6-30), SEQ ID NO: 36(GIP6-30), or a functional variant thereof, is substituted with E. An advantage of having E at position 15 is that the potency and/or physical stability, such as solubility, may be increased. E in position 15 may also prevent agonistic activity.

In one embodiment it is provided a GIP peptide analogue or a functional variant thereof, wherein the D at position 9 and/or at position 15 of any one of SEQ ID NO: 1 GIP(3-30)X$_1$-X$_2$, SEQ ID NO: 30 GIP(3-30)X$_2$, SEQ ID NO: 31 GIP(3-30)X$_1$, SEQ ID NO:32 GIP(3-30), SEQ ID NO:33 GIP(4-30)X$_2$, SEQ ID NO: 34 GIP(4-30), SEQ ID NO: 35 GIP(5-30), SEQ ID NO: 36 GIP(6-30) or a functional variant thereof, is substituted with E.

In one embodiment it is provided a GIP peptide analogue or a functional variant thereof, wherein the K at position 16 of any one of SEQ ID NO: 1 GIP(3-30)X$_1$-X$_2$, SEQ ID NO: 30 GIP(3-30)X$_2$, SEQ ID NO: 31 GIP(3-30)X$_1$, SEQ ID NO:32 GIP(3-30), SEQ ID NO:33 GIP(4-30)X$_2$, SEQ ID NO: 34 GIP(4-30), SEQ ID NO: 35 GIP(5-30), SEQ ID NO: 36 GIP(6-30), or of the functional variant thereof, is substituted with any amino acid.

In one embodiment it is provided a GIP peptide analogue or a functional variant thereof, wherein the K at position 16 of any one of SEQ ID NO: 1 GIP(3-30)X$_1$-X$_2$, SEQ ID NO: 30 GIP(3-30)X$_2$, SEQ ID NO: 31 GIP(3-30)X$_1$, SEQ ID NO:32 GIP(3-30), SEQ ID NO:33 GIP(4-30)X$_2$, SEQ ID NO: 34 GIP(4-30), SEQ ID NO: 35 GIP(5-30), SEQ ID NO: 36 GIP(6-30), or of the functional variant thereof, is substituted with a conservative amino acid substitution.

In one embodiment it is provided a GIP peptide analogue or a functional variant thereof, wherein the K at position 16 of any one of SEQ ID NO: 1 GIP(3-30)X$_1$-X$_2$, SEQ ID NO: 30 GIP(3-30)X$_2$, SEQ ID NO: 31 GIP(3-30)X$_1$, SEQ ID NO:32 GIP(3-30), SEQ ID NO:33 GIP(4-30)X$_2$, SEQ ID NO: 34 GIP(4-30), SEQ ID NO: 35 GIP(5-30), SEQ ID NO: 36 GIP(6-30), or of the functional variant thereof, is substituted with an amino acid selected from the group consisting of R, A and E.

In one embodiment it is provided a GIP peptide analogue or a functional variant thereof, wherein the K at position 16 of any one of SEQ ID NO: 1 GIP(3-30)X$_1$-X$_2$, SEQ ID NO: 30 GIP(3-30)X$_2$, SEQ ID NO: 31 GIP(3-30)X$_1$, SEQ ID NO:32 GIP(3-30), SEQ ID NO:33 GIP(4-30)X$_2$, SEQ ID NO: 34 GIP(4-30), SEQ ID NO: 35 GIP(5-30), SEQ ID NO: 36 GIP(6-30), or of the functional variant thereof, is substituted with R.

In one embodiment it is provided a GIP peptide analogue or a functional variant thereof, wherein the I at position 17 of any one of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36 GIP(6-30), or of the functional variant thereof, is substituted with any amino acid.

In one embodiment it is provided a GIP peptide analogue or a functional variant thereof, wherein the I at position 17 of any one of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36 GIP(6-30), or of the functional variant thereof, is substituted with a conservative amino acid.

In one embodiment it is provided a GIP peptide analogue or a functional variant thereof, wherein the I at position 17 of any one of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36 GIP(6-30), or of the functional variant thereof, is substituted with K or Orn.

In one embodiment it is provided a GIP peptide analogue or a functional variant thereof, wherein the H at position 18 of any one of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36 GIP(6-30), or a functional variant thereof, is substituted with any amino acid.

In one embodiment it is provided a GIP peptide analogue or a functional variant thereof, wherein the H at position 18 of any one of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36 GIP(6-30), or of the functional variant thereof, is substituted with a conservative amino acid.

In one embodiment it is provided a GIP peptide analogue or a functional variant thereof, wherein the H at position 18 of any one of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36 GIP(6-30), or of a functional variant thereof, is substituted with an amino acid selected from the group consisting of A, R, K and Orn.

In one embodiment it is provided a GIP peptide analogue or a functional variant thereof, wherein the H at position 18 of any one of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36 GIP(6-30), or of a functional variant thereof, is substituted with a K or a Orn.

In one embodiment it is provided a GIP peptide analogue or a functional variant thereof, wherein the S at position 11 and/or the H at position 18 of any one of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36 GIP(6-30) or a functional variant thereof, is substituted with K.

In one embodiment it is provided a GIP peptide analogue or a functional variant thereof, wherein the Q at position 20 of any one of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36 GIP(6-30), or of the functional variant thereof, is substituted with any amino acid.

In one embodiment it is provided a GIP peptide analogue or a functional variant thereof, wherein the Q at position 20 of any one of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36 GIP(6-30), or of the functional variant thereof, is substituted with a conservative amino acid.

In one embodiment it is provided a GIP peptide analogue or a functional variant thereof, wherein the Q at position 20 of any one of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36 GIP(6-30), or of the functional variant thereof, is substituted with K or Orn.

In one embodiment it is provided a GIP peptide analogue or a functional variant thereof, wherein the D at position 21 of any one of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36 GIP(6-30), or of the functional variant thereof, is substituted with any amino acid.

In one embodiment it is provided a GIP peptide analogue or a functional variant thereof, wherein the D at position 21 of any one of SEQ ID NO:1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36 GIP(6-30), or of the functional variant thereof, is substituted with a conservative amino acid.

In one embodiment it is provided a GIP peptide analogue or a functional variant thereof, wherein the D at position 21 of any one of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36 GIP(6-30), or of the functional variant thereof, is substituted with E. An advantage of having E at position 21 is that the potency and/or physical stability, such as solubility, may be increased.

In one embodiment it is provided a GIP peptide analogue or a functional variant thereof, wherein the N at position 24 of any one of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36 GIP(6-30), or of the functional variant thereof, is substituted with any amino acid.

In one embodiment it is provided a GIP peptide analogue or a functional variant thereof, wherein the N at position 24 of any one of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO:

36 GIP(6-30), or of the functional variant thereof, is substituted with a conservative amino acid.

In one embodiment it is provided a GIP peptide analogue or a functional variant thereof, wherein the N at position 24 of any one of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36 GIP(6-30), or of the functional variant thereof, is substituted with an amino acid selected from Q, A and E.

In one embodiment it is provided a GIP peptide analogue or a functional variant thereof, wherein the N at position 24 of any one of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36 GIP(6-30), or of the functional variant thereof, is substituted with E. An advantage of having an E at position 24 is that the physical stability, such as solubility, may be increased. It may also reduce the susceptibility to aggregate.

In one embodiment it is provided a GIP peptide analogue or a functional variant thereof, wherein the A at position 28 of any one of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36 GIP(6-30), or of the functional variant thereof, is substituted with any amino acid.

In one embodiment it is provided a GIP peptide analogue or a functional variant thereof, wherein the A at position 28 of any one of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36 GIP(6-30), or of the functional variant thereof, is substituted with a conservative amino acid.

In one embodiment it is provided a GIP peptide analogue or a functional variant thereof, wherein the A at position 28 of any one of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36 GIP(6-30), or of the functional variant thereof, is substituted with E.

In one embodiment it is provided a GIP peptide analogue or a functional variant thereof, wherein the Q at position 29 of any one of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36 GIP(6-30), or of the functional variant thereof, is substituted with any amino acid.

In one embodiment it is provided a GIP peptide analogue or a functional variant thereof, wherein the Q at position 29 of any one of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36 GIP(6-30), or of the functional variant thereof, is substituted with a conservative amino acid.

In one embodiment it is provided a GIP peptide analogue or a functional variant thereof, wherein the Q at position 29 of any one of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36 GIP(6-30), or of the functional variant thereof, is substituted with G.

In one embodiment it is provided a GIP peptide analogue or a functional variant thereof, wherein the K at position 30 of any one of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36 GIP(6-30), or of the functional variant thereof, is substituted with any amino acid.

In one embodiment it is provided a GIP peptide analogue or a functional variant thereof, wherein the K at position 30 of any one of SEQ ID NO:1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36 GIP(6-30), or of the functional variant thereof, is substituted with a conservative amino acid substitution.

In one embodiment it is provided a GIP peptide analogue or a functional variant thereof, wherein the K at position 30 of any one of SEQ ID NO: 1 (GIP3-30 $X_1$-$X_2$), SEQ ID NO:30 (GIP3-30 $X_2$), SEQ ID NO: 31 (GIP3-30 $X_1$), SEQ ID NO:32 (GIP3-30), SEQ ID NO: 33 (GIP4-30 $X_2$), SEQ ID NO:34(GIP4-30), SEQ ID NO: 35 (GIP5-30), SEQ ID NO:36 (GIP6-30), or of the functional variant thereof, is substituted with an amino acid selected from the group consisting of R, A, E and G, preferably with an amino acid selected from the group consisting of R, A and G.

In one embodiment it is provided a GIP peptide analogue or a functional variant thereof, wherein the amino acid residues at positions 9, 15, 21, and 24 are all individually an alfa-helix stabilizing amino acid residue selected from the group consisting of A, L, E and K.

In one embodiment it is provided a GIP peptide analogue or a functional variant thereof, wherein said GIP peptide analogue comprises at least one substitution to K and one substitution to E or Aib at any one of amino acid residues 3 to 30 of SEQ ID NO:1, such as of any one of SEQ ID NO:1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36 GIP(6-30).

In one embodiment it is provided a GIP peptide analogue or a functional variant thereof, wherein said GIP peptide analogue comprises at least one substitution to K and one substitution to E or Aib at any one of amino acid residues 3 to 30 of SEQ ID NO:1, such as of any one of SEQ ID NO:1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36 GIP(6-30), wherein at least one of the amino acid residues at any one of positions 11, 14 and/or 18 is substituted to a K, and wherein at least one of the amino acid residues at any one of positions 9, 15, 21 and/or 24 is substituted to a E.

In one embodiment it is provided a GIP peptide analogue (SEQ ID NO:1) or a functional variant thereof, wherein
the amino acid at position 5 is T;
the amino acid at position 6 is F;
the amino acid at position 10 is Y;
the amino acid at position 22 is F;
the amino acid at position 23 is V;
the amino acid at position 25 is W;
the amino acid at position 26 is L;
the amino acid at position 27 is L.

In one embodiment it is provided a GIP peptide analogue (SEQ ID NO:1) or a functional variant thereof, wherein the amino acid at position 5 is T.

In one embodiment it is provided a GIP peptide analogue (SEQ ID NO:1) or a functional variant thereof, wherein the amino acid at position 6 is F.

In one embodiment it is provided a GIP peptide analogue (SEQ ID NO:1) or a functional variant thereof, wherein the amino acid at position 7 is I.

In one embodiment it is provided a GIP peptide analogue (SEQ ID NO:1) or a functional variant thereof, wherein the amino acid at position 10 is Y.

In one embodiment it is provided a GIP peptide analogue (SEQ ID NO:1) or a functional variant thereof, wherein the amino acid at position 22 is F.

In one embodiment it is provided a GIP peptide analogue (SEQ ID NO:1) or a functional variant thereof, wherein the amino acid at position 23 is V.

In one embodiment it is provided a GIP peptide analogue (SEQ ID NO:1) or a functional variant thereof, wherein the amino acid at position 25 is W.

In one embodiment it is provided a GIP peptide analogue (SEQ ID NO:1) or a functional variant thereof, wherein the amino acid at position 26 is L.

In one embodiment it is provided a GIP peptide analogue (SEQ ID NO:1) or a functional variant thereof, wherein the amino acid at position 27 is L.

In one embodiment it is provided a GIP peptide analogue (SEQ ID NO:1) or a functional variant thereof, wherein the amino acid residues at positions 29 and 30 are not both G.

In one embodiment it is provided a GIP peptide analogue (SEQ ID NO:1) or a functional variant thereof, wherein only one of the amino acid residues at positions 29 and 30 is G.

In one embodiment it is provided a GIP peptide analogue (SEQ ID NO:1) or a functional variant thereof, wherein the amino acid residues at positions 29 and 30 individually selected from the group consisting of Q, E and K.

In one embodiment it is provided a GIP peptide analogue (SEQ ID NO:1) or a functional variant thereof, wherein the amino acid at position 29 is Q.

In one embodiment it is provided a GIP peptide analogue (SEQ ID NO:1) or a functional variant thereof, wherein the amino acid at position 30 is K.

In one embodiment it is provided a GIP peptide analogue (SEQ ID NO:1) wherein
the amino acid residue at position 3 is E or glutaric acid or absent,
the amino acid residue at position 4 is G or absent,
the amino acid residue at position 5 is T,
the amino acid residue at position 6 is F,
the amino acid residue at position 7 is I,
the amino acid residue at position 8 is S,
the amino acid residue at position 9 is D or E,
the amino acid residue at position 10 is Y,
the amino acid residue at position 11 is K or S,
the amino acid residue at position 12 is I or K,
the amino acid residue at position 13 is A or Aib or K,
the amino acid residue at position 14 is M, L, Nle or K,
the amino acid residue at position 15 is D or E,
the amino acid residue at position 16 is K,
the amino acid residue at position 17 is I or K,
the amino acid residue at position 18 is H or K,
the amino acid residue at position 19 is Q,
the amino acid residue at position 20 is Q,
the amino acid residue at position 21 is D or E,
the amino acid residue at position 22 is F,
the amino acid residue at position 23 is V,
the amino acid residue at position 24 is N, A, Q or E,
the amino acid residue at position 25 is W,
the amino acid residue at position 26 is L,
the amino acid residue at position 27 is L,
the amino acid residue at position 28 is A, E or K,
the amino acid residue at position 29 is Q, G or K, and
the amino acid residue at position 30 is K or G,
or a functional variant thereof.

In one embodiment it is provided a GIP peptide analogue (SEQ ID NO:1) wherein
the amino acid at position 3 is E or glutaric acid or absent;
the amino acid at position 4 is Gly or absent;
the amino acid at position 5 is T;
the amino acid at position 9 is selected from D, E;
the amino acid at position 11 is selected from S, K and A;
the amino acid at position 12 is selected from I and K;
the amino acid at position 13 is selected from A and Aib;
the amino acid at position 14 is selected from M, L and Nle;
the amino acid at position 15 is selected from D and E;
the amino acid at position 16 is selected from K and R;
the amino acid at position 17 is selected from I and K;
the amino acid at position 18 is selected from H and K;
the amino acid at position 20 is selected from Q and K;
the amino acid at position 21 is selected from D and E;
the amino acid at position 24 is selected from N, Q and E;
the amino acid at position 28 is selected from A and E;
the amino acid at position 29 is selected from Q and G; and/or
the amino acid at position 30 is selected from K, R, G and A.

In one embodiment it is provided a GIP peptide analogue (SEQ ID NO:1) wherein
the amino acid at position 3 is Glu or glutaric acid or absent
the amino acid at position 4 is Gly or absent
the amino acid at position 5 is T;
the amino acid at position 6 is F;
the amino acid at position 7 is I;
the amino acid at position 9 is selected from D and E;
the amino acid at position 10 is Y;
the amino acid at position 11 is selected from S, K and A;
the amino acid at position 12 is selected from I and K;
the amino acid at position 13 is selected from A and Aib;
the amino acid at position 14 is selected from M, L and Nle;
the amino acid at position 15 is selected from D and E;
the amino acid at position 16 is selected from K and R;
the amino acid at position 17 is selected from I and K;
the amino acid at position 18 is selected from H and K;
the amino acid at position 20 is selected from Q and K;
the amino acid at position 21 is selected from D and E;
the amino acid at position 22 is F;
the amino acid at position 23 is V;
the amino acid at position 24 is selected from N, Q and E;
the amino acid at position 25 is W;
the amino acid at position 26 is L;
the amino acid at position 27 is L;
the amino acid at position 29 is Q; and/or
the amino acid at position 30 is K or R.

In one embodiment the present disclosure provides a GIP peptide analogue consisting of SEQ ID NO:1 (GIP3-30 $X_1$-$X_2$):

```
 3 -  4 - 5 - 6  7   8   9  10  11
X₁ - X₂ - T - F - I - S - D - Y - S -

12  13  14  15  16  17
 I - A - M - D - K - I 18  19  20  21  22  23  24  25
 H - Q - Q - D - F - V - N - W -

26  27  28  29  30
 L - L - A - Q - K - Z.
```

In one embodiment the present disclosure provides a GIP peptide analogue consisting of SEQ ID NO:30 (GIP3-30 $X_2$):

```
 3 - 4 - 5 - 6  7   8   9  10  11
 E - X₂ - T - F - I - S - D - Y - S -

12  13  14  15  16  17
 I - A - M - D - K - I 18 19 20 21 22 23 24 25
 H - Q - Q - D - F - V -

26 27 28 29 30
 N - W - L - L - A - Q - K - Z.
```

In one embodiment the present disclosure provides a GIP peptide analogue consisting of SEQ ID NO: 31 (GIP3-30 $X_1$):

```
 3 -  4 - 5 - 6  7   8   9  10  11  12  13  14
X₁ - G - T - F - I - S - D - Y - S - I - A - M -

15  16  17 18  19  20  21  22  23  24  25  26
 D - K - I H - Q - Q - D - F - V - N - W - L -

27  28  29  30
 L - A - Q - K - Z.
```

In one embodiment the present disclosure provides a GIP peptide analogue consisting of SEQ ID NO:32 (GIP3-30):

```
 3 - 4 - 5 - 6  7   8   9  10  11  12  13  14
 E - G - T - F - I - S - D - Y - S - I - A - M -

15  16  17 18  19  20  21  22  23  24  25  26
 D - K - I H - Q - Q - D - F - V - N - W - L -

27  28  29  30
 L - A - Q - K - Z.
```

In one embodiment the present disclosure provides a GIP peptide analogue consisting of SEQ ID NO: 33(GIP4-30 $X_2$):

```
 4 - 5 - 6  7   8   9  10  11  12  13  14  15
X₂ - T - F - I - S - D - Y - S - I - A - M - D -

16 17 18  19  20  21  22  23  24  25  26  27
 K - I H - Q - Q - D - F - V - N - W - L - L -

28  29  30
 A - Q - K - Z.
```

In one embodiment the present disclosure provides a GIP peptide analogue consisting of SEQ ID NO:34 (GIP4-30):

```
 4 - 5 - 6  7   8   9  10  11  12  13  14  15
 G - T - F - I - S - D - Y - S - I - A - M - D -

16 17 18  19  20  21  22  23  24  25  26  27
 K - I H - Q - Q - D - F - V - N - W - L - L -

28  29  30
 A - Q - K - Z.
```

In one embodiment the present disclosure provides a GIP peptide analogue wherein the amino acid residue at position 4 is absent when the amino acid residue at position 3 is absent.

In one embodiment the present disclosure provides a GIP peptide analogue consisting of SEQ ID NO:35 (GIP5-30):

```
5 - 6  7   8   9  10  11  12  13  14  15  16  17
T - F - I - S - D - Y - S - I - A - M - D - K - I 18  19  20  21  22  23  24  25  26  27  28  29
 H - Q - Q - D - F - V - N - W - L - L - A - Q -

30
 K - Z.
```

In one embodiment the present disclosure provides a GIP peptide analogue consisting of SEQ ID NO:36 (GIP6-30):

```
 6  7   8   9  10  11  12  13  14  15  16  17
 F - I - S - D - Y - S - I - A - M - D - K - I 18  19  20  21  22  23  24  25  26  27  28
 H - Q - Q - D - F - V - N - W - L - A -

29  30
 Q - K - Z.
```

One feature of the GIP peptide analogue of the present disclosure is the presence of the moiety referred to as Z, Z peptide, or peptide Z. As provided herein, Z is a peptide comprising one or more amino acid residues of GIP(31-42) (GKKNDWKHNITQ; SEQ ID NO: 2) or one or more amino acid residues of Exendin-4 (HGEGTFTSDLSKQMEEE-AVRLFIEWLKNGGPSSGAPPPS; SEQ ID NO: 3). The presence of the Z peptide is advantageous as it improves both the half-life and the antagonistic potency of the GIP peptide analogue.

In one embodiment of the present disclosure, Z consists of one or more consecutive amino acid residues of GIP(31-42) (SEQ ID NO: 2).

In one embodiment of the present disclosure, Z consists of one or more consecutive amino acid residues of Exendin-4 (SEQ ID NO: 3).

In one embodiment of the present disclosure, Z consists of one or more amino consecutive acid residues of the C-terminus of Exendin-4(30-39) (PSSGAPPPS; SEQ ID NO: 4 CE30-39).

In one embodiment of the present disclosure, Z consists of one or more amino consecutive acid residues of the C-terminus of Exendin-4(29-39) (GPSSGAPPPS; SEQ ID NO: 5 CE29-39).

In one embodiment of the present disclosure, Z comprises at least one G or one P. Without wishing to be bound by theory it is believed that when Z comprises a G or P, such as e.g. in position 31 and/or 32, the half-life of the GIP peptide analogue increases, which may be due to decreased degradation from the C-terminus, which increases the in vivo stability of the GIP peptide analogue.

In one embodiment of the present disclosure, Z comprises at least two P.

In one embodiment of the present disclosure, Z is a peptide selected from the group consisting of
- a glycine or a proline,
- GP, GPS, GPSS (SEQ ID NO: 6), GPSSG (SEQ ID NO: 7), GPSSGA (SEQ ID NO: 8), GPSSGAP (SEQ ID NO: 9), GPSSGAPP (SEQ ID NO: 10), GPSSGAPPP (SEQ ID NO: 11) and GPSSGAPPPS (SEQ ID NO: 5),
- PS, PSS, PSSG (SEQ ID NO: 12), PSSGA (SEQ ID NO: 13), PSSGAP (SEQ ID NO: 14), PSSGAPP (SEQ ID NO: 15), PSSGAPPP (SEQ ID NO: 16) and PSSGAPPPS (SEQ ID NO: 4),
- GK, GKK, GKKN (SEQ ID NO: 17), GKKND (SEQ ID NO: 18), GKKNDW (SEQ ID NO: 19), GRKNDW (SEQ ID NO: 20), GKRNDW (SEQ ID NO: 21), GRRNDW (SEQ ID NO: 22), GKKNDWK (SEQ ID NO: 23), GKKNDWKH (SEQ ID NO: 24), GKKNDWKHN (SEQ ID NO: 25), GKKNDWKHNI (SEQ ID NO: 26), GKKNDWKHNIT (SEQ ID NO: 27) and GKKNDWKHNITQ (SEQ ID NO:2),
- GPSSGA (SEQ ID NO: 8), GPSSGAP (SEQ ID NO: 9), GPSSGAPP (SEQ ID NO: 10), GPSSGAPPP (SEQ ID NO: 11), GPSSGAPPPS (SEQ ID NO: 5), GKKNDW (SEQ ID NO: 19), GKKKDW (SEQ ID NO: 28), GKKNDK (SEQ ID NO: 29), GRKNDW (SEQ ID NO: 20), GKRNDW (SEQ ID NO: 21), GRRNDW (SEQ ID NO: 22), GKKNDWK (SEQ ID NO: 23), GKKNDWKH (SEQ ID NO: 24), GKKNDWKHN (SEQ ID NO: 25), GKKNDWKHNI (SEQ ID NO: 26), GKKNDWKHNIT (SEQ ID NO: 27) and GKKNDWKHNITQ (SEQ ID NO:2), or a variant thereof comprising 1 or 2 individual amino acid substitutions at any one of the amino acid residues, or
- PSSG (SEQ ID NO: 12), PSSGA (SEQ ID NO: 13), PSSGAP (SEQ ID NO: 14), PSSGAPP (SEQ ID NO: 15), PSSGAPPP (SEQ ID NO: 16) and PSSGAPPPS (SEQ ID NO: 4), or a variant thereof comprising 1 or 2 individual amino acid substitutions at any one of the amino acid residues.

In one embodiment of the present disclosure a fatty acid molecule a fatty acid molecule is not attached at the amino acid residue at position 3 of SEQ ID NO:1 or a variant thereof.

In one embodiment a fatty acid molecule is not attached at the N-terminal amino group of the amino acid residue at position 3 of SEQ ID NO:1 GIP(3-30)$X_1$-$X_2$, SEQ ID NO: 30 GIP(3-30)$X_2$, SEQ ID NO:31 GIP(3-30)$X_1$, or SEQ ID NO:32 GIP(3-30).

In one embodiment a fatty acid molecule is not attached at the N-terminal amino group of the amino acid residue at position 4 of SEQ ID NO: 33 GIP(4-30)$X_2$ or SEQ ID NO: 34 GIP(4-30).

In one embodiment a fatty acid molecule is not attached at the N-terminal amino group of the amino acid residue at position 5 of SEQ ID NO: 35 GIP(5-30).

In one embodiment a fatty acid molecule is not attached to an amino acid residue of Z.

In one embodiment the GIP peptide analogue of the present disclosure has a free N-terminus. Thus, the N-terminus of the GIP peptide analogue comprises an amino (—$NH_2$) moiety which is not substituted, such as which is not acetylated, acylated or alkylated. Hence, the N-terminus of the GIP peptide analogue may comprise a free amino (—$NH_2$) moiety.

In one embodiment a fatty acid molecule is attached to an amino acid residue at any one of positions 7 to 29 of said GIP peptide analogue, such as of SEQ ID NO:1. In one embodiment a fatty acid molecule is attached to an amino acid residue at any one of positions 7 to 29 of any one of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36 GIP(6-30), or a variant thereof.

In one embodiment a fatty acid molecule is attached to an amino acid residue at any one of positions 6 to 29 of said GIP peptide analogue, such as of SEQ ID NO:1. In one embodiment a fatty acid molecule is attached to an amino acid residue at any one of positions 6 to 29 of any one of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36 GIP(6-30), or a variant thereof.

In one embodiment a fatty acid molecule is attached to an amino acid residue at any one of positions 4 to 29 of said GIP peptide analogue, such as of SEQ ID NO:1. In one embodiment a fatty acid molecule is attached to an amino acid residue at any one of positions 4 to 29 of any one of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO:32 GIP(3-30), SEQ ID NO:33 GIP(4-30)$X_2$, SEQ ID NO: 34 GIP(4-30), SEQ ID NO: 35 GIP(5-30), SEQ ID NO: 36 GIP(6-30), or a variant thereof.

In one embodiment a fatty acid molecule is attached to an amino acid residue at position 5, position 6, position 7, position 8, position 9, position 10, position 11, position 12, position 13, position 14, position 15, position 16, position 17, position 18, position 19, position 20, position 21, position 22, position 23, position 24, position 25, position 26, position 27, position 28 or position 29 of said GIP peptide analogue, such as of SEQ ID NO:1, or a functional variant thereof.

In one embodiment a fatty acid molecule is attached to an amino acid residue at position 6, position 7, position 8, position 9, position 10, position 11, position 12, position 13, position 14, position 15, position 16, position 17, position 18, position 19, position 20, position 21, position 22, position 23, position 24, position 25, position 26, position 27, position 28 or position 29 of SEQ ID NO:36 hGIP(6-30), or a functional variant thereof.

In one embodiment a fatty acid molecule is attached to an amino acid residue at position 5, position 6, position 7, position 8, position 9, position 10, position 11, position 12, position 13, position 14, position 15, position 16, position 17, position 18, position 19, position 20, position 21, position 22, position 23, position 24, position 25, position 26, position 27, position 28 or position 29 of SEQ ID NO:35 hGIP(5-30), or a functional variant thereof.

In one embodiment a fatty acid molecule is attached to an amino acid residue at position 4, position 5, position 6, position 7, position 8, position 9, position 10, position 11, position 12, position 13, position 14, position 15, position 16, position 17, position 18, position 19, position 20, position 21, position 22, position 23, position 24, position 25, position 26, position 27, position 28 or position 29 of SEQ ID NO:32 hGIP(3-30), or a functional variant thereof.

In one embodiment a fatty acid molecule is attached to one or more amino acid residues in the mid-region of any one of SEQ ID NO: 1 GIP(3-30)$X_1$-$X_2$, SEQ ID NO: 30 GIP(3-30)$X_2$, SEQ ID NO: 31 GIP(3-30)$X_1$, SEQ ID NO:32

GIP(3-30), SEQ ID NO:33 GIP(4-30)X$_2$, SEQ ID NO: 34 GIP(4-30), SEQ ID NO: 35 GIP(5-30), SEQ ID NO: 36 GIP(6-30), or a functional variant thereof.

In one embodiment a fatty acid molecule is attached to one or more amino acid residues at any one of positions 11 to 21 any one of SEQ ID NO: 1 GIP(3-30)X$_1$-X$_2$, SEQ ID NO: 30 GIP(3-30)X$_2$, SEQ ID NO: 31 GIP(3-30)X$_1$, SEQ ID NO:32 GIP(3-30), SEQ ID NO:33 GIP(4-30)X$_2$, SEQ ID NO: 34 GIP(4-30), SEQ ID NO: 35 GIP(5-30), SEQ ID NO: 36 GIP(6-30), or a functional variant thereof.

In one embodiment a fatty acid molecule is attached to one or more amino acid residues at any one of positions 11, 12, 17, 18 and 20 of any one of SEQ ID NO: 1 GIP(3-30)X$_1$-X$_2$, SEQ ID NO: 30 GIP(3-30)X$_2$, SEQ ID NO: 31 GIP(3-30)X$_1$, SEQ ID NO:32 GIP(3-30), SEQ ID NO:33 GIP(4-30)X$_2$, SEQ ID NO: 34 GIP(4-30), SEQ ID NO: 35 GIP(5-30), SEQ ID NO: 36 GIP(6-30), or a functional variant thereof.

In one embodiment a fatty acid molecule is attached to one or more amino acid residues at any one of positions 11, 12, 17 and 18 of any one of SEQ ID NO: 1 GIP(3-30)X$_1$-X$_2$, SEQ ID NO: 30 GIP(3-30)X$_2$, SEQ ID NO: 31 GIP(3-30)X$_1$, SEQ ID NO:32 GIP(3-30), SEQ ID NO:33 GIP(4-30)X$_2$, SEQ ID NO: 34 GIP(4-30), SEQ ID NO: 35 GIP(5-30), SEQ ID NO: 36 GIP(6-30), or a functional variant thereof. Attachment of a fatty acid at any one of these positions may result in a GIP peptide analogue with particularly long half-life and having a particularly high antagonistic potency.

In one embodiment a fatty acid molecule is attached to the epsilon-amino group of a K residue or of an Orn residue of said GIP peptide analogue, such as of any one of SEQ ID NO: 1 GIP(3-30)X$_1$-X$_2$, SEQ ID NO: 30 GIP(3-30)X$_2$, SEQ ID NO: 31 GIP(3-30)X$_1$, SEQ ID NO:32 GIP(3-30), SEQ ID NO:33 GIP(4-30)X$_2$, SEQ ID NO: 34 GIP(4-30), SEQ ID NO: 35 GIP(5-30), SEQ ID NO: 36 GIP(6-30), or a functional variant thereof comprising at least one K or Orn residue.

In one embodiment a fatty acid molecule is attached to the side chain amino group of the amino acid residue at position 16 of said GIP peptide analogue, such as of any one of SEQ ID NO: 1 GIP(3-30)X$_1$-X$_2$, SEQ ID NO: 30 GIP(3-30)X$_2$, SEQ ID NO: 31 GIP(3-30)X$_1$, SEQ ID NO:32 GIP(3-30), SEQ ID NO:33 GIP(4-30)X$_2$, SEQ ID NO: 34 GIP(4-30), SEQ ID NO: 35 GIP(5-30), SEQ ID NO: 36 GIP(6-30), or a functional variant thereof.

In one embodiment a fatty acid molecule is attached to the K at position 16 of said GIP peptide analogue, such as of any one of SEQ ID NO: 1 GIP(3-30)X$_1$-X$_2$, SEQ ID NO: 30 GIP(3-30)X$_2$, SEQ ID NO: 31 GIP(3-30)X$_1$, SEQ ID NO:32 GIP(3-30), SEQ ID NO:33 GIP(4-30)X$_2$, SEQ ID NO: 34 GIP(4-30), SEQ ID NO: 35 GIP(5-30), SEQ ID NO: 36 GIP(6-30), or a functional variant thereof.

In one embodiment a fatty acid molecule is attached to the side chain amino group of the amino acid residue at position 18 of said GIP peptide analogue, such as of any one of SEQ ID NO: 1 GIP(3-30)X$_1$-X$_2$, SEQ ID NO: 30 GIP(3-30)X$_2$, SEQ ID NO: 31 GIP(3-30)X$_1$, SEQ ID NO:32 GIP(3-30), SEQ ID NO:33 GIP(4-30)X$_2$, SEQ ID NO: 34 GIP(4-30), SEQ ID NO: 35 GIP(5-30), SEQ ID NO: 36 GIP(6-30), or a variant thereof, wherein H at position 18 has been substituted with K or Orn in said GIP peptide analogue. Attachment of a fatty acid to the side chain amino group of the amino acid residue at position 18 may result in a GIP peptide analogue with particularly long half-life and having a particularly high antagonistic potency.

In one embodiment a fatty acid molecule is attached to the side chain amino group of the amino acid residue at position 11 of said GIP peptide analogue, such as of any one of SEQ ID NO: 1 GIP(3-30)X$_1$-X$_2$, SEQ ID NO: 30 GIP(3-30)X$_2$, SEQ ID NO: 31 GIP(3-30)X$_1$, SEQ ID NO:32 GIP(3-30), SEQ ID NO:33 GIP(4-30)X$_2$, SEQ ID NO: 34 GIP(4-30), SEQ ID NO: 35 GIP(5-30), SEQ ID NO: 36 GIP(6-30), or a variant thereof, wherein S at position 11 has been substituted with K or Orn in said GIP peptide analogue.

In one embodiment a fatty acid molecule is attached to the side chain amino group of the amino acid residue at position 12 of said GIP peptide analogue, such as of any one of SEQ ID NO: 1 GIP(3-30)X$_1$-X$_2$, SEQ ID NO: 30 GIP(3-30)X$_2$, SEQ ID NO: 31 GIP(3-30)X$_1$, SEQ ID NO:32 GIP(3-30), SEQ ID NO:33 GIP(4-30)X$_2$, SEQ ID NO: 34 GIP(4-30), SEQ ID NO: 35 GIP(5-30), SEQ ID NO: 36 GIP(6-30), or a variant thereof, wherein I at position 12 has been substituted with K or Orn in said GIP peptide analogue.

In one embodiment at least one fatty acid molecule is attached at the amino acid residue at positions 11 of said GIP peptide analogue, such as of any one of SEQ ID NO: 1 GIP(3-30)X$_1$-X$_2$, SEQ ID NO: 30 GIP(3-30)X$_2$, SEQ ID NO: 31 GIP(3-30)X$_1$, SEQ ID NO:32 GIP(3-30), SEQ ID NO:33 GIP(4-30)X$_2$, SEQ ID NO: 34 GIP(4-30), SEQ ID NO: 35 GIP(5-30), SEQ ID NO: 36 GIP(6-30), or a functional variant thereof.

In one embodiment a fatty acid molecule is attached to the K at position 11 of said GIP peptide analogue, such as of any one of SEQ ID NO: 1 GIP(3-30)X$_1$-X$_2$, SEQ ID NO: 30 GIP(3-30)X$_2$, SEQ ID NO: 31 GIP(3-30)X$_1$, SEQ ID NO:32 GIP(3-30), SEQ ID NO:33 GIP(4-30)X$_2$, SEQ ID NO: 34 GIP(4-30), SEQ ID NO: 35 GIP(5-30), SEQ ID NO: 36 GIP(6-30), or a functional variant thereof.

In one embodiment at least one fatty acid molecule is attached at the amino acid residue at positions 12 of said GIP peptide analogue, such as of any one of SEQ ID NO: 1 GIP(3-30)X$_1$-X$_2$, SEQ ID NO: 30 GIP(3-30)X$_2$, SEQ ID NO: 31 GIP(3-30)X$_1$, SEQ ID NO:32 GIP(3-30), SEQ ID NO:33 GIP(4-30)X$_2$, SEQ ID NO: 34 GIP(4-30), SEQ ID NO: 35 GIP(5-30), SEQ ID NO: 36 GIP(6-30), or a functional variant thereof.

In one embodiment a fatty acid molecule is attached to the K at position 12 of said GIP peptide analogue, such as of any one of SEQ ID NO: 1 GIP(3-30)X$_1$-X$_2$, SEQ ID NO: 30 GIP(3-30)X$_2$, SEQ ID NO: 31 GIP(3-30)X$_1$, SEQ ID NO:32 GIP(3-30), SEQ ID NO:33 GIP(4-30)X$_2$, SEQ ID NO: 34 GIP(4-30), SEQ ID NO: 35 GIP(5-30), SEQ ID NO: 36 GIP(6-30), or a functional variant thereof.

In one embodiment at least one fatty acid molecule is attached at the amino acid residue at positions 17 of said GIP peptide analogue, such as of any one of SEQ ID NO: 1 GIP(3-30)X$_1$-X$_2$, SEQ ID NO: 30 GIP(3-30)X$_2$, SEQ ID NO: 31 GIP(3-30)X$_1$, SEQ ID NO:32 GIP(3-30), SEQ ID NO:33 GIP(4-30)X$_2$, SEQ ID NO: 34 GIP(4-30), SEQ ID NO: 35 GIP(5-30), SEQ ID NO: 36 GIP(6-30), or a functional variant thereof.

In one embodiment a fatty acid molecule is attached to the K at position 17 of said GIP peptide analogue, such as of any one of SEQ ID NO: 1 GIP(3-30)X$_1$-X$_2$, SEQ ID NO: 30 GIP(3-30)X$_2$, SEQ ID NO: 31 GIP(3-30)X$_1$, SEQ ID NO:32 GIP(3-30), SEQ ID NO:33 GIP(4-30)X$_2$, SEQ ID NO: 34 GIP(4-30), SEQ ID NO: 35 GIP(5-30), SEQ ID NO: 36 GIP(6-30), or a functional variant thereof.

In one embodiment at least one fatty acid molecule is attached at the amino acid residue at positions 18 of said GIP peptide analogue, such as of any one of SEQ ID NO: 1 GIP(3-30)X$_1$-X$_2$, SEQ ID NO: 30 GIP(3-30)X$_2$, SEQ ID NO: 31 GIP(3-30)X$_1$, SEQ ID NO:32 GIP(3-30), SEQ ID NO:33 GIP(4-30)X$_2$, SEQ ID NO: 34 GIP(4-30), SEQ ID NO: 35 GIP(5-30), SEQ ID NO: 36 GIP(6-30), or a functional variant thereof.

In one embodiment a fatty acid molecule is attached to the K at position 18 of said GIP peptide analogue, such as of any one of SEQ ID NO: 1 GIP(3-30)X$_1$-X$_2$, SEQ ID NO: 30 GIP(3-30)X$_2$, SEQ ID NO: 31 GIP(3-30)X$_1$, SEQ ID NO:32 GIP(3-30), SEQ ID NO:33 GIP(4-30)X$_2$, SEQ ID NO: 34 GIP(4-30), SEQ ID NO: 35 GIP(5-30), SEQ ID NO: 36 GIP(6-30), or a functional variant thereof.

In one embodiment at least one fatty acid molecule is attached at a Lysine at position 18 of said GIP peptide analogue, such as of any one of SEQ ID NO: 1 GIP(3-30)X$_1$-X$_2$, SEQ ID NO: 30 GIP(3-30)X$_2$, SEQ ID NO: 31 GIP(3-30)X$_1$, SEQ ID NO:32 GIP(3-30), SEQ ID NO:33 GIP(4-30)X$_2$, SEQ ID NO: 34 GIP(4-30), SEQ ID NO: 35 GIP(5-30), SEQ ID NO: 36 GIP(6-30), and at least two of the amino acids at position 9, 15, and 24 of any one of SEQ ID NO: 1 GIP(3-30)X$_1$-X$_2$, SEQ ID NO: 30 GIP(3-30)X$_2$, SEQ ID NO: 31 GIP(3-30)X$_1$, SEQ ID NO:32 GIP(3-30), SEQ ID NO:33 GIP(4-30)X$_2$, SEQ ID NO: 34 GIP(4-30), SEQ ID NO: 35 GIP(5-30), SEQ ID NO: 36 GIP(6-30) are E.

In one embodiment at least one fatty acid molecule is attached to an amino acid in the middle of the GIP peptide analogue, such as at any one of positions 11 to 18, such as at position 11 or 18 of the GIP peptide analogue.

In one embodiment it is provided a GIP peptide analogue or functional variant thereof, said peptide being an analogue of any one of SEQ ID NO:1 GIP(3-30)X$_1$-X$_2$, SEQ ID NO: 30 GIP(3-30)X$_2$, SEQ ID NO: 31 GIP(3-30)X$_1$, SEQ ID NO:32 GIP(3-30), and having a sequence selected from the group consisting of:

```
GIP(3-30),                                    SEQ ID NO: 32
EGTFISDYSIAMDKIHQQDFVNWLLAQK-Z;;

GIP(3-30)[H18K],                              SEQ ID NO: 38
EGTFISDYSIAMDKIKQQDFVNWLLAQK-Z;;

GIP(3-30)[E3S;H18K],                          SEQ ID NO: 39
SGTFISDYSIAMDKIKQQDFVNWLLAQK-Z;;

GIP(3-30)[E3S;K16R;H18K;K30R],                SEQ ID NO: 42
SGTFISDYSIAMDRIKQQDFVNWLLAQR-Z;;

GIP(3-30)[S11K],                              SEQ ID NO: 43
EGTFISDYKIAMDKIHQQDFVNWLLAQK-Z;;

GIP(3-30)[I12K],                              SEQ ID NO: 44
EGTFISDYSKAMDKIHQQDFVNWLLAQK-Z;;

GIP(3-30)[Q20K],                              SEQ ID NO: 45
EGTFISDYSIAMDKIHQKDFVNWLLAQK-Z;;

GIP(3-30)[N24K],                              SEQ ID NO: 46
EGTFISDYSIAMDKIHQQDFVKWLLAQK-Z;;

GIP(3-30)[I17K],                              SEQ ID NO: 47
EGTFISDYSIAMDKKHQQDFVNWLLAQK-Z;;

GIP(3-30)[H18K;K30G],                         SEQ ID NO: 48
EGTFISDYSIAMDKIKQQDFVNWLLAQG-Z;;

GIP(3-30)[H18K;Q29G;K30G],                    SEQ ID NO: 49
EGTFISDYSIAMDKIKQQDFVNWLLAGG-Z;;

GIP(3-30)[D9E;D15E;H18K;D21E;N24Q],           SEQ ID NO: 50
EGTFISEYSIAMEKIKQQEFVQWLLAQK-Z;;

GIP(3-30)[D9E;D15E;H18K;N24Q],                SEQ ID NO: 51
EGTFISEYSIAMEKIKQQDFVQWLLAQK-Z;;

GIP(3-30)[D9E;I12Aib;M14Nle;D15E;H18K;N24E],  SEQ ID NO: 52
EGTFISEYSAibANleEKIKQQDFVEWLLAQK-Z;;

GIP(3-30)[D9E;A13Aib;D15E;H18K;N24E],         SEQ ID NO: 53
EGTFISEYSIAibMEKIKQQDFVEWLLAQK-Z;;

GIP(3-30)[H18K;N24E],                         SEQ ID NO: 54
EGTFISDYSIAMDKIKQQDFVEWLLAQK-Z;;

GIP(3-30)[M14L;H18K],                         SEQ ID NO: 55
EGTFISDYSIALDKIKQQDFVNWLLAQK-Z;;

GIP(3-30)[M14Nle;H18K],                       SEQ ID NO: 56
EGTFISDYSIANleDKIKQQDFVNWLLAQK-Z;;

GIP(3-30)[M14E;H18K],                         SEQ ID NO: 57
EGTFISDYSIAEDKIKQQDFVNWLLAQK-Z;;

GIP(3-30)[M14K;H18K],                         SEQ ID NO: 58
EGTFISDYSIAKDKIKQQDFVNWLLAQK-Z;;

GIP(3-30)[M14S;H18K],                         SEQ ID NO: 59
EGTFISDYSIASDKIKQQDFVNWLLAQK-Z;;

GIP(3-30)[H18K;N24E;K30A],                    SEQ ID NO: 60
EGTFISDYSIAMDKIKQQDFVEWLLAQA-Z;;

GIP(3-30)[H18K;A28E],                         SEQ ID NO: 61
EGTFISDYSIAMDKIKQQDFVNWLLEQK-Z;;

GIP(3-30)[E3V;H18K],                          SEQ ID NO: 62
VGTFISDYSIAMDKIKQQDFVNWLLAQK-Z;;

GIP(3-30)[E3Aib;H18K],                        SEQ ID NO: 63
AibGTFISDYSIAMDKIKQQDFVNWLLAQK-Z;;

GIP(3-30)[E3P;H18K],                          SEQ ID NO: 64
PGTFISDYSIAMDKIKQQDFVNWLLAQK-Z;;

GIP(3-30)[E3V;G4E;H18K],                      SEQ ID NO: 65
VETFISDYSIAMDKIKQQDFVNWLLAQK-Z;;

GIP(3-30)[E3Aib;G4E;H18K],                    SEQ ID NO: 66
AibETFISDYSIAMDKIKQQDFVNWLLAQK-Z;;

GIP(3-30)[E3G;G4E;H18K],                      SEQ ID NO: 67
GETFISDYSIAMDKIKQQDFVNWLLAQK-Z;;
```

```
GIP(3-30)[E3P;G4E;H18K],
                                            SEQ ID NO: 68
PETFISDYSIAMDKIKQQDFVNWLLAQK-Z;;

GIP(3-30)[E3D;G4T;H18K],
                                            SEQ ID NO: 69
DTTFISDYSIAMDKIKQQDFVNWLLAQK-Z;;

GIP(3-30)[E3G;G4E;S11A;M14L;H18K;N24E;K30G],
                                            SEQ ID NO: 70
GETFISDYAIALDKIKQQDFVEWLLAQG-Z;;

GIP(3-30)[E3G;G4E;D9T;M14L;H18K;N24E],
                                            SEQ ID NO: 71
GETFISTYSIALDKIKQQDFVEWLLAQG-Z;;

GIP(3-30)[D9T;S11K;M14L;N24E],
                                            SEQ ID NO: 72
EGTFISTYKIALDKIHQQDFVEWLLAQK-Z;;

GIP(3-30)[A13Aib;H18K;N24E],
                                            SEQ ID NO: 73
EGTFISDYSIAibMDKIKQQDFVEWLLAQK-Z;;

GIP(3-30)[A13Aib;M14L;H18K;N24E],
                                            SEQ ID NO: 74
EGTFISDYSIAibLDKIKQQDFVEWLLAQK-Z;;

GIP(3-30)[A13Aib;M14Nle;H18K;N24E],
                                            SEQ ID NO: 75
EGTFISDYSIAibNleDKIKQQDFVEWLLAQK-Z;;

GIP(3-30)[M14L;H18K;N24E],
                                            SEQ ID NO: 76
EGTFISDYSIALDKIKQQDFVEWLLAQK-Z;;

GIP(3-30)[M14Nle;H18K;N24E],
                                            SEQ ID NO: 77
EGTFISDYSIANleDKIKQQDFVEWLLAQK-Z;;

GIP(3-30)[M14K;H18K;N24E],
                                            SEQ ID NO: 78
EGTFISDYSIAKDKIKQQDFVEWLLAQK-Z;;

GIP(3-30)[M14Nle;H18K;Q29G;K30G],
                                            SEQ ID NO: 79
EGTFISDYSIANleDKIKQQDFVNWLLAGG-Z;;

GIP(3-30)[M14Nle;H18K;N24E;Q29G;K30G],
                                            SEQ ID NO: 80
EGTFISDYSIANleDKIKQQDFVEWLLAGG-Z;;

GIP(3-30)[D9E;A13Aib;M14L;D15E;H18K;D21E;N24E],
                                            SEQ ID NO: 81
EGTFISEYSIAibLEKIKQQEFVEWLLAQK-Z;;

GIP(3-30)[D9E;A13Aib;M14Nle;D15E;H18K;D21E;N24E],
                                            SEQ ID NO: 82
EGTFISEYSIAibNleEKIKQQEFVEWLLAQK-Z;;

GIP(3-30)[E3yGlu;H18K],
                                            SEQ ID NO: 83
yGluGTFISDYSIAMDKIKQQDFVNWLLAQK-Z;;

GIP(3-30)[E3βGlu;H18K],
                                            SEQ ID NO: 84
βGluGTFISDYSIAMDKIKQQDFVNWLLAQK-Z;;

GIP(3-30)[E3Glutaric acid(X);H18K],
                                            SEQ ID NO: 85
XGTFISDYSIAMDKIKQQDFVNWLLAQK-Z;;

GIP(3-30)[M14L;H18K;N24E;Q29G;K30G],
                                            SEQ ID NO: 86
EGTFISDYSIALDKIKQQDFVEWLLAGG-Z;;

GIP(3-30)[D9E;M14L;D15E;H18K;D21E;N24E],
                                            SEQ ID NO: 87
EGTFISEYSIALEKIKQQEFVEWLLAQK-Z;;

GIP(3-30)[D9E;M14Nle;D15E;H18K;D21E;N24E],
                                            SEQ ID NO: 88
EGTFISEYSIANleEKIKQQEFVEWLLAQK-Z;;

GIP(3-30)[E3yGlu(L-isomer);M14Nle;H18K;N24E],
                                            SEQ ID NO: 89
yGluGTFISDYSIANleDKIKQQDFVEWLLAQK-Z;;

GIP(3-30)[E3yGlu(D-isomer);M14Nle;H18K;N24E],
                                            SEQ ID NO: 90
yGluGTFISDYSIANleDKIKQQDFVEWLLAQK-Z;;

GIP(3-30)[E3βGlu;M14Nle;H18K;N24E],
                                            SEQ ID NO: 91
βGluGTFISDYSIANleDKIKQQDFVEWLLAQK-Z;;

GIP(3-30)[E3Glutaric acid(X);M14Nle;H18K;N24E],
                                            SEQ ID NO: 92
XGTFISDYSIANleDKIKQQDFVEWLLAQK-Z;;

GIP(3-30)[E3βGlu;A13Aib;M14Nle;H18K],
                                            SEQ ID NO: 93
βGluGTFISDYSIAibNleDKIKQQDFVNWLLAQK-Z;;

GIP(3-30)[M14L;H18K;A28E],
                                            SEQ ID NO: 40
EGTFISDYSIALDKIKQQDFVNWLLEQK-Z;;

GIP(3-30)[M14Nle;H18K;A28E],
                                            SEQ ID NO: 95
EGTFISDYSIANleDKIKQQDFVNWLLEQK-Z;;
and GIP(3-30)[M14L;H18K;A28E;Q29G;K30G]
                                            SEQ ID NO: 94
EGTFISDYSIALDKIKQQDFVNWLLEGG-Z;;
``` wherein said peptide is modified by attaching at least one fatty acid molecule at one or more amino acid residues at positions 4 to 29 of any one of any one of the above sequences, and wherein said peptide may be C-terminal carboxylated.

In one embodiment it is provided a GIP peptide analogue or functional variant thereof, said peptide being an analogue of hGIP5-30 (SEQ ID NO: 35 GIP(5-30)), and having a sequence selected from the group consisting of:

```
GIP(5-30)
                                            SEQ ID NO: 35
TFISDYSIAMDKIHQQDFVNWLLAQK-Z;;

GIP(5-30)[S11K],
                                            SEQ ID NO: 97
TFISDYKIAMDKIHQQDFVNWLLAQK-Z;;

GIP(5-30)[H18K],
                                            SEQ ID NO: 100
TFISDYSIAMDKIKQQDFVNWLLAQK-Z;;

GIP(5-30)[S11K;K16R;K30R],
                                            SEQ ID NO: 101
TFISDYKIAMDRIHQQDFVNWLLAQR-Z;;

GIP(5-30)[I12K],
                                            SEQ ID NO: 102
TFISDYSKAMDKIHQQDFVNWLLAQK-Z;;

GIP(5-30)[Q20K],
                                            SEQ ID NO: 103
TFISDYSIAMDKIHQKDFVNWLLAQK-Z;;
and GIP(5-30)[N24K],
                                            SEQ ID NO: 104
TFISDYSIAMDKIHQQDFVKWLLAQK-Z;;
``` wherein said peptide is modified by attaching at least one fatty acid molecule at one or more amino acid residues at positions 4 to 29 of any one of any one of the above sequences, and wherein said peptide may be C-terminal carboxylated.

In one embodiment it is provided a GIP peptide analogue or functional variant thereof, said peptide being an analogue of hGIP6-30 (SEQ ID NO:36 GIP(6-30)), and having a sequence selected from the group consisting of:

FISDYSIAMDKIKQQDFVNWLLAQK-Z; SEQ ID NO:105; GIP(6-30) [H18K], wherein said peptide is modified by attaching at least one fatty acid molecule at one or more amino acid residues at positions 4 to 29 of any one of any one of the above sequences, and wherein said peptide may be C-terminal carboxylated.

In one embodiment, the GIP peptide analogue of the present disclosure is C-terminally amidated (—NH$_2$).

In one embodiment, the GIP peptide analogue of the present disclosure is C-terminally carboxylated (—COOH), such as wherein the C-terminus is a free carboxylic acid.

Functional Variants—Mutants

In one embodiment, one or more, or all, of said amino acid substitutions are conservative amino acid substitutions (or synonymous substitutions). A conservative substitution is the substitution of amino acids whose side chains have similar biochemical properties and thus do not affect the function of the peptide.

Particular amino acid substitutions as disclosed herein are K to R, A, G; E to D, S, P, G, V, 2-Aminoisobutyric acid (Aib), γ-glutamic acid (γGlu), D-γ-glutamic acid (D-γGlu), β-Glutamic acid (βGlu), pyroE (pyroglutamic acid), glutaric acid; L to M; Q to E; I to V; I to L, K, Aib; A to S, Aib, E; Y to W; K to Q; S to T, K; N to S; M to L, Nle, E, S, K; H to K; N, I, S, G to A; N, I, S to T; D to E, T; N to Q, E; Q to R, K, G; G to E, T, K.

In another embodiment, a functional variant as defined herein includes sequences wherein an alkyl amino acid is substituted for an alkyl amino acid, wherein an aromatic amino acid is substituted for an aromatic amino acid, wherein a sulfur-containing amino acid is substituted for a sulfur-containing amino acid, wherein a hydroxy-containing amino acid is substituted for a hydroxy-containing amino acid, wherein an acidic amino acid is substituted for an acidic amino acid, wherein a basic amino acid is substituted for a basic amino acid, and/or wherein a dibasic monocarboxylic amino acid is substituted for a dibasic monocarboxylic amino acid.

Conservative substitutions may be introduced in any one or more of the above specified positions of a GIP peptide analogue selected from any one of SEQ ID NO: 1 GIP(3-30)X$_1$-X$_2$, SEQ ID NO: 30 GIP(3-30)X$_2$, SEQ ID NO: 31 GIP(3-30)X$_1$, SEQ ID NO:32 GIP(3-30), SEQ ID NO:33 GIP(4-30)X$_2$, SEQ ID NO: 34 GIP(4-30), SEQ ID NO: 35 GIP(5-30), SEQ ID NO: 36 GIP(6-30) as long as the resulting variant remains functional. It may however also be desirable to introduce non-conservative substitutions in one or more positions (non-synonymous substitutions).

A non-conservative substitution leading to the formation of a variant of a GIP peptide analogue selected from any one of SEQ ID NO: 1 GIP(3-30)X$_1$-X$_2$, SEQ ID NO: 30 GIP(3-30)X$_2$, SEQ ID NO: 31 GIP(3-30)X$_1$, SEQ ID NO:32 GIP(3-30), SEQ ID NO:33 GIP(4-30)X$_2$, SEQ ID NO: 34 GIP(4-30), SEQ ID NO: 35 GIP(5-30), SEQ ID NO: 36 GIP(6-30) in one embodiment comprises substitution of amino acid residues that i) differ substantially in polarity, for example a residue with a non-polar side chain (Ala, Leu, Pro, Trp, Val, Ile, Leu, Phe or Met) substituted for a residue with a polar side chain such as Gly, Ser, Thr, Cys, Tyr, Asn, or Gln or a charged amino acid such as Asp, Glu, Arg, or Lys, or substituting a charged or a polar residue for a non-polar one; and/or ii) differ substantially in its effect on peptide backbone orientation such as substitution of or for Pro or Gly by another residue; and/or iii) differ substantially in electric charge, for example substitution of a negatively charged residue such as Glu or Asp for a positively charged residue such as Lys, His or Arg (and vice versa); and/or iv) differ substantially in steric bulk, for example substitution of a bulky residue such as His, Trp, Phe or Tyr for one having a minor side chain, e.g. Ala, Gly or Ser (and vice versa).

Substitution of amino acids can in one embodiment be made based upon their hydrophobicity and hydrophilicity values and the relative similarity of the amino acid side-chain substituents, including charge, size, and the like.

The GIP peptide analogues or their functional variant counterparts as defined herein comprise proteinogenic or natural amino acids, i.e. the 22 amino acids naturally incorporated into polypeptides. Of these, 20 are encoded by the universal genetic code and the remaining 2; selenocysteine (Sec, U) and pyrrolysine (Pyl, O), are incorporated into proteins by unique synthetic mechanisms.

A GIP peptide analogue as defined herein in one embodiment comprises one or more non-naturally occurring amino acid residues (unnatural, non-proteinogenic or non-standard amino acids) or amino acid mimetics, such as glutaric acid. Non-naturally occurring amino acids include e.g., without limitation, beta-2-naphthyl-alanine, trans-3-methylproline, 2,4-methanoproline, cis-4-hydroxyproline, ornithine (Orn), trans-4-hydroxyproline, N-methylglycine, allo-threonine, methylthreonine, hydroxyethylcysteine, hydroxyethylhomocysteine, nitroglutamnine, homoglutamine, pipecolic acid, thiazolidine carboxylic acid, dehydroproline, 3- and 4-methylproline, 3,3-dimethylproline, tert-leucine, norleucine (Nle), methoxinine (Mox), norvaline, 2-azaphenylalanine, 3-azaphenylalanine, 4-azaphenylalanine, and 4-fluorophenylalanine.

In one embodiment the amino acid Met is substituted with an oxidation resistant amino acid analogue, for example, norleucine (Nle) or Leu which preserves the length of the amino acid side chain important for hydrophobic interactions but not its hydrogen-bonding properties; or methoxinine (Mox), a non-canonical amino acid that resembles more closely the electronic properties of Met in comparison to Nle; or Lys.

The standard and/or non-standard amino acids may be linked by peptide bonds (to form a linear peptide chain), or by non-peptide bonds (e.g. via the variable side-chains of the amino acids). Preferably, the amino acids of the peptides defined herein are linked by peptide bonds.

The term peptide also embraces post-translational modifications introduced by chemical or enzyme-catalyzed reactions, as are known in the art. These include acetylation, phosphorylation, methylation, glucosylation, glycation, amidation, hydroxylation, deimination, deamidation, carbamylation and sulfation of one or more amino acid residues, and also proteolytic modification by known proteinases including lysosomal kathepsins, and also calpains, secretases and matrix-metalloproteinases.

Also, functional equivalents of the peptides may comprise chemical modifications such as ubiquitination, labeling (e.g., with radionuclides, various enzymes, etc.), pegylation (derivatization with polyethylene glycol), or by insertion (or substitution by chemical synthesis) of amino acids such as ornithine, which do not normally occur in human proteins (non-proteinogenic).

Sterically similar compounds may be formulated to mimic the key portions of the peptide structure. This may be achieved by techniques of modelling and chemical designing known to those of skill in the art. For example, esterification and other alkylations may be employed to modify the amino terminus of e.g. a di-arginine peptide backbone, to mimic a tetra peptide structure. It will be understood that all such sterically similar constructs fall within the scope of the present invention. Peptides with N-terminal and C-terminal alkylations and esterifications are also encompassed within the present invention. For example, glutaric acid is a sterically similar compound that mimics Glutamic acid.

In one embodiment the N-terminal amino acid of the GIP peptide analogues of the present disclosure does not have any chemical modifications. It may be advantageous that the amino group at the N-terminus of the GIP peptide analogue is free, i.e. not substituted, since substitution may lead to agonistic effects at the GIPR.

It appears that extending the length of the fatty acid or the linker, if present, may decrease the antagonistic potency. However, simultaneously incorporating an Aib residue at position 13 appears to compensate for some or all of the reduced potency, especially in combination with E at one or more of positions 9, 15, 21 and 24, such as in combination with E at one or more of positions 9, 15 and 21.

Attachment of Fatty Acid Molecules

In one embodiment a fatty acid molecule is attached to one or more amino acid residues having a side-chain aminoalkyl group (—$C_nH_{2n}NH_2$).

In one embodiment a fatty acid molecule is attached to one or more amino acid residues having a side-chain amino group ($NH_2$).

In one embodiment a fatty acid molecule is attached to an amino group ($NH_2$) of an amino acid residue.

In one embodiment a fatty acid molecule is attached to the side-chain amino group of an amino acid residue.

In one embodiment a fatty acid molecule is attached to the E (epsilon) side-chain amino group of a lysine residue (Lys, K).

In one embodiment a fatty acid molecule is attached to the b (delta) side-chain amino group of an ornithine residue (Orn).

In one embodiment the amino acid residue having a fatty acid molecule attached is selected from the group consisting of Lys and Orn.

In one embodiment the amino acid residue having a fatty acid molecule attached is Lys.

In one embodiment the fatty acid molecule is attached to the delta-amino group of a Orn residue of said GIP peptide analogue, such as of SEQ ID NO:1, or a functional variant comprising an Orn amino acid residue.

In one embodiment the fatty acid molecule is attached to the epsilon-amino group of a K residue of said GIP peptide analogue, such as of SEQ ID NO:1, or a functional variant thereof.

In one embodiment the amino acid residue having a fatty acid molecule attached is the most N-terminal amino acid residue, such as the most N-terminal amino acid residue of said GIP peptide analogue, such as of SEQ ID NO:1, or a variant thereof, wherein said fatty acid is attached to an amino group comprised in the side chain of the N-terminal amino acid.

In one embodiment the fatty acid molecule according to the present disclosure is a straight-chain fatty acid.

In one embodiment the fatty acid molecule according to the present disclosure is a branched fatty acid.

In one embodiment the fatty acid molecule according to the present disclosure is a monoacyl fatty acid molecule, comprising one fatty acid. A monoacyl fatty acid molecule is a fatty acid molecule comprising only one carboxyl group. Preferably, the carboxyl group is located at one end of the fatty acid molecule.

For example, a GIP peptide may be conjugated to a monoacyl fatty acid (such as Hexadecanoyl) via a linker, as depicted in Formula I:

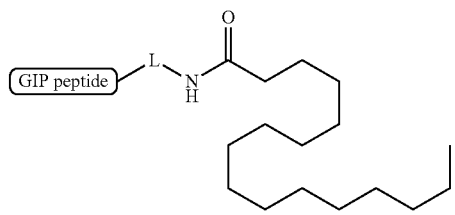

Formula I

In one embodiment the fatty acid molecule according to the present disclosure is a diacyl fatty acid molecule. A diacyl fatty acid molecule is a fatty acid molecule comprising two carboxyl groups. Preferably, one or both the carboxyl groups are located at one or each of the endings of the fatty acid molecule.

For example, a GIP peptide may be conjugated to a diacyl fatty, acid also referred to as "diacid", (such as 15-carboxypentadecanoyl) via a linker, as depicted in Formula II:

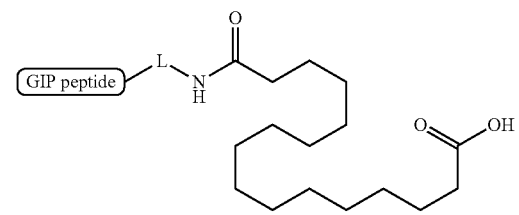

Formula II

In one embodiment the fatty acid molecule according to the present disclosure is a diacyl fatty acid molecule comprising two fatty acids.

In one embodiment the fatty acid molecule according to the present disclosure is a diacyl fatty acid molecule containing two carboxyl functional groups.

In one embodiment the fatty acid molecule according to the present disclosure comprises an acyl group of the formula $CH_3(CH_2)_nCO$—, wherein n is an integer from 4 to 24.

In one embodiment said fatty acid molecule comprises an acyl group selected from the group consisting of $CH_3(CH_2)_6CO$—, $CH_3(CH_2)_8CO$—, $CH_3(CH_2)_{10}CO$—, $CH_3(CH_2)_{12}CO$—, $CH_3(CH_2)14CO$—, $CH_3(CH_2)_{16}CO$—, $CH_3(CH_2)_{18}CO$—, $CH_3(CH_2)_{20}CO$— and $CH_3(CH_2)_{22}CO$—.

In one embodiment said fatty acid molecule is a (mono) acyl fatty acid selected from the group consisting of $CH_3(CH_2)_{10}CO$— (lauryl, C12), $CH_3(CH_2)_{12}CO$— (myristoyl, C14), $CH_3(CH_2)_{14}CO$— (palmitoyl, C16), $CH_3(CH_2)_{16}CO$— (stearyl, C18), $CH_3(CH_2)_{18}CO$— (arachidyl, C20) and $CH_3(CH_2)_{20}CO$— (behenyl, C22).

In one embodiment said fatty acid molecule is a (di)acyl fatty acid selected from the group consisting of HOOC—

CH₃(CH₂)₁₀CO— (dodecanoyl, C12), HOOC—CH₃(CH₂)₁₂CO— (1-tetradecanoyl, C14), HOOC—CH₃(CH₂)₁₄CO— (hexadecanoyl, C16), HOOC—CH₃(CH₂)₁₅CO— (15-carboxy-pentadecanoyl, C17), HOOC—CH₃(CH₂)₁₆CO— (octadecanoyl, C18), HOOC—CH₃(CH₂)₁₇CO— (17-carboxy-heptadecanoyl, C19), HOOC—CH₃(CH₂)₁₈CO— (eicosanoyl, C20), HOOC—CH₃(CH₂)₁₉CO— (19-carboxy-nonadecanoyl, C21) and HOOC—CH₃(CH₂)₂₀CO— (behenyl, C22).

In one embodiment said fatty acid molecule comprises two fatty acids each selected from the group consisting of CH₃(CH₂)₁₀CO— (lauryl, C12), CH₃(CH₂)₁₂CO— (myristoyl, C14), CH₃(CH₂)₁₄CO— (palmitoyl, C16), CH₃(CH₂)₁₆CO— (stearyl, C18), CH₃(CH₂)₁₈CO— (arachidyl, C20) and CH₃(CH₂)₂₀CO— (behenyl, C22).

In one embodiment said fatty acid molecule comprises an acyl group of the formula COOH(CH₂)ₙCO— (dicarboxylic acid), wherein n is an integer from 4 to 24.

In one embodiment said fatty acid molecule comprises an acyl group selected from the group consisting of COOH(CH₂)₁₄CO— (C16 diacid), COOH(CH₂)₁₆CO— (C18 diacid), COOH(CH₂)₁₈CO— (C20 diacid) and COOH(CH₂)₂₀CO— (C22 diacid).

In one embodiment said fatty acid molecule is selected from C12, C14, C16, C18, C20 and C22.

In one embodiment said fatty acid molecule is selected from C14 diacid, C16 diacid, C18 diacid, C20 diacid and C22 diacid.

In one embodiment said fatty acid molecule is palmitoyl.

In one embodiment said fatty acid molecule is 1,16-Hexadecanedioic acid/hexadecanedioic acid.

In one embodiment said fatty acid molecule is 15-carboxy-pentadecanoyl.

In one embodiment said fatty acid molecule is stearyl.

In one embodiment said fatty acid molecule is 1,18-Octadecanedioic acid/octadecanedioic acid.

In one embodiment said fatty acid molecule is 17-carboxy-heptadecanoyl.

In one embodiment said fatty acid molecule is arachidyl.

In one embodiment said fatty acid molecule is 1,20-Eicosanoic acid/eicosanoic acid.

In one embodiment said fatty acid molecule is 19-carboxy-nonadecanoyl.

In one embodiment said fatty acid molecule is behenyl.

In one embodiment said fatty acid molecule is 1,22-Docosanoic acid/docosanoic acid.

In one embodiment said fatty acid molecule comprises or consists of COOH(CH₂)₁₄CO—. In one embodiment said fatty acid molecule comprises or consists of COOH(CH₂)₁₆CO—. In one embodiment said fatty acid molecule comprises or consists of COOH(CH₂)₁₈CO—.

A fatty acid molecule may be attached to an amino acid residue directly, in such a way that a carboxyl group of the fatty acid molecule forms an amide bond with an amino group of the amino acid residue.

Attachment of Fatty Acid Molecules Via a Linker

Attachment of fatty acid molecules to a peptide herein can occur either directly in indirectly, i.e. via a linker or spacer.

In one embodiment the fatty acid molecule according to the present disclosure is attached to an amino acid residue directly.

In one embodiment the fatty acid molecule according to the present disclosure is directly attached to the alpha-amino group of an amino acid residue, wherein said amino acid residue is the N-terminal amino acid residue.

In one embodiment the fatty acid molecule according to the present disclosure is directly attached to the epsilon-amino group of a Lys residue.

In one embodiment the fatty acid molecule according to the present disclosure is directly attached to the delta-amino group of an Orn residue.

In one embodiment the fatty acid molecule according to the present disclosure is attached to an amino acid residue via a linker or spacer as depicted in Formula III:

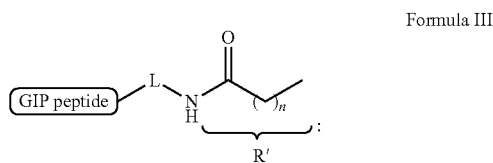

Formula III

In one embodiment the fatty acid molecule according to the present disclosure is attached to the epsilon-amino group of a Lys residue via linker or spacer.

In one embodiment the fatty acid molecule according to the present disclosure is attached to the delta-amino group of an Orn residue via linker or spacer.

In one embodiment the fatty acid molecule may be attached to an amino acid residue by means of a spacer (or linker) in such a way that an amino group of the linker forms an amide bond with a carboxyl group of the fatty acid molecule.

In one embodiment the linker is an α,ω-amino acid. Examples of suitable linkers are succinic acid, Lys, Glu or Asp, or a dipeptide such as Gly-Lys. When the linker is succinic acid, one carboxyl group thereof may form an amide bond with an amino group of the amino acid residue, and the other carboxyl group thereof may form an amide bond with an amino group of the fatty acid molecule. When the linker is Lys, Glu or Asp, the carboxyl group thereof may form an amide bond with an amino group of the amino acid residue, and the amino group thereof may form an amide bond with a carboxyl group of the fatty acid molecule. When Lys is used as the linker, a further linker may in some instances be inserted between the ε-amino group of Lys and the fatty acid molecule. In one embodiment such a further linker is succinic acid which forms an amide bond with the ε-amino group of Lys and with an amino group present in the fatty acid molecule. Other linkers are Nε-(γ-L-glutamyl), Nε-(β-L-asparagyl), Nε-glycyl, and Nε-(α-(γ-aminobutanoyl)).

In one embodiment the linker comprises one or more moieties individually selected from the group consisting of:
  a. α-amino acid, γ-amino acid or ω-amino acid,
  b. one or more amino acids selected from the group consisting of succinic acid, Lys, Glu, Asp,
  c. one or more of γ-aminobutanoyl (γ-aminobutyric acid), γ-Glu (γ-glutamic acid), β-Asp β-asparagyl), β-Ala (β-alanyl) and Gly, and
  d. [8-amino-3,6-dioxaoctanoic acid]ₙ (AEEAcₙ), wherein n is an integer between 1 and 50, such as an integer between 1-4, 1-3 or 1-2.

In one embodiment the linker is a hydrophilic linker. In one embodiment the linker is a non-natural amino acid hydrophilic linker.

In one embodiment the linker is selected from the group consisting of γ-aminobutanoyl (γ-aminobutyric acid), γ-glutamyl (γ-glutamic acid), β-asparagyl, β-alanyl and glycyl. In one embodiment the linker comprises one or more of γ-aminobutanoyl (γ-aminobutyric acid), γ-glutamyl (γ-glutamic acid), β-asparagyl, β-alanyl and glycyl.

In one embodiment the linker is a repeat of individual linker moieties. In one embodiment the linker is a repeat of identical linker moieties. In one embodiment the linker is a repeat of different linker moieties.

In one embodiment the linker is γ-glutamic acid.

In one embodiment the linker is γ-glutamic acid—8-amino-3,6-dioxaoctanoic acid (γ-Glu)-(AEEAc), or a repeat thereof.

In one embodiment the linker comprises one or more repeats of γ-glutamic acid-8-amino-3,6-dioxaoctanoic acid (γ-Glu)-(AEEAc$_n$).

The examples of linkers disclosed herein are such that they can be attached to an amino acid residue of the GIP peptide analogue via any one of the extremities of the linker. Thus, if for example the linker comprises one or more repeats of γ-glutamic acid-8-amino-3,6-dioxaoctanoic acid In one embodiment the linker is [8-amino-3,6-dioxaoctanoic acid]$_n$ AEEAc$_n$), wherein n is an integer selected from the group consisting of 1, 2, 3.

In one embodiment the linker is [γ-glutamic acid]—[8-amino-3,6-dioxaoctanoic acid]$_n$(γ-Glu)-AEEAc$_n$), wherein n is an integer selected from the group consisting of 1, 2, 3.

In one embodiment the linker is [γ-glutamic acid]—[8-amino-3,6-dioxaoctanoic acid](γ-Glu)-AEEAc or [8-amino-3,6-dioxaoctanoic acid]—[γ-glutamic acid](AEEAc-γ-Glu). For example, a GIP peptide may be conjugated to a fatty acid (for example C16 or palmitic acid/palmitoyl in Formula IV, but any other fatty acid may be used) via [γ-glutamic acid]—[8-amino-3,6-dioxaoctanoic acid] as depicted in Formula IV:

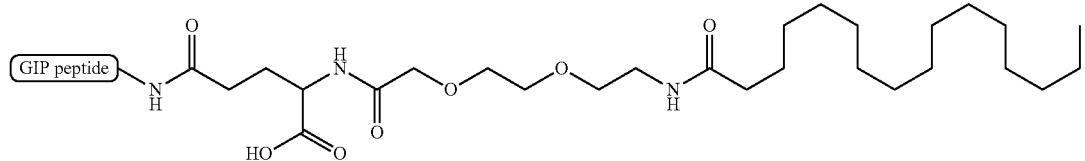 [SMILES: CCCCCCCCCCCCCCCC(=O)NCCOCCOCC(=O)NC(CCC(=O)NC)C(=O)O]

(γ-Glu)-(AEEAc$_n$), said linker can be attached to an amino acid residue of the GIP peptide analogue either via a γ-Glu or via a AEEAc$_n$.

In one embodiment the linker is [γ-glutamic acid]-[8-amino-3,6-dioxaoctanoic acid]$_n$(γ-Glu)-(AEEAc$_n$), wherein n is an integer between 1 and 50.

In one embodiment the linker is [γ-glutamic acid]—[8-amino-3,6-dioxaoctanoic acid]$_n$(γ-Glu)-(AEEAc$_n$), wherein n is an integer between 1 and 50, such as an integer between 1-2, 2-3, 3-4, 4-5, 5-6, 6-7, 7-8, 8-9, 9-10, 10-11, 11-12, 12-13, 13-14, 14-15, 15-20, 20-25, 25-30, 30-35, 35-40, 40-45, 45-50.

In one embodiment the linker is [γ-glutamic acid]—[8-amino-3,6-dioxaoctanoic acid]$_n$(γ-Glu)-(AEEAc$_n$), wherein n is an integer selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 and 50.

In one embodiment the linker is [8-amino-3,6-dioxaoctanoic acid]$_n$ (AEEAc$_n$), wherein n is an integer between 1 and 50, such as an integer between 1-2, 2-3, 3-4, 4-5, 5-6, 6-7, 7-8, 8-9, 9-10, 10-11, 11-12, 12-13, 13-14, 14-15, 15-20, 20-25, 25-30, 30-35, 35-40, 40-45, 45-50.

In one embodiment the linker is [8-amino-3,6-dioxaoctanoic acid]$_n$ (AEEAc$_n$), wherein n is an integer selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 and 50.

Formula IV: the formula does not depict the stereochemistry, usually, the natural L-form is used, unless otherwise specified.

For example, a GIP peptide may be conjugated to a fatty acid (for example C16 or palmitic acid/palmitoyl in Formula IV, but any other fatty acid may be used) via [8-amino-3,6-dioxaoctanoic acid]—[γ-glutamic acid] as depicted in Formula V:

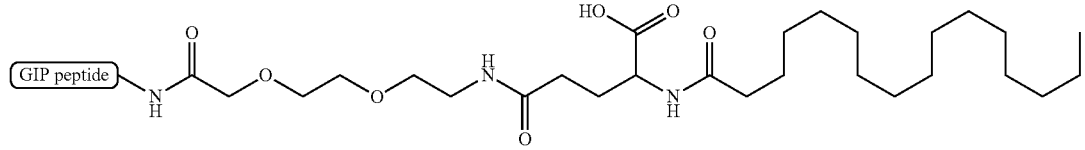 [SMILES: CCCCCCCCCCCCCCCC(=O)NC(CCC(=O)NCCOCCOCC(=O)NC)C(=O)O]

Formula V: the formula does not depict the stereochemistry, usually, the natural L-form is used, unless otherwise specified.

In one embodiment the linker is [γ-glutamic acid]—[8-amino-3,6-dioxaoctanoic acid]$_2$ (γ-Glu)-(AEEAc)$_2$. For example, the linker may comprise or consist of γGlu-AEEAc-AEEAc- or AEEAc-γGlu-AEEAc- or AEEAc-AEEAc-γGlu-.

In one embodiment the linker is [γ-glutamic acid]—[8-amino-3,6-dioxaoctanoic acid]$_3$ (γ-Glu)-(AEEAc)$_3$. For example, the linker may comprise or consist of γGlu-AEEAc-AEEAc-AEEAc- or AEEAc-γGlu-AEEAc-AEEAc- or AEEAc-AEEAc-γGlu-AEEAc- or AEEAc-AEEAc-AEEAc-γGlu-.

As provided herein, a linker comprising or consisting of one γ-glutamic acid and one, two or three 8-amino-3,6-dioxaoctanoic acid moieties can be attached to an amino acid residue of the GIP peptide analogue either via a γ-Glu or via a AEEAc$_n$.

In one embodiment the linker is an amino acid residue except Cys. In one embodiment the linker is 4-Abu. In one embodiment the linker is γ-aminobuturic acid.

In another embodiment the linker is a dipeptide, such as a dipeptide wherein the C-terminal amino acid residue is Lys, His or Trp, preferably Lys, and wherein the N-terminal amino acid residue is selected from the group comprising Ala, Arg, Asp, Asn, Gly, Glu, Gln, Ile, Leu, Val, Phe and Pro. In one embodiment the dipeptide linker is Gly-Lys.

In one embodiment the linker comprises one or more moieties selected from the group consisting of γ-aminobutanoyl (γ-aminobutyric acid), γ-glutamyl (γ-glutamic acid), β-asparagyl, β-alanyl and glycyl. In one embodiment the linker comprises one or more of γ-aminobutanoyl (γ-aminobutyric acid), γ-glutamyl (γ-glutamic acid), β-asparagyl, β-alanyl, glycyl, γ-glutamic acid—8-amino-3,6-dioxaoctanoic acid (γ-Glu-AEEAc$_n$, wherein n is an integer between 1 and 50), an amino acid residue except Cys, 4-Abu, γ-aminobuturic acid and a dipeptide.

In another embodiment linker is an unbranched alkane α, ω-dicarboxylic acid group having from 1 to 7 methylene groups, preferably two methylene groups, which linker forms a bridge between an amino group of the parent peptide and an amino group of the fatty acid molecule.

In one embodiment the GIP peptide analogue disclosed herein comprises a fatty acid, and the fatty acid molecule is attached to an amino acid residue via a linker so that the combination of linker and fatty acid is selected from the group consisting of:
  i. Hexadecanoyl-γ-Glu-
  ii. Hexadecanoyl-γ-Glu-γ-Glu-
  iii. Hexadecanoyl-γ-Glu-AEEAc-
  iv. Hexadecanoyl-γ-Glu-AEEAc-AEEAc-
  v. Hexadecanoyl-γ-Glu-AEEAc-AEEAc-AEEAc-
  vi. [15-carboxy-pentadecanoyl]-γ-Glu-
  vii. [15-carboxy-pentadecanoyl]-γ-Glu-γ-Glu-
  viii. [15-carboxy-pentadecanoyl]-γ-Glu-AEEAc-
  ix. [15-carboxy-pentadecanoyl]-γ-Glu-AEEAc-AEEAc-
  x. [15-carboxy-pentadecanoyl]-γ-Glu-AEEAc-AEEAc-AEEAc-
  xi. Octadecanoyl-γ-Glu-
  xii. Octadecanoyl-γ-Glu-γ-Glu-
  xiii. Octadecanoyl-γ-Glu-AEEAc-
  xiv. Octadecanoyl-γ-Glu-AEEAc-AEEAc-
  xv. Octadecanoyl-γ-Glu-AEEAc-AEEAc-AEEAc-
  xvi. [17-carboxy-heptadecanoyl]-γ-Glu-
  xvii. [17-carboxy-heptadecanoyl]-γ-Glu-γ-Glu-
  xviii. [17-carboxy-heptadecanoyl]-γ-Glu-AEEAc-
  xix. [17-carboxy-heptadecanoyl]-γ-Glu-AEEAc-AEEAc-
  xx. [17-carboxy-heptadecanoyl]-γ-Glu-AEEAc-AEEAc-AEEAc-
  xxi. Eicosanoyl-γ-Glu-
  xxii. Eicosanoyl-γ-Glu-γ-Glu-
  xxiii. Eicosanoyl-γ-Glu-AEEAc-
  xxiv. Eicosanoyl-γ-Glu-AEEAc-AEEAc-
  xxv. Eicosanoyl-γ-Glu-AEEAc-AEEAc-AEEAc-
  xxvi. [19-carboxy-nonadecanoyl]-γ-Glu-
  xxvii. [19-carboxy-nonadecanoyl]-γ-Glu-γ-Glu-
  xxviii. [19-carboxy-nonadecanoyl]-γ-Glu-AEEAc-
  xxix. [19-carboxy-nonadecanoyl]-γ-Glu-AEEAc-AEEAc-
  xxx. [19-carboxy-nonadecanoyl]-γ-Glu-AEEAc-AEEAc-AEEAc- In one embodiment the GIP peptide analogue disclosed herein comprises a fatty acid, and the fatty acid molecule is attached to an amino acid residue via a linker so that the combination of linker and fatty acid is selected from the group consisting of:
  i. [15-Carboxy pentadecanoyl-γGlu
  ii. [17-carboxy-heptadecanoyl]-γ-Glu-AEEAc-AEEAc-, and
  iii. [17-carboxy-heptadecanoyl]-γGlu-γGlu GIP Peptides with Fatty Acid In one embodiment the GIP analogue as defined herein is selected from the group consisting of:

```
GIP(3-36)[H18K],
                                              SEQ ID NO: 106
EGTFISDYSIAMDKIKQQDFVNWLLAQKGKKNDW-2xAEEAc + y-glu-C16-diacid/K18;

GIP(3-36)[H18K],
                                              SEQ ID NO: 106
EGTFISDYSIAMDKIKQQDFVNWLLAQKGKKNDW-3xAEEAc + y-glu-C16-diacid/K18;

GIP(3-36)[H18K],
                                              SEQ ID NO: 106
EGTFISDYSIAMDKIKQQDFVNWLLAQKGKKNDW-3xAEEAc + y-glu-C18-diacid/K18;

GIP(3-30) + Cex(31-39)[H18K],
                                              SEQ ID NO: 107
EGTFISDYSIAMDKIKQQDFVNWLLAQKPSSGAPPPS-C16-diacid/K18;

GIP(3-30) + Cex(31-39)[CexH18K],
                                              SEQ ID NO: 108
EGTFISDYSIAMDKIKQQDFVNWLLAQKPSSGAPPPS(NH2)-2)(AEEAc + yGlu-C18-diacid/K18;

GIP(3-30) + Cex(31-39)[CexH18K],
                                              SEQ ID NO: 107
EGTFISDYSIAMDKIKQQDFVNWLLAQKPSSGAPPPS-2)(AEEAc + yGlu-C18-diacid/K18;

GIP(3-30) + Cex(31-39)[CexH18K],
                                              SEQ ID NO: 108
EGTFISDYSIAMDKIKQQDFVNWLLAQKPSSGAPPPS(NH2)-2)(AEEAc + yGlu-C18-diacid/K18;

GIP(3-30) + Cex(31-39)[CexH18K],
                                              SEQ ID NO: 107
EGTFISDYSIAMDKIKQQDFVNWLLAQKPSSGAPPPS-C16-diacid/K18;

GIP(3-30) + Cex(31-39)[CexH18K],
                                              SEQ ID NO: 107
EGTFISDYSIAMDKIKQQDFVNWLLAQKPSSGAPPPS-C18-diacid/K18;
```

-continued

```
GIP(3-30) + Cex(31-39)[CexH18K],
                                                         SEQ ID NO: 107
EGTFISDYSIAMDKIKQQDFVNWLLAQKPSSGAPPPS-C18/K18;

GIP(3-30) + Cex(31-39)[CexH18K],
                                                         SEQ ID NO: 107
EGTFISDYSIAMDKIKQQDFVNWLLAQKPSSGAPPPS-2)(AEEAc + yGlu-C16-diacid/K18;

GIP(3-30) + Cex(31-39)[CexH18K],
                                                         SEQ ID NO: 107
EGTFISDYSIAMDKIKQQDFVNWLLAQKPSSGAPPPS-yGlu-C16-diacid/K18;

GIP(3-30) + Cex[H18K],
                                                         SEQ ID NO: 109
EGTFISDYSIAMDKIKQQDFVNWLLAQKGPSSGAPPPS-C16-diacid/K18;

GIP(3-30) + Cex[CexH18K],
                                                         SEQ ID NO: 109
EGTFISDYSIAMDKIKQQDFVNWLLAQKGPSSGAPPPS-2)(AEEAc + y-glu-C16-diacid/K18:

GIP(3-30) + Cex[CexH18K],
                                                         SEQ ID NO: 109
EGTFISDYSIAMDKIKQQDFVNWLLAQKGPSSGAPPPS-3)(AEEAc + y-glu-C16-diacid/K18:

GIP(3-30) + Cex[CexH18K],
                                                         SEQ ID NO: 109
EGTFISDYSIAMDKIKQQDFVNWLLAQKGPSSGAPPPS-2)(AEEAc + y-glu-C18-diacid/K18:

GIP(3-30) + Cex[CexH18K],
                                                         SEQ ID NO: 109
EGTFISDYSIAMDKIKQQDFVNWLLAQKGPSSGAPPPS-3)(AEEAc + y-glu-C18-diacid/K18:

GIP(3-30) + Cex(31-39)[CexH18K],
                                                         SEQ ID NO: 110
EGTFISDYSIAMDKIKQQDFVNWLLAQKGPSSGAPPPS(NH2)-2)(AEEAc + yGlu-C18-diacid/K18;

GIP(3-30) + Cex(31-39)[CexH18K],
                                                         SEQ ID NO: 109
EGTFISDYSIAMDKIKQQDFVNWLLAQKGPSSGAPPPS-2)(AEEAc + yGlu-C18-diacid/K18;

GIP(3-30) + Cex(9)[CexH18K],
                                                         SEQ ID NO: 111
EGTFISDYSIAMDKIKQQDFVNWLLAQKGPSSGAPPP-C16-diacid/K18:

GIP(3-30) + Cex(Cex8)[H18K],
                                                         SEQ ID NO: 112
EGTFISDYSIAMDKIKQQDFVNWLLAQKGPSSGAPP-C16-diacid/K18:

GIP(3-30) + Cex(Cex7)[H18K],
                                                         SEQ ID NO: 113
EGTFISDYSIAMDKIKQQDFVNWLLAQKGPSSGAP-C16-diacid/K18:

GIP(3-30) + Cex(Cex6)[H18K],
                                                         SEQ ID NO: 114
EGTFISDYSIAMDKIKQQDFVNWLLAQKGPSSGA-C16-diacid/K18:

GIP(3-30) + Cex(Cex5)[H18K],
                                                         SEQ ID NO: 115
EGTFISDYSIAMDKIKQQDFVNWLLAQKGPSSG-C16-diacid/K18:

GIP(3-30) + Cex(Cex4)[H18K],
                                                         SEQ ID NO: 116
EGTFISDYSIAMDKIKQQDFVNWLLAQKGPSS-C16-diacid/K18:

GIP(3-30) + Cex(Cex3)[H18K],
                                                         SEQ ID NO: 117
EGTFISDYSIAMDKIKQQDFVNWLLAQKGPS-C16-diacid/K18:

GIP(3-30) + Cex(Cex2)[H18K],
                                                         SEQ ID NO: 118
EGTFISDYSIAMDKIKQQDFVNWLLAQKGP-C16-diacid/K18:

GIP(3-31)[H18K],
                                                         SEQ ID NO: 119
EGTFISDYSIAMDKIKQQDFVNWLLAQKG-C16-diacid/K18:

GIP(3-32)[H18K],
                                                         SEQ ID NO: 120
EGTFISDYSIAMDKIKQQDFVNWLLAQKGK-C16-diacid/K18:
```

-continued

GIP(3-33)[H18K],
SEQ ID NO: 121
EGTFISDYSIAMDKIKQQDFVNWLLAQKGKK-C16-diacid/K18:

GIP(3-34)[H18K],
SEQ ID NO: 122
EGTFISDYSIAMDKIKQQDFVNWLLAQKGKKN-C16-diacid/K18:

GIP(3-35)[H18K],
SEQ ID NO: 123
EGTFISDYSIAMDKIKQQDFVNWLLAQKGKKND-C16-diacid/K18:

GIP(3-36)[H18K],
SEQ ID NO: 106
EGTFISDYSIAMDKIKQQDFVNWLLAQKGKKNDW-C16-diacid/K18:

GIP(3-37)[H18K],
SEQ ID NO: 124
EGTFISDYSIAMDKIKQQDFVNWLLAQKGKKNDWK-C16-diacid/K18:

GIP(3-38)[H18K],
SEQ ID NO: 125
EGTFISDYSIAMDKIKQQDFVNWLLAQKGKKNDWKH-C16-diacid/K18:

GIP(3-39)[H18K],
SEQ ID NO: 126
EGTFISDYSIAMDKIKQQDFVNWLLAQKGKKNDWKHN-C16-diacid/K18:

GIP(3-40)[H18K],
SEQ ID NO: 127
EGTFISDYSIAMDKIKQQDFVNWLLAQKGKKNDWKHNI-C16-diacid/K18:

GIP(3-41)[H18K],
SEQ ID NO: 128
EGTFISDYSIAMDKIKQQDFVNWLLAQKGKKNDWKHNIT-C16-diacid/K18:

GIP(3-42)[H18K],
SEQ ID NO: 129
EGTFISDYSIAMDKIKQQDFVNWLLAQKGKKNDWKHNITQ-C16-diacid/K18:

GIP(3-36)[E35;H18K],
SEQ ID NO: 130
SGTFISDYSIAMDKIKQQDFVNWLLAQKGKKNDW-2xAEEAc + y-glu-C16-diacid/K18;

GIP(3-36)[E35;H18K],
SEQ ID NO: 130
SGTFISDYSIAMDKIKQQDFVNWLLAQKGKKNDW-3xAEEAc + y-glu-C16-diacid/K18;

GIP(3-36)[E35;H18K],
SEQ ID NO: 130
SGTFISDYSIAMDKIKQQDFVNWLLAQKGKKNDW-3xAEEAc + y-glu-C18-diacid/K18;

GIP(3-30) + Cex[E35;H18K],
SEQ ID NO: 131
SGTFISDYSIAMDKIKQQDFVNWLLAQKGPSSGAPPPS-2xAEEAc + y-glu-C16-diacid/K18:

GIP(3-30) + Cex[CexE3S;H18K],
SEQ ID NO: 131
SGTFISDYSIAMDKIKQQDFVNWLLAQKGPSSGAPPPS-3xAEEAc + y-glu-C16-diacid/K18:

GIP(3-30) + Cex[CexE3S;H18K],
SEQ ID NO: 131
SGTFISDYSIAMDKIKQQDFVNWLLAQKGPSSGAPPPS-2xAEEAc + y-glu-C18-diacid/K18:

GIP(3-30) + Cex[CexE3S;H18K],
SEQ ID NO: 131
SGTFISDYSIAMDKIKQQDFVNWLLAQKGPSSGAPPPS-3xAEEAc + y-glu-C18-diacid/K18:

GIP(3-36)[E35;K16R;H18K;K30R],
SEQ ID NO: 132
SGTFISDYSIAMDRIKQQDFVNWLLAQRGRRNDW-2xAEEAc + y-glu-C16-diacid/K18;

GIP(3-36)[E35;K16R;H18K;K30R],
SEQ ID NO: 132
SGTFISDYSIAMDRIKQQDFVNWLLAQRGRRNDW-3xAEEAc + y-glu-C16-diacid/K18;

GIP(3-36)[E35;K16R;H18K;K30R],
SEQ ID NO: 132
SGTFISDYSIAMDRIKQQDFVNWLLAQRGRRNDW-3xAEEAc + y-glu-C18-diacid/K18;

GIP(3-30) + Cex[E35;K16R;H18K;K30R],
SEQ ID NO: 133
SGTFISDYSIAMDRIKQQDFVNWLLAQRGPSSGAPPPS-2xAEEAc + y-glu-C16-diacid/K18:

GIP(3-30) + Cex[CexE3S;K16R;H18K;K30R],
SEQ ID NO: 133
SGTFISDYSIAMDRIKQQDFVNWLLAQRGPSSGAPPPS-3xAEEAc + y-glu-C18-diacid/K18:

GIP(3-30) + Cex[CexE3S;K16R;H18K;K30R],
SEQ ID NO: 133
SGTFISDYSIAMDRIKQQDFVNWLLAQRGPSSGAPPPS-2xAEEAc + y-glu-C16-diacid/K18:

GIP(3-30) + Cex[CexE3S;K16R;H18K;K30R],
SEQ ID NO: 133
SGTFISDYSIAMDRIKQQDFVNWLLAQRGPSSGAPPPS-3xAEEAc + y-glu-C18-diacid/K18:

GIP(3-36)[S11K],
SEQ ID NO: 134
EGTFISDYKIAMDKIHQQDFVNWLLAQKGKKNDW-2xAEEAc + yGlu-C18-diacid/K11;

GIP(3-36)[I12K],
SEQ ID NO: 135
EGTFISDYSKAMDKIHQQDFVNWLLAQKGKKNDW-2xAEEAc + yGlu-C18-diacid/K12;

GIP(3-30) + Cex(31-39)[CexQ20K],
SEQ ID NO: 136
EGTFISDYSIAMDKIHQKDFVNWLLAQKPSSGAPPPS(NH2)-2xAEEAc + yGlu-C18-diacid/K20;

GIP(3-30) + Cex(31-39)[Cex117K],
SEQ ID NO: 137
EGTFISDYSIAMDKKHQQDFVNWLLAQKPSSGAPPPS(NH2)-2xAEEAc + yGlu-C18-diacid/K17;

GIP(3-30) + Cex(31-39)[CexH18K;K30G],
SEQ ID NO: 138
EGTFISDYSIAMDKIKQQDFVNWLLAQGPSSGAPPPS(NH2)-2xAEEAc + yGlu-C18-diacid;

GIP(3-30) + Cex(31-39)[CexH18K;Q29G;K30G],
SEQ ID NO: 139
EGTFISDYSIAMDKIKQQDFVNWLLAGGPSSGAPPPS(NH2)-2xAEEAc + yGlu-C18-diacid;

GIP(3-30) + Cex(31-39)[CexH18K;Q29G;K30G],
SEQ ID NO: 140
EGTFISDYSIAMDKIKQQDFVNWLLAGGPSSGAPPPS-2xAEEAc + yGlu-C18-diacid;

GIP(3-30) + Cex(31-39)[CexD9E;D15E;H18K;D21E;N24Q],
SEQ ID NO: 141
EGTFISEYSIAMEKIKQQEFVQWLLAQKPSSGAPPPS-C16-diacid;

GIP(3-30) + Cex(31-39)[D9E;D15E;H18K;N24E],
SEQ ID NO: 142
EGTFISEYSIAMEKIKQQDFVEWLLAQKPSSGAPPPS-C16-diacid;

GIP(3-30) + Cex(31-39)[D9E;112Aib;M14Nle;D15E;H18K;N24E],
SEQ ID NO: 143
EGTFISEYSAibANleEKIKQQDFVEWLLAQKPSSGAPPPS-C16-diacid/18K;

GIP(3-30) + Cex(31-39)[D9E;A13Aib;D15E;H18K;N24E],
SEQ ID NO: 144
EGTFISEYSIAAibMEKIKQQDFVEWLLAQKPSSGAPPPS-C16-diacid/18K;

GIP(3-30) + Cex(31-39)[H18K;N24E],
SEQ ID NO: 145
EGTFISDYSIAMDKIKQQDFVEWLLAQKPSSGAPPPS-C16-diacid/18K;

GIP(3-30) + Cex(31-39)[M14L;H18K],
SEQ ID NO: 146
EGTFISDYSIALDKIKQQDFVNWLLAQKPSSGAPPPS-C16-diacid/18K;

GIP(3-30) + Cex(31-39)[M14L;H18K],
SEQ ID NO: 146
EGTFISDYSIALDKIKQQDFVNWLLAQKPSSGAPPPS-2xAEEAc + yGlu-C18-diacid/18K;

GIP(3-30) + Cex(31-39)[M14Nle;H18K],
SEQ ID NO: 147
EGTFISDYSIANleDKIKQQDFVNWLLAQKPSSGAPPPS-C16-diacid/18K;

GIP(3-30) + Cex(31-39)[M14E;H18K],
SEQ ID NO: 148
EGTFISDYSIAEDKIKQQDFVNWLLAQKPSSGAPPPS-C16-diacid/18K;

```
GIP(3-30) + Cex(31-39)[M14K;H18K],
                                                        SEQ ID NO: 149
EGTFISDYSIAKDKIKQQDFVNWLLAQKPSSGAPPPS-C16-diacid/18K;

GIP(3-30) + Cex(31-39)[M14K;H18K],
                                                        SEQ ID NO: 149
EGTFISDYSIAKDKIKQQDFVNWLLAQKPSSGAPPPS-2xAEEAc + yGlu-C18-diacid/18K;

GIP(3-30) + Cex(31-39)[M14S;H18K],
                                                        SEQ ID NO: 150
EGTFISDYSIASDKIKQQDFVNWLLAQKPSSGAPPPS-C16-diacid/18K;

GIP(3-30) + Cex(31-39)[H18K;N24E;K30A],
                                                        SEQ ID NO: 151
EGTFISDYSIAMDKIKQQDFVEWLLAQAPSSGAPPPS-C16-diacid/18K;

GIP(3-30) + Cex(31-39)[H18K;L27E],
                                                        SEQ ID NO: 152
EGTFISDYSIAMDKIKQQDFVNWLEAQKPSSGAPPPS-C16-diacid/18K;

GIP(3-30) + Cex(31-39)[H18K;A28E],
                                                        SEQ ID NO: 153
EGTFISDYSIAMDKIKQQDFVNWLLEQKPSSGAPPPS-C16-diacid/18K;

GIP(3-30) + Cex(31-39)[E3V;H18K],
                                                        SEQ ID NO: 154
VGTFISDYSIAMDKIKQQDFVNWLLAQKPSSGAPPPS-C16-diacid/18K;

GIP(3-30) + Cex(31-39)[E3Aib;H18K],
                                                        SEQ ID NO: 155
AibGTFISDYSIAMDKIKQQDFVNWLLAQKPSSGAPPPS-C16-diacid/18K;

GIP(3-30) + Cex(31-39)[E3P;H18K],
                                                        SEQ ID NO: 156
PGTFISDYSIAMDKIKQQDFVNWLLAQKPSSGAPPPS-C16-diacid/18K;

GIP(3-30) + Cex(31-39)[E3V;G4E;H18K],
                                                        SEQ ID NO: 157
VETFISDYSIAMDKIKQQDFVNWLLAQKPSSGAPPPS-C16-diacid/18K;

GIP(3-30) + Cex(31-39)[E3Aib;G4E;H18K],
                                                        SEQ ID NO: 158
AibETFISDYSIAMDKIKQQDFVNWLLAQKPSSGAPPPS-C16-diacid/18K;

GIP(3-30) + Cex(31-39)[E3G;G4E;H18K],
                                                        SEQ ID NO: 159
GETFISDYSIAMDKIKQQDFVNWLLAQKPSSGAPPPS-C16-diacid/18K;

GIP(3-30) + Cex(31-39)[E3P;G4E;H18K],
                                                        SEQ ID NO: 160
PETFISDYSIAMDKIKQQDFVNWLLAQKPSSGAPPPS-C16-diacid/18K;

GIP(3-30) + Cex(31-39)[E3D;G4T;H18K],
                                                        SEQ ID NO: 161
DTTFISDYSIAMDKIKQQDFVNWLLAQKPSSGAPPPS-C16-diacid/18K;

GIP(3-30) + Cex(31-39)[E3G;G4E;S11A;M14L;H18K;N24E;K30G],
                                                        SEQ ID NO: 162
GETFISDYAIALDKIKQQDFVEWLLAQGPSSGAPPPS-C16-diacid/18K;

GIP(3-30) + Cex(31-39)[E3G;G4E;D9T;M14L;H18K;N24E],
                                                        SEQ ID NO: 163
GETFISTYSIALDKIKQQDFVEWLLAQKPSSGAPPPS-C16-diacid/18K;

GIP(3-30) + Cex(31-39)[D9T;S11K;M14L;N24E],
                                                        SEQ ID NO: 164
EGTFISTYKIALDKIHQQDFVEWLLAQKPSSGAPPPS-yGlu-C16-diacid/18K;

GIP(3-30) + Cex(31-39)[E3G;G4E;S11A;M14L;H18K;N24E;K30G],
                                                        SEQ ID NO: 162
GETFISDYAIALDKIKQQDFVEWLLAQG(NH₂)PSSGAPPPS-C16-diacid/18K;

GIP(3-30) + Cex(31-39)[A13Aib;H18K;N24E],
                                                        SEQ ID NO: 166
EGTFISDYSIAibMDKIKQQDFVEWLLAQKPSSGAPPPS-C16-diacid/18K;

GIP(3-30) + Cex(31-39)[A13Aib;M14L;H18K;N24E],
                                                        SEQ ID NO: 167
EGTFISDYSIAibLDKIKQQDFVEWLLAQKPSSGAPPPS-C16-diacid/18K;
```

-continued

```
GIP(3-30) + Cex(31-39)[A13Aib;M14L;H18K;N24E],
                                                       SEQ ID NO: 167
EGTFISDYSIAibLDKIKQQDFVEWLLAQKPSSGAPPPS-2xAEEAc + yGlu-C18-diacid/18K;

GIP(3-30) + Cex(31-39)[A13Aib;M14Nle;H18K;N24E],
                                                       SEQ ID NO: 168
EGTFISDYSIAibNleDKIKQQDFVEWLLAQKPSSGAPPPS-C16-diacid/18K;

GIP(3-30) + Cex(31-39)[A13Aib;M14Nle;H18K;N24E],
                                                       SEQ ID NO: 168
EGTFISDYSIAibNleDKIKQQDFVEWLLAQKPSSGAPPPS-2xAEEAc + yGlu-C18-diacid/18K;

GIP(3-30) + Cex(31-39)[M14L;H18K;N24E],
                                                       SEQ ID NO: 169
EGTFISDYSIALDKIKQQDFVEWLLAQKPSSGAPPPS-C16-diacid/18K;

GIP(3-30) + Cex(31-39)[M14L;H18K;N24E],
                                                       SEQ ID NO: 169
EGTFISDYSIALDKIKQQDFVEWLLAQKPSSGAPPPS-2xAEEAc + yGlu-C18-diacid/18K;

GIP(3-30) + Cex(31-39)[M14Nle;H18K;N24E],
                                                       SEQ ID NO: 170
EGTFISDYSIANleDKIKQQDFVEWLLAQKPSSGAPPPS-C16-diacid/18K;

GIP(3-30) + Cex(31-39)[M14Nle;H18K;N24E],
                                                       SEQ ID NO: 170
EGTFISDYSIANleDKIKQQDFVEWLLAQKPSSGAPPPS-2xAEEAc + yGlu-C18-diacid/18K;

GIP(3-30) + Cex(31-39)[M14K;H18K;N24E],
                                                       SEQ ID NO: 171
EGTFISDYSIAKDKIKQQDFVEWLLAQKPSSGAPPPS-C16-diacid/18K;

GIP(3-30) + Cex(31-39)[M14Nle;H18K;Q29G;K30G],
                                                       SEQ ID NO: 172
EGTFISDYSIANleDKIKQQDFVNWLLAGGPSSGAPPPS-C16-diacid/18K;

GIP(3-30) + Cex(31-39)[M14Nle;H18K;N24E;Q29G;K30G],
                                                       SEQ ID NO: 173
EGTFISDYSIANleDKIKQQDFVEWLLAGGPSSGAPPPS-C16-diacid/18K;

GIP(3-30) + Cex(31-39)[D9E;A13Aib;M14L;D15E;H18K;D21E;N24E],
                                                       SEQ ID NO: 174
EGTFISEYSIAibLEKIKQQEFVEWLLAQKPSSGAPPPS-C16-diacid/18K;

GIP(3-30) + Cex(31-39)[D9E;A13Aib;M14L;D15E;H18K;D21E;N24E],
                                                       SEQ ID NO: 174
EGTFISEYSIAibLEKIKQQEFVEWLLAQKPSSGAPPPS-2xAEEAc + yGlu-C18-diacid/18K;

GIP(3-30) + Cex(31-39)[D9E;A13Aib;M14Nle;D15E;H18K;D21E;N24E],
                                                       SEQ ID NO: 175
EGTFISEYSIAibNleEKIKQQEFVEWLLAQKPSSGAPPPS-C16-diacid/18K;

GIP(3-30) + Cex(31-39)[D9E;A13Aib;M14Nle;D15E;H18K;D21E;N24E],
                                                       SEQ ID NO: 175
EGTFISEYSIAibNleEKIKQQEFVEWLLAQKPSSGAPPPS-2xAEEAc + yGlu-C18-diacid/18K;

GIP(3-30) + Cex(31-39)[E3yGlu;H18K],
                                                       SEQ ID NO: 176
yGluGTFISDYSIAMDKIKQQDFVNWLLAQKPSSGAPPPS-C16-diacid/18K;

GIP(3-30) + Cex(31-39)[E3βGlu;H18K],
                                                       SEQ ID NO: 177
βGluGTFISDYSIAMDKIKQQDFVNWLLAQKPSSGAPPPS-C16-diacid/18K;

GIP(3-30) + Cex(31-39)[E3Glutaric acid(X);H18K],
                                                       SEQ ID NO: 178
XGTFISDYSIAMDKIKQQDFVNWLLAQKPSSGAPPPS-C16-diacid/18K;

GIP(3-30) + Cex(31-39)[M14L;H18K;N24E;Q29G;K30G],
                                                       SEQ ID NO: 179
EGTFISDYSIALDKIKQQDFVEWLLAGGPSSGAPPPS-2xAEEAc + yGlu-C18-diacid/18K;

GIP(3-30) + Cex(31-39)[D9E;M14L;D15E;H18K;D21E;N24E],
                                                       SEQ ID NO: 180
EGTFISEYSIALEKIKQQEFVEWLLAQKPSSGAPPPS-2xAEEAc + yGlu-C18-diacid/18K;

GIP(3-30) + Cex(31-39)[D9E;M14Nle;D15E;H18K;D21EN24E],
                                                       SEQ ID NO: 181
EGTFISEYSIANleEKIKQQEFVEWLLAQKPSSGAPPPS-2xAEEAc + yGlu-C18-diacid/18K;
```

```
GIP(3-30) + Cex(31-39)[E3yGlu(L-isomer);M14Nle;H18K;N24E],
                                                         SEQ ID NO: 182
yGluGTFISDYSIANleDKIKQQDFVEWLLAQKPSSGAPPPS-C16-diacid/18K;

GIP(3-30) + Cex(31-39)[E3yGlu(D-isomer);M14Nle;H18K;N24E],
                                                         SEQ ID NO: 183
yGluGTFISDYSIANleDKIKQQDFVEWLLAQKPSSGAPPPS-C16-diacid/18K;

GIP(3-30) + Cex(31-39)[E3βGlu;M14Nle;H18K;N24E],
                                                         SEQ ID NO: 184
βGluGTFISDYSIANleDKIKQQDFVEWLLAQKPSSGAPPPS-C16-diacid/18K;

GIP(3-30) + Cex(31-39)[E3βGlu;M14Nle;H18K;N24E],
                                                         SEQ ID NO: 184
βGluGTFISDYSIANleDKIKQQDFVEWLLAQKPSSGAPPPS-2xAEEAc + yGlu-C18-diacid/18K;

GIP(3-30) + Cex(31-39)[E3Glutaric acid(X);M14Nle;H18K;N24E],
                                                         SEQ ID NO: 185
XGTFISDYSIANleDKIKQQDFVEWLLAQKPSSGAPPPS-C16-diacid/18K;

GIP(3-30) + Cex(31-39)[E3Glutaric acid(X);M14Nle;H18K;N24E],
                                                         SEQ ID NO: 185
XGTFISDYSIANleDKIKQQDFVEWLLAQKPSSGAPPPS-2xAEEAc + yGlu-C18-diacid/18K;

GIP(3-30) + Cex(31-39)[E3βGlu;A13Aib;M14Nle;H18K],
                                                         SEQ ID NO: 186
βGluGTFISDYSIAibNleDKIKQQDFVNWLLAQKPSSGAPPPS-C16-diacid/18K;

GIP(3-30) + Cex(32-39)[H18K;Q29G;K30P]),
                                                         SEQ ID NO: 41
EGTFISDYSIAMDKIKQQDFVNWLLAQPSSGAPPPS(NH2)-2xAEEAc + yGlu-C18-diacid/K18;;

GIP(3-30)Cex(31-39)[M14L;H18K;A28E],
                                                         SEQ ID NO: 217
EGTFISDYSIALDKIKQQDFVNWLLEQKPSSGAPPPS-2xAEEAc + yGlu-C18-diacid/K18;;

GIP(3-30)Cex(31-39)[M14Nle;H18K;A28E],
                                                         SEQ ID NO: 218
EGTFISDYSIANleDKIKQQDFVNWLLEQKPSSGAPPPS-2xAEEAc + yGlu-C18-diacid/K18;;

GIP(3-30)Cex(31-39)[M14L;H18K;A28E;Q29G;K30G], AT691,
                                                         SEQ ID NO: 219
EGTFISDYSIALDKIKQQDFVNWLLEGGPSSGAPPPS-2xAEEAc + yGlu-C18-diacid/K18;;

GIP(3-30 + CEX31-39[H18K], AT650
                                                         SEQ ID NO: 165
EGTFISDYSIAMDKIKQQDFVNWLLAQK(NH2)PSSGAPPPSC16-diacid/18K;

GIP(3-30) + Cex(31-39), AT626,
                                                         SEQ ID NO: 220
EGTFISDYSIAMDKIKQQDFVNWLLEGGPSSGAPPPS-C16-diacid/K18;
``` or a functional variant thereof,
wherein said fatty acid is attached directly or via a linker/spacer as defined herein.

It follows that C16 is the fatty acid $CH_3(CH_2)_{14}CO-$ (palmitoyl) and C18 is the fatty acid $CH_3(CH_2)_{16}CO-$ (stearyl). The suffix "-diacid" means that the fatty acid molecule is a diacyl fatty acid molecule. No such suffix refers to a monoacyl fatty acid molecule.

It follows that C20 is the fatty acid $CH_3(CH_2)_{18}CO-$ (arachidyl). The suffix "-diacid" means that the fatty acid molecule is a diacyl fatty acid molecule. No such suffix refers to a monoacyl fatty acid molecule.

It follows that C22 is the fatty acid $CH_3(CH_2)_{20}CO-$ (behenyl). The suffix "-diacid" means that the fatty acid molecule is a diacyl fatty acid molecule. No such suffix refers to a monoacyl fatty acid molecule.

In one embodiment the GIP analogue as defined herein is selected from the group consisting of:

```
GIP(5-33)[S11K],
                                                         SEQ ID NO: 189
TFISDYKIAMDKIHQQDFVNWLLAQKGKK-y-glu-C16diacid/K11

GIP(5-36)[S11K],
                                                         SEQ ID NO: 190
TFISDYKIAMDKIHQQDFVNWLLAQKGKKNDW-y-glu-C16diacid/K11

GIP(5-36)[S11K],
                                                         SEQ ID NO: 190
TFISDYKIAMDKIHQQDFVNWLLAQKGKKNDW-2xAEEAc + yGlu-C18-diacid/K11,
```

```
GIP(5-36)[S11K],
                                                     SEQ ID NO: 191
TFISDYKIAMDKIHQQDFVNWLLAQKGKKNDW(NH2)-2xAEEAc + yGlu-C18-diacid/K11, GIP(5-36)[S11K],
                                                     SEQ ID NO: 190
TFISDYKIAMDKIHQQDFVNWLLAQKGKKNDW-2xAEEAc + yGlu-C18/K11, GIP(5-36)[S11K],
                                                     SEQ ID NO: 190
TFISDYKIAMDKIHQQDFVNWLLAQKGKKNDW-yGlu-yGlu-C18/K11, GIP(5-36)[I12K],
                                                     SEQ ID NO: 192
TFISDYSKAMDKIHQQDFVNWLLAQKGKKNDW-2xAEEAc + yGlu-C18diacid/K12

GIP(5-39)[S11K],
                                                     SEQ ID NO: 193
TFISDYKIAMDKIHQQDFVNWLLAQKGKKNDWKHN-y-glu-C16diacid/K11

GIP(5-42)[S11K],
                                                     SEQ ID NO: 194
TFISDYKIAMDKIHQQDFVNWLLAQKGKKNDWKHNITQ-y-glu-C16diacid/K11

GIP(5-31)[S11K],
                                                     SEQ ID NO: 195
TFISDYKIAMDKIHQQDFVNWLLAQKG-y-glu-C16diacid/K11

GIP(5-32)[S11K],
                                                     SEQ ID NO: 196
TFISDYKIAMDKIHQQDFVNWLLAQKGK-y-glu-C16diacid/K11

GIP(5-34)[S11K],
                                                     SEQ ID NO: 197
TFISDYKIAMDKIHQQDFVNWLLAQKGKKN-y-glu-C16diacid/K11

GIP(5-35)[S11K],
                                                     SEQ ID NO: 198
TFISDYKIAMDKIHQQDFVNWLLAQKGKKND-y-glu-C16diacid/K11

GIP(5-37)[S11K],
                                                     SEQ ID NO: 199
TFISDYKIAMDKIHQQDFVNWLLAQKGKKNDWK-y-glu-C16diacid/K11

GIP(5-38)[S11K],
                                                     SEQ ID NO: 200
TFISDYKIAMDKIHQQDFVNWLLAQKGKKNDWKH-y-glu-C16diacid/K11

GIP(5-40)[S11K],
                                                     SEQ ID NO: 201
TFISDYKIAMDKIHQQDFVNWLLAQKGKKNDWKHNI-y-glu-C16diacid/K11

GIP(5-41)[S11K],
                                                     SEQ ID NO: 202
TFISDYKIAMDKIHQQDFVNWLLAQKGKKNDWKHNIT-y-glu-C16diacid/K11

GIP(5-30) + Cex31-39[S11K],
                                                     SEQ ID NO: 203
TFISDYKIAMDKIHQQDFVNWLLAQKPSSGAPPPS(NH2)-2xPEG + yGlu-C18-diacid/K11;

GIP(5-36)[S11K;K16R;K30R;K32R;K33R],
                                                     SEQ ID NO: 204
TFISDYKIAMDRIHQQDFVNWLLAQRGRRNDW-3xAEEAc + y-glu-C16diacid/K11;

GIP(5-36)[S11K;K16R;K30R;K32R;K33R],
                                                     SEQ ID NO: 204
TFISDYKIAMDRIHQQDFVNWLLAQRGRRNDW-3xAEEAc + y-glu-C18diacid/K11;

GIP(5-30) + Cex[S11K;K16R;K30R],
                                                     SEQ ID NO: 205
TFISDYKIAMDRIHQQDFVNWLLAQRGPSSGAPPPS-2AEEAc + y-glu-C16diacid/K11;

GIP(5-30) + Cex[S11K;K16R;K30R],
                                                     SEQ ID NO: 205
TFISDYKIAMDRIHQQDFVNWLLAQRGPSSGAPPPS-3AEEAc + y-glu-C16diacid/K11;

GIP(5-30) + Cex[S11K;K16R;K30R],
                                                     SEQ ID NO: 205
TFISDYKIAMDRIHQQDFVNWLLAQRGPSSGAPPPS-2}(AEEAc + y-glu-C18diacid/K11;
```

-continued

GIP(5-30) + Cex[S11K;K16R;K30R],
SEQ ID NO: 205
TFISDYKIAMDRIHQQDFVNWLLAQRGPSSGAPPPS-3)(AEEAc + y-glu-C18diacid/K11;

GIP(5-36)[H18K],
SEQ ID NO: 206
TFISDYSIAMDKIKQQDFVNWLLAQKGKKNDW-2xAEEAc + y-glu-C18diacid/K18;

GIP(5-30) + Cex(31-39)[H18K],
SEQ ID NO: 221
TFISDYSIAMDKIKQQDFVNWLLAQKPSSGAPPPS(NH2)-2xPEG + yGlu-C18-diacid/K18;

GIP(5-30) + Cex(31-39)[H18K],
SEQ ID NO: 222
TFISDYSIAMDKIKQQDFVNWLLAQKPSSGAPPPS-yGlu-C16-diacid/K18;

GIP(5-36)[Q20K],
SEQ ID NO: 209
TFISDYSIAMDKIHQKDFVNWLLAQKGKKNDW-2xAEEAc + y-glu-C18diacid/K20;

GIP(5-36)[Q20K],
SEQ ID NO: 223
TFISDYSIAMDKIHQKDFVNWLLAQKGKKNDW(NH2)-2xAEEAc + y-glu-C18diacid/K20;

GIP(5-36[N24K],
SEQ ID NO: 210
TFISDYSIAMDKIHQQDFVKWLLAQKGKKNDW-2xAEEAc + y-glu-C18diacid/K24;

GIP(5-30) + Cex(31-39)[S11K;Q29G;K30G],
SEQ ID NO: 216
TFISDYKIAMDKIHQQDFVNWLLAGGPSSGAPPPS(NH$_2$)-2xPEG + yGlu-C18-diacid/K11;

AT597,
SEQ ID NO: 203
TFISDYKIAMDKIHQQDFVNWLLAQKPSSGAPPPS(NH$_2$)2xPEG + yGlu-C18-diacid/K11, and
or a functional variant thereof.
In one embodiment the GIP analogue is selected from the group consisting of:

GIP(6-33)[H18K],
SEQ ID NO: 211
FISDYSIAMDKIKQQDFVNWLLAQKGKK-C16diacid/K18;

GIP(6-36)[H18K],
SEQ ID NO: 212
FISDYSIAMDKIKQQDFVNWLLAQKGKKNDW-C16diacid/K18;

GIP(6-39)[H18K],
SEQ ID NO: 213
FISDYSIAMDKIKQQDFVNWLLAQKGKKNDWKHN-C16diacid/K18;

GIP(6-42)[H18K], and
SEQ ID NO: 214
FISDYSIAMDKIKQQDFVNWLLAQKGKKNDWKHNITQ-C16diacid/K18;

GIP(6-30) + Cex[H18K],
SEQ ID NO: 215
FISDYSIAMDKIKQQDFVNWLLAQKGPSSGAPPPS-C16diacid/K18;

or a functional variant thereof,
wherein said fatty acid is attached directly or via a linker/spacer as defined herein.

Compound

It is a further aspect to provide a compound comprising or consisting of a peptide as defined herein. In one embodiment, said compound is formulated as a peptide monomer (i.e. comprising 1 copy of the peptide), whereas in another embodiment, said compound is formulated as a peptide multimer.

Multimeric Compound

In one embodiment the peptide according to the present disclosure is formulated as a multimer. A multimer is a protein comprising or consisting of multiple peptide monomers. A multimer is an aggregate of multiple molecules that is usually held together with non-covalent bonds. This definition distinguishes a multimer from a polymer, which is a series of monomers that are held together with covalent bonds.

A peptide sequence of the present disclosure is in one embodiment connected to another (identical or non-identical) peptide sequence of the present disclosure by a chemical bond or through a linker group. In some embodiments a peptide of the disclosure is formulated as an oligomer or multimer of monomers, wherein each monomer is as a peptide sequence as defined according to the present disclosure.

Thus, according to the disclosure a multimeric compound is in one embodiment a polymer comprising two or more peptide sequences of the disclosure, said peptide sequences being identical or non-identical, wherein at least one of the two or more peptide sequences is a peptide according to the present disclosure. Preferably, both peptide sequences are a peptide according to the present disclosure.

In one embodiment the multimeric compound is a dimer, comprising two peptides according to the present disclosure, said two peptides being identical or non-identical with respect to each other.

In another embodiment the multimeric compound is a trimer, comprising three peptides according to the present disclosure, said peptides being identical or non-identical with respect to each other.

In another embodiment the multimeric compound is a tetramer, comprising four peptides according to the present disclosure, said peptides being identical or non-identical with respect to each other.

In one embodiment the multimeric compound is a dendrimer, such as a tetrameric or octameric dendrimer. Dendrimers are repeatedly branched, roughly spherical large molecules, typically symmetric around the core, and often adopts a spherical three-dimensional morphology.

Dendrimers according to the present disclosure may comprise 4 peptides, 8 peptides, 16 peptides, or 32 peptides. In one particular embodiment said dendrimer comprises four peptides (i.e. a tetrameric dendrimer) or eight peptides (octameric dendrimer).

In some particular embodiments, the multimeric compound comprises two identical amino acid sequences of the present invention (dimer) or the compound comprises four identical copies of an amino acid sequence of the present disclosure (tetrameric dendrimer).

The multimers according to the disclosure is in one embodiment made by linking two or more peptide monomers via a peptide bond or a linker group. In one embodiment they are linked to a lysine backbone, such as a lysine residue (each peptide chain is linked to a single lysine residue), or coupled to a polymer carrier, for example a protein carrier. Said linker group in one embodiment comprises a plurality of lysine residues, such as a core moiety having a plurality of lysine residues, such as seen in a lysine-based dendromeric structure containing three, seven, fifteen and more lysine residues However, any other linking of peptide monomers known to the skilled person may be envisioned.

The linking in one embodiment occurs at the N-terminal and/or C-terminal end of the peptide monomers.

In one embodiment there is provided a multimeric compound, consisting of:
A) one or more glucose-dependent insulinotropic peptide (GIP) analogues selected from the group consisting of:
a glucose-dependent insulinotropic peptide (GIP) analogue consisting of amino acid sequence SEQ ID NO:1:

```
 3    4   - 5 - 6   7   8   9   10  11  12  13  14
X₁ - X₂ - T - F - I - S - D - Y - S - I - A - M -

15  16  17 18  19  20  21  22  23  24  25  26  27
D - K - I  H - Q - Q - D - F - V - N - W - L - L -

28  29  30
A - Q - K - Z,
``` wherein X₁ and X₂ are individually any amino acid or omitted; or a functional variant thereof, wherein said variant has 1 to 7, such as 1 to 4 individual amino acid substitutions at any amino acid of SEQ ID NO:1,
wherein said peptide is modified by attaching at least one fatty acid molecule at one or more amino acid residues at positions 3 to 29 of SEQ ID NO:1, or said functional variant thereof,
wherein Z is a peptide comprising one or more amino acid residues of GIP(31-42) (GKKNDWKHNITQ; SEQ ID NO: 2) or one or more amino acid residues of Exendin-4 (HGEGTFTSDLSKQMEEE-AVRLFIEWLKNGGPSSGAPPPS; SEQ ID NO: 3); and
a glucose-dependent insulinotropic peptide (GIP) analogue selected from the group consisting of:
a peptide having an amino acid sequence consisting of SEQ ID NO:32 hGIP(3-30):

```
 3    4   - 5 - 6   7   8   9   10  11  12  13  14
E  - G  - T - F - I - S - D - Y - S - I - A - M -
```

```
15  16  17 18  19  20  21  22  23  24  25  26
D - K - I  H - Q - Q - D - F - V - N - W - L -

27  28  29  30
L - A - Q - K - Z,
``` a peptide having an amino acid sequence consisting of SEQ ID NO:35 hGIP(5-30):

```
 5  - 6   7   8   9  10  11  12  13  14  15  16  17
T - F  - I - S - D - Y - S - I - A - M - D - K - I 18  19  20  21  22  23  24  25  26  27  28  29
H - Q - Q - D - F - V - N - W - L - L - A - Q -

30
K - Z
``` and
a peptide having an amino acid sequence consisting of SEQ ID NO:36 hGIP(6-30):

```
 6   7   8   9  10  11  12  13  14  15  16  17
F - I - S - D - Y - S - I - A - M - D - K - I 18  19  20  21  22  23  24  25  26  27  28
H - Q - Q - D - F - V - N - W - L - L - A -

29  30
Q - K - Z
``` or a functional variant thereof, wherein said variant has 1 to 4 individual amino acid substitutions at any one of SEQ ID NO: hGIP(5-30) and SEQ ID NO: hGIP(6-30),
wherein said peptide is modified by attaching at least one fatty acid molecule at one or more amino acid residues at positions 4 to 29 of any one of SEQ ID NO; and SEQ ID NO: or a functional variant thereof comprising between 1 and 4 amino acid substitutions at any one of SEQ ID NO: hGIP(5-30) and SEQ ID NO: hGIP(6-30), with or without a linker,
wherein Z is:
a. a glycine or a proline,
b. a fragment selected from the group consisting of: GP, GPS, GPSS (SEQ ID NO: 6), GPSSG (SEQ ID NO: 7), GPSSGA (SEQ ID NO: 8), GPSSGAP (SEQ ID NO: 9), GPSSGAPP (SEQ ID NO: 10), GPSSGAPPP (SEQ ID NO:11) and GPSSGAPPPS (SEQ ID NO: 5),
b1. a fragment selected from the group consisting of: PS, PSS, PSSG (SEQ ID NO: 12), PSSGA (SEQ ID NO: 13), PSSGAP (SEQ ID NO: 14), PSSGAPP (SEQ ID NO: 15), PSSGAPPP (SEQ ID NO: 16) and PSSGAPPPS (SEQ ID NO: 4),
c. a fragment selected from the group consisting of: GK, GKK, GKKN (SEQ ID NO: 17), GKKND (SEQ ID NO: 18), GKKNDW (SEQ ID NO: 19), GRKNDW (SEQ ID NO: 20), GKRNDW (SEQ ID NO: 21), GRRNDW (SEQ ID NO: 22), GKKNDWK (SEQ ID NO: 23), GKKNDWKH (SEQ ID NO: 24), GKKNDWKHN (SEQ ID NO: 25), GKKNDWKHNI (SEQ ID NO: 26), GKKNDWKHNIT (SEQ ID NO: 27) and GKKNDWKHNITQ (SEQ ID NO:2), or
d. a fragment selected from the group consisting of: GPSSGA (SEQ ID NO: 8), GPSSGAP (SEQ ID NO: 9), GPSSGAPP (SEQ ID NO: 10), GPSSGAPPP (SEQ ID NO: 11), GPSSGAPPPS (SEQ ID NO: 5), GKKNDW (SEQ ID NO: 19), GRKNDW (SEQ ID NO: 20), GKRNDW (SEQ ID NO: 21), GRRNDW (SEQ ID NO: 22), GKKNDWK (SEQ ID NO: 23), GKKNDWKH (SEQ ID NO: 24), GKKNDWKHN (SEQ ID NO: 25), GKKNDWKHNI (SEQ ID NO: 26), GKKNDWKHNIT (SEQ ID NO: 27) and GKKNDWKHNITQ (SEQ ID NO:2), or a variant thereof comprising 1 or 2 individual amino acid substitutions at any one of the amino acid residues, or
- e. a fragment selected from the group consisting of:
  PSSG (SEQ ID NO: 12), PSSGA (SEQ ID NO: 13), PSSGAP (SEQ ID NO: 14), PSSGAPP (SEQ ID NO: 15), PSSGAPPP (SEQ ID NO: 16) and PSSGAPPPS (SEQ ID NO: 4),
  or a variant thereof comprising 1 or 2 individual amino acid substitutions at any one of the amino acid residues;

B) optionally one or more linker groups.

Determining Antagonist Properties and Affinity

In order to determine whether a peptide is an antagonist of the GIPR, methods known in the art may be employed, for example by determining the IC50 of the peptide. This can be done by constructing a dose-response curve and examining the effect of different concentrations of the peptide on reversing agonist activity. The agonist can be GIP1-42, for example hGIP-1-42 or hGIP1-30. The GIPR can be hGIPR, rGIPR, mGIPR, dog GIPR, pig GIPR or the *Macaca mulatta* GIPR. IC50 values can be calculated for a given antagonist by determining the concentration needed to inhibit half of the maximum biological response of the agonist. A method for determining whether a peptide is an antagonist is described in example 4, but other methods known in the art may also be used. For example, Schild plot analysis may be performed on hGIP1-42 cAMP dose-response curves with increasing concentrations of GIP-derived peptides. In this way, the type of antagonist activity may also be determined.

The GIP peptide analogues of the present disclosure are characterized by having antagonistic activity towards GIPR. In particular, the GIP peptide analogues of the present disclosure are potent antagonists of GIPR, due to a large extent to the presence of a fatty acid in the core of the GIP peptide (residues 3 to 29 of GIP) as well as to the presence of an elongation at the C-terminus of the GIP peptide.

In one embodiment, the GIP peptide analogue of the present disclosure is an antagonist of GIPR.

In one embodiment, the GIP peptide analogue of the present disclosure inhibits, such as is capable of inhibiting, GIPR activity of at least 70%, such as of at least 75%, such as of at least 80%, such as of at least 85%, such as of at least 90%, such as of at least 95%, such as of about 100%, as measured via an assay that determines the decrease in intracellular cAMP, such as via a CisBio cAMP assay and/or via a DiscoveRx cAMP assay, which are described in "Materials and methods".

In one embodiment, the GIP peptide analogue of the present disclosure inhibits GIPR activity of at least 80%, such as of at least 85%, such as of at least 90%, such as of at least 95%, such as of about 100%, wherein inhibition of GIPR activity is determined as a decrease in intracellular cAMP, for example via an assay that determines the decrease in intracellular cAMP, such as via a CisBio cAMP assay and/or via a DiscoveRx cAMP assay, which are described in "Materials and methods". The % inhibition is a % of inhibition of Emax, which means that if a peptide inhibits Emax of 85%, there is 15% activity left of the GIPR.

In one embodiment, the GIP peptide analogue of the present disclosure has a GIPR antagonistic activity corresponding to an IC50 of 50 nM or less, such as of 45 nM or less, such as of 40 nM or less, such as of 35 nM or less, such as of 30 nM or less, such as of 25 nM or less, such as of 20 nM or less, such as of 15 nM or less, such as of 10 nM or less, such as of 5 nM or less, such as of between 1 and 5 nM, wherein antagonistic activity (also referred to as "potency") is measured via an assay that determines the decrease in intracellular cAMP, such as via a CisBio cAMP assay and/or via a DiscoveRx cAMP assay, which are described in "Materials and methods".

Methods for determining antagonistic activity of a compound, such as of a GIP peptide analogue, are known to the person of skills in the art. Exemplary methods that can be used for determining antagonistic activity of a compound, such as of a GIP peptide analogue, can be found herein in the "Examples", for example, these methods comprise measuring intracellular cAMP and determining a decrease in intracellular cAMP resulting from treatment of cells with a GIP peptide analogue.

The GIP peptide analogues of the present disclosure are also characterized by having low or no agonistic activity towards GIPR. GIP peptide analogues having low or no agonistic activity towards GIPR, such as an agonistic activity of 20% or less, preferably of 10% or less, ever more preferably of 5% or less, are also referred to as "silent antagonists".

In one embodiment the GIP peptide analogue of the present disclosure is capable of stimulating GIPR activity of at most 30%, such as of at most 25%, such as of at the most 20%, such as of at the most 15%, such as of at the most 10%, such as of at the most 5%, in one embodiment the GIP peptide analogue of the present disclosure has no agonistic activity towards GIPR, that is it stimulates GIPR activity of about 0%.

Agnostic activity of a GIP peptide analogue towards GIPR can be determined in the same way as antagonistic activity, but an increase in intracellular cAMP is measured, instead of a decrease, as described in "Materials and methods".

Method of Treatment

It is also an aspect to provide a peptide as defined herein, or a composition comprising the peptide, for use as a medicament.

In one embodiment there is provided a glucose-dependent insulinotropic peptide (GIP) analogue consisting of amino acid sequence SEQ ID NO:1:

```
3 - 4 - 5 - 6   7   8   9   10  11  12  13  14
X₁- X₂- T - F - I - S - D - Y - S - I - A - M -

15  16  17 18  19  20  21  22  23  24  25  26  27
D - K - I  H - Q - Q - D - F - V - N - W - L - L -

28  29  30
A - Q - K - Z,
```

- wherein X₁ and X₂ are individually any amino acid or omitted;
- or a functional variant thereof, wherein said variant has 1 to 8, such as 1 to 4 individual amino acid substitutions at any amino acid of SEQ ID NO:1,
- wherein said peptide is modified by attaching at least one fatty acid molecule at one or more amino acid residues at positions 3 to 29 of SEQ ID NO:1, or said functional variant thereof, wherein Z is a peptide comprising one or more amino acid residues of GIP(31-42) (GKKNDWKHNITQ; SEQ ID NO: 2) or one or more amino acid residues of Exendin-4 (HGEGTFTSDLSKQMEEEAVRLFIEWLKNGGPSSGAPPPS; SEQ ID NO: 3) for use as a medicament.

In one embodiment there is provided a GIP analogue selected from the group consisting of:
a peptide having an amino acid sequence consisting of SEQ ID NO:32 hGIP(3-30):

```
3 - 4 - 5 - 6   7   8   9   10  11  12  13  14
E - G - T - F - I - S - D - Y - S - I - A - M -

15  16  17 18  19  20  21  22  23  24  25  26  27
D - K - I  H - Q - Q - D - F - V - N - W - L - L -

28  29  30
A - Q - K - Z,
``` a peptide having an amino acid sequence consisting of SEQ ID NO:35 hGIP(5-30):

```
5 - 6   7   8   9   10  11  12  13  14  15  16  17
T - F - I - S - D - Y - S - I - A - M - D - K - I 18  19  20  21  22  23  24  25  26  27  28  29  30
H - Q - Q - D - F - V - N - W - L - L - A - Q - K -
Z
``` and
a peptide having an amino acid sequence consisting of SEQ ID NO:36 hGIP(6-30):

```
6   7   8   9   10  11  12  13  14  15  16  17 18
F - I - S - D - Y - S - I - A - M - D - K - I  H -

19  20  21  22  23  24  25  26  27  28  29  30
Q - Q - D - F - V - N - W - L - L - A - Q - K - Z
``` or a functional variant thereof, wherein said variant has 1 to 4 individual amino acid substitutions at any one of the amino acid residues of SEQ ID NO: hGIP(3-30), SEQ ID NO: hGIP(5-30) and SEQ ID NO: hGIP(6-30),
wherein said peptide is modified by attaching at least one fatty acid molecule at one or more amino acid residues at positions 6 to 29 of any one of SEQ ID NO: hGIP(3-30), SEQ ID NO: hGIP(5-30) and SEQ ID NO: hGIP(6-30), or a functional variant thereof comprising between 1 and 4 amino acid substitutions at any one of the amino acid residues of SEQ ID NO: hGIP(3-30), SEQ ID NO: hGIP(5-30) and SEQ ID NO: hGIP(6-30), with or without a linker,
wherein Z is:
a glycine or a proline,
a fragment selected from the group consisting of:
GP, GPS, GPSS (SEQ ID NO: 6), GPSSG (SEQ ID NO: 7), GPSSGA (SEQ ID NO: 8), GPSSGAP (SEQ ID NO: 9), GPSSGAPP (SEQ ID NO: 10), GPSSGAPPP (SEQ ID NO:11) and GPSSGAPPPS (SEQ ID NO: 5),
a fragment selected from the group consisting of:
PS, PSS, PSSG (SEQ ID NO: 12), PSSGA (SEQ ID NO: 13), PSSGAP (SEQ ID NO: 14), PSSGAPP (SEQ ID NO: 15), PSSGAPPP (SEQ ID NO: 16) and PSSGAPPPS (SEQ ID NO: 4),
a fragment selected from the group consisting of:
GK, GKK, GKKN (SEQ ID NO: 17), GKKND (SEQ ID NO: 18), GKKNDW (SEQ ID NO: 19), GRKNDW (SEQ ID NO: 20), GKRNDW (SEQ ID NO: 21), GRRNDW (SEQ ID NO: 22), GKKNDWK (SEQ ID NO: 23), GKKNDWKH (SEQ ID NO: 24), GKKNDWKHN (SEQ ID NO: 25), GKKNDWKHNI (SEQ ID NO: 26), GKKNDWKHNIT (SEQ ID NO: 27) and GKKNDWKHNITQ (SEQ ID NO:2), or
a fragment selected from the group consisting of:
GPSSGA (SEQ ID NO: 8), GPSSGAP (SEQ ID NO: 9), GPSSGAPP (SEQ ID NO: 10), GPSSGAPPP (SEQ ID NO: 11), GPSSGAPPPS (SEQ ID NO: 5), GKKNDW (SEQ ID NO: 19), GRKNDW (SEQ ID NO: 20), GKRNDW (SEQ ID NO: 21), GRRNDW (SEQ ID NO: 22), GKKNDWK (SEQ ID NO: 23), GKKNDWKH (SEQ ID NO: 24), GKKNDWKHN (SEQ ID NO: 25), GKKNDWKHNI (SEQ ID NO: 26), GKKNDWKHNIT (SEQ ID NO: 27) and GKKNDWKHNITQ (SEQ ID NO:2),
or a variant thereof comprising 1 or 2 individual amino acid substitutions at any one of the amino acid residues, or
a fragment selected from the group consisting of:
PSSG (SEQ ID NO: 12), PSSGA (SEQ ID NO: 13), PSSGAP (SEQ ID NO: 14), PSSGAPP (SEQ ID NO: 15), PSSGAPPP (SEQ ID NO: 16) and PSSGAPPPS (SEQ ID NO: 4),
or a variant thereof comprising 1 or 2 individual amino acid substitutions at any one of the amino acid residues, for use as a medicament.

In one embodiment there is provided a glucose-dependent insulinotropic peptide (GIP) analogue consisting of amino acid sequence SEQ ID NO:1:

```
3 -  4 -  5 - 6   7   8   9   10  11  12  13  14
X₁ - X₂ - T - F - I - S - D - Y - S - I - A - M -

15  16  17 18  19  20  21  22  23  24  25  26  27
D - K - I  H - Q - Q - D - F - V - N - W - L - L -

28  29  30
A - Q - K - Z,
``` wherein $X_1$ and $X_2$ are individually any amino acid or omitted;
or a functional variant thereof, wherein said variant has 1 to 8, such as 1 to 4 individual amino acid substitutions at any amino acid of SEQ ID NO:1,
wherein said peptide is modified by attaching at least one fatty acid molecule at one or more amino acid residues at positions 3 to 29 of SEQ ID NO:1, or said functional variant thereof,
wherein Z is a peptide comprising one or more amino acid residues of GIP(31-42) (GKKNDWKHNITQ; SEQ ID NO: 2) or one or more amino acid residues of Exendin-4 (HGEGTFTSDLSKQMEEEAVRLFIEWLKNGGPSSGAPPPS; SEQ ID NO: 3) for use in a method of inhibiting or reducing one or more of i) GIP-induced glucagon secretion, ii) GIP-induced insulin secretion, iii) GIP-induced somatostatin secretion, iv) GIP-induced glucose uptake, v) GIP-induced fatty acid synthesis and/or fatty acid incorporation, vi) high or increased expression or activity of a GIPR, vii) post-prandial GIP release, viii) serum levels of free fatty acids and/or triglycerides, ix) GIP-induced appetite increases, x) GIP-induced reduction in energy expenditure, xi) GIP-induced increase in absorption of nutrients from the gut, xii) GIP-induced decrease in GLP-1's appetite suppressive effect, xiii) GIP-induced leptin resistance.

In one embodiment there is provided a GIP analogue selected from the group consisting of:

a peptide having an amino acid sequence consisting of SEQ ID NO:32 hGIP(3-30):

```
3 - 4 - 5 - 6   7   8   9  10  11  12  13  14  15
E - G - T - F - I - S - D - Y - S - I - A - M - D -

16  17 18  19  20  21  22  23  24  25  26  27  28
K - I H - Q - Q - D - F - V - N - W - L - L - A -

29  30
Q - K - Z,
``` a peptide having an amino acid sequence consisting of SEQ ID NO:35 hGIP(5-30):

```
5 - 6   7   8   9  10  11  12  13  14  15  16  17
T - F - I - S - D - Y - S - I - A - M - D - K - I 18  19  20  21  22  23  24  25  26  27  28  29  30
H - Q - Q - D - F - V - N - W - L - L - A - Q - K -
Z
``` and
a peptide having an amino acid sequence consisting of SEQ ID NO:36 hGIP(6-30):

```
6   7   8   9  10  11  12  13  14  15  16  17 18
F - I - S - D - Y - S - I - A - M - D - K - I H -

19  20  21  22  23  24  25  26  27  28  29  30
Q - Q - D - F - V - N - W - L - L - A - Q - K - Z
``` or a functional variant thereof, wherein said variant has 1 to 4 individual amino acid substitutions at any one of the amino acid residues of SEQ ID NO:32 hGIP(3-30), SEQ ID NO:35 hGIP(5-30) and SEQ ID NO:36 hGIP(6-30), wherein said peptide is modified by attaching at least one fatty acid molecule at one or more amino acid residues at positions 6 to 29 of any one of SEQ ID NO:32 hGIP(3-30), SEQ ID NO:35 hGIP(5-30) and SEQ ID NO:36 hGIP(6-30), or a functional variant thereof comprising between 1 and 4 amino acid substitutions at any one of the amino acid residues of SEQ ID NO:32 hGIP(3-30), SEQ ID NO:35 hGIP(5-30) and SEQ ID NO:36 hGIP(6-30), with or without a linker, wherein Z is:
a glycine or a proline,
a fragment selected from the group consisting of:
GP, GPS, GPSS (SEQ ID NO: 6), GPSSG (SEQ ID NO: 7), GPSSGA (SEQ ID NO: 8), GPSSGAP (SEQ ID NO: 9), GPSSGAPP (SEQ ID NO: 10), GPSSGAPPP (SEQ ID NO:11) and GPSSGAPPPS (SEQ ID NO: 5),
a fragment selected from the group consisting of: PS, PSS, PSSG (SEQ ID NO: 12), PSSGA (SEQ ID NO: 13), PSSGAP (SEQ ID NO: 14), PSSGAPP (SEQ ID NO: 15), PSSGAPPP (SEQ ID NO: 16) and PSSGAPPPS (SEQ ID NO: 4),
a fragment selected from the group consisting of:
GK, GKK, GKKN (SEQ ID NO: 17), GKKND (SEQ ID NO: 18), GKKNDW (SEQ ID NO: 19), GRKNDW (SEQ ID NO: 20), GKRNDW (SEQ ID NO: 21), GRRNDW (SEQ ID NO: 22), GKKNDWK (SEQ ID NO: 23), GKKNDWKH (SEQ ID NO: 24), GKKNDWKHN (SEQ ID NO: 25), GKKNDWKHNI (SEQ ID NO: 26), GKKNDWKHNIT (SEQ ID NO: 27) and GKKNDWKHNITQ (SEQ ID NO:2), or a fragment selected from the group consisting of:
GPSSGA (SEQ ID NO: 8), GPSSGAP (SEQ ID NO: 9), GPSSGAPP (SEQ ID NO: 10), GPSSGAPPP (SEQ ID NO: 11), GPSSGAPPPS (SEQ ID NO: 5), GKKNDW (SEQ ID NO: 19), GRKNDW (SEQ ID NO: 20), GKRNDW (SEQ ID NO: 21), GRRNDW (SEQ ID NO: 22), GKKNDWK (SEQ ID NO: 23), GKKNDWKH (SEQ ID NO: 24), GKKNDWKHN (SEQ ID NO: 25), GKKNDWKHNI (SEQ ID NO: 26), GKKNDWKHNIT (SEQ ID NO: 27) and GKKNDWKHNITQ (SEQ ID NO:2), or a variant thereof comprising 1 or 2 individual amino acid substitutions at any one of the amino acid residues, or a fragment selected from the group consisting of:
PSSG (SEQ ID NO: 12), PSSGA (SEQ ID NO: 13), PSSGAP (SEQ ID NO: 14), PSSGAPP (SEQ ID NO: 15), PSSGAPPP (SEQ ID NO: 16) and PSSGAPPPS (SEQ ID NO: 4), or a variant thereof comprising 1 or 2 individual amino acid substitutions at any one of the amino acid residues, for use in a method of inhibiting or reducing one or more of i) GIP-induced glucagon secretion, ii) GIP-induced insulin secretion, iii) GIP-induced somatostatin secretion, iv) GIP-induced glucose uptake, v) GIP-induced fatty acid synthesis and/or fatty acid incorporation, vi) high or increased expression or activity of a GIPR, vii) post-prandial GIP release, viii) serum levels of free fatty acids and/or triglycerides, ix) GIP-induced reduction of bone resorption.

In one embodiment there is provided a glucose-dependent insulinotropic peptide (GIP) analogue consisting of amino acid sequence SEQ ID NO:1:

```
3  -  4  -  5 - 6   7   8   9   10  11  12  13  14
X₁ - X₂ - T - F - I - S - D - Y - S - I - A - M -

15  16  1718  19  20  21  22  23  24  25  26  27
D - K - I H - Q - Q - D - F - V - N - W - L - L -

28  29  30
A - Q - K - Z,
``` wherein X₁ and X₂ are individually any amino acid or omitted;

or a functional variant thereof, wherein said variant has 1 to 8, such as 1 to 4 individual amino acid substitutions at any amino acid of SEQ ID NO:1, wherein said peptide is modified by attaching at least one fatty acid molecule at one or more amino acid residues at positions 3 to 29 of SEQ ID NO:1, or said functional variant thereof, wherein Z is a peptide comprising one or more amino acid residues of GIP(31-42) (GKKNDWKHNITQ; SEQ ID NO: 2) or one or more amino acid residues of Exendin-4 (HGEGTFTSDLSKQMEEEAVRLFIEW-LKNGGPSSGAPPPS; SEQ ID NO: 3), for use in a method of treating a condition selected from the group consisting of metabolic syndrome, obesity, pre-diabetes, type I diabetes, type 2 diabetes, insulin resistance, elevated fasting glucose, hyperglycemia, elevated fasting serum triglyceride levels, low levels of very low-density lipoprotein (VLDL), low high-density lipoprotein (HDL) levels, dyslipidemia, increased/decreased low-density lipoprotein (LDL), high cholesterol levels, abnormal deposition of lipids, a cardiovascular disease, elevated blood pressure and atherosclerosis.

In one embodiment there is provided a GIP analogue selected from the group consisting of:

a peptide having an amino acid sequence consisting of SEQ ID NO:32 hGIP(3-30):

```
 3 - 4 - 5 - 6   7   8   9  10  11  12  13  14
 E - G - T - F - I - S - D - Y - S - I - A - M -

15  16  17  18  19  20  21  22  23  24  25  26
 D - K - I   H - Q - Q - D - F - V - N - W - L -

27  28  29  30
 L - A - Q - K - Z,
``` a peptide having an amino acid sequence consisting of SEQ ID NO:35 hGIP(5-30):

```
 5 - 6   7   8   9  10  11  12  13  14  15  16
 T - F - I - S - D - Y - S - I - A - M - D - K -

17  18  19  20  21  22  23  24  25  26  27  28
 I   H - Q - Q - D - F - V - N - W - L - L - A -

29  30
 Q - K - Z
``` and a peptide having an amino acid sequence consisting of SEQ ID NO:36 hGIP(6-30):

```
 6   7   8   9  10  11  12  13  14  15  16  17
 F - I - S - D - Y - S - I - A - M - D - K - I 18  19  20  21  22  23  24  25  26  27  28  29
 H - Q - Q - D - F - V - N - W - L - L - A - Q -

30
 K - Z
``` or a functional variant thereof, wherein said variant has 1 to 4 individual amino acid substitutions at any one of the amino acid residues of SEQ ID NO:32 hGIP(3-30), SEQ ID NO:35 hGIP(5-30) and SEQ ID NO:36 hGIP(6-30), wherein said peptide is modified by attaching at least one fatty acid molecule at one or more amino acid residues at positions 6 to 29 of any one of SEQ ID NO:32 hGIP(3-30), SEQ ID NO:35 hGIP(5-30) and SEQ ID NO:36 hGIP(6-30), or a functional variant thereof comprising between 1 and 4 amino acid substitutions at any one of the amino acid residues of SEQ ID NO:32 hGIP(3-30), SEQ ID NO:35 hGIP(5-30) and SEQ ID NO:36 hGIP(6-30), with or without a linker, wherein Z is:

a glycine or a proline, a fragment selected from the group consisting of: GP, GPS, GPSS (SEQ ID NO: 6), GPSSG (SEQ ID NO: 7), GPSSGA (SEQ ID NO: 8), GPSSGAP (SEQ ID NO: 9), GPSSGAPP (SEQ ID NO: 10), GPSSGAPPP (SEQ ID NO:11) and GPSSGAPPPS (SEQ ID NO: 5), a fragment selected from the group consisting of: PS, PSS, PSSG (SEQ ID NO: 12), PSSGA (SEQ ID NO: 13), PSSGAP (SEQ ID NO: 14), PSSGAPP (SEQ ID NO: 15), PSSGAPPP (SEQ ID NO: 16) and PSSGAPPPS (SEQ ID NO: 4), a fragment selected from the group consisting of: GK, GKK, GKKN (SEQ ID NO: 17), GKKND (SEQ ID NO: 18), GKKNDW (SEQ ID NO: 19), GRKNDW (SEQ ID NO: 20), GKRNDW (SEQ ID NO: 21), GRRNDW (SEQ ID NO: 22), GKKNDWK (SEQ ID NO: 23), GKKNDWKH (SEQ ID NO: 24), GKKNDWKHN (SEQ ID NO: 25), GKKNDWKHNI (SEQ ID NO: 26), GKKNDWKHNIT (SEQ ID NO: 27) and GKKNDWKHNITQ (SEQ ID NO:2), or a fragment selected from the group consisting of: GPSSGA (SEQ ID NO: 8), GPSSGAP (SEQ ID NO: 9), GPSSGAPP (SEQ ID NO: 10), GPSSGAPPP (SEQ ID NO: 11), GPSSGAPPPS (SEQ ID NO: 5), GKKNDW (SEQ ID NO: 19), GRKNDW (SEQ ID NO: 20), GKRNDW (SEQ ID NO: 21), GRRNDW (SEQ ID NO: 22), GKKNDWK (SEQ ID NO: 23), GKKNDWKH (SEQ ID NO: 24), GKKNDWKHN (SEQ ID NO: 25), GKKNDWKHNI (SEQ ID NO: 26), GKKNDWKHNIT (SEQ ID NO: 27) and GKKNDWKHNITQ (SEQ ID NO:2), or a variant thereof comprising 1 or 2 individual amino acid substitutions at any one of the amino acid residues, or a fragment selected from the group consisting of: PSSG (SEQ ID NO: 12), PSSGA (SEQ ID NO: 13), PSSGAP (SEQ ID NO: 14), PSSGAPP (SEQ ID NO: 15), PSSGAPPP (SEQ ID NO: 16) and PSSGAPPPS (SEQ ID NO: 4), or a variant thereof comprising 1 or 2 individual amino acid substitutions at any one of the amino acid residues, for use for use in a method of treating a condition selected from the group consisting of metabolic syndrome, obesity, over-weight, an obesity-related disorder, pre-diabetes, type I diabetes, type 2 diabetes, a diabetes-related disorder, insulin resistance, elevated fasting glucose, hyperglycemia, elevated fasting serum triglyceride levels, low levels of very low-density lipoprotein (VLDL), low high-density lipoprotein (HDL) levels, dyslipidemia, increased/decreased low-density lipoprotein (LDL), high cholesterol levels, abnormal deposition of lipids, a cardiovascular disease, elevated blood pressure and atherosclerosis.

In one embodiment there is provided a glucose-dependent insulinotropic peptide (GIP) analogue consisting of amino acid sequence SEQ ID NO:1:

```
 3 -  4 -  5 - 6   7   8   9  10  11  12  13  14
 X₁ - X₂ - T - F - I - S - D - Y - S - I - A - M -

15  16  17 18  19  20  21  22  23  24  25  26  27
 D - K - I  H - Q - Q - D - F - V - N - W - L - L -

28  29  30
 A - Q - K - Z,
``` wherein $X_1$ and $X_2$ are individually any amino acid or omitted;

or a functional variant thereof, wherein said variant has 1 to 8, such as 1 to 4 individual amino acid substitutions at any amino acid of SEQ ID NO:1, wherein said peptide is modified by attaching at least one fatty acid molecule at one or more amino acid residues at positions 3 to 29 of SEQ ID NO:1, or said functional variant thereof, wherein Z is a peptide comprising one or more amino acid residues of GIP(31-42) (GKKNDWKHNITQ; SEQ ID NO: 2) or one or more amino acid residues of Exendin-4 (HGEGTFTSDLSKQMEEEAVRLFIEWLKNGGPSSGAPPPS; SEQ ID NO: 3), for use in a method of inducing weight-loss.

In one embodiment there is provided a GIP analogue selected from the group consisting of:
a peptide having an amino acid sequence consisting of SEQ ID NO:32 hGIP(3-30):

```
3 - 4 - 5 - 6   7   8   9   10  11  12  13  14
E - G - T - F - I - S - D - Y - S - I - A - M -

15  16  17 18  19  20  21  22  23  24  25  26
D - K - I H - Q - Q - D - F - V - N - W - L -

27  28  29  30
L - A - Q - K - Z,
``` a peptide having an amino acid sequence consisting of SEQ ID NO:35 hGIP(5-30):

```
5 - 6   7   8   9   10  11  12  13  14  15  16  17
T - F - I - S - D - Y - S - I - A - M - D - K - I 18  19  20  21  22  23  24  25  26  27  28  29
H - Q - Q - D - F - V - N - W - L - L - A - Q -

30
K - Z
``` and
a peptide having an amino acid sequence consisting of SEQ ID NO:36 hGIP(6-30):

```
6   7   8   9   10  11  12  13  14  15  16  17
F - I - S - D - Y - S - I - A - M - D - K - I 18  19  20  21  22  23  24  25  26  27  28  29
H - Q - Q - D - F - V - N - W - L - L - A - Q -

30
K - Z
``` or a functional variant thereof, wherein said variant has 1 to 4 individual amino acid substitutions at any one of the amino acid residues of SEQ ID NO:32 hGIP(3-30), SEQ ID NO:35 hGIP(5-30) and SEQ ID NO:36 hGIP (6-30),
wherein said peptide is modified by attaching at least one fatty acid molecule at one or more amino acid residues at positions 6 to 29 of any one of SEQ ID NO:32 hGIP(3-30), SEQ ID NO:35 hGIP(5-30) and SEQ ID NO:36 hGIP(6-30), or a functional variant thereof comprising between 1 and 4 amino acid substitutions at any one of the amino acid residues of SEQ ID NO:32 hGIP(3-30), SEQ ID NO:35 hGIP(5-30) and SEQ ID NO:36 hGIP(6-30), with or without a linker,
wherein Z is:
a glycine or a proline,
a fragment selected from the group consisting of:
GP, GPS, GPSS (SEQ ID NO: 6), GPSSG (SEQ ID NO: 7), GPSSGA (SEQ ID NO: 8), GPSSGAP (SEQ ID NO: 9), GPSSGAPP (SEQ ID NO: 10), GPSSGAPPP (SEQ ID NO:11) and GPSSGAPPPS (SEQ ID NO: 5),
a fragment selected from the group consisting of:
PS, PSS, PSSG (SEQ ID NO: 12), PSSGA (SEQ ID NO: 13), PSSGAP (SEQ ID NO: 14), PSSGAPP (SEQ ID NO: 15), PSSGAPPP (SEQ ID NO: 16) and PSSGAPPPS (SEQ ID NO: 4), a fragment selected from the group consisting of:
GK, GKK, GKKN (SEQ ID NO: 17), GKKND (SEQ ID NO: 18), GKKNDW (SEQ ID NO: 19), GRKNDW (SEQ ID NO: 20), GKRNDW (SEQ ID NO: 21), GRRNDW (SEQ ID NO: 22), GKKNDWK (SEQ ID NO: 23), GKKNDWKH (SEQ ID NO: 24), GKKNDWKHN (SEQ ID NO: 25), GKKNDWKHNI (SEQ ID NO: 26), GKKNDWKHNIT (SEQ ID NO: 27) and GKKNDWKHNITQ (SEQ ID NO:2), or
a fragment selected from the group consisting of:
GPSSGA (SEQ ID NO:8), GPSSGAP (SEQ ID NO: 9), GPSSGAPP (SEQ ID NO: 10), GPSSGAPPP (SEQ ID NO: 11), GPSSGAPPPS (SEQ ID NO: 5), GKKNDW (SEQ ID NO: 19), GRKNDW (SEQ ID NO: 20), GKRNDW (SEQ ID NO: 21), GRRNDW (SEQ ID NO: 22), GKKNDWK (SEQ ID NO: 23), GKKNDWKH (SEQ ID NO: 24), GKKNDWKHN (SEQ ID NO: 25), GKKNDWKHNI (SEQ ID NO: 26), GKKNDWKHNIT (SEQ ID NO: 27) and GKKNDWKHNITQ (SEQ ID NO:2),
or a variant thereof comprising 1 or 2 individual amino acid substitutions at any one of the amino acid residues, or
a fragment selected from the group consisting of:
PSSG (SEQ ID NO: 12), PSSGA (SEQ ID NO: 13), PSSGAP (SEQ ID NO: 14), PSSGAPP (SEQ ID NO: 15), PSSGAPPP (SEQ ID NO: 16) and PSSGAPPPS (SEQ ID NO: 4),
or a variant thereof comprising 1 or 2 individual amino acid substitutions at any one of the amino acid residues,
for use in a method of inducing weight-loss.

In one embodiment there is provided a glucose-dependent insulinotropic peptide (GIP) analogue consisting of amino acid sequence SEQ ID NO:1:

```
3  -  4  -  5  -  6   7   8   9   10  11  12  13  14  15  16  17
X₁ -  X₂ -  T  -  F - I - S - D - Y - S - I - A - M - D - K - I 18  19  20  21  22  23  24  25  26  27  28  29  30
H - Q - Q - D - F - V - N - W - L - L - A - Q - K - Z,
``` wherein $X_1$ and $X_2$ are individually any amino acid or omitted;
or a functional variant thereof, wherein said variant has 1 to 8, such as 1 to 4 individual amino acid substitutions at any amino acid of SEQ ID NO:1,
wherein said peptide is modified by attaching at least one fatty acid molecule at one or more amino acid residues at positions 3 to 29 of SEQ ID NO:1, or said functional variant thereof,
wherein Z is a peptide comprising one or more amino acid residues of GIP(31-42) (GKKNDWKHNITQ; SEQ ID NO: 2) or one or more amino acid residues of Exendin-4 (HGEGTFTSDLSKQMEEEAVRLFIEW-LKNGGPSSGAPPPS; SEQ ID NO: 3), for use in the manufacture of a medicament for
treating a condition selected from the group consisting of metabolic syndrome, obesity, over-weight, an obesity-related disorder, pre-diabetes, type I diabetes, type 2 diabetes, a diabetes-related disorder, insulin resistance, elevated fasting glucose, hyperglycemia, elevated fasting serum triglyceride levels, low levels of very low-density lipoprotein (VLDL), low high-density lipoprotein (HDL) levels, dyslipidemia, increased/decreased low-density lipoprotein (LDL), high cholesterol levels, abnormal deposition of lipids, a cardiovascular disease, elevated blood pressure and atherosclerosis, or inducing weight-loss, or treating cancer, including but not limited to colon cancer, a neuroendocrine cancer and adrenal adenoma.

In one embodiment there is provided a GIP analogue selected from the group consisting of:

a peptide having an amino acid sequence consisting of SEQ ID NO:32 hGIP(3-30):

```
3 - 4 - 5 - 6   7   8   9   10  11  12  13  14  15  16  17
E - G - T - F - I - S - D - Y - S - I - A - M - D - K - I 18  19  20  21  22  23  24  25  26  27  28  29  30
H - Q - Q - D - F - V - N - W - L - L - A - Q - K - Z,
``` a peptide having an amino acid sequence consisting of SEQ ID NO:35 hGIP(5-30):

```
5 - 6   7   8   9   10  11  12  13  14  15  16  17
T - F - I - S - D - Y - S - I - A - M - D - K - I 18  19  20  21  22  23  24  25  26  27  28  29  30
H - Q - Q - D - F - V - N - W - L - L - A - Q - K - Z
``` and
a peptide having an amino acid sequence consisting of SEQ ID NO:36 hGIP(6-30):

```
6   7   8   9   10  11  12  13  14  15  16  17
F - I - S - D - Y - S - I - A - M - D - K - I 18  19  20  21  22  23  24  25  26  27  28  29  30
H - Q - Q - D - F - V - N - W - L - L - A - Q - K - Z
``` or a functional variant thereof, wherein said variant has 1 to 4 individual amino acid substitutions at any one of the amino acid residues of SEQ ID NO:32 hGIP(3-30), SEQ ID NO:35 hGIP(5-30) and SEQ ID NO:36 hGIP (6-30), wherein said peptide is modified by attaching at least one fatty acid molecule at one or more amino acid residues at positions 6 to 29 of any one of SEQ ID NO:32 hGIP(3-30), SEQ ID NO:35 hGIP(5-30) and SEQ ID NO:36 hGIP(6-30), or a functional variant thereof comprising between 1 and 4 amino acid substitutions at any one of the amino acid residues of SEQ ID NO:32 hGIP(3-30), SEQ ID NO:35 hGIP(5-30) and SEQ ID NO:36 hGIP(6-30), with or without a linker, wherein Z is:

a glycine or a proline, a fragment selected from the group consisting of:

GP, GPS, GPSS (SEQ ID NO: 6), GPSSG (SEQ ID NO: 7), GPSSGA (SEQ ID NO: 8), GPSSGAP (SEQ ID NO: 9), GPSSGAPP (SEQ ID NO: 10), GPSSGAPPP (SEQ ID NO:11) and GPSSGAPPPS (SEQ ID NO: 5), a fragment selected from the group consisting of:

PS, PSS, PSSG (SEQ ID NO: 12), PSSGA (SEQ ID NO: 13), PSSGAP (SEQ ID NO: 14), PSSGAPP (SEQ ID NO: 15), PSSGAPPP (SEQ ID NO: 16) and PSSGAPPPS (SEQ ID NO: 4), a fragment selected from the group consisting of:

GK, GKK, GKKN (SEQ ID NO: 17), GKKND (SEQ ID NO: 18), GKKNDW (SEQ ID NO: 19), GRKNDW (SEQ ID NO: 20), GKRNDW (SEQ ID NO: 21), GRRNDW (SEQ ID NO: 22), GKKNDWK (SEQ ID NO: 23), GKKNDWKH (SEQ ID NO: 24), GKKNDWKHN (SEQ ID NO: 25), GKKNDWKHNI (SEQ ID NO: 26), GKKNDWKHNIT (SEQ ID NO: 27) and GKKNDWKHNITQ (SEQ ID NO:2), or a fragment selected from the group consisting of:

GPSSGA (SEQ ID NO:8), GPSSGAP (SEQ ID NO: 9), GPSSGAPP (SEQ ID NO: 10), GPSSGAPPP (SEQ ID NO: 11), GPSSGAPPPS (SEQ ID NO: 5), GKKNDW (SEQ ID NO: 19), GRKNDW (SEQ ID NO: 20), GKRNDW (SEQ ID NO: 21), GRRNDW (SEQ ID NO: 22), GKKNDWK (SEQ ID NO: 23)GKKNDWKH (SEQ ID NO: 24), GKKNDWKHN , (SEQ ID NO: 25), GKKNDWKHNI (SEQ ID NO: 26), GKKNDWKHNIT (SEQ ID NO: 27) and GKKNDWKHNITQ (SEQ ID NO:2), or a variant thereof comprising 1 or 2 individual amino acid substitutions at any one of the amino acid residues, or a fragment selected from the group consisting of:

PSSG (SEQ ID NO: 12), PSSGA (SEQ ID NO: 13), PSSGAP (SEQ ID NO: 14), PSSGAPP (SEQ ID NO: 15), PSSGAPPP (SEQ ID NO: 16) and PSSGAPPPS (SEQ ID NO: 4), or a variant thereof comprising 1 or 2 individual amino acid substitutions at any one of the amino acid residues, for use in the manufacture of a medicament for treating a condition selected from the group consisting of metabolic syndrome, obesity, over-weight, an obesity-related disorder, pre-diabetes, type I diabetes, type 2 diabetes, a diabetes-related disorder, insulin resistance, elevated fasting glucose, hyperglycemia, elevated fasting serum triglyceride levels, low levels of very low-density lipoprotein (VLDL), low high-density lipoprotein (HDL) levels, dyslipidemia, increased/decreased low-density lipoprotein (LDL), high cholesterol levels, abnormal deposition of lipids, a cardiovascular disease, elevated blood pressure and atherosclerosis, or inducing weight-loss, or
treating cancer, including but not limited to colon cancer, a neuroendocrine cancer and adrenal adenoma.

In one particular embodiment there is provided a GIP peptide analogue as defined herein for use in a method of treating obesity.

In one particular embodiment there is provided a GIP peptide analogue as defined herein for use in a method of treating diabetes mellitus, including diabetes mellitus type I and type II.

In one particular embodiment there is provided a GIP peptide analogue as defined herein for use in a method of treating insulin resistance.

It is a further aspect to provide a GIP peptide analogue as defined herein for use in a method of treating cancer.

An obesity related disorders may be any one of: increased food-intake, increased appetite, binge eating, bulimia nervosa, obesity induced by administration of an antipsychotic or a steroid, reduced/increased gastric motility, delayed/increased gastric emptying, decreased physical mobility, osteoarthritis, dyslipidemia, increased/decreased low-density lipoprotein (LDL), high cholesterol levels, and abnormal deposition of lipids.

In some embodiments, dyslipidemia, increased/decreased low-density lipoprotein (LDL), cholesterol, and abnormal deposition of lipids are referred to as fatty acid metabolism disorders.

A diabetes related disorders may be any one of: impaired glucose tolerance (IGT), progression from IGT to type 2 diabetes, progression of non-insulin requiring type 2 diabetes to insulin requiring type 2 diabetes, decreased beta-cell function, decreased beta-cell mass, increased beta-cell apoptosis, decreased glucose sensitivity to beta-cells.

A cardiovascular disease may be any one of coronary heart disease, myocardial infarction, reperfusion injury, stroke, cerebral ischemia, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (also referred to as atherosclerosis oblitterens), diastolic dysfunction, and systolic dysfunction, and combinations thereof.

In one embodiment the cancer is selected from the group consisting of colon cancer, a neuroendocrine cancer and adrenal adenoma.

It is a further aspect to provide a GIP peptide analogue as defined herein for use in a method of treating a bone density disorder (or a bone volume disorder).

In one embodiment there is provided a GIP peptide analogue as defined herein for use in a method of inhibiting activity of bone cells. In one embodiment there is provided a peptide as defined herein for use in a method of inhibiting (or antagonizing) GIP-induced postprandial reduction in bone resorption. In one embodiment there is provided a peptide as defined herein for use in a method of treating bone cancer.

In one embodiment, the bone density (or volume) disorder is selected from the group consisting of osteoporosis, disorders characterized by low bone density and/or reduced bone volume, disorders characterized by high bone density and/or increased bone volume and osteoporosis.

It is a further aspect to provide a GIP peptide analogue as defined herein for use in a method of characterizing or examining aspects of a disorder, and/or characterizing or examining aspects of the human physiology associated with a disorder, wherein said disorder in one embodiment is selected from metabolic syndrome, obesity, diabetes mellitus, insulin resistance, obesity related disorders as defined herein or diabetes related disorders as defined herein. In other aspects the invention relates to methods of treating cancer, such as colon cancer or adrenal adenoma. In other aspects the invention relates to methods of treating a bone density disorder characterized by high bone density and/or increased bone volume or osteoporosis. In other aspects the invention relates to methods of treating atherosclerosis.

Also provided is a method for treating metabolic syndrome, obesity, over-weight, diabetes mellitus, insulin resistance, an obesity related disorder as defined herein, or a diabetes related disorder as defined herein; a cancer such as colon cancer or adrenal adenoma; a bone density disorder, such as bone density disorders characterized by high bone density and/or increased bone volume; or atherosclerosis; said method comprising the step of administering to an individual in need thereof an effective amount of a peptide as defined herein.

An individual in need as referred to herein, is an individual that may benefit from the administration of a peptide or pharmaceutical composition according to the present disclosure. Such an individual may suffer from metabolic syndrome, and/or from a metabolic disorder such as obesity, over-weight, diabetes, insulin resistance, an obesity related disorder as defined herein, or a diabetes related disorder as defined herein, a cancer such as colon cancer or adrenal adenoma, a bone density disorder, or be in risk of suffering therefrom. The individual may be any human being, male or female, infant, middle-aged or old. The disorder to be treated or prevented in the individual may relate to the age of the individual, the general health of the individual, the medications used for treating the individual and whether or not the individual has a prior history of suffering from diseases or disorders that may have or have induced metabolic syndrome, and/or a metabolic disorder such as obesity, over-weight, diabetes, insulin resistance, an obesity related disorder as defined herein, or a diabetes related disorder as defined herein, a cancer such as colon cancer or adrenal adenoma, atherosclerosis, a bone density disorder. In some embodiments, the disorder to be treated is linked to GIP-induced glucagon secretion, GIP-induced insulin secretion, to GIP-induced somatostatin secretion, to GIP-induced glucose uptake, to GIP-induced fatty acid synthesis and/or fatty acid incorporation, to high expression and/or activity of a GIPR, to release of GIP following a meal; wherein the term "high" is to be construed as referring to levels greater than the corresponding levels observed in individuals not in need of treatment.

Method of Preparation (Peptide)

The peptides according to the present disclosure may be prepared by any methods known in the art. Thus, the GIP-derived peptides may be prepared by standard peptide-preparation techniques such as solution synthesis or Merrifield-type solid phase synthesis.

In one embodiment, a peptide as defined herein is a non-naturally occurring peptide; being derived from naturally occurring protein native GIP, such as GIP(1-42).

In one embodiment a peptide according to the present disclosure is purified from a naturally occurring source thereof, such as serum. Protein purification is a series of processes intended to isolate a single type of protein from a complex mixture. The starting material is usually a biological tissue. The various steps in the purification process may free the protein from a matrix that confines it, separate the protein and non-protein parts of the mixture, and finally separate the desired protein from all other proteins. Separation steps may exploit differences in (for example) protein size, physico-chemical properties, binding affinity and biological activity.

In one embodiment a peptide according to the disclosure is synthetically made or produced.

The methods for synthetic production of peptides are well known in the art. Detailed descriptions as well as practical advice for producing synthetic peptides may be found in Synthetic Peptides: A User's Guide (Advances in Molecular Biology), Grant G. A. ed., Oxford University Press, 2002, or in: Pharmaceutical Formulation: Development of Peptides and Proteins, Frokjaer and Hovgaard eds., Taylor and Francis, 1999.

In one embodiment the peptide or peptide sequences of the invention are produced synthetically, in particular, by the Sequence Assisted Peptide Synthesis (SAPS) method, by solution synthesis, by Solid-phase peptide synthesis (SPPS) such as Merrifield-type solid phase synthesis, by recombinant techniques (production by host cells comprising a first nucleic acid sequence encoding the peptide operably associated with a second nucleic acid capable of directing expression in said host cells) or enzymatic synthesis. These are well-known to the skilled person.

Peptides may be synthesised either batch-wise on a fully automated peptide synthesiser using 9-fluorenylmethyloxy-carbonyl (Fmoc) or tert-Butyloxycarbonyl (Boc) as N-α-amino protecting group and suitable common protection groups for side-chain functionalities.

After purification such as by reversed phase HPLC, peptides may be further processed to obtain for example cyclic or C- or N-terminal modified isoforms. The methods for cyclization and terminal modification are well-known in the art.

Peptides according to the invention may be synthesized as monomers or multimers such as dimers or tetramers.

Pharmaceutical Composition and Formulation

Whilst it is possible for the bioactive agent of the present disclosure to be administered as the raw chemical (peptide), it is sometimes preferred to present them in the form of a pharmaceutical formulation. Such a pharmaceutical formulation may be referred to as a pharmaceutical composition, pharmaceutically acceptable composition or pharmaceutically safe composition.

Accordingly, further provided is a pharmaceutical formulation, which comprises a bioactive agent of the present invention, or a pharmaceutically acceptable salt or ester thereof, and a pharmaceutically acceptable carrier, excipient and/or diluent. The pharmaceutical formulations may be prepared by conventional techniques, e.g. as described in Remington: The Science and Practice of Pharmacy 2005, Lippincott, Williams & Wilkins.

Pharmaceutically acceptable salts of the instant peptide compounds, where they can be prepared, are also intended to be covered by this invention. These salts will be ones which are acceptable in their application to a pharmaceutical use. By that it is meant that the salt will retain the biological activity of the parent compound and the salt will not have untoward or deleterious effects in its application and use in treating diseases.

Pharmaceutically acceptable salts are prepared in a standard manner. If the parent compound is a base it is treated with an excess of an organic or inorganic acid in a suitable solvent. If the parent compound is an acid, it is treated with an inorganic or organic base in a suitable solvent.

The peptide compounds as disclosed herein may be administered in the form of an alkali metal or earth alkali metal salt thereof, concurrently, simultaneously, or together with a pharmaceutically acceptable carrier or diluent, especially and preferably in the form of a pharmaceutical composition thereof, whether by oral, rectal, or parenteral (including subcutaneous) route, in an effective amount.

Examples of pharmaceutically acceptable acid addition salts for use in the present inventive pharmaceutical composition include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, p-toluenesulphonic acids, and arylsulphonic, for example.

In a particular embodiment, the peptide according to the disclosure is formulated as an acetate salt, a HCl (hydrochloride) salt or TFA (trifluoroacetate) salt.

Administration and Dosage

According to the present disclosure, a peptide, or a composition comprising a peptide as defined herein is administered to individuals in need of treatment in pharmaceutically effective doses or a therapeutically effective amount. The dosage requirements will vary with the particular drug composition employed, the route of administration and the particular subject being treated, which depend on the severity and the sort of the disorder as well as on the weight and general state of the subject. It will also be recognized by one skilled in the art that the optimal quantity and spacing of individual dosages of a peptide compound will be determined by the nature and extent of the condition being treated, the form, route and site of administration, and the particular patient being treated, and that such optima can be determined by conventional techniques. It will also be appreciated by one of skill in the art that the optimal course of treatment, i.e., the number of doses of a compound given per day for a defined number of days, can be ascertained using conventional course of treatment determination tests.

In one embodiment the bioactive agent is administered at least once daily, such as once daily, such as twice daily, such as thrice daily, such as four times daily, such as five times daily.

A dose may also be administered in intermittent intervals, or intervals, whereby a dose is not administered every day. Rather one or more doses may be administered every second day, every third day, every fourth day, every fifth day, every sixth day, every week, every second week, every third week, every fourth week, every fifth week, every sixth week, or intervals within those ranges (such as every 2 to 4 weeks, or 4 to 6 weeks).

In one embodiment, a dose is administered once every week, such as once weekly, such as in one dose per week.

Routes of Administration

It will be appreciated that the preferred route of administration will depend on the general condition and age of the subject to be treated, the nature of the condition to be treated, the location of the tissue to be treated in the body and the active ingredient chosen.

Systemic Treatment

For systemic treatment according to the present disclosure the route of administration is capable of introducing the bioactive agent into the blood stream to ultimately target the sites of desired action.

Such routes of administration are any suitable routes, such as an enteral route (including the oral, rectal, nasal, pulmonary, buccal, sublingual, transdermal, intracisternal and intraperitoneal administration), and/or a parenteral route (including subcutaneous, intramuscular, intrathecal, intracerebral, intravenous and intradermal administration).

Parenteral Administration

Parenteral administration is any administration route not being the oral/enteral route whereby the medicament avoids first-pass degradation in the liver. Accordingly, parenteral administration includes any injections and infusions, for example bolus injection or continuous infusion, such as intravenous administration, intramuscular administration or subcutaneous administration. Furthermore, parenteral administration includes inhalations and topical administration.

Accordingly, the bioactive agent may be administered topically to cross any mucosal membrane of an animal to which the biologically active substance is to be given, e.g. in the nose, vagina, eye, mouth, genital tract, lungs, gastro-intestinal tract, or rectum, preferably the mucosa of the nose, or mouth, and accordingly, parenteral administration may also include buccal, sublingual, nasal, rectal, vaginal and intraperitoneal administration as well as pulmonal and bronchial administration by inhalation or installation. Also, the agent may be administered topically to cross the skin.

According to an advantageous embodiment of the invention, the GIP analogue is administered subcutaneously.

Local Treatment

The bioactive agent according to the invention may in one embodiment be used as a local treatment, i.e. be introduced directly to the site(s) of action. Accordingly, the bioactive agent may be applied to the skin or mucosa directly, or the bioactive agent may be injected into the site of action, for example into the diseased tissue or to an end artery leading directly to the diseased tissue. These administration forms preferably avoid the blood brain barrier.

Kit-of-Parts

The present disclosure also relates to a kit-of-parts comprising one or more of the bioactive agents described above and at least one additional or further component, such as one or more second active ingredients.

REFERENCES

1. Baggio L L, Drucker D J. Biology of Incretins: GLP-1 and GIP. Gastroenterology 2007; 132(6):2131-2157.
2. Holst J J. On the Physiology of GIP and GLP-1. Horm Metab Res 2004; 36(11/12):747-754.
3. Heer J, Rasmussen C, Coy D H, Holst J J. Glucagon-like peptide-1, but not glucose-dependent insulinotropic peptide, inhibits glucagon secretion via somatostatin (receptor subtype 2) in the perfused rat pancreas. Diabetologia 2008; 51(12):2263-2270.
4. Gutniak M, Orskov C, Holst J J, Ahrén B, Efendic S. Antidiabetogenic Effect of Glucagon-like Peptide-1 (7-36)amide in Normal Subjects and Patients with Diabetes Mellitus. N Engl J Med 1992; 326(20):1316-1322.
5. Christensen M, Vedtofte L, Holst J J, Vilsboell T, Knop F K. Glucose-Dependent Insulinotropic Polypeptide: A Bifunctional Glucose-Dependent Regulator of Glucagon and Insulin Secretion in Humans. Diabetes 2011; 60(12): 3103-3109.
6. Pederson R, Brown J. Interaction of Gastric Inhibitory Polypeptide, Glucose, and Arginine on Insulin and Glucagon Secretion from the Perfused Rat Pancreas. Endocrinology 1978; 103(2):610-615.
7. Adrian T E, Bloom S R, Hermansen K, Iversen J. Pancreatic polypeptide, glucagon and insulin secretion from the isolated perfused canine pancreas. Diabetologia 1978; 14(6):413-417.
8. Brunicardi F C, Druck P, Seymour N E, Sun Y S, Elahi D, Andersen D K. Selective neurohormonal interactions in islet cell secretion in the isolated perfused human pancreas. Journal of Surgical Research 1990; 48(4):273-278.
9. Dupre J, Caussignac Y, McDonald T J, Van Vliet S. Stimulation of Glucagon Secretion by Gastric Inhibitory Polypeptide in Patients with Hepatic Cirrhosis and Hyperglucagonemia. The Journal of Clinical Endocrinology & Metabolism 1991; 72(1):125-129.
10. Ding W G, Renstrom E, Rorsman P, Buschard K, Gromada J. Glucagon-like peptide I and glucose-dependent insulinotropic polypeptide stimulate Ca2+-induced secretion in rat alpha-cells by a protein kinase A-mediated mechanism. Diabetes 1997; 46(5):792-800.
11. Meier J J, Gallwitz B, Siepmann N et al. Gastric inhibitory polypeptide (GIP) dose-dependently stimulates glucagon secretion in healthy human subjects at euglycaemia. Diabetologia 2003; 46(6):798-801.
12. Christensen M B, Calanna S, Holst J J, Vilsboell T, Knop F K. Glucose-dependent Insulinotropic Polypeptide: Blood Glucose Stabilizing Effects in Patients With Type 2 Diabetes. The Journal of Clinical Endocrinology & Metabolism 2013; 99(3):E418-E426.
13. Christensen M, Calanna S, Sparre-Ulrich A H et al. Glucose-Dependent Insulinotropic Polypeptide Augments Glucagon Responses to Hypoglycemia in Type 1 Diabetes. Diabetes 2014.
14. Song D H, Getty-Kaushik L, Tseng E, Simon J, Corkey B E, Wolfe M M. Glucose-Dependent Insulinotropic Polypeptide Enhances Adipocyte Development and Glucose Uptake in Part Through Akt Activation. Gastroenterology 2007; 133(6):1796-1805.
15. Miyawaki K, Yamada Y, Ban N et al. Inhibition of gastric inhibitory polypeptide signaling prevents obesity. Nat Med 2002; 8(7):738-742.
16. Starich G H, Bar R S, Mazzaferri E L. GIP increases insulin receptor affinity and cellular sensitivity in adipocytes. Am J Physiol 1985; 249(6 Pt 1):E603-E607.
17. Getty-Kaushik L, Song D H, Boylan M O, Corkey B E, Wolfe M M. Glucose-Dependent Insulinotropic Polypeptide Modulates Adipocyte Lipolysis and Reesterification. Obesity 2006; 14(7):1124-1131.
18. Hauner H, Glatting G, Kaminska D, Pfeiffer E F. Effects of gastric inhibitory polypeptide on glucose and lipid metabolism of isolated rat adipocytes. Ann Nutr Metab 1988; 32(5-6):282-288.
19. Kim S J, Nian C, Karunakaran S, Clee S M, Isales C M, McIntosh CHS. GIP-Overexpressing Mice Demonstrate Reduced Diet-Induced Obesity and Steatosis, and Improved Glucose Homeostasis. PLoS ONE 2012; 7(7): e40156.
20. Nasteska D, Harada N, Suzuki K et al. Chronic Reduction of GIP Secretion Alleviates Obesity and Insulin Resistance Under High-Fat Diet Conditions. Diabetes 2014; 63(7):2332-2343.
21. Miyawaki K, Yamada Y, Yano H et al. Glucose intolerance caused by a defect in the entero-insular axis: A study in gastric inhibitory polypeptide receptor knockout mice. Proceedings of the National Academy of Sciences 1999; 96(26):14843-14847.
22. Ahlqvist E, Osmark P, Kuulasmaa T et al. Link Between GIP and Osteopontin in Adipose Tissue and Insulin Resistance. Diabetes 2013; 62(6):2088-2094.
23. Calanna S, Christensen M, Holst J J et al. Secretion of Glucose-Dependent Insulinotropic Polypeptide in Patients With Type 2 Diabetes: Systematic review and meta-analysis of clinical studies. Diabetes Care 2013; 36(10):3346-3352.
24. Asmar M, Simonsen L, Madsbad S, Stallknecht B, Holst J J, Bulow J. Glucose-Dependent Insulinotropic Polypeptide May Enhance Fatty Acid Re-esterification in Subcutaneous Abdominal Adipose Tissue in Lean Humans. Diabetes 2010; 59(9):2160-2163.
25. Deschamps I, Heptner W, Desjeux J F, Baltakse V, Machinot S, Lestradet H. Effects of diet on insulin and gastric inhibitory polypeptide levels in obese children. Pediatr Res 1980; 14(4 Pt 1):300-303.
26. Brøns C, Jensen C B, Storgaard H et al. Impact of short-term high-fat feeding on glucose and insulin metabolism in young healthy men. The Journal of Physiology 2009; 587(10):2387-2397.
27. Raufman J P, Singh L, Eng J. Exendin-3, a novel peptide from Heloderma horridum venom, interacts with vasoactive intestinal peptide receptors and a newly described receptor on dispersed acini from guinea pig pancreas. Description of exendin-3(9-39) amide, a specific exendin receptor antagonist. Journal of Biological Chemistry 1991; 266(5):2897-2902.
28. Jørgensen NB, Dirksen C, Bojsen-Møller K N et al. Exaggerated Glucagon-Like Peptide 1 Response Is Important for Improved β-Cell Function and Glucose Tolerance After Roux-en-Y Gastric Bypass in Patients With Type 2 Diabetes. Diabetes 2013; 62(9):3044-3052.
29. Nakamura T, Tanimoto H, Mizuno Y, Tsubamoto Y, Noda H. Biological and functional characteristics of a novel lowGçômolecular weight antagonist of glucose-dependent insulinotropic polypeptide receptor, SKL-14959, in vitro and in vivo. Diabetes, Obesity and Metabolism 2012; 14(6):511-517.
30. Ebert R, Illmer K, Creutzfeldt W. Release of gastric inhibitory polypeptide (GIP) by intraduodenal acidification in rats and humans and abolishment of the incretin effect of acid by GIP-antiserum in rats. Gastroenterology 1979; 76(3):515-523.
31. Fulurija A, Lutz T A, Sladko K et al. Vaccination against GIP for the Treatment of Obesity. PLoS ONE 2008; 3(9):e3163.
32. Irwin N, McClean P L, Patterson S, Hunter K, Flatt P R. Active immunisation against gastric inhibitory polypeptide (GIP) improves blood glucose control in an animal model of obesity-diabetes. Biological Chemistry. bchm 390, 75. 2009. 16-7-2014.
33. Hinke S A, Manhart S, Pamir N et al. Identification of a bioactive domain in the amino-terminus of glucose-dependent insulinotropic polypeptide (GIP). Biochimica et Biophysica Acta (BBA)—Protein Structure and Molecular Enzymology 2001; 1547(1):143-155.
34. Tseng C C, Kieffer T J, Jarboe L A, Usdin T B, Wolfe M M. Postprandial stimulation of insulin release by glucose-dependent insulinotropic polypeptide (GIP). Effect of a specific glucose-dependent insulinotropic polypeptide receptor antagonist in the rat. J Clin Invest 1996; 98(11): 2440-2445.
35. Irwin N, Green B D, Parker J C, Gault V A, O'Harte FPM, Flatt P R. Biological activity and antidiabetic potential of synthetic fragment peptides of glucose-dependent insulinotropic polypeptide, GIP(1-16) and (Pro3)GIP(1-16). Regulatory Peptides 2006; 135(1GQ62):45-53.
36. Kerr B D, Flatt AJS, Flatt P R, Gault V A. Characterization and biological actions of N-terminal truncated forms of glucose-dependent insulinotropic polypeptide. Biochemical and Biophysical Research Communications 2011; 404(3):870-876.
37. Gelling R W, Coy D H, Pederson R A et al. GIP(6-30 amide) contains the high affinity binding region of GIP and is a potent inhibitor of GIP1-42 action in vitro. Regulatory Peptides 1997; 69(3):151-154.
38. Deacon CFP. GIP-(3-42) does not antagonize insulinotropic effects of GIP at physiological concentrations. American Journal of Physiology—Endocrinology and Metabolism 2006; 291(3):E468-E475.
39. Gault V A, O'Harte FPM, Harriott P, Flatt P R. Characterization of the Cellular and Metabolic Effects of a Novel Enzyme-Resistant Antagonist of Glucose-Dependent Insulinotropic Polypeptide. Biochemical and Biophysical Research Communications 2002; 290(5):1420-1426.
40. Ravn P, Madhurantakam C, Kunze S et al. Structural and Pharmacological Characterization of Novel Potent and Selective Monoclonal Antibody Antagonists of Glucose-dependent Insulinotropic Polypeptide Receptor. Journal of Biological Chemistry 2013; 288(27):19760-19772.
41. Deacon C F, Plamboeck A, Rosenkilde M M, de Heer J, Holst J J. GIP-(3-42) does not antagonize insulinotropic effects of GIP at physiological concentrations. American Journal of Physiology—Endocrinology and Metabolism 2006; 291(3):E468-E475.
42. Goetze J P, Hunter I, Lippert S K, Bardram L, Rehfeld J F. Processing-independent analysis of peptide hormones and prohormones in plasma. Front Biosci 2012; 17:1804-1815.
43. Goetze J P, Rehfeld J F. Peptide hormones and their prohormones as biomarkers. Biomarkers Med 2009; 3(4): 335-338.
44. Fujita Y, Asadi A, Yang G K, Kwok Y N, Kieffer T J. Differential processing of pro-glucose-dependent insulinotropic polypeptide in gut. American Journal of Physiology—Gastrointestinal and Liver Physiology 2010; 298 (5):G608-G614.
45. Widenmaier S B, Kim S J, Yang G K et al. A GIP Receptor Agonist Exhibits beta-Cell Anti-Apoptotic Actions in Rat Models of Diabetes Resulting in Improved beta-Cell Function and Glycemic Control. PLoS ONE 2010; 5(3):e9590.
46. Graham F L, van der Eb A J. A new technique for the assay of infectivity of human adenovirus 5 DNA. Virology 1973; 52(2):456-467.
47. Kissow H, Hartmann B, Holst J J et al. Glucagon-like peptide-1 (GLP-1) receptor agonism or DPP-4 inhibition does not accelerate neoplasia in carcinogen treated mice. Regulatory Peptides 2012; 179(1-3):91-100.
48. Hoejberg P V, Vilsboell T, Raboel R et al. Four weeks of near-normalisation of blood glucose improves the insulin response to glucagon-like peptide-1 and glucose-dependent insulinotropic polypeptide in patients with type 2 diabetes. Diabetologia 2009; 52(2):199-207.
49. Hansen L S, Sparre-Ulrich A H, et al., N-terminally and C-terminally truncated forms of glucosedependent insulinotropic polypeptide are high-affinity competitive antagonists of the human GIP receptor. British Journal of Pharmacology 2016; 173 826-838.

EXAMPLES

The present examples support the following conclusions:
1) Individual amino acid substitutions at certain sites result in improved antagonistic profile 2) Several acylation sites show great potential on both GIP(3-30)+extension and GIP(5-30)+extension
3) Extension with C-terminal amino acid residues from GIP(1-42) or Exendin-4 result in improved effects, such as antagonistic effect and/or extended in vivo half-life and/or selectivity
4) The GIP peptide analogues according to embodiments of the present invention have increased physical stability, such as increased solubility.
5) The GIP peptide analogues according to embodiments of the present invention have decreased or no agonistic activity at the GIPR.

Materials and Methods

The generation and action of GIP(3-30) and GIP(5-30) peptides per se is disclosed in WO 2016/034186.
Materials
Human GIP(1-42) was purchased from Bachem, Bubendorf, Switzerland (H5645) while the remaining ligands were synthesized by Caslo™, Lyngby, Denmark and Almac Group, Craigavon, United Kingdom, Peptides & Elephants GmbH, Henningsdorf, Germany, and WuXi AppTec, China. cDNA of the human GIP receptor was purchased from Origene, Rockville, Maryland, USA (SC110906) and cloned into a pCMV-Script vector. Iodinated human GIP(1-42) was purchased from PerkinElmer Life Sciences, Skovlunde, Denmark (NEX402025UC).
Animals
Gottingen mini-pigs or Male Wistar rats were housed in the animal facility at the Faculty of Health and Medical Sciences.
Transfections and Tissue Culture
COS-7 cells were cultured at 10% $CO_2$ and 37° C. in Dulbecco's modified Eagle's medium 1885 supplemented with 10% fetal bovine serum, 2 mM glutamine, 180 units/ml penicillin, and 45 g/ml streptomycin. Transient transfection of the COS-7 cells for cAMP accumulation and competition binding was performed using the calcium phosphate precipitation method with the addition of chloroquine[46-47].
cAMP Assay
Alternative 1 (Also Referred to as DiscoveRx Assay):
Transient transfected COS-7 cells expressing the human GIP receptor were seeded in white 96-well plates with a density of $3.5*10^4$/well. The day after, the cells were washed twice with Hepes buffered saline (HBS) buffer and incubated with HBS and 1 mM 3-isobutyl-1-methylxanthine (IBMX) for 30 min at 37° C. To test for agonistic properties, ligands were added and incubated for 30 min at 37° C. In order to test for antagonistic properties, the cells were preincubated with the antagonists for 10 min prior to the addition of the agonist and subsequent incubated for 20 additional min. The HitHunter™ cAMP XS assay (DiscoveRx) was carried out according to the manufacturer's instructions.
Alternative 2 (Also Referred to as CisBio Assay):
The in vitro functional activity of compounds towards human GIP receptor can also be determined in HEK-293 cells transiently expressing the receptor. On the day of the assay, cells were resuspended in HBSS buffer (Gibco, 14025-50) supplemented with 20 mM HEPES (Gibco, 15630-106), 0.1% Pluronic F-68 (Gibco, 24040-032) and 0.1% casein (Sigma, C4765), and plated in 384-well plates at a density of 5000 cells/well. The GIP peptide analogues of the present disclosure were diluted in HBSS buffer supplemented with 20 mM HEPES, 0.1% pluronic, 0.1% casein and 500 uM IBMX. To test for antagonistic properties, the GIP peptide analogues to be tested were each independently added to the cells and incubated for 20 min. at 37° C. prior to addition of agonist (GIP1-42) at an EC50 concentration, and subsequent incubation at 37° C. for 30 min. The resulting decrease in intracellular cAMP was quantitatively determined using the CisBio cAMP Dynamic 2 HTRF Assay Kit. The assay is based on a competition between native cAMP produced by cells and cAMP labeled with the dye d2 for binding to a cryptate labeled antibody. The specific signal (i.e. energy transfer signal) is inversely proportional to the concentration of cAMP in the sample.

The cAMP-d2 conjugate and the antibody anti-cAMP-Cryptate, both diluted in lysis buffer provided in the kit, were added to the cells according to the manufacturer's protocol. The resulting competitive assay was incubated for 60 minutes at room temperature, and the signal was detected by using a PerkinElmer Envision® instrument with excitation at 320 nm and emission at 665 nm and 620 nm. The HTRF ratio (emission at 665 nm/620 nm*10,000) is inversely proportional to the amount of cAMP present and is converted to nM cAMP per well using a cAMP standard curve. The dose-response curves were fitted using the non-linear regression analysis (four-logistic parameter equation) in GraphPad Prism, whereby pIC50 values were estimated.

To test for agonistic properties at the GIP receptor, compounds were diluted and added to cells as described above and incubated for 30 min at 37° C. The resulting increase in intracellular cAMP was determined using the CisBio cAMP Dynamic 2 HTRF Assay Kit as described above.
Elimination Half-Life ($T_{1/2}$) Estimated in Gottingen Minipigs
2-3 Gottingen minipigs were subcutaneously administered one of the GIP analogues of the present invention (1-10 nmol/kg, total volume 2-6 mL) and blood samples were collected before and up to 432 hours post subcutaneous administration.) from a central venous catheter. The catheter was flushed with saline and heparin between samples. Blood was collected into cold EDTA tubes, centrifuged and plasma was kept at −20° C. pending analyses.
Elimination Half-Life ($T_{1/2}$) Estimated in Wistar Rats
3 Wistar rats were administered one of the GIP analogues intravenously of the present invention (7 nmol/kg, total dose volume 1 ml/kg) and blood samples were collected from the tail-tip before and up to 72 hours post administration. Blood was collected into cold EDTA tubes, centrifuged and plasma was kept at −20° C. pending analyses.
Determination of Plasma Concentration of the Modified GIP Peptide Analogues
Göttingen mini-pig, or Male Wistar rat plasma concentrations of a GIP analogue according to the present invention was either analyzed by radioimmunoassay (RIA) or by liquid chromatography-mass spectrometry (LC/MS). For RIA-based determination, analogues' immunoreactivity were determined using antiserum Ab95234, Ab95235, or Ab95236, which are polyclonal in-house antibodies raised in rabbits specific for either the mid region of GIP(1-30)$NH_2$ or amidated C-terminus of GIP(3-30)$NH_2$. For LC/MS-based determination, the plasma samples were precipitated by addition of 3 parts ethanol followed by thorough mixing. After centrifugation and dilution of the supernatant, the samples were analyzed by LC-MS/MS and compared with a 9-point calibration curve. The calibration curves were prepared in naïve plasma matrix from Göttingen minipigs. The LC/MS was performed by Red Glead Discovery AB, Lund, Sweden.

Data Analysis $IC_{50}$, $EC_{50}$, and Emax values were determined by non-linear regression. These were carried out with the GraphPad Prism 6.0 software (GraphPad, San Diego, California, USA) and Microsoft Excel™. The pharmacokinetic parameters, including elimination $T_{1/2}$, were calculated with the software PK solutions 2.0 (Summit Research services, US).

Example 1—Antagonistic Properties of Human GIP (3-30) and GIP(5-30) Extended with 1 to 12 C-Terminal Amino Acid Residues from GIP(1-42) or Exendin-4 are Preserved or Improved Following Addition of Extra C-Terminal Amino Acid Residues The effect of the addition of between 1 and 12 extra C-terminal amino acid residues to GIP(3-30) and GIP(5-30) on their antagonistic activity as well as T % was tested as described below. The GIP analogues were also acylated with or without a linker at e.g. position 11, 12, 17, 18 or 20, where the Serine-11, Isoleucine-12, Isoleucine-17, Histidine-18 or Glutamine-20 had previously been substituted with a Lysine.

Results:

GIP(3-36) analogues e.g. AT361, which is lipidated with a C16 diacid in position 18, display improved $IC_{50}$ value of 2 nM compared to e.g. AT158. AT361 also had a very high $T_{1/2}$ of 31 h. The half-life is surprisingly long compared to analogous GIP(3-30) variants lipidated with C16 diacid in position 18, such as AT158 which only has a half-life of 14 hours. The long half-life is accomplished without N-capping or other types of stabilization at the N-terminus as e.g. AT361 has a free amine group at the N-terminus.

GIP(3-30)+amino acids from the C-terminal part of Exendin-4, such as e.g. AT631, were generally high-potent antagonists. AT631 displayed improved $IC_{50}$-value of 1.9 nM compared to e.g. AT158. The half-life of AT631 is also more than 30 hours in vivo, as a very long $T_{1/2}$ of 56 h was determined, and surprisingly long compared to e.g. AT158 (see FIG. 1) or liraglutide, which also has a C16 fatty acid. The long half-life is accomplished without N-capping or other types of stabilization at the N-terminus as e.g. AT631 has a free amine group at the N-terminus.

Taken together GIP(3-30) antagonists with C-terminal extensions, such as e.g. AT361 and AT631, were better antagonists than reported in PCT/EP2018/064355. The antagonists that were tested in pigs for $T_{1/2}$ investigation were much better than reported in PCT/EP2018/064355. Both AT361 and AT631 also show extraordinarily long $T_{1/2}$ of more than 30 hours compared to e.g. the GIP(3-30) analogue AT158 (see Table 1B and FIG. 1) and other C16 lipidated peptides known in the art, such as e.g. Liraglutide (a once-daily GLP-1 analogue). Also AT437, AT632, AT587, AT589, AT614, AT616, AT618, AT619 have very long half-lives. The combination of a C-terminal extension of GIP(3-30) (as for example in AT361 and AT631) and acylation i.e. attachment of a fatty acid in specific positions, such as e.g. on a lysine in position 18, can generate a surprisingly long half-life.

Without being bound to any theory, the presence of a carboxylic acid at the C-terminus (as in AT361 and AT631) may also contribute to an improved half-life.

When assessing and comparing the pharmacokinetic properties of various compounds, it can be beneficial to use more than one species. So far in the above, the half-life discussed has solely been determined in minipigs. Although it is generally accepted that elimination half-life is shorter in rats than in minipigs, the following will discuss our pharmacokinetic findings in rats. From Table 3A and 3B, the average and time-dependent plasma concentrations in Wistar rats, it can be seen that exposure and half-life is much higher for analogues in which the fatty acid is attached to the mid regions of the peptide compared to e.g. a GIP analogue with a fatty acid attached at position 40 at the C-terminus, such as in AT651. The exposure at every time point is also much higher compared to e.g. a GIP analogue with a fatty acid attached at position 40 at the C-terminus, such as in AT651, for all the tested peptides according to embodiments of the present invention. Thus, attaching a fatty acid to the mid regions of GIP(3-30) while having a C-terminal extension, e.g. position 11 and 18, produces pharmacokinetically superior analogues than fatty acid attachment to position 40 of the C-terminus. It is also important to note, that although many of the tested analogues have a C16 fatty acid attached (AT361, AT631, AT366, AT632, AT447) there is a surprisingly long $T_{1/2}$ (11 h, 7 h, 7 h, 8 h, 5.8 h, respectively) when compared to similar peptides with the same fatty acid length attached, e.g. Liraglutide which has a T % of 4 h in rats. Without being bound to any theory, the C-terminal extended GIP peptides could constitute advantageous molecules for half-life extension by lipidation.

From Table 2B, it can also be seen that specific substitutions may be advantageous. The introduction of alfa helix stabilizing amino acids, such as E, L, K, A and Aib, at specific positions, such as at individually at any of positions 9, 13, 14, 15, 18, 21 and 24, may be especially beneficial with regard to increasing antagonistic potency. For example, substitution with E in position 24 retains or increases potency. Substitution at position 14 with L, Nle or K retains or even increases potency, as seen e.g. from AT618, AT619 and AT621. The substitution of D at position 9 and/or at position 15 and/or position 21 with E seem to increase potency as can be seen from e.g. AT613, AT614, AT616 and AT617, as well as e.g. AT693, AT695, AT696 and AT700. It may generally also be seen that a free C-terminus carboxylic acid increases potency. When the length of the fatty acid increases, such as from C16 diacid to C18 diacid, the potency often decreases. However, certain substitutions may compensate for this. For example Aib at position 13 or substitution with E in for example position 9 and/or 15 and/or 21. Substitution with E in position 24 gives retained or improved antagonistic potency as well as improved solubility for example at physiological pH around 7.5. It can also be seen from table 2B that various Z retain or increases potency as in e.g. AT467, AT468, AT469, AT470, AT471, AT472, AT473 and AT474. From e.g. AT633 and AT635 it can be seen that N-terminal acetylation leads to (partial) agonism at the GIPR.

TABLE 1A

Name and structure of the GIP antagonists with extensions. When the linker consists of more than one unit, it is intended that the first named unit is linked to peptide, and the last named unit is linked to the fatty acid. However, the units of the linker may be placed in a different order with no or minor effects on the function of the linker.

| ID | Backbone | C-term mod | FA posi. | FA linker | FA | Mutations |
|---|---|---|---|---|---|---|
| AT415 | 3-36 | COOH | 18 | 2xAEEAc + y-glu | C16-diacid | [H18K] |
| AT416 | 3-36 | COOH | 18 | 3xAEEAc + y-glu | C16-diacid | [H18K] |
| AT418 | 3-36 | COOH | 18 | 3xAEEAc + y-glu | C18-diacid | [H18K] |
| AT419 | 3-36 | COOH | 18 | 2xAEEAc + y-glu | C16-diacid | [E3S][H18K] |
| AT420 | 3-36 | COOH | 18 | 3xAEEAc + y-glu | C16-diacid | [E3S][H18K] |
| AT422 | 3-36 | COOH | 18 | 3xAEEAc + y-glu | C18-diacid | [E3S][H18K] |
| AT423 | 3-36 | COOH | 18 | 2xAEEAc + y-glu | C16-diacid | [E3S][K16R][H18K][K30R][K32R][K33R] |
| AT424 | 3-36 | COOH | 18 | 3xAEEAc + y-glu | C16-diacid | [E3S][K16R][H18K][K30R][K32R][K33R] |
| AT426 | 3-36 | COOH | 18 | 3xAEEAc + y-glu | C18-diacid | [E3S][K16R][H18K][K30R][K32R][K33R] |
| AT431 | 3-30 + Cex | COOH | 18 | 2xAEEAc + y-glu | C16-diacid | [H18K] |
| AT432 | 3-30 + Cex | COOH | 18 | 3xAEEAc + y-glu | C16-diacid | [H18K] |
| AT433 | 3-30 + Cex | COOH | 18 | 2xAEEAc + y-glu | C18-diacid | [H18K] |
| AT434 | 3-30 + Cex | COOH | 18 | 3xAEEAc + y-glu | C18-diacid | [H18K] |
| AT435 | 3-30 + Cex | COOH | 18 | 2xAEEAc + y-glu | C16-diacid | [E3S][H18K] |
| AT436 | 3-30 + Cex | COOH | 18 | 3xAEEAc + y-glu | C16-diacid | [E3S][H18K] |
| AT437 | 3-30 + Cex | COOH | 18 | 2xAEEAc + y-glu | C18-diacid | [E3S][H18K] |
| AT438 | 3-30 + Cex | COOH | 18 | 3xAEEAc + y-glu | C18-diacid | [E3S][H18K] |
| AT439 | 3-30 + Cex | COOH | 18 | 2xAEEAc + y-glu | C16-diacid | [E3S][K16R][H18K][K30R] |
| AT440 | 3-30 + Cex | COOH | 18 | 3xAEEAc + y-glu | C16-diacid | [E3S][K16R][H18K][K30R] |
| AT441 | 3-30 + Cex | COOH | 18 | 2xAEEAc + y-glu | C18-diacid | [E3S][K16R][H18K][K30R] |
| AT442 | 3-30 + Cex | COOH | 18 | 3xAEEAc + y-glu | C18-diacid | [E3S][K16R][H18K][K30R] |
| AT467 | 3-30 + Cex9 | COOH | 18 | | C16-diacid | [H18K] |
| AT468 | 3-30 + Cex8 | COOH | 18 | | C16-diacid | [H18K] |
| AT469 | 3-30 + Cex7 | COOH | 18 | | C16-diacid | [H18K] |
| AT470 | 3-30 + Cex6 | COOH | 18 | | C16-diacid | [H18K] |
| AT471 | 3-30 + Cex5 | COOH | 18 | | C16-diacid | [H18K] |
| AT472 | 3-30 + Cex4 | COOH | 18 | | C16-diacid | [H18K] |
| AT473 | 3-30 + Cex3 | COOH | 18 | | C16-diacid | [H18K] |
| AT474 | 3-30 + Cex2 | COOH | 18 | | C16-diacid | [H18K] |
| AT447 | 3-31 | COOH | 18 | | C16-diacid | [H18K] |
| AT448 | 3-32 | COOH | 18 | | C16-diacid | [H18K] |
| AT360 | 3-33 | COOH | 18 | | C16-diacid | [H18K] |
| AT449 | 3-34 | COOH | 18 | | C16-diacid | [H18K] |
| AT450 | 3-35 | COOH | 18 | | C16-diacid | [H18K] |
| AT361 | 3-36 | COOH | 18 | | C16-diacid | [H18K] |
| AT451 | 3-37 | COOH | 18 | | C16-diacid | [H18K] |
| AT452 | 3-38 | COOH | 18 | | C16-diacid | [H18K] |
| AT362 | 3-39 | COOH | 18 | | C16-diacid | [H18K] |
| AT453 | 3-40 | COOH | 18 | | C16-diacid | [H18K] |
| AT454 | 3-41 | COOH | 18 | | C16-diacid | [H18K] |
| AT363 | 3-42 | COOH | 18 | | C16-diacid | [H18K] |
| AT364 | 3-30 + Cex | COOH | 18 | | C16-diacid | [H18K] |
| AT365 | 5-33 | COOH | 11 | y-glu | C16diacid | [S11K] |
| AT366 | 5-36 | COOH | 11 | y-glu | C16diacid | [S11K] |
| AT367 | 5-39 | COOH | 11 | y-glu | C16diacid | [S11K] |
| AT368 | 5-42 | COOH | 11 | y-glu | C16diacid | [S11K] |
| AT428 | 5-36 | COOH | 11 | 3xAEEAc + y-glu | C16diacid | [S11K][K16R][K30R][K32R][K33R] |
| AT430 | 5-36 | COOH | 11 | 3xAEEAc + y-glu | C18diacid | [S11K][K16R][K30R][K32R][K33R] |
| AT443 | 5-30 + Cex | COOH | 11 | 2xAEEAc + y-glu | C16diacid | [S11K][K16R][K30R] |
| AT444 | 5-30 + Cex | COOH | 11 | 3xAEEAc + y-glu | C16diacid | [S11K][K16R][K30R] |
| AT445 | 5-30 + Cex | COOH | 11 | 2xAEEAc + y-glu | C18diacid | [S11K][K16R][K30R] |
| AT446 | 5-30 + Cex | COOH | 11 | 3xAEEAc + y-glu | C18diacid | [S11K][K16R][K30R] |
| AT455 | 5-31 | COOH | 11 | y-glu | C16diacid | [S11K] |
| AT456 | 5-32 | COOH | 11 | y-glu | C16diacid | [S11K] |
| AT457 | 5-34 | COOH | 11 | y-glu | C16diacid | [S11K] |
| AT458 | 5-35 | COOH | 11 | y-glu | C16diacid | [S11K] |
| AT459 | 5-37 | COOH | 11 | y-glu | C16diacid | [S11K] |
| AT460 | 5-38 | COOH | 11 | y-glu | C16diacid | [S11K] |
| AT461 | 5-40 | COOH | 11 | y-glu | C16diacid | [S11K] |
| AT462 | 5-41 | COOH | 11 | y-glu | C16diacid | [S11K] |
| AT463 | 6-33 | COOH | 18 | | C16diacid | [H18K] |
| AT464 | 6-36 | COOH | 18 | | C16diacid | [H18K] |
| AT465 | 6-39 | COOH | 18 | | C16diacid | [H18K] |
| AT466 | 6-42 | COOH | 18 | | C16diacid | [H18K] |
| AT475 | 6-30 + Cex | COOH | 18 | | C16diacid | [H18K] |
| AT631 | 3-30 + Cex(31-39) | COOH | 18 | | C16diacid | [H18K] |

TABLE 1A-continued

Name and structure of the GIP antagonists with extensions. When the linker
consists of more than one unit, it is intended that the first named unit is linked to
peptide, and the last named unit is linked to the fatty acid. However, the units of the
linker may be placed in a different order with no or minor effects on the function of
the linker.

| ID | Backbone | C-term mod | FA posi. | FA linker | FA | Mutations |
|---|---|---|---|---|---|---|
| AT543 | GIP(3-36) | COOH | 11 | 2xAEEAc + yGlu | C18-diacid | [S11K] |
| AT544 | GIP(3-36) | COOH | 12 | 2xAEEAc + yGlu | C18-diacid | [I12K] |
| AT545 | GIP(3-36) | NH2 | 18 | 2xAEEAc + yGlu | C18-diacid | [H18K] |
| AT546 | GIP(3-36) | COOH | 18 | 2xAEEAc + yGlu | C18 | [H18K] |
| AT547 | GIP(3-36) | COOH | 18 | yGlu-yGlu | C18 | [H18K] |
| AT548 | GIP(3-36) | COOH | 20 | 2xAEEAc + yGlu | C18-diacid | [Q20K] |
| AT549 | GIP(3-36) | NH2 | 20 | 2xAEEAc + yGlu | C18-diacid | [Q20K] |
| AT550 | GIP(3-36) | COOH | 24 | 2xAEEAc + yGlu | C18-diacid | [N24K] |
| AT558 | GIP(5-36) | COOH | 11 | 2xAEEAc + yGlu | C18-diacid | [S11K] |
| AT559 | GIP(5-36) | NH2 | 11 | 2xAEEAc + yGlu | C18-diacid | [S11K] |
| AT560 | GIP(5-36) | COOH | 11 | 2xAEEAc + yGlu | C18 | [S11K] |
| AT561 | GIP(5-36) | COOH | 11 | yGlu-yGlu | C18 | [S11K] |
| AT562 | GIP(5-36) | COOH | 12 | 2xAEEAc + yGlu | C18-diacid | [I12K] |
| AT563 | GIP(5-36) | COOH | 18 | 2xAEEAc + yGlu | C18-diacid | [H18K] |
| AT564 | GIP(5-36) | COOH | 20 | 2xAEEAc + yGlu | C18-diacid | [Q20K] |
| AT565 | GIP(5-36) | NH2 | 20 | 2xAEEAc + yGlu | C18-diacid | [Q20K] |
| AT566 | GIP(5-36) | COOH | 24 | 2xAEEAc + yGlu | C18-diacid | [N24K] |
| AT586 | GIP(3-30)Cex(31-39) | NH2 | 17 | 2xAEEAc + yGlu | C18-diacid | [I17K] |
| AT587 | GIP(3-30)Cex(31-39) | NH2 | 18 | 2xAEEAc + yGlu | C18-diacid | [H18K] |
| AT588 | GIP(3-31)Cex(31-39) | NH2 | 18 | 2xAEEAc + yGlu | C18-diacid | [H18K] |
| AT589 | GIP(3-31)Cex(31-39) | COOH | 18 | 2xAEEAc + yGlu | C18-diacid | [H18K] |
| AT590 | GIP(3-30)Cex(31-39) | NH2 | 18 | 2xAEEAc + yGlu | C18-diacid | [H18K][K30G] |
| AT591 | GIP(3-30)Cex(31-39) | NH2 | 18 | 2xAEEAc + yGlu | C18-diacid | [H18K][Q29G][K30G] |
| AT592 | GIP(3-30)Cex(31-39) | COOH | 18 | 2xAEEAc + yGlu | C18-diacid | [H18K][Q29G][K30G] |
| AT593 | GIP(3-30)Cex(32-39) | NH2 | 18 | 2xAEEAc + yGlu | C18-diacid | [H18K][Q29G][K30P] |
| AT594 | GIP(3-30)Cex(31-39) | NH2 | 20 | 2xAEEAc + yGlu | C18-diacid | [Q20K] |
| AT597 | GIP(5-30)Cex(31-39) | NH2 | 11 | 2xPEG + yGlu | C18-diacid | [S11K] |
| AT602 | GIP(5-30)Cex(31-39) | COOH | 11 | 2xPEG + yGlu | C18-diacid | [S11K][Q29G][K30G] |
| AT605 | GIP(5-30)Cex(31-39) | NH2 | 18 | 2xPEG + yGlu | C18-diacid | [H18K] |
| AT613 | GIP(3-30)Cex(31-39) | COOH | 18 | none | C16-diacid | [D9E; D15E; H18K; D21E; N24Q] |
| AT614 | GIP(3-30)Cex(31-39) | COOH | 18 | none | C16-diacid | [D9E; D15E; H18K; N24E] |
| AT615 | GIP(3-30)Cex(31-39) | COOH | 18 | none | C16-diacid | [D9E; I12Aib; M14Nle; D15E; H18K; N24E] |
| AT616 | GIP(3-30)Cex(31-39) | COOH | 18 | none | C16-diacid | [D9E; A13Aib; D15E; H18K; N24E] |
| AT617 | GIP(3-30)Cex(31-39) | COOH | 18 | none | C16-diacid | [H18K; N24E] |
| AT618 | GIP(3-30)Cex(31-39) | COOH | 18 | none | C16-diacid | [M14L; H18K] |
| AT619 | GIP(3-30)Cex(31-39) | COOH | 18 | none | C16-diacid | [M14Nle; H18K] |
| AT620 | GIP(3-30)Cex(31-39) | COOH | 18 | none | C16-diacid | [M14E; H18K] |
| AT621 | GIP(3-30)Cex(31-39) | COOH | 18 | none | C16-diacid | [M14K; H18K] |
| AT622 | GIP(3-30)Cex(31-39) | COOH | 18 | none | C16-diacid | [M14S; H18K] |
| AT623 | GIP(3-30)Cex(31-39) | COOH | 18 | none | C16-diacid | [H18K; N24E; K30A] |
| AT624 | GIP(3-30)Cex(31-39) | COOH | 18 | none | C16-diacid | [H18K; L27E] |
| AT625 | GIP(3-30)Cex(31-39) | COOH | 18 | none | C16-diacid | [H18K; A28E] |
| AT626 | GIP(3-30)Cex(31-39) | COOH | 18 | none | C16-diacid | [H18K; A28E; Q29G; K30G] |
| AT627 | GIP(3-30)Cex(31-39) | COOH | 18 | none | C18-diacid | [H18K] |
| AT628 | GIP(3-30)Cex(31-39) | COOH | 18 | none | C18 | [H18K] |
| AT629 | GIP(3-30)Cex(31-39) | COOH | 18 | 2xAEEAc + yGlu | C16-diacid | [H18K] |
| AT630 | GIP(3-30)Cex(31-39) | COOH | 18 | yGlu | C16-diacid | [H18K] |
| AT631 | GIP(3-30)Cex(31-39) | COOH | 18 | none | C16diacid | [H18K] |
| AT632 | GIP(5-30)Cex(31-39) | COOH | 11 | yGlu | C16diacid | [S11K] |
| AT633 | GIP(3-30)Cex(31-39) | COOH | 18 | none | C16diacid | [H18K], N-terminal acetylation |
| AT635 | GIP(3-30)Cex(31-39) | COOH | 18 | none | C16diacid | [D9E; D15E; H18K], N-terminal acetylation |
| AT636 | GIP(3-30)Cex(31-39) | COOH | 18 | none | C16-diacid | [E3V; H18K] |
| AT637 | GIP(3-30)Cex(31-39) | COOH | 18 | none | C16-diacid | [E3Aib; H18K] |
| AT638 | GIP(3-30)Cex(31-39) | COOH | 18 | none | C16-diacid | [E3P; H18K] |
| AT639 | GIP(3-30)Cex(31-39) | COOH | 18 | none | C16-diacid | [E3V; G4E; H18K] |
| AT640 | GIP(3-30)Cex(31-39) | COOH | 18 | none | C16-diacid | [E3Aib; G4E; H18K] |
| AT641 | GIP(3-30)Cex(31-39) | COOH | 18 | none | C16-diacid | [E3G; G4E; H18K] |
| AT642 | GIP(3-30)Cex(31-39) | COOH | 18 | none | C16-diacid | [E3P; G4E; H18K] |
| AT643 | GIP(3-30)Cex(31-39) | COOH | 18 | none | C16-diacid | [E3D; G4T; H18K] |
| AT644 | GIP(3-30)Cex(31-39) | COOH | 18 | none | C16-diacid | [E3G; G4E; S11A; M14L; H18K; N24E; K30G] |
| AT646 | GIP(3-30)Cex(31-39) | COOH | 18 | none | C16-diacid | [E3G; G4E; D9T; M14L; H18K; N24E] |
| AT647 | GIP(5-30)Cex(31-39) | COOH | 11 | yGlu | C16-diacid | [D9T; S11K; M14L; N24E] |
| AT650 | GIP(3-30)Cex(31-39) | NH2 | 18 | none | C16-diacid | [H18K] |

TABLE 1A-continued

Name and structure of the GIP antagonists with extensions. When the linker consists of more than one unit, it is intended that the first named unit is linked to peptide, and the last named unit is linked to the fatty acid. However, the units of the linker may be placed in a different order with no or minor effects on the function of the linker.

| ID | Backbone | C-term mod | FA posi. | FA linker | FA | Mutations |
|---|---|---|---|---|---|---|
| AT651 | GIP(3-30)Cex(31-39)K | NH2 | 40 | none | C16 | [40K] + Phenyl lactic acid at N-terminus |
| AT652 | GIP(3-30)Cex(31-39)K | NH2 | 40 | none | C16 | [E3P; 40K] + Phenyl lactic acid at N-terminus |
| AT665 | GIP(3-30)Cex(31-39) | COOH | 18 | none | C16-diacid | [A13Aib; H18K; N24E] |
| AT666 | GIP(3-30)Cex(31-39) | COOH | 18 | none | C16-diacid | [A13Aib; M14L; H18K; N24E] |
| AT667 | GIP(3-30)Cex(31-39) | COOH | 18 | none | C16-diacid | [A13Aib; M14Nle; H18K; N24E] |
| AT668 | GIP(3-30)Cex(31-39) | COOH | 18 | none | C16-diacid | [M14L; H18K; N24E] |
| AT669 | GIP(3-30)Cex(31-39) | COOH | 18 | none | C16-diacid | [M14Nle; H18K; N24E] |
| AT670 | GIP(3-30)Cex(31-39) | COOH | 18 | none | C16-diacid | [M14K; H18K; N24E] |
| AT671 | GIP(3-30)Cex(31-39) | COOH | 18 | none | C16-diacid | [M14Nle; H18K; Q29G; K30G] |
| AT672 | GIP(3-30)Cex(31-39) | COOH | 18 | none | C16-diacid | [M14Nle; H18K; N24E; Q29G; K30G] |
| AT673 | GIP(3-30)Cex(31-39) | COOH | 18 | none | C16-diacid | [D9E; A13Aib; M14L; D15E; H18K; D21E; N24E] |
| AT674 | GIP(3-30)Cex(31-39) | COOH | 18 | none | C16-diacid | [D9E; A13Aib; M14Nle; D15E; H18K; D21E; N24E] |
| AT675 | GIP(3-30)Cex(31-39) | COOH | 18 | none | C16-diacid | [E3γGlu; H18K] |
| AT676 | GIP(3-30)Cex(31-39) | COOH | 18 | none | C16-diacid | [E3βGlu; H18K] |
| AT677 | GIP(3-30)Cex(31-39) | COOH | 18 |  | C16-diacid | [[E3Glutaric acid; H18K] |
| AT680 | GIP(3-30)Cex(31-39) | COOH | 18 | 2xAEEAc + γGlu | C18-diacid | [H18K] |
| AT681 | GIP(3-30)Cex(31-39) | COOH | 18 | 2xAEEAc + γGlu | C18-diacid | [M14L; H18K] |
| AT682 | GIP(3-30)Cex(31-39) | COOH | 18 | 2xAEEAc + γGlu | C18-diacid | [M14L; H18K; N24E] |
| AT683 | GIP(3-30)Cex(31-39) | COOH | 18 | 2xAEEAc + γGlu | C18-diacid | [M14Nle; H18K; N24E] |
| AT684 | GIP(3-30)Cex(31-39) | COOH | 18 | 2xAEEAc + γGlu | C18-diacid | [M14K; H18K] |
| AT685 | GIP(3-30)Cex(31-39) | COOH | 18 | 2xAEEAc + γGlu | C18-diacid | [A13Aib; M14L; H18K; N24E] |
| AT686 | GIP(3-30)Cex(31-39) | COOH | 18 | 2xAEEAc + γGlu | C18-diacid | [A13Aib; M14Nle; H18K; N24E] |
| AT687 | GIP(3-30)Cex(31-39) | COOH | 18 | 2xAEEAc + γGlu | C18-diacid | [M14L; H18K; N24E; Q29G; K30G] |
| AT689 | GIP(3-30)Cex(31-39) | COOH | 18 | 2xAEEAc + γGlu | C18-diacid | [M14L; H18K; A28E] |
| AT690 | GIP(3-30)Cex(31-39) | COOH | 18 | 2xAEEAc + γGlu | C18-diacid | [M14Nle; H18K; A28E] |
| AT691 | GIP(3-30)Cex(31-39) | COOH | 18 | 2xAEEAc + γGlu | C18-diacid | [M14L; H18K; A28E; Q29G; K30G] |
| AT693 | GIP(3-30)Cex(31-39) | COOH | 18 | 2xAEEAc + γGlu | C18-diacid | [D9E; M14L; D15E; H18K; D21E; N24E] |
| AT694 | GIP(3-30)Cex(31-39) | COOH | 18 | 2xAEEAc + γGlu | C18-diacid | [D9E; M14Nle; D15E; H18K; D21E; N24E] |
| AT695 | GIP(3-30)Cex(31-39) | COOH | 18 | 2xAEEAc + γGlu | C18-diacid | [D9E; A13Aib; M14L; D15E; H18K; D21E; N24E] |
| AT696 | GIP(3-30)Cex(31-39) | COOH | 18 | 2xAEEAc + γGlu | C18-diacid | [D9E; A13Aib; M14Nle; D15E; H18K; D21E; N24E] |
| AT697 | GIP(3-30)Cex(31-39) | COOH | 18 | none | C16-diacid | [E3γGlu(L-isomer); M14Nle; H18K; N24E] |
| AT698 | GIP(3-30)Cex(31-39) | COOH | 18 | none | C16-diacid | [E3γGlu(D-isomer); M14Nle; H18K; N24E] |
| AT699 | GIP(3-30)Cex(31-39) | COOH | 18 | none | C16-diacid | [E3βGlu; M14Nle; H18K; N24E] |
| AT700 | GIP(3-30)Cex(31-39) | COOH | 18 | none | C16-diacid | [E3Glutaric acid; M14Nle; H18K; N24E] |
| AT701 | GIP(3-30)Cex(31-39) | COOH | 18 | 2xAEEAc + γGlu | C18-diacid | [E3βGlu; M14Nle; H18K; N24E] |
| AT702 | GIP(3-30)Cex(31-39) | COOH | 18 | 2xAEEAc + γGlu | C18-diacid | [E3Glutaric acid; M14Nle; H18K; N24E] |
| AT703 | GIP(3-30)Cex(31-39) | COOH | 18 | none | C16-diacid | [E3βGlu; A13Aib; M14Nle; H18K] |

TABLE 1B

Antagonistic, agonistic properties and for some the half-life, T½ of the GIP antagonists with extensions. The data were obtained with the cAMP Assay (DiscoveRx assay).

| ID | cAMP antagonism | | | | | cAMP agonism | | | T½ |
|---|---|---|---|---|---|---|---|---|---|
|  | log | SEM | nM | % inhib | n | Emax | SEM | n |  |
| AT415 | −7.3 | 0.2 | 55 | 87 | 2 | 4.6 | 1.0 | 2 |  |
| AT416 | −7.3 | 0.2 | 52 | 90 | 2 | No Agonism | | 2 |  |
| AT418 | −7.2 | 0.3 | 68 | 95 | 2 | 7.8 | 2.6 | 2 |  |
| AT419 | −6.7 | 0.6 | 215 | 78 | 2 | 4.9 | 0.8 | 2 |  |
| AT420 | −6.6 | 0.4 | 237 | 100 | 2 | No Agonism | | 2 |  |
| AT422 | −8.5 | 0.3 | 3 | 90 | 2 | 6.0 | 2.6 | 2 |  |
| AT423 | −8.2 | 0.5 | 6 | 95 | 2 | No Agonism | | 2 |  |
| AT424 | −7.5 | 0.3 | 35 | 100 | 2 | No Agonism | | 2 |  |
| AT426 | −7.6 | 0.2 | 28 | 80 | 2 | No Agonism | | 2 |  |
| AT431 | −8.1 | 0.2 | 7 | 75 | 3 | No Agonism | | 3 |  |
| AT432 | −7.7 | 0.3 | 19 | 92 | 3 | No Agonism | | 3 |  |
| AT433 | −7.2 | 0.2 | 62 | 100 | 3 | No Agonism | | 3 |  |
| AT434 | −7.9 | 0.2 | 14 | 100 | 3 | No Agonism | | 3 |  |
| AT435 | −7.1 | 0.4 | 75 | 100 | 3 | No Agonism | | 3 |  |
| AT436 | −7.7 | 0.2 | 18 | 100 | 3 | No Agonism | | 3 |  |
| AT437 | −8.1 | 0.1 | 8 | 100 | 3 | No Agonism | | 3 |  |
| AT438 | −7.3 | 0.4 | 54 | 100 | 3 | No Agonism | | 3 |  |
| AT439 | −8.0 | 0.3 | 9 | 100 | 3 | No Agonism | | 3 |  |
| AT440 | −7.0 | 0.1 | 103 | 100 | 3 | No Agonism | | 3 |  |
| AT441 | −7.6 | 0.6 | 25 | 55 | 2 | No Agonism | | 3 |  |
| AT442 | −7.6 | 0.4 | 26 | 77 | 2 | No Agonism | | 3 |  |
| AT467 | −8.2 | 0.2 | 6 | 100 | 3 | No Agonism | | 3 |  |
| AT468 | −7.9 | 0.2 | 13 | 95 | 2 | 4.6 | 1.1 | 2 |  |
| AT469 | −8.5 | 0.2 | 3 | 90 | 2 | No Agonism | | 2 |  |
| AT470 | −7.8 | 0.2 | 14 | 100 | 2 | No Agonism | | 2 |  |
| AT471 | −7.9 | 0.2 | 11 | 100 | 2 | No Agonism | | 2 |  |
| AT472 | −7.8 | 0.3 | 15 | 100 | 2 | No Agonism | | 2 |  |
| AT473 | −7.6 | 0.3 | 26 | 100 | 2 | No Agonism | | 2 |  |
| AT474 | −8.4 | 0.2 | 4 | 100 | 2 | 5.9 | 2.8 | 2 |  |
| AT447 | −8.1 | 0.2 | 9 | 82 | 3 | 4.2 | 1.5 | 3 |  |
| AT448 | −8.2 | 0.3 | 6 | 77 | 3 | 6.2 | 1.4 | 3 |  |
| AT360 | −7.1 | 0.1 | 86 | 85 | 2 | 20.0 | 5.6 | 3 |  |
| AT449 | −8.4 | 0.2 | 4 | 95 | 3 | 8.6 | 1.6 | 3 |  |
| AT450 | −8.5 | 0.4 | 3 | 57 | 3 | 5.8 | 1.0 | 3 |  |
| AT361 | −8.8 | 0.1 | 2 | 100 | 3 | 5.0 | 1.2 | 3 | 31 |
| AT451 | −8.1 | 0.5 | 8 | 75 | 3 | 9.2 | 2.0 | 3 |  |
| AT452 | −8.3 | 0.2 | 5 | 75 | 3 | 7.2 | 1.9 | 3 |  |
| AT362 | −8.3 | 0.2 | 5 | 86 | 3 | 7.0 | 2.3 | 3 |  |
| AT453 | −7.2 | 0.5 | 57 | 65 | 3 | 6.1 | 1.0 | 3 |  |
| AT454 | −7.3 | 0.4 | 54 | 82 | 3 | 8.9 | 0.7 | 3 |  |
| AT363 | −8.3 | 0.3 | 5 | 82 | 3 | 7.0 | 2.2 | 3 |  |
| AT364 | −8.9 | 0.1 | 1 | 100 | 3 | No Agonism | | 3 |  |
| AT365 | −8.2 | 0.1 | 6 | 100 | 3 | No Agonism | | 3 |  |
| AT366 | −8.5 | 0.3 | 3 | 100 | 4 | No Agonism | | 3 |  |
| AT367 | −8.3 | 0.2 | 6 | 100 | 2 | No Agonism | | 3 |  |
| AT368 | −8.1 | 0.1 | 9 | 100 | 3 | No Agonism | | 3 |  |
| AT369 | −8.8 | 0.1 | 2 | 100 | 3 | No Agonism | | 3 |  |
| AT428 | −6.5 | 0.2 | 296 | 90 | 2 | No Agonism | | 2 |  |
| AT430 | −6.8 | 0.1 | 153 | 100 | 2 | No Agonism | | 2 |  |
| AT443 | −6.8 | 0.2 | 171 | 100 | 2 | No Agonism | | 2 |  |
| AT444 | −6.8 | 0.4 | 153 | 100 | 2 | No Agonism | | 2 |  |
| AT445 | −7.3 | 0.5 | 47 | 85 | 2 | No Agonism | | 2 |  |
| AT446 | −6.8 | 0.2 | 152 | 100 | 2 | No Agonism | | 2 |  |
| AT455 | −7.5 | 0.2 | 31 | 95 | 3 | No Agonism | | 3 |  |
| AT456 | −7.2 | 0.2 | 60 | 85 | 3 | No Agonism | | 3 |  |
| AT457 | −7.9 | 0.1 | 14 | 100 | 3 | No Agonism | | 3 |  |
| AT458 | −7.4 | 0.1 | 38 | 100 | 3 | No Agonism | | 3 |  |
| AT459 | −7.5 | 0.2 | 31 | 88 | 3 | No Agonism | | 3 |  |
| AT460 | −7.4 | 0.1 | 40 | 100 | 3 | No Agonism | | 3 |  |
| AT461 | −7.6 | 0.1 | 23 | 100 | 3 | No Agonism | | 3 |  |
| AT462 | −7.4 | 0.2 | 37 | 85 | 3 | No Agonism | | 3 |  |
| AT463 | −7.8 | 0.3 | 14 | 88 | 3 | No Agonism | | 3 |  |
| AT464 | −7.3 | 0.2 | 50 | 100 | 3 | No Agonism | | 3 |  |
| AT465 | −7.6 | 0.5 | 28 | 86 | 3 | No Agonism | | 3 |  |
| AT466 | −7.8 | 0.1 | 16 | 90 | 3 | No Agonism | | 3 |  |
| AT475 | −8.4 | 0.3 | 4 | 100 | 2 | No Agonism | | 2 |  |

TABLE 1C

Antagonistic, agonistic properties and for some the half-life, Elimination T½ of the GIP antagonists with extensions. The CisBio Assay (Alternative 2 above) was used to determine antagonistic and agonistic activities of the GIP peptide analogues listed in Table 1B.

| ID | cAMP antagonism | | | | | cAMP agonism | | | T½ (hours) |
|---|---|---|---|---|---|---|---|---|---|
|  | pIC50 | SD | nM | % inhib | n | % Emax | SD | n |  |
| AT631 | 9.0 | 0.3 | 1.12 | 98 | 4 | 0 | | 5 | 56 |
| AT361 | 8.4 | 0.3 | 3.76 | 99 | 4 | 0 | | 5 | 31 |
| AT415 | 7.9 | 0.5 | 13.6 | 87 | 3 | 0 | | 2 |  |
| AT422 | 8.4 | 0.2 | 3.69 | 94 | 3 | 0 | | 2 |  |
| AT423 | 7.1 | 0.2 | 79.4 | 71 | 4 | 0 | | 4 | 14 |
| AT431 | 7.5 | 0.2 | 34.2 | 77 | 3 | 0 | | | |
| AT433 | 8.1 | 0.6 | 7.94 | 89 | 4 | 0 | | 2 |  |
| AT434 | 7.5 | 0.4 | 35.48 | 95 | | | | | |
| AT435 | 7.1 | 0.0 | 79.4 | 84 | | | | | |
| AT437 | 7.5 | 0.2 | 35.5 | 83 | 2 | 0 | | 2 | 48 |
| AT439 | 7.8 | 0.4 | 14.7 | 93 | 3 | 0 | | 2 |  |
| AT441 | 7.7 | 0.3 | 21.5 | 89 | 3 | 0 | | 2 |  |
| AT467 | 7.8 | 0.6 | 14.7 | 86 | 3 | 0 | | 4 |  |
| AT468 | 7.9 | 0.3 | 12.6 | 92 | 3 | 0 | | 2 |  |
| AT469 | 8.4 | 0.6 | 3.80 | 93 | 5 | 0 | | 4 |  |
| AT470 | 7.7 | 0.0 | 20.0 | 91 | 3 | 0 | | 2 |  |
| AT471 | 8.2 | 0.5 | 6.81 | 87 | 3 | 0 | | 2 |  |
| AT472 | 8.1 | 0.2 | 7.94 | 90 | 3 | 0 | | 2 |  |
| AT473 | 8.5 | 0.5 | 2.93 | 88 | 3 | 0 | | 2 |  |
| AT474 | 7.9 | 0.3 | 13.6 | 86 | 3 | 0 | | 2 |  |
| AT447 | 7.9 | 0.2 | 11.9 | 93 | 4 | 0 | | 4 |  |
| AT448 | 8.9 | 0.5 | 1.36 | 96 | 3 | 0 | | 4 |  |
| AT360 | 7.9 | 0.5 | 12.6 | 96 | 3 | 0 | | 2 |  |
| AT449 | 8.2 | 0.4 | 5.84 | 89 | 3 | 0 | | 2 |  |
| AT450 | 8.6 | 0.5 | 2.29 | 97 | 5 | 0 | | 4 |  |
| AT361 | 8.4 | 0.3 | 3.76 | 99 | 4 | 0 | | 5 |  |
| AT451 | 8.6 | 0.3 | 2.33 | 99 | 3 | 0 | | 2 |  |
| AT452 | 8.1 | 0.5 | 7.59 | 97 | 5 | 0 | | 4 |  |
| AT362 | 7.8 | 0.2 | 14.7 | 94 | 4 | 0 | | 2 |  |
| AT453 | 8.2 | 0.1 | 6.31 | 95 | 3 | 0 | | 2 |  |
| AT454 | 8.2 | 0.3 | 6.81 | 84 | 3 | 0 | | 2 |  |
| AT363 | 7.9 | 0.0 | 12.6 | 90 | 3 | 0 | | 2 |  |
| AT364 | 7.9 | 0.5 | 13.8 | 87 | 5 | 0 | | 4 |  |
| AT365 | 7.9 | 0.5 | 13.6 | 100 | 3 | 0 | | 2 |  |
| AT366 | 7.8 | 0.1 | 17.8 | 100 | 5 | 0 | | 5 | 17 |
| AT369 | 8.1 | 0.2 | 8.25 | 100 | 5 | 0 | | 5 | 27 |
| AT475 | 8.1 | 0.7 | 7.9 | 96 | 4 | 0 | | 2 |  |
| AT545 | 7.8 | 0.4 | 17.8 | 77 | 3 | 0 | | 2 |  |
| AT546 | 7.9 | 0.1 | 12.6 | 95 | 2 | 0 | | 2 |  |
| AT547 | 8.1 | 0.1 | 7.94 | 100 | 2 | 0 | | 2 |  |
| AT548 | 6.9 | 0.1 | 126 | 86 | 2 | 0 | | 2 |  |
| AT549 | 6.7 | 0.3 | 200 | 80 | 2 | 0 | | 2 |  |
| AT560 | 7.6 | 0.2 | 23.3 | 100 | 3 | | | | |
| AT561 | 8.0 | 0.4 | 11.2 | 97 | 4 | 0 | | 3 |  |
| AT562 | 8.4 | 0.3 | 3.98 | 82 | 2 | 0 | | 2 |  |
| AT563 | 8.3 | 0.5 | 4.64 | 80 | 3 | 0 | | 2 |  |
| AT586 | 7.6 | 0.4 | 25.1 | 80 | 3 | 0 | | 2 |  |
| AT587 | 8.4 | 0.3 | 3.98 | 90 | 3 | 0 | | 2 | 99 |
| AT588 | 7.6 | 0.2 | 23.3 | 97 | 3 | 0 | | 2 |  |
| AT589 | 8.2 | 0.7 | 5.84 | 95 | 6 | 0 | | 3 | 67 |
| AT590 | 8.3 | 0.4 | 5.41 | 93 | 3 | 0 | | 3 |  |
| AT591 | 7.7 | 0.3 | 21.5 | 92 | 3 | 0 | | 3 |  |
| AT592 | 8.2 | 0.1 | 6.31 | 88 | 3 | 0 | | 3 |  |
| AT593 | 7.2 | 0.1 | 63.1 | 86 | 3 | 0 | | 2 |  |
| AT594 | 7.1 | 0.3 | 79.4 | 80 | 3 | 0 | | 2 |  |
| AT597 | 7.1 | 0.3 | 79.4 | 81 | 2 | 0 | | 0 |  |
| AT602 | 7.5 | 0.5 | 35.5 | 100 | 2 | 0 | | 3 |  |
| AT605 | 8.1 | 0.0 | 7.93 | 85 | 2 | 0 | | 2 |  |
| AT613 | 8.8 | 0.4 | 1.47 | 100 | 3 | 0 | | 3 |  |
| AT614 | 9.0 | 0.2 | 1.08 | 100 | 3 | 0 | | 3 | 43 |
| AT615 | 8.1 | 0.2 | 7.94 | 97 | 3 | 0 | | 3 |  |
| AT616 | 9.3 | 0.5 | 0.473 | 100 | 4 | 0 | | 4 | 49 |
| AT617 | 9.1 | 0.4 | 0.794 | 91 | 3 | 0 | | 4 |  |
| AT618 | 8.4 | 0.4 | 3.98 | 100 | 3 | 0 | | 3 | 35 |
| AT619 | 8.7 | 0.5 | 2.19 | 87 | 5 | 0 | | 3 | 36 |
| AT620 | 7.5 | 0.1 | 31.6 | 83 | 2 | 0 | | 2 |  |
| AT621 | 8.9 | 0.5 | 1.36 | 93 | 3 | 0 | | 2 |  |
| AT622 | 7.5 | 0.4 | 31.6 | 77 | 2 | 14 | 11 | 2 |  |
| AT623 | 8.5 | 0.3 | 3.16 | 98 | 2 | 0 | | 2 |  |

TABLE 1C-continued

Antagonistic, agonistic properties and for some the half-life, Elimination T½ of the GIP antagonists with extensions. The CisBio Assay (Alternative 2 above) was used to determine antagonistic and agonistic activities of the GIP peptide analogues listed in Table 1B.

| ID | cAMP antagonism | | | | | cAMP agonism | | | T½ (hours) |
|---|---|---|---|---|---|---|---|---|---|
| | pIC50 | SD | nM | % inhib | n | % Emax | SD | n | |
| AT624 | ~7 | | 100 | ~90 | 3 | 0 | | 2 | |
| AT625 | 8.4 | 0.4 | 3.98 | 93 | 2 | 0 | | 2 | |
| AT626 | 8.4 | 0.4 | 4.47 | 100 | 2 | 0 | | 2 | |
| AT627 | 7.8 | 0.2 | 15.9 | 97 | 3 | 0 | | 2 | |
| AT628 | 7.2 | 0.2 | 58.4 | 94 | 3 | 0 | | 2 | |
| AT629 | 7.8 | 0.4 | 17.1 | 93 | 3 | 0 | | 2 | |
| AT630 | 8.0 | 0.5 | 11.2 | 85 | 4 | 0 | | 3 | |
| AT631 | 7.9 | 0.5 | 13.8 | 87 | 5 | 0 | | 4 | |
| AT632 | 8.1 | 0.2 | 8.41 | 100 | 4 | 0 | | 5 | |
| AT633 | ~8.8 | | | | 3 | 23 | 7 | 2 | |
| AT635 | 9.0 | 0.4 | 1.12 | 87 | 2 | 5 | 7 | 2 | |
| AT636 | 8.8 | 0.8 | 1.71 | 87 | 3 | 0 | | 2 | |
| AT637 | 8.7 | 0.1 | 2.23 | 89 | 2 | 0 | | 2 | |
| AT638 | 7.8 | 0.6 | 14.7 | 85 | 3 | 0 | | 2 | |
| AT639 | 7.2 | 0.6 | 66.8 | 100 | 3 | 0 | | 4 | 27 |
| AT640 | 8.2 | 0.2 | 7.08 | 90 | 2 | 0 | | 2 | |
| AT641 | 8.1 | 0.3 | 7.94 | 91 | 2 | 0 | | 2 | |
| AT642 | 7.5 | 0.1 | 35.5 | 92 | 2 | 0 | | 2 | |
| AT643 | 8.0 | 0.1 | 11.2 | 90 | 2 | 0 | | 2 | |
| AT644 | 7.8 | 0.4 | 17.13 | 93 | 3 | 0 | | 2 | |
| AT646 | 8.0 | 0.3 | 10.0 | 96 | 2 | 0 | | 2 | |
| AT647 | 7.7 | 0.1 | 18.8 | 100 | 4 | 0 | | 5 | |
| AT650 | 8.4 | 0.2 | 3.69 | 94 | 3 | 0 | | 2 | |
| AT651 | ~8.9 | | | 36 | 3 | 19 | 12 | 2 | |
| AT652 | 8.0 | 0.6 | 10.593 | 60 | 4 | 17 | 12 | 2 | |
| AT665 | 9.8 | 0.9 | 0.150 | 88 | 3 | 0 | | 2 | |
| AT666 | | | | | | | | | |
| AT667 | 9.1 | 0.8 | 0.736 | 86 | 3 | 4 | 3 | 2 | |
| AT668 | 9.0 | 0.7 | 0.944 | 92 | 4 | 0 | | 2 | |
| AT669 | 8.5 | 0.5 | 3.35 | 95 | 4 | 0 | | 2 | |
| AT670 | 8.0 | 0.6 | 10.0 | 92 | 3 | 0 | 0 | 2 | |
| AT671 | | | | | | | | | |
| AT672 | | | | | | | | | |
| AT673 | 9.9 | 0.5 | 0.136 | 94 | 3 | 0 | 0 | 2 | |
| AT674 | 9.4 | 0.1 | 0.447 | 93 | 3 | 0 | 0 | 2 | |
| AT675 | 8.4 | 0.2 | 4.30 | 90 | 3 | 3 | 4 | 2 | |
| AT676 | 8.6 | 0.6 | 2.33 | 91 | 3 | 0 | 0 | 2 | |
| AT677 | 9.4 | 0.4 | 0.447 | 93 | 3 | 0 | 0 | 2 | |
| AT680 | 8.4 | 0.2 | 4.30 | 93 | 3 | 0 | 0 | 2 | |
| AT681 | 8.5 | 0.4 | 3.42 | 85 | 3 | 7 | 1 | 2 | |
| AT682 | 7.9 | 0.2 | 13.6 | 89 | 3 | 0 | 0 | 2 | |
| AT683 | 7.8 | 0.1 | 15.9 | 93 | 3 | 0 | 0 | 2 | |
| AT684 | | | | | | | | | |
| AT685 | | | | | | | | | |
| AT686 | | | | | | | | | |
| AT687 | | | | | | | | | |
| AT689 | 8.0 | 0.3 | 10.0 | 82 | 3 | 3 | 4 | 2 | |
| AT690 | 7.8 | 0.4 | 15.9 | 76 | 3 | 6 | 1 | 2 | |
| AT691 | 7.8 | 0.6 | 20.0 | 75 | 4 | 7 | 1 | 2 | |
| AT693 | 8.9 | 0.3 | 1.26 | 96 | 3 | 0 | | 2 | |
| AT694 | 8.8 | 0.4 | 1.47 | 88 | 3 | 4 | 5 | 2 | |
| AT695 | 9.1 | 0.3 | 0.794 | 98 | 3 | 0 | | 2 | |
| AT696 | 9.2 | 0.4 | 0.584 | 97 | 3 | 0 | | 2 | |
| AT697 | 8.6 | 0.4 | 2.82 | 81 | 3 | 8 | 0 | 2 | |
| AT698 | 8.0 | 0.5 | 9.26 | 78 | 3 | 8 | 1 | 2 | |
| AT699 | 8.2 | 0.3 | 6.31 | 88 | 3 | 0 | | 2 | |
| AT700 | 9.2 | 0.4 | 0.708 | 89 | 3 | 3 | 4 | 2 | |
| AT701 | 7.9 | 0.1 | 12.6 | 63 | 3 | 13 | 0 | 2 | |
| AT702 | 8.5 | 0.1 | 3.55 | 85 | 3 | 0 | | 2 | |
| AT703 | 8.6 | 0.1 | 4.30 | 93 | 3 | 0 | 0 | 2 | |

The half-life of AT631 is determined based on RIA and the half-life of AT361 is determined based on LC/MS (see "Materials and methods").

TABLE 2A

The average and time-dependent plasma concentrations in Wistar rats are displayed for a selected number of compounds. Plasma concentrations were determined by LC/MS (see "Materials and methods").

| Sample times (hours) | AT361 | AT631 | AT366 | AT632 | AT433 | AT447 | AT449 | AT452 | AT651 |
|---|---|---|---|---|---|---|---|---|---|
| Pre-dose | <1 | <1 | <1 | <0.2 | <0.2 | <10 | <2 | <4 | <2 |
| 0.5 | 66 | 67 | 117 | 84 | 101 | 124 | 100 | 136 | 19 |
| 1 | 55 | 48 | 94 | 58 | 74 | na | na | na | na |
| 1.5 | 55 | 43 | 82 | 57 | 65 | 82 | 72 | 85 | 2 |
| 3 | 42 | 37 | 62 | 43 | 50 | 59 | 48 | 62 | <2 |
| 6 | 33 | 25 | 44 | 35 | 38 | 45 | 39 | 44 | <2 |
| 24 | 4.6 | 3.2 | 6.5 | 5.5 | 9.9 | <10 | 2 | <4 | <2 |
| 26 | 3.4 | 2.4 | 6.9 | 5.1 | 8.7 | na | na | na | na |
| 28 | 2.7 | 2.4 | 4.9 | 4.4 | 7.9 | na | na | na | na |
| 30 | 1.9 | 1.6 | 4.5 | 3.4 | 6.9 | <10 | <2 | <4 | <2 |
| 48 | 0.8 | <1 | <1 | 0.6 | 1.9 | <10 | <2 | <4 | <2 |
| 72 | 0.4 | <1 | <1 | <0.2 | <0.2 | na | na | na | na | na: indicates that this timepoint/plasma samples was not taken and is thus, not available

TABLE 2B

Elimination T½ in Wistar are displayed for a selected number of compounds where the data sets enabled the calculations (see "Materials and methods").

| ID | T½ (hours) |
|---|---|
| AT361 | 11 |
| AT631 | 7 |
| AT366 | 7 |
| AT632 | 8 |
| AT433 | 8 |
| AT447 | 5.8 |
| AT449 | 4.1 |
| AT452 | 4 |

Example 2—Selectivity cAMP Assay—Selectivity

Transient transfected COS-7 cells expressing the either of the GLP1 receptor (GLP1R), GLP2 receptor (GLP2R), glucagon receptor (GcgR) or secretin receptor (SCTR) were seeded in white 96-well plates with a density of 3.5*10⁴/ well. The day after, the cells were washed twice with Hepes buffered saline (HBS) buffer and incubated with HBS and 1 mM 3-isobutyl-1-methylxanthine (IBMX) for 30 min at 37° C. To test for agonistic properties, ligands were added and incubated for 30 min at 37° C. In order to test for antagonistic properties, the cells were preincubated with the antagonists for 10 min prior to the addition the natural agonist for the expressed receptor (GLP1 for GLP1R expressing cells, GLP2 for GLP2R expressing cells, glucagon for the GcgR and secretin for the SCTR) and subsequent incubated for 20 additional min. To determine the IC50, a concentration of the natural agonist was used corresponding to 50-80% of maximal cAMP accumulation. The Hit-Hunter™ cAMP XS assay (DiscoveRx) was carried out according to the manufacturer's instructions.

Results:

We compared the selectivity data of the best antagonists from PCT/EP2018/064355 to the best antagonists in this application. This was done by determining antagonistic properties of the peptides for GIPR, Glucagon receptor and GLP-1 receptor. As shown by the data in Table 3, antagonists in this application were more selective than the ones from PCT/EP2018/064355. The combination of a C-terminal extension of GIP(3-30) (as in e.g. AT361 and AT631) and acylation on a lysine in e.g. position 18 seems to generate surprisingly selective antagonists.

TABLE 3A

Antagonistic properties in relation to GIPR, Glucagon receptor and GLP-1 receptor of GIP antagonists of the present disclosure and previously described in PCT/EP2018/064355.

| | GIPR, Antagonism | | GLP-1R, Antagonism | | | | | Glucagon R, Antagonism | | | | |
|---|---|---|---|---|---|---|---|---|---|---|---|---|
| ID | nM | % inhib | index | log | nM | % inhib | n | index | log | nM | % inhib | n |
| *AT117* | *15* | *NA* | *2.7* | *−7.4* | *41* | *41* | *3* | *Not tested* | | | | |
| *AT158* | *5* | *NA* | *57* | *−6.5* | *336* | *54* | *3* | *92* | *−6.3* | *548* | *54* | *2* |
| *AT198* | *11* | *NA* | *62* | *−6.2* | *617* | *91* | *3* | *629* | *−5.2* | *6918* | *50* | *4* |
| AT361 | 2 | 100.0 | 888 | −6.3 | 497 | 28 | 2 | No antagonism | | | | 2 |
| AT631 | 1.9 | | | no antagonism | | | 2 | No antagonism | | | | 2 |

NA = not available

Italics indicates previously described antagonists

Furthermore, antagonistic properties of the peptides for GIPR, GLP-2 receptor and secretin receptor were determined. As shown by the data in Table 3B, GIP analogues of the present invention, such as e.g. AT361 and AT631, do not antagonize the GLP-2 or secretin receptor and are thus very selective for the GIP receptor.

TABLE 3B

Antagonistic properties in relation to GIPR, GLP-2 receptor and Secretin receptor of GIP antagonists of the present disclosure.

| | GIPR, Antagonism | GLP-2R, Antagonism | | | | Secretin R, Antagonism | | | |
|---|---|---|---|---|---|---|---|---|---|
| ID | nM | index | log | nM | % inhib | n | indeX | log | nM | % inhib | n |
| AT361 | 2 | No antagonism | | | | 2 | No antagonism | | | | 2 |
| AT631 | 1.9 | No antagonism | | | | 2 | No antagonism | | | | 2 |

SEQUENCE LISTING

```
<SEQ ID NO: 1; PRT1; Artificial sequence> XXTFISDYSIAMDKIHQQDFVNWLLAQK
(SEQ ID NO: 1)

<SEQ ID NO: 2; PRT1; Artificial sequence> GKKNDWKHNITQ GIP(31-42) (SEQ ID
NO: 2)

<SEQ ID NO: 3; PRT1; Artificial sequence>
HGEGTFTSDLSKQMEEEAVRLFIEWLKNGGPSSGAPPPS Exendin-4 (; SEQ ID NO:
3)

<SEQ ID NO: 4; PRT1; Artificial sequence> PSSGAPPPS (; SEQ ID NO: 4 CE31-39)

<SEQ ID NO: 5; PRT1; Artificial sequence> GPSSGAPPPS (; SEQ ID NO: 5 CE30-39)

<SEQ ID NO: 6; PRT1; Artificial sequence> GPSS

<SEQ ID NO: 7; PRT1; Artificial sequence> GPSSG

<SEQ ID NO: 8; PRT1; Artificial sequence> GPSSGA

<SEQ ID NO: 9; PRT1; Artificial sequence> GPSSGAP

<SEQ ID NO: 10; PRT1; Artificial sequence> GPSSGAPP

<SEQ ID NO: 11; PRT1; Artificial sequence> GPSSGAPPP

<SEQ ID NO: 12; PRT1; Artificial sequence> PSSG

<SEQ ID NO: 13; PRT1; Artificial sequence> PSSGA

<SEQ ID NO: 14; PRT1; Artificial sequence> PSSGAP

<SEQ ID NO: 15; PRT1; Artificial sequence> PSSGAPP

<SEQ ID NO: 16; PRT1; Artificial sequence> PSSGAPPP

<SEQ ID NO: 17; PRT1; Artificial sequence> GKKN

<SEQ ID NO: 18; PRT1; Artificial sequence> GKKND

<SEQ ID NO: 19; PRT1; Artificial sequence> GKKNDW

<SEQ ID NO: 20; PRT1; Artificial sequence> GRKNDW

<SEQ ID NO: 21; PRT1; Artificial sequence> GKRNDW

<SEQ ID NO: 22; PRT1; Artificial sequence> GRRNDW

<SEQ ID NO: 23; PRT1; Artificial sequence> GKKNDWK

<SEQ ID NO: 24; PRT1; Artificial sequence> GKKNDWKH

<SEQ ID NO: 25; PRT1; Artificial sequence> GKKNDWKHN

<SEQ ID NO: 26; PRT1; Artificial sequence> GKKNDWKHNI

<SEQ ID NO: 27; PRT1; Artificial sequence> GKKNDWKHNIT

<SEQ ID NO: 28; PRT1; Artificial sequence> GKKKDW

<SEQ ID NO: 29; PRT1; Artificial sequence> GKKNDK

<SEQ ID NO: 30; PRT1; Artificial sequence> EXTFISDYSIAMDKIHQQDFVNWLLAQK
SEQ ID NO: 30 (GIP3-30 $X_2$), <SEQ ID NO: 31; PRT1; Artificial sequence> XGTFISDYSIAMDKIHQQDFVNWLLAQK
SEQ ID NO: 31 (GIP3-30 $X_1$), <SEQ ID NO: 32; PRT1; Artificial sequence> EGTFISDYSIAMDKIHQQDFVNWLLAQK
SEQ ID NO: 32 (GIP3-30), <SEQ ID NO: 33; PRT1; Artificial sequence> XTFISDYSIAMDKIHQQDFVNWLLAQK
SEQ ID NO: 33 (GIP4-30 $X_2$), <SEQ ID NO: 34; PRT1; Artificial sequence> GTFISDYSIAMDKIHQQDFVNWLLAQK
SEQ ID NO:3 4 (GIP4-30),
```

-continued

<SEQ ID NO: 35; PRT1; Artificial sequence> TFISDYSIAMDKIHQQDFVNWLLAQK
SEQ ID NO: 35 (GIP5-30), <SEQ ID NO: 36; PRT1; Artificial sequence> FISDYSIAMDKIHQQDFVNWLLAQK
SEQ ID NO: 36 (GIP6-30), <SEQ ID NO: 37; PRT1; Artificial sequence> EGTFISDYSIAMDKIHQQDFVNWLLAQK
SEQ ID NO: 37; GIP(3-30), <SEQ ID NO: 38; PRT1; Artificial sequence> EGTFISDYSIAMDKIKQQDFVNWLLAQK
SEQ ID NO: 38; GIP(3-30) [H18K]

<SEQ ID NO: 39; PRT1; Artificial sequence> SGTFISDYSIAMDKIKQQDFVNWLLAQK
SEQ ID NO: 39 ; GIP(3-30) [E3S; H18K], <SEQ ID NO: 40; PRT1; Artificial sequence> EGTFISDYSIALDKIKQQDFVNWLLEQK
GIP(3-30) Cex(31-39) [M14L; H18K; A28E]

<SEQ ID NO: 41; PRT1; Artificial sequence>
EGTFISDYSIAMDKIKQQDFVNWLLAQPSSGAPPPS(NH$_2$)2xAEEAc + yGlu-C18-
diacid/K18; (3-30 + CEX32-39 [H18L][Q29G][K30P]), AT593

<SEQ ID NO: 42; PRT1; Artificial sequence> SGTFISDYSIAMDRIKQQDFVNWLLAQR
GIP(3-30) [E3S; K16R; H18K; K30R], <SEQ ID NO: 43; PRT1; Artificial sequence> EGTFISDYKIAMDKIHQQDFVNWLLAQK
GIP(3-30) [S11K], <SEQ ID NO: 44; PRT1; Artificial sequence>
EGTFISDYSKAMDKIHQQDFVNWLLAQK GIP(3-30) [I12K], <SEQ ID NO: 45; PRT1; Artificial sequence> EGTFISDYSIAMDKIHQKDFVNWLLAQK
GIP(3-30) [Q20K], <SEQ ID NO: 46; PRT1; Artificial sequence> EGTFISDYSIAMDKIHQQDFVKWLLAQK
GIP(3-30) [N24K], <SEQ ID NO: 47; PRT1; Artificial sequence>
EGTFISDYSIAMDKKHQQDFVNWLLAQK GIP(3-30) [I17K], <SEQ ID NO: 48; PRT1; Artificial sequence> EGTFISDYSIAMDKIKQQDFVNWLLAQG
GIP(3-30) [H18K; K30G], <SEQ ID NO: 49; PRT1; Artificial sequence> EGTFISDYSIAMDKIKQQDFVNWLLAGG
GIP(3-30) [H18K; Q29G; K30G], <SEQ ID NO: 50; PRT1; Artificial sequence> EGTFISEYSIAMEKIKQQEFVQWLLAQK
GIP(3-30) [D9E; D15E; H18K; D21E; N24Q], <SEQ ID NO: 51; PRT1; Artificial sequence> EGTFISEYSIAMEKIKQQDFVQWLLAQK
GIP(3-30) [D9E; D15E; H18K; N24Q], <SEQ ID NO: 52; PRT1; Artificial sequence>
EGTFISEYSAibANleEKIKQQDFVEWLLAQK GIP(3-30)
[D9E; I12Aib; M14Nle; D15E; H18K; N24E], <SEQ ID NO: 53; PRT1; Artificial sequence>
EGTFISEYSIAibMEKIKQQDFVEWLLAQK GIP(3-30)
[D9E; A13Aib; D15E; H18K; N24E], <SEQ ID NO: 54; PRT1; Artificial sequence> EGTFISDYSIAMDKIKQQDFVEWLLAQK
GIP(3-30) [H18K; N24E], <SEQ ID NO: 55; PRT1; Artificial sequence> EGTFISDYSIALDKIKQQDFVNWLLAQK
GIP(3-30) [M14L; H18K], <SEQ ID NO: 56; PRT1; Artificial sequence>
EGTFISDYSIANleDKIKQQDFVNWLLAQK GIP(3-30) [M14Nle; H18K], <SEQ ID NO: 57; PRT1; Artificial sequence> EGTFISDYSIAEDKIKQQDFVNWLLAQK
GIP(3-30) [M14E; H18K], <SEQ ID NO: 58; PRT1; Artificial sequence> EGTFISDYSIAKDKIKQQDFVNWLLAQK
GIP(3-30) [M14K; H18K], <SEQ ID NO: 59; PRT1; Artificial sequence> EGTFISDYSIASDKIKQQDFVNWLLAQK
GIP(3-30) [M14S; H18K], <SEQ ID NO: 60; PRT1; Artificial sequence> EGTFISDYSIAMDKIKQQDFVEWLLAQA GIP(3-30) [H18K; N24E; K30A], <SEQ ID NO: 61; PRT1; Artificial sequence> EGTFISDYSIAMDKIKQQDFVNWLLEQK GIP(3-30) [H18K; A28E], <SEQ ID NO: 62; PRT1; Artificial sequence> VGTFISDYSIAMDKIKQQDFVNWLLAQK GIP(3-30) [E3V; H18K], <SEQ ID NO: 63; PRT1; Artificial sequence> AibGTFISDYSIAMDKIKQQDFVNWLLAQK GIP(3-30) [E3Aib; H18K], <SEQ ID NO: 64; PRT1; Artificial sequence> PGTFISDYSIAMDKIKQQDFVNWLLAQK GIP(3-30) [E3P; H18K], <SEQ ID NO: 65; PRT1; Artificial sequence> VETFISDYSIAMDKIKQQDFVNWLLAQK GIP(3-30) [E3V; G4E; H18K], <SEQ ID NO: 66; PRT1; Artificial sequence> AibETFISDYSIAMDKIKQQDFVNWLLAQK GIP(3-30) [E3Aib; G4E; H18K], <SEQ ID NO: 67; PRT1; Artificial sequence> GETFISDYSIAMDKIKQQDFVNWLLAQK GIP(3-30) [E3G; G4E; H18K], <SEQ ID NO: 68; PRT1; Artificial sequence> PETFISDYSIAMDKIKQQDFVNWLLAQK GIP(3-30) [E3P; G4E; H18K], <SEQ ID NO: 69; PRT1; Artificial sequence> DTTFISDYSIAMDKIKQQDFVNWLLAQK GIP(3-30) [E3D; G4T; H18K], <SEQ ID NO: 70; PRT1; Artificial sequence> GETFISDYAIALDKIKQQDFVEWLLAQG GIP(3-30) [E3G; G4E; S11A; M14L; H18K; N24E; K30G], <SEQ ID NO: 71; PRT1; Artificial sequence> GETFISTYSIALDKIKQQDFVEWLLAQG GIP(3-30) [E3G; G4E; D9T; M14L; H18K; N24E], <SEQ ID NO: 72; PRT1; Artificial sequence> EGTFISTYKIALDKIHQQDFVEWLLAQK GIP(3-30) [D9T; S11K; M14L; N24E], <SEQ ID NO: 73; PRT1; Artificial sequence> EGTFISDYSIAibMDKIKQQDFVEWLLAQK GIP(3-30) [A13Aib; H18K; N24E], <SEQ ID NO: 74; PRT1; Artificial sequence> EGTFISDYSIAibLDKIKQQDFVEWLLAQK GIP(3-30) [A13Aib; M14L; H18K; N24E], <SEQ ID NO: 75; PRT1; Artificial sequence> EGTFISDYSIAibNleDKIKQQDFVEWLLAQK GIP(3-30) [A13Aib; M14Nle; H18K; N24E], <SEQ ID NO: 76; PRT1; Artificial sequence> EGTFISDYSIALDKIKQQDFVEWLLAQK GIP(3-30) [M14L; H18K; N24E], <SEQ ID NO: 77; PRT1; Artificial sequence> EGTFISDYSIANleDKIKQQDFVEWLLAQK GIP(3-30) [M14Nle; H18K; N24E], <SEQ ID NO: 78; PRT1; Artificial sequence> EGTFISDYSIAKDKIKQQDFVEWLLAQK GIP(3-30) [M14K; H18K; N24E], <SEQ ID NO: 79; PRT1; Artificial sequence> EGTFISDYSIANleDKIKQQDFVNWLLAGG GIP(3-30) [M14Nle; H18K; Q29G; K30G], <SEQ ID NO: 80; PRT1; Artificial sequence> EGTFISDYSIANleDKIKQQDFVEWLLAGG GIP(3-30) [M14Nle; H18K; N24E; Q29G; K30G], <SEQ ID NO: 81; PRT1; Artificial sequence> EGTFISEYSIAibLEKIKQQEFVEWLLAQK GIP(3-30)[D9E; A13Aib; M14L; D15E; H18K; D21E; N24E], <SEQ ID NO: 82; PRT1; Artificial sequence> EGTFISEYSIAibNleEKIKQQEFVEWLLAQK GIP(3-30) [D9E; A13Aib; M14Nle; D15E; H18K; D21E; N24E], <SEQ ID NO: 83; PRT1; Artificial sequence> yGluGTFISDYSIAMDKIKQQDFVNWLLAQK GIP(3-30) [E3yGlu; H18K], <SEQ ID NO: 84; PRT1; Artificial sequence> βGluGTFISDYSIAMDKIKQQDFVNWLLAQK GIP(3-30) [E3βGlu; H18K], <SEQ ID NO: 85; PRT1; Artificial sequence> XGTFISDYSIAMDKIKQQDFVNWLLAQK GIP(3-30) [E3Glutaric acid(X); H18K], -continued <SEQ ID NO: 86; PRT1; Artificial sequence> EGTFISDYSIALDKIKQQDFVEWLLAGG
GIP(3-30) [M14L; H18K; N24E; Q29G; K30G], <SEQ ID NO: 87; PRT1; Artificial sequence> EGTFISEYSIALEKIKQQEFVEWLLAQK
GIP(3-30)[D9E; M14L; D15E; H18K; D21E; N24E], <SEQ ID NO: 88; PRT1; Artificial sequence>
EGTFISEYSIANleEKIKQQEFVEWLLAQK GIP(3-30)
[D9E; M14Nle; D15E; H18K; D21E; N24E], <SEQ ID NO: 89; PRT1; Artificial sequence>
yGluGTFISDYSIANleDKIKQQDFVEWLLAQK GIP(3-30) [E3yGlu(L-
isomer); M14Nle; H18K; N24E], <SEQ ID NO: 90; PRT1; Artificial sequence>
yGluGTFISDYSIANleDKIKQQDFVEWLLAQK GIP(3-30) [E3yGlu(D-
isomer); M14Nle; H18K; N24E], <SEQ ID NO: 91; PRT1; Artificial sequence>
βGluGTFISDYSIANleDKIKQQDFVEWLLAQK GIP(3-30)
[E3βGlu; M14Nle; H18K; N24E], <SEQ ID NO: 92; PRT1; Artificial sequence>
XGTFISDYSIANleDKIKQQDFVEWLLAQK GIP(3-30) [E3Glutaric
acid(X); M14Nle; H18K; N24E], <SEQ ID NO: 93; PRT1; Artificial sequence>
βGluGTFISDYSIAibNleDKIKQQDFVNWLLAQK (3-30 E3βGlu A13Aib M14Nle H18K)

<SEQ ID NO: 94; PRT1; Artificial sequence> EGTFISDYSIALDKIKQQDFVNWLLEGG
GIP(3-30) [M14L; H18K; A28E; Q29G; K30G]

<SEQ ID NO: 95; PRT1; Artificial sequence>
EGTFISDYSIANleDKIKQQDFVNWLLEQK GIP(3-30) Cex(31-39)
[M14Nle; H18K; A28E]

<SEQ ID NO: 96; PRT1; Artificial sequence> TFISDYSIAMDKIHQQDFVNWLLAQK
GIP(5-30)

<SEQ ID NO: 97; PRT1; Artificial sequence> TFISDYKIAMDKIHQQDFVNWLLAQK
GIP(5-30) [S11K], <SEQ ID NO: 98; PRT1; Artificial sequence>
EGTFISDYSIAMDKIKQQDFVNWLLAQKPSSGAPPPSK(NH2) C16-diacid/K40; GIP(3-
30 + CEX31-39 + K), Phenyl lactic acid at N-terminus, AT651

<SEQ ID NO: 99; PRT1; Artificial sequence>
PGTFISDYSIAMDKIKQQDFVNWLLAQKPSSGAPPPSK(NH2) C16-diacid/K40; GIP(3-
30 + CEX31-39 + K), Phenyl lactic acid at N-terminus, AT652

<SEQ ID NO: 100; PRT1; Artificial sequence> TFISDYSIAMDKIKQQDFVNWLLAQK
GIP(5-30) [H18K], <SEQ ID NO: 101; PRT1; Artificial sequence> TFISDYKIAMDRIHQQDFVNWLLAQR
GIP(5-30) [S11K; K16R; K30R], <SEQ ID NO: 102; PRT1; Artificial sequence> TFISDYSKAMDKIHQQDFVNWLLAQK
GIP(5-30) [I12K], <SEQ ID NO: 103; PRT1; Artificial sequence> TFISDYSIAMDKIHQKDFVNWLLAQK
GIP(5-30) [Q20K], and <SEQ ID NO: 104; PRT1; Artificial sequence> TFISDYSIAMDKIHQQDFVKWLLAQK
GIP(5-30) [N24K], <SEQ ID NO: 105; PRT1; Artificial sequence> FISDYSIAMDKIKQQDFVNWLLAQK
GIP(6-30) [H18K], <SEQ ID NO: 106; PRT1; Artificial sequence>
EGTFISDYSIAMDKIKQQDFVNWLLAQKGKKNDW 2xAEEAc + y-glu-C16-diacid/K18;
GIP(3-36 H18K), AT415

<SEQ ID NO: 107; PRT1; Artificial sequence>
EGTFISDYSIAMDKIKQQDFVNWLLAQKPSSGAPPPS-
C16-diacid/K18; GIP(3-30 + CEX31-39 H18K), AT631, <SEQ ID NO: 108; PRT1; Artificial sequence>
EGTFISDYSIAMDKIKQQDFVNWLLAQKPSSGAPPPS(NH2) 2xAEEAc + yGlu-C18-
diacid/K18; GIP(3-30 + CEX31-39 H18K), AT587

<SEQ ID NO: 109; PRT1; Artificial sequence>
EGTFISDYSIAMDKIKQQDFVNWLLAQKGPSSGAPPPS
2xAEEAc + y-glu-C16-diacid/K18: GIP(3-30 + CEX H18K), AT431

<SEQ ID NO: 110; PRT1; Artificial sequence>
EGTFISDYSIAMDKIKQQDFVNWLLAQKGPSSGAPPPS(NH2)
2xAEEAc + yGlu-C18-diacid/K18; GIP(3-30 + CEX31-39 H18K), AT588, <SEQ ID NO: 111; PRT1; Artificial sequence>
EGTFISDYSIAMDKIKQQDFVNWLLAQKGPSSGAPPP C16-diacid/K18; GIP(3-
30 + CEX 9 H18K), AT467

<SEQ ID NO: 112; PRT1; Artificial sequence>
EGTFISDYSIAMDKIKQQDFVNWLLAQKGPSSGAPP C16-diacid/K18; GIP(3-30 + CEX
8 H18K), AT468

<SEQ ID NO: 113; PRT1; Artificial sequence>
EGTFISDYSIAMDKIKQQDFVNWLLAQKGPSSGAP C16-diacid/K18; GIP(3-30 + CEX 7
H18K), AT469

<SEQ ID NO: 114; PRT1; Artificial sequence>
EGTFISDYSIAMDKIKQQDFVNWLLAQKGPSSGA C16-diacid/K18; GIP(3-30 + CEX 6
H18K), AT470

<SEQ ID NO: 115; PRT1; Artificial sequence>
EGTFISDYSIAMDKIKQQDFVNWLLAQKGPSSG C16-diacid/K18; GIP(3-30 + CEX 5
H18K), AT471

<SEQ ID NO: 116; PRT1; Artificial sequence>
EGTFISDYSIAMDKIKQQDFVNWLLAQKGPSS C16-diacid/K18; GIP(3-30 + CEX 4
H18K), AT472

<SEQ ID NO: 117; PRT1; Artificial sequence>
EGTFISDYSIAMDKIKQQDFVNWLLAQKGPS C16-diacid/K18 GIP(3-30 + CEX 3
H18K), AT473

<SEQ ID NO: 118; PRT1; Artificial sequence>
EGTFISDYSIAMDKIKQQDFVNWLLAQKGP C16-diacid/K18 GIP(3-30 + CEX 2 H18K),
AT474

<SEQ ID NO: 119; PRT1; Artificial sequence>
EGTFISDYSIAMDKIKQQDFVNWLLAQKG-C16-diacid/K18 GIP(3-31 H18K), AT447

<SEQ ID NO: 120; PRT1; Artificial sequence>
EGTFISDYSIAMDKIKQQDFVNWLLAQKGK C16-diacid/K18 GIP(3-32 H18K), AT448

<SEQ ID NO: 121; PRT1; Artificial sequence>
EGTFISDYSIAMDKIKQQDFVNWLLAQKGKK C16-diacid/K18 GIP(3-33 H18K), AT360

<SEQ ID NO: 122; PRT1; Artificial sequence>
EGTFISDYSIAMDKIKQQDFVNWLLAQKGKKN C16-diacid/K18 GIP(3-34 H18K),
AT449

<SEQ ID NO: 123; PRT1; Artificial sequence>
EGTFISDYSIAMDKIKQQDFVNWLLAQKGKKND C16-diacid/K18 GIP(3-35 H18K),
AT450

<SEQ ID NO: 124; PRT1; Artificial sequence>
EGTFISDYSIAMDKIKQQDFVNWLLAQKGKKNDWK C16-diacid/K18 GIP(3-37 H18K),
AT451

<SEQ ID NO: 125; PRT1; Artificial sequence>
EGTFISDYSIAMDKIKQQDFVNWLLAQKGKKNDWKH C16-diacid/K18 GIP(3-38
H18K), AT452

<SEQ ID NO: 126; PRT1; Artificial sequence>
EGTFISDYSIAMDKIKQQDFVNWLLAQKGKKNDWKHN C16-diacid/K18 GIP(3-39
H18K), AT462

<SEQ ID NO: 127; PRT1; Artificial sequence>
EGTFISDYSIAMDKIKQQDFVNWLLAQKGKKNDWKHNI C16-diacid/K18 GIP(3-40
H18K), AT453

<SEQ ID NO: 128; PRT1; Artificial sequence>
EGTFISDYSIAMDKIKQQDFVNWLLAQKGKKNDWKHNIT C16-diacid/K18: SEQ ID
NO: (3-41 H18K), AT454

<SEQ ID NO: 129; PRT1; Artificial sequence>
EGTFISDYSIAMDKIKQQDFVNWLLAQKGKKNDWKHNITQ C16-diacid/K18 GIP(3-42
H18K), AT363

<SEQ ID NO: 130; PRT1; Artificial sequence>
SGTFISDYSIAMDKIKQQDFVNWLLAQKGKKNDW 2xAEEAc + y-glu-C16-diacid/K18;
GIP(3-36 E3S H18K), AT419

<SEQ ID NO: 131; PRT1; Artificial sequence>
SGTFISDYSIAMDKIKQQDFVNWLLAQKGPSSGAPPPS 2xAEEAc + y-glu-C16-
diacid/K18 GIP(3-30 + CEX E35 H18K), AT435

<SEQ ID NO: 132; PRT1; Artificial sequence>
SGTFISDYSIAMDRIKQQDFVNWLLAQRGRRNDW 2xAEEAc + y-glu-C16-diacid/K18;
GIP(3-30 E35 K16R H18K K30R), AT423

<SEQ ID NO: 133; PRT1; Artificial sequence>
SGTFISDYSIAMDRIKQQDFVNWLLAQRGPSSGAPPPS 2xAEEAc+30y-glu-C16-
diacid/K18 GIP(3-30 + CEX E35 K16R H18K K30R), AT439

<SEQ ID NO: 134; PRT1; Artificial sequence>
EGTFISDYKIAMDKIHQQDFVNWLLAQKGKKNDW 2xAEEAc + yGlu-C18-diacid/K11;
GIP(3-36 S11K), AT543

<SEQ ID NO: 135; PRT1; Artificial sequence>
EGTFISDYSKAMDKIHQQDFVNWLLAQKGKKNDW 2xAEEAc + yGlu- C18-diacid/K12;
GIP(3-36 I12K), AT544, <SEQ ID NO: 136; PRT1; Artificial sequence>
EGTFISDYSIAMDKIHQKDFVNWLLAQKPSSGAPPPS(NH$_2$)2xAEEAc + yGlu-C18-
diacid/K20; GIP(3-30 + CEX31-39 Q20K), AT594, <SEQ ID NO: 137; PRT1; Artificial sequence>
EGTFISDYSIAMDKKHQQDFVNWLLAQKPSSGAPPPS(NH$_2$)2xAEEAc + yGlu-C18-
diacid/K17; GIP(3-30 + CEX31-39 I17K), AT586, <SEQ ID NO: 138; PRT1; Artificial sequence>
EGTFISDYSIAMDKIKQQDFVNWLLAQGPSSGAPPPS(NH$_2$)2xAEEAc + yGlu-C18-
diacid; GIP (3-30 + CEX31-39 H18K K30G), AT590

<SEQ ID NO: 139; PRT1; Artificial sequence>
EGTFISDYSIAMDKIKQQDFVNWLLAGGPSSGAPPPS(NH$_2$)2xAEEAc + yGlu-C18-
diacid; GIP(3-30 + CEX31-39 H18K Q29G K30G), AT591

<SEQ ID NO: 140; PRT1; Artificial sequence>
EGTFISDYSIAMDKIKQQDFVNWLLAGGPSSGAPPPS 2xAEEAc + yGlu-C18-diacid;
GIP(3-30 + CEX31-39 H18K Q29G K30G), AT592

<SEQ ID NO: 141; PRT1; Artificial sequence>
EGTFISEYSIAMEKIKQQEFVQWLLAQKPSSGAPPPS C16-diacid; GIP(3-30 + CEX31-
39 D9E; D15E; H18K; D21E; N24Q), AT613, <SEQ ID NO: 142; PRT1; Artificial sequence>
EGTFISEYSIAMEKIKQQDFVEWLLAQKPSSGAPPPS C16-diacid; GIP(3-30) Cex(31-
39) [D9E; D15E; H18K; N24E], AT614

<SEQ ID NO: 143; PRT1; Artificial sequence>
EGTFISEYSAibANleEKIKQQDFVEWLLAQKPSSGAPPPS C16-diacid/18K; GIP(3-
30 + CEX31-39 D9E; I12Aib; M14Nle; D15E; H18K; N24E), AT615, <SEQ ID NO: 144; PRT1; Artificial sequence>
EGTFISEYSIAibMEKIKQQDFVEWLLAQKPSSGAPPPS C16-diacid/18K; GIP(3-30 +
CEX31-39 D9E; A13Aib; D15E; H18K; N24E), AT616, <SEQ ID NO: 145; PRT1; Artificial sequence>
EGTFISDYSIAMDKIKQQDFVEWLLAQKPSSGAPPPS C16-diacid/18K; GIP(3-
30 + CEX31-39 H18K N24E), AT617, <SEQ ID NO: 146; PRT1; Artificial sequence>
EGTFISDYSIALDKIKQQDFVNWLLAQKPSSGAPPPS C16-diacid/18K; GIP(3-
30 + CEX31-39 M14L H18K), AT618,

```
<SEQ ID NO: 147; PRT1; Artificial sequence>
EGTFISDYSIANleDKIKQQDFVNWLLAQKPSSGAPPPS C16-diacid/18K; GIP(3-
30 + CEX31-39 M14Nle H18K), AT619, <SEQ ID NO: 148; PRT1; Artificial sequence>
EGTFISDYSIAEDKIKQQDFVNWLLAQKPSSGAPPPS C16-diacid/18K; GIP(3-
30 + CEX31-39 M14E H18K), AT620, <SEQ ID NO: 149; PRT1; Artificial sequence>
EGTFISDYSIAKDKIKQQDFVNWLLAQKPSSGAPPPS C16-diacid/18K; GIP(3-
30 + CEX31-39 M14K H18K), AT621, <SEQ ID NO: 150; PRT1; Artificial sequence>
EGTFISDYSIASDKIKQQDFVNWLLAQKPSSGAPPPS C16-diacid/18K; GIP(3-
30 + CEX31-39 M14S H18K), AT622

<SEQ ID NO: 151; PRT1; Artificial sequence>
EGTFISDYSIAMDKIKQQDFVEWLLAQAPSSGAPPPS C16-diacid/18K; GIP(3-
30 + CEX31-39 H18K N24E K30A), AT623, <SEQ ID NO: 152; PRT1; Artificial sequence>
EGTFISDYSIAMDKIKQQDFVNWLEAQKPSSGAPPPS C16-diacid/18K; GIP(3-
30 + CEX31-39 H18K L27E), AT624, <SEQ ID NO: 153; PRT1; Artificial sequence>
EGTFISDYSIAMDKIKQQDFVNWLLEQKPSSGAPPPS C16-diacid/18K; GIP(3-
30 + CEX31-39 H18K A28E), AT625, <SEQ ID NO: 154; PRT1; Artificial sequence>
VGTFISDYSIAMDKIKQQDFVNWLLAQKPSSGAPPPS C16-diacid/18K; GIP(3-
30 + CEX31-39 E3V H18K), AT636, <SEQ ID NO: 155; PRT1; Artificial sequence>
AibGTFISDYSIAMDKIKQQDFVNWLLAQKPSSGAPPPS C16-diacid/18K; GIP(3-
30 + CEX31-39 E3Aib H18K), AT637, <SEQ ID NO: 156; PRT1; Artificial sequence>
PGTFISDYSIAMDKIKQQDFVNWLLAQKPSSGAPPPS C16-diacid/18K; GIP(3-
30 + CEX31-39 E3P H18K), AT638, <SEQ ID NO: 157; PRT1; Artificial sequence>
VETFISDYSIAMDKIKQQDFVNWLLAQKPSSGAPPPS C16-diacid/18K; GIP(3-
30 + CEX31-39 E3V G4E H18K), AT639, <SEQ ID NO: 158; PRT1; Artificial sequence>
AibETFISDYSIAMDKIKQQDFVNWLLAQKPSSGAPPPS C16-diacid/18K; GIP(3-
30 + CEX31-39 E3Aib G4E H18K), AT640, <SEQ ID NO: 159; PRT1; Artificial sequence>
GETFISDYSIAMDKIKQQDFVNWLLAQKPSSGAPPPS C16-diacid/18K; GIP(3-
30 + CEX31-39 E3G G4E H18K), AT641, <SEQ ID NO: 160; PRT1; Artificial sequence>
PETFISDYSIAMDKIKQQDFVNWLLAQKPSSGAPPPS C16-diacid/18K; GIP(3-
30 + CEX31-39 E3P G4E H18K), AT642, <SEQ ID NO: 161; PRT1; Artificial sequence>
DTTFISDYSIAMDKIKQQDFVNWLLAQKPSSGAPPPS C16-diacid/18K; GIP(3-
30 + CEX31-39 E3D G4T H18K), AT643, <SEQ ID NO: 162; PRT1; Artificial sequence>
GETFISDYAIALDKIKQQDFVEWLLAQGPSSGAPPPS C16-diacid/18K; GIP(3-
30 + CEX31-39 E3G; G4E; S11A; M14L; H18K; N24E; K30G),AT644, <SEQ ID NO: 163; PRT1; Artificial sequence>
GETFISTYSIALDKIKQQDFVEWLLAQKPSSGAPPPS C16-diacid/18K; GIP(3-
30 + CEX31-39 E3G; G4E; D9T; M14L; H18K; N24E), AT646, <SEQ ID NO: 164; PRT1; Artificial sequence>
EGTFISTYKIALDKIHQQDFVEWLLAQKPSSGAPPPS yGlu-C16-diacid/18K; GIP(3-
30 + CEX31-39 D9T; S11K; M14L; N24E), AT647, <SEQ ID NO: 165; PRT1; Artificial sequence>
EGTFISDYSIAMDKIKQQDFVNWLLAQK(NH2)PSSGAPPPS C16-diacid/18K; GIP(3-
30 + CEX31-39 AT650,
```

-continued

<SEQ ID NO: 166; PRT1; Artificial sequence>
EGTFISDYSIAibMDKIKQQDFVEWLLAQKPSSGAPPPS C16-diacid/18K; GIP(3-30 + CEX31-39 A13Aib H18K N24E), AT665, <SEQ ID NO: 167; PRT1; Artificial sequence>
EGTFISDYSIAibLDKIKQQDFVEWLLAQKPSSGAPPPS C16-diacid/18K; GIP(3-30 + CEX31-39 A13Aib M14L H18K N24E), AT666, <SEQ ID NO: 168; PRT1; Artificial sequence>
EGTFISDYSIAibNleDKIKQQDFVEWLLAQKPSSGAPPPS C16-diacid/18K; GIP(3-30 + CEX31-39 A13Aib M14Nle H18K N24E), AT667, <SEQ ID NO: 169; PRT1; Artificial sequence>
EGTFISDYSIALDKIKQQDFVEWLLAQKPSSGAPPPS C16-diacid/18K; GIP(3-30 + CEX31-39 M14L H18K N24E), AT668, <SEQ ID NO: 170; PRT1; Artificial sequence>
EGTFISDYSIANleDKIKQQDFVEWLLAQKPSSGAPPPS C16-diacid/18K; GIP(3-30 + CEX31-39 M14Nle H18K N24E), AT669, <SEQ ID NO: 171; PRT1; Artificial sequence>
EGTFISDYSIAKDKIKQQDFVEWLLAQKPSSGAPPPS C16-diacid/18K; GIP(3-30) + Cex(31-39) [M14K H18K N24E], AT670, <SEQ ID NO: 172; PRT1; Artificial sequence>
EGTFISDYSIANleDKIKQQDFVNWLLAGGPSSGAPPPS C16-diacid/18K; GIP(3-30) + Cex(31-39) [M14Nle H18K Q29G K30G], AT671, <SEQ ID NO: 173; PRT1; Artificial sequence>
EGTFISDYSIANleDKIKQQDFVEWLLAGGPSSGAPPPS C16-diacid/18K; GIP(3-30) + Cex(31-39) [M14Nle H18K N24E Q29G K30G], AT672, <SEQ ID NO: 174; PRT1; Artificial sequence>
EGTFISEYSIAibLEKIKQQEFVEWLLAQKPSSGAPPPS C16-diacid/18K; GIP(3-30) + Cex(31-39) [D9E; A13Aib M14L D15E H18K D21E N24E], AT673, <SEQ ID NO: 175; PRT1; Artificial sequence>
EGTFISEYSIAibNleEKIKQQEFVEWLLAQKPSSGAPPPS C16-diacid/18K; GIP(3-30) + Cex(31-39) [D9E; A13Aib M14Nle D15E H18K D21E N24E], AT674, <SEQ ID NO: 176; PRT1; Artificial sequence>
yGluGTFISDYSIAMDKIKQQDFVNWLLAQKPSSGAPPPS C16-diacid/18K; GIP(3-30) + Cex(31-39) [E3yGlu H18K], AT675, <SEQ ID NO: 177; PRT1; Artificial sequence>
βGluGTFISDYSIAMDKIKQQDFVNWLLAQKPSSGAPPPS C16-diacid/18K; GIP(3-30) + Cex(31-39) [E3βGlu H18K], AT676, <SEQ ID NO: 178; PRT1; Artificial sequence>
XGTFISDYSIAMDKIKQQDFVNWLLAQKPSSGAPPPS C16-diacid/18K; GIP(3-30) + Cex(31-39) [E3Glutaric acid(X) H18K], AT677, <SEQ ID NO: 179; PRT1; Artificial sequence>
EGTFISDYSIALDKIKQQDFVEWLLAGGPSSGAPPPS 2xAEEAc + yGlu-C18-diacid/18K; GIP(3-30) + Cex(31-39) [M14L H18K N24E Q29G K30G], AT687, <SEQ ID NO: 180; PRT1; Artificial sequence>
EGTFISEYSIALEKIKQQEFVEWLLAQKPSSGAPPPS 2xAEEAc + yGlu-C18-diacid/18K; GIP(3-30) + Cex(31-39) [D9E; M14L D15E H18K D21E N24E], AT693, <SEQ ID NO: 181; PRT1; Artificial sequence>
EGTFISEYSIANleEKIKQQEFVEWLLAQKPSSGAPPPS 2xAEEAc + yGlu-C18-diacid/18K; GIP(3-30) + Cex(31-39) [D9E; M14Nle D15E H18K D21E N24E], AT694, <SEQ ID NO: 182; PRT1; Artificial sequence>
yGluGTFISDYSIANleDKIKQQDFVEWLLAQKPSSGAPPPS C16-diacid/18K; GIP(3-30) + Cex(31-39) [E3yGlu(L-isomer) M14Nle H18K N24E], AT697, <SEQ ID NO: 183; PRT1; Artificial sequence>
yGluGTFISDYSIANleDKIKQQDFVEWLLAQKPSSGAPPPS C16-diacid/18K; GIP(3-30) + Cex(31-39) [E3yGlu(D-isomer) M14Nle H18K N24E], AT698, <SEQ ID NO: 184; PRT1; Artificial sequence>
βGluGTFISDYSIANleDKIKQQDFVEWLLAQKPSSGAPPPS C16-diacid/18K; GIP(3-30) + Cex(31-39) [E3βGlu M14Nle H18K N24E], AT699, <SEQ ID NO: 185; PRT1; Artificial sequence>
XGTFISDYSIANleDKIKQQDFVEWLLAQKPSSGAPPPS C16-diacid/18K; GIP(3-30) + Cex(31-39) [E3Glutaric acid(X) M14Nle H18K N24E], AT700, <SEQ ID NO: 186; PRT1; Artificial sequence>
βGluGTFISDYSIAibNleDKIKQQDFVNWLLAQKPSSGAPPPS C16-diacid/18K; GIP(3-30) + Cex(31-39) [E3βGlu A13Aib M14Nle H18K], AT703, <SEQ ID NO: 187; PRT1; Artificial sequence>
Ac-EGTFISDYSIAMDKIKQQDFVNWLLAQKPSSGAPPPS-
C16-diacid/K18; GIP(3-30 + CEX31-39 H18K), AT 633

<SEQ ID NO: 188; PRT1; Artificial sequence>
Ac-EGTFISEYSIAMEKIKQQDFVNWLLAQKPSSGAPPPS-
C16-diacid/K18; GIP(3-30 + CEX31-39 D9E; D15E; H18K), AT635

<SEQ ID NO: 189; PRT1; Artificial sequence>
TFISDYKIAMDKIHQQDFVNWLLAQKGKK y-glu-C16diacid/K11 GIP(5-33 S11K),
AT365

<SEQ ID NO: 190; PRT1; Artificial sequence>
TFISDYKIAMDKIHQQDFVNWLLAQKGKKNDW y-glu-C16diacid/K11 GIP(5-36 S11K),
AT 366

<SEQ ID NO: 191; PRT1; Artificial sequence>
TFISDYKIAMDKIHQQDFVNWLLAQKGKKNDW(NH$_2$)2xAEEAc + yGlu-C18-
diacid/K11, GIP(5-36 S11K), AT559

<SEQ ID NO: 192; PRT1; Artificial sequence>
TFISDYSKAMDKIHQQDFVNWLLAQKGKKNDW 2xAEEAc + yGlu-C18diacid/K12
GIP(5-36 I12K), AT562

<SEQ ID NO: 193; PRT1; Artificial sequence>
TFISDYKIAMDKIHQQDFVNWLLAQKGKKNDWKHN-y-glu-C16diacid/K11 GIP(5-39
S11K), AT367

<SEQ ID NO: 194; PRT1; Artificial sequence>
TFISDYKIAMDKIHQQDFVNWLLAQKGKKNDWKHNITQ y-glu-C16diacid/K11 GIP(5-
42 S11K), AT368

<SEQ ID NO: 195; PRT1; Artificial sequence>
TFISDYKIAMDKIHQQDFVNWLLAQKG y-glu-C16diacid/K11 GIP(5-31 S11K), AT455

<SEQ ID NO: 196; PRT1; Artificial sequence>
TFISDYKIAMDKIHQQDFVNWLLAQKGK y-glu-C16diacid/K11 GIP(5-32 S11K),
AT456

<SEQ ID NO: 197; PRT1; Artificial sequence>
TFISDYKIAMDKIHQQDFVNWLLAQKGKKN y-glu-C16diacid/K11 GIP(5-34 S11K),
AT457

<SEQ ID NO: 198; PRT1; Artificial sequence>
TFISDYKIAMDKIHQQDFVNWLLAQKGKKND y-glu-C16diacid/K11 GIP(5-35 S11K),
AT458

<SEQ ID NO: 199; PRT1; Artificial sequence>
TFISDYKIAMDKIHQQDFVNWLLAQKGKKNDWK y-glu-C16diacid/K11 GIP(5-37
S11K), AT459

<SEQ ID NO: 200; PRT1; Artificial sequence>
TFISDYKIAMDKIHQQDFVNWLLAQKGKKNDWKH y-glu-C16diacid/K11 GIP(5-38
S11K), AT460

<SEQ ID NO: 201; PRT1; Artificial sequence>
TFISDYKIAMDKIHQQDFVNWLLAQKGKKNDWKHNI y-glu-C16diacid/K11 GIP(5-40
S11K), AT461

<SEQ ID NO: 202; PRT1; Artificial sequence>
TFISDYKIAMDKIHQQDFVNWLLAQKGKKNDWKHNIT y-glu-C16diacid/K11 GIP(5-41
S11K), AT462

<SEQ ID NO: 203; PRT1; Artificial sequence>
TFISDYKIAMDKIHQQDFVNWLLAQKPSSGAPPPS(NH$_2$)2xPEG + yGlu-C18-
diacid/K11; GIP(5-30 + CEX31-39 S11K), AT597, -continued <SEQ ID NO: 204; PRT1; Artificial sequence>
TFISDYKIAMDRIHQQDFVNWLLAQRGRRNDW 3xAEEAc + y-glu-C16diacid/K11;
GIP(5-36 S11K K16R K30R K32R K33R), AT428

<SEQ ID NO: 205; PRT1; Artificial sequence>
TFISDYKIAMDRIHQQDFVNWLLAQRGPSSGAPPPS 2xAEEAc + y-glu-C16diacid/K11;
GIP(5-30 + CEX S11K K16R K30R), AT443

<SEQ ID NO: 206; PRT1; Artificial sequence>
TFISDYSIAMDKIKQQDFVNWLLAQKGKKNDW 2xAEEAc + y-glu-C18diacid/K18;
GIP(5-36 H18K), AT563

<SEQ ID NO: 207; PRT1; Artificial sequence>
TFISDYKIAMDKIHQQDFVNWLLAQKGPSSGAPPPS(NH$_2$)2xPEG + yGlu-C18-
diacid/K11; GIP(5-30 + CEX31-39 S11K), AT605, <SEQ ID NO: 208; PRT1; Artificial sequence>
TFISDYKIAMDKIHQQDFVNWLLAQKPSSGAPPPS yGlu-C16-diacid/K11; GIP(5-
30 + CEX31-39 S11K), AT632, <SEQ ID NO: 209; PRT1; Artificial sequence>
TFISDYSIAMDKIHQKDFVNWLLAQKGKKNDW 2xAEEAc + y-glu-C18diacid/K20;
GIP(5-36 Q20K), AT564

<SEQ ID NO: 210; PRT1; Artificial sequence>
TFISDYSIAMDKIHQQDFVKWLLAQKGKKNDW 2xAEEAc + y-glu-C18diacid/K24;
GIP(5-36 N24K), AT566

<SEQ ID NO: 211; PRT1; Artificial sequence>
FISDYSIAMDKIKQQDFVNWLLAQKGKK C16diacid/K18; GIP(6-33 H18K), AT463

<SEQ ID NO: 212; PRT1; Artificial sequence>
FISDYSIAMDKIKQQDFVNWLLAQKGKKNDW C16diacid/K18; GIP(6-36 H18K),
AT464

<SEQ ID NO: 213; PRT1; Artificial sequence>
FISDYSIAMDKIKQQDFVNWLLAQKGKKNDWKHN C16diacid/K18; GIP(6-39 H18K),
AT465

<SEQ ID NO: 214; PRT1; Artificial sequence>
FISDYSIAMDKIKQQDFVNWLLAQKGKKNDWKHNITQ C16diacid/K18; GIP(6-
342H18K), AT466

<SEQ ID NO: 215; PRT1; Artificial sequence>
FISDYSIAMDKIKQQDFVNWLLAQKGPSSGAPPPS C16diacid/K18; GIP(6-30 + CEX
H18K), AT475

<SEQ ID NO: 216; PRT1; Artificial sequence>
TFISDYKIAMDKIHQQDFVNWLLAGGPSSGAPPPS(NH$_2$)2xPEG + yGlu-C18-
diacid/K11; GIP(5-30 + CEX31-39 [S11K Q29G K30G], AT602, <SEQ ID NO: 217; PRT1; Artificial sequence>
EGTFISDYSIALDKIKQQDFVNWLLEQKPSSGAPPPS 2xAEEAc + yGlu-C18-
diacid/K18; GIP(3-30) Cex(31-39) [M14L; H18K; A28E], AT689

<SEQ ID NO: 218; PRT1; Artificial sequence>
EGTFISDYSIANleDKIKQQDFVNWLLEQKPSSGAPPPS 2xAEEAc + yGlu-C18-
diacid/K18; GIP(3-30) Cex(31-39) [M14Nle; H18K; A28E], AT690

<SEQ ID NO: 219; PRT1; Artificial sequence>
EGTFISDYSIALDKIKQQDFVNWLLEGGPSSGAPPPS-2xAEEAc + yGlu-C18-
diacid/K18; GIP(3-30) Cex(31-39) [M14L; H18K; A28E; Q29G; K30G], AT691

<SEQ ID NO: 220; PRT1; Artificial sequence>
EGTFISDYSIAMDKIKQQDFVNWLLEGGPSSGAPPPS-C16-diacid/K18; GIP(3-
30) + Cex(31-39) [H18K; A28E; Q29G; K30G]

The invention claimed is:

1. A glucose-dependent insulinotropic peptide (GIP) analogue consisting of the amino acid sequence of SEQ ID NO: 81:

```
                                                (SEQ ID NO: 81)
3   4   5   6   7   8   9   10  11  12  13    14  15  16  17
E - G - T - F - I - S - E - Y - S - I - Aib - L - E - K - I 18  19  20  21  22  23  24  25  26  27  28  29  30
K - Q - Q - E - F - V - E - W - L - L - A - Q - K - Z,
``` wherein said amino acid sequence is modified by attaching a fatty acid molecule at one or more amino acid residue, directly or via a linker, at any one of positions 3 to 29 of SEQ ID NO: 81, wherein Z is a peptide of one or more amino acid residues of GIP(31-42) (GKKNDWKHNITQ; SEQ ID NO: 2) or wherein Z is a peptide of one or more amino acid residues of Exendin-4 (HGEGTFTSDLSKQMEEE-AVRLFIEWLKNGGPSSGAPPPS; SEQ ID NO: 3), wherein said amino acid sequence is optionally C-terminally amidated (—NH2) or C-terminally carboxylated (—COOH), and wherein said GIP analogue is an antagonist of GIPR.

2. The GIP analogue according to claim 1,
wherein said GIP analogue inhibits GIPR activity of at least 80%, and/or
wherein inhibition of GIPR activity is determined as a decrease in intracellular cAMP, and/or
wherein said GIP analogue has a GIPR antagonistic potency corresponding to an IC50 value of 50 nM or less than 50 nM.

3. The GIP analogue according to claim 1, wherein Z consists of one or more consecutive amino acid residues of:
(a) the C-terminus of Exendin-4(30-39) (PSSGAPPPS; SEQ ID NO: 4; CE31-39); or
(b) the C-terminus of Exendin-4(29-39) (GPSSGAPPPS; SEQ ID NO: 5; CE30-39).

4. The GIP analogue according to claim 1, wherein Z is a peptide selected from:
a glycine, a proline, GP, PS, PSS, GPS, GPSS (SEQ ID NO: 6), PSSG (SEQ ID NO: 12), PSSGA (SEQ ID NO: 13), GPSSG (SEQ ID NO: 7), GPSSGA (SEQ ID NO: 8), PSSGAP (SEQ ID NO: 14), PSSGAPP (SEQ ID NO: 15), GPSSGAP (SEQ ID NO: 9), GPSSGAPP (SEQ ID NO: 10), PSSGAPPP (SEQ ID NO: 16), PSSGAPPPS (SEQ ID NO: 4), GPSSGAPPP (SEQ ID NO: 11), GPSSGAPPPS (SEQ ID NO: 5), GK, GKK, GKKN (SEQ ID NO: 17), GKKND (SEQ ID NO: 18), GKKNDW (SEQ ID NO: 19), GRKNDW (SEQ ID NO: 20), GKRNDW (SEQ ID NO: 21), GRRNDW (SEQ ID NO: 22), GKKKDW (SEQ ID NO: 28), GKKNDK (SEQ ID NO: 29), GKKNDWK (SEQ ID NO: 23), GKKNDWKH (SEQ ID NO: 24), GKKNDWKHN (SEQ ID NO: 25), GKKNDWKHNI (SEQ ID NO: 26), GKKNDWKHNIT (SEQ ID NO: 27), and GKKNDWKHNITQ (SEQ ID NO: 2).

5. The GIP analogue according to claim 1, wherein said fatty acid molecule is attached to an amino acid residue at any one of positions 11 to 21 of SEQ ID NO: 81.

6. The GIP analogue according to claim 1, wherein a fatty acid molecule is attached to the side chain amino group of the K amino acid residue at position 18 of SEQ ID NO: 81.

7. The GIP analogue according to claim 1, wherein said GIP analogue peptide is C-terminally amidated (–NH$_2$) or C-terminally carboxylated (—COOH).

8. The GIP analogue according to claim 1, wherein said fatty acid molecule is a straight-chain fatty acid or a branched fatty acid.

9. The GIP analogue according to claim 1, wherein:
a) said fatty acid molecule is a monoacyl fatty acid molecule comprising one fatty acid;
b) said fatty acid molecule is a diacyl fatty acid molecule;
c) said fatty acid molecule comprises an acyl group of the formula $CH_3(CH_2)_nCO$—, wherein n is in an integer of 4 to 24; or
d) said fatty acid molecule comprises an acyl group selected from $COOH(CH_2)_{14}CO$—, $COOH(CH_2)_{16}CO$—, $COOH(CH_2)_{18}CO$— and $COOH(CH_2)_{20}CO$—.

10. The GIP analogue according to claim 1, wherein said GIP analogue is modified by attaching a fatty acid molecule at an amino acid residue via a linker, wherein said linker comprises one or more moieties individually selected from:
a) α-amino acid, γ-amino acid, and ω-amino acid;
b) one or more amino acids selected from Lys, Glu, and Asp;
c) one or more of γ-aminobutanoyl (γ-aminobutyric acid), γ-Glu (γ-glutamic acid), β-Asp (β-asparagyl), β-Ala (β-alanyl) and Gly;

d) [8-amino-3,6-dioxaoctanoic acid]$_n$ (AEEAc$_n$), wherein n is an integer of 1 to 50, or an integer of 1-4, 1-3, or 1-2; and (e) succinic acid.

11. The GIP analogue according to claim 1, wherein the GIP analogue is

EGTFISEYSIAibLEKIKQQEFVEWL-LAQKPSSGAPPPS-C16-diacid/18K; SEQ ID NO: 174 GIP(3-30)+Cex(31-39).

12. The GIP analogue according to claim 1, wherein said GIP analogue is

EGTFISEYSIAibLEKIKQQEFVEWL-LAQKPSSGAPPPS-C16-diacid/18K; SEQ ID NO: 174 GIP(3-30)+Cex(31-39).

13. The GIP analogue according to claim 1, wherein said GIP analogue is EGTFISEYSIAibLEKIKQQEFVEWL-LAQKPSSGAPPPS-C16-diacid/18K; SEQ ID NO: 174 GIP(3-30)+Cex(31-39), wherein said GIP analogue is C-terminally carboxylated.

14. The GIP analogue according to claim 1, wherein said GIP analogue is EGTFISEYSIAibLEKIKQQEFVEWL-LAQKPSSGAPPPS-C16-diacid/18K; SEQ ID NO: 174 GIP(3-30)+Cex(31-39), wherein said GIP analogue is C-terminally amidated.

15. A method of treating obesity in a subject, wherein said method comprises administering to the subject the GIP analogue EGTFISEYSIAibLEKIKQQEFVEWL-LAQKPSSGAPPPS-C16-diacid/18K; SEQ ID NO: 174 GIP(3-30)+Cex(31-39), wherein said GIP analogue is C-terminally carboxylated.

16. A method of reducing one or more of i) GIP-induced glucagon secretion, ii) GIP-induced insulin secretion, iii) GIP-induced somatostatin secretion, iv) GIP-induced glucose uptake, and v) GIP-induced leptin resistance in a subject, wherein said method comprising administering a GIP analogue according to claim 1 to the subject.

17. A method of treating a condition in a subject, wherein said method comprises administering a GIP analogue according to claim 1 to the subject, wherein the condition is selected from the group consisting of obesity, pre-diabetes, type 2 diabetes, insulin resistance, elevated fasting glucose, and hyperglycemia.

* * * * *

SEQUENCE LISTING

<160> NUMBER OF SEQ ID NOS: 223

<210> SEQ ID NO 1
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(2)
<223> OTHER INFORMATION: Xaa can be any amino acid or absent

<400> SEQUENCE: 1

Xaa Xaa Thr Phe Ile Ser Asp Tyr Ser Ile Ala Met Asp Lys Ile His
1               5                   10                  15

Gln Gln Asp Phe Val Asn Trp Leu Leu Ala Gln Lys
            20                  25

<210> SEQ ID NO 2
<211> LENGTH: 12
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(1)
<220> FEATURE:
<221> NAME/KEY: MISC_FEATURE
<222> LOCATION: (2)..(2)

<400> SEQUENCE: 2

Gly Lys Lys Asn Asp Trp Lys His Asn Ile Thr Gln
1               5                   10

<210> SEQ ID NO 3
<211> LENGTH: 39
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(39)
<223> OTHER INFORMATION: Exendin-4

<400> SEQUENCE: 3

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 4
<211> LENGTH: 9
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(9)
<223> OTHER INFORMATION: Exendin 31-39

<400> SEQUENCE: 4

Pro Ser Ser Gly Ala Pro Pro Pro Ser

```
<210> SEQ ID NO 5
<211> LENGTH: 10
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(10)
<223> OTHER INFORMATION: Exendin 30-39

<400> SEQUENCE: 5

Gly Pro Ser Ser Gly Ala Pro Pro Pro Ser
1               5                   10

<210> SEQ ID NO 6
<211> LENGTH: 4
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(4)
<223> OTHER INFORMATION: Exendin fragment

<400> SEQUENCE: 6

Gly Pro Ser Ser
1

<210> SEQ ID NO 7
<211> LENGTH: 5
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(5)
<223> OTHER INFORMATION: Exendin fragment

<400> SEQUENCE: 7

Gly Pro Ser Ser Gly
1               5

<210> SEQ ID NO 8
<211> LENGTH: 6
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(6)
<223> OTHER INFORMATION: Exendin fragment

<400> SEQUENCE: 8

Gly Pro Ser Ser Gly Ala
1               5

<210> SEQ ID NO 9
<211> LENGTH: 7
<212> TYPE: PRT
<213> ORGANISM: Artificial sequence
<220> FEATURE:
<223> OTHER INFORMATION: peptide
<220> FEATURE:
<221> NAME/KEY: PEPTIDE
```

```
<222> LOCATION: (1)..(7)
<223> OTHER INFORMATION: Exendin fragment

<400> SEQUENCE: 9

Gly Pro Ser Ser Gly Ala Pro
1               5

<210> SEQ ID NO 10
<211> LENGTH: 8
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(8)
<223> OTHER INFORMATION: Exendin fragment

<400> SEQUENCE: 10

Gly Pro Ser Ser Gly Ala Pro Pro
1               5

<210> SEQ ID NO 11
<211> LENGTH: 9
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(9)
<223> OTHER INFORMATION: Exendin fragment

<400> SEQUENCE: 11

Gly Pro Ser Ser Gly Ala Pro Pro Pro
1               5

<210> SEQ ID NO 12
<211> LENGTH: 4
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(4)
<223> OTHER INFORMATION: Exendin fragment

<400> SEQUENCE: 12

Pro Ser Ser Gly
1

<210> SEQ ID NO 13
<211> LENGTH: 5
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(5)
<223> OTHER INFORMATION: Exendin fragment

<400> SEQUENCE: 13

Pro Ser Ser Gly Ala
1               5

<210> SEQ ID NO 14
<211> LENGTH: 6
```

```
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(6)
<223> OTHER INFORMATION: Exendin fragment

<400> SEQUENCE: 14

Pro Ser Ser Gly Ala Pro
1               5

<210> SEQ ID NO 15
<211> LENGTH: 7
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(7)
<223> OTHER INFORMATION: Exendin fragment

<400> SEQUENCE: 15

Pro Ser Ser Gly Ala Pro Pro
1               5

<210> SEQ ID NO 16
<211> LENGTH: 8
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(8)
<223> OTHER INFORMATION: Exendin fragment

<400> SEQUENCE: 16

Pro Ser Ser Gly Ala Pro Pro Pro
1               5

<210> SEQ ID NO 17
<211> LENGTH: 4
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(4)
<223> OTHER INFORMATION: GIP fragment

<400> SEQUENCE: 17

Gly Lys Lys Asn
1

<210> SEQ ID NO 18
<211> LENGTH: 5
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(5)
<223> OTHER INFORMATION: GIP fragment

<400> SEQUENCE: 18
```

```
Gly Lys Lys Asn Asp
1               5

<210> SEQ ID NO 19
<211> LENGTH: 6
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(6)
<223> OTHER INFORMATION: GIP fragment

<400> SEQUENCE: 19

Gly Lys Lys Asn Asp Trp
1               5

<210> SEQ ID NO 20
<211> LENGTH: 6
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(6)
<223> OTHER INFORMATION: GIP fragment

<400> SEQUENCE: 20

Gly Arg Lys Asn Asp Trp
1               5

<210> SEQ ID NO 21
<211> LENGTH: 6
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(6)
<223> OTHER INFORMATION: GIP fragment

<400> SEQUENCE: 21

Gly Lys Arg Asn Asp Trp
1               5

<210> SEQ ID NO 22
<211> LENGTH: 6
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(6)
<223> OTHER INFORMATION: GIP fragment

<400> SEQUENCE: 22

Gly Arg Arg Asn Asp Trp
1               5

<210> SEQ ID NO 23
<211> LENGTH: 7
<212> TYPE: PRT
<213> ORGANISM: Artificial sequence
<220> FEATURE:
<223> OTHER INFORMATION: peptide
<220> FEATURE:
```

```
<221> NAME/KEY: PEPTIDE
<222> LOCATION: (1)..(7)
<223> OTHER INFORMATION: GIP fragment

<400> SEQUENCE: 23

Gly Lys Lys Asn Asp Trp Lys
1               5

<210> SEQ ID NO 24
<211> LENGTH: 8
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(8)
<223> OTHER INFORMATION: GIP fragment

<400> SEQUENCE: 24

Gly Lys Lys Asn Asp Trp Lys His
1               5

<210> SEQ ID NO 25
<211> LENGTH: 9
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(9)
<223> OTHER INFORMATION: GIP fragment

<400> SEQUENCE: 25

Gly Lys Lys Asn Asp Trp Lys His Asn
1               5

<210> SEQ ID NO 26
<211> LENGTH: 10
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(10)
<223> OTHER INFORMATION: GIP fragment

<400> SEQUENCE: 26

Gly Lys Lys Asn Asp Trp Lys His Asn Ile
1               5                   10

<210> SEQ ID NO 27
<211> LENGTH: 11
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(11)
<223> OTHER INFORMATION: GIP fragment

<400> SEQUENCE: 27

Gly Lys Lys Asn Asp Trp Lys His Asn Ile Thr
1               5                   10

<210> SEQ ID NO 28
```

```
<211> LENGTH: 6
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(6)
<223> OTHER INFORMATION: GIP fragment

<400> SEQUENCE: 28

Gly Lys Lys Lys Asp Trp
1               5

<210> SEQ ID NO 29
<211> LENGTH: 6
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(6)
<223> OTHER INFORMATION: GIP fragment

<400> SEQUENCE: 29

Gly Lys Lys Asn Asp Lys
1               5

<210> SEQ ID NO 30
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: Xaa can be any amino acid or absent

<400> SEQUENCE: 30

Glu Xaa Thr Phe Ile Ser Asp Tyr Ser Ile Ala Met Asp Lys Ile His
1               5                   10                  15

Gln Gln Asp Phe Val Asn Trp Leu Leu Ala Gln Lys
            20                  25

<210> SEQ ID NO 31
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: Xaa can be any amino acid or absent

<400> SEQUENCE: 31

Xaa Gly Thr Phe Ile Ser Asp Tyr Ser Ile Ala Met Asp Lys Ile His
1               5                   10                  15

Gln Gln Asp Phe Val Asn Trp Leu Leu Ala Gln Lys
            20                  25

<210> SEQ ID NO 32
<211> LENGTH: 28
<212> TYPE: PRT
<213> ORGANISM: Artificial sequence
<220> FEATURE:
<223> OTHER INFORMATION: peptide
```

```
<220> FEATURE:
<221> NAME/KEY: PEPTIDE
<222> LOCATION: (1)..(28)
<223> OTHER INFORMATION: GIP3-30

<400> SEQUENCE: 32

Glu Gly Thr Phe Ile Ser Asp Tyr Ser Ile Ala Met Asp Lys Ile His
1               5                   10                  15

Gln Gln Asp Phe Val Asn Trp Leu Leu Ala Gln Lys
            20                  25

<210> SEQ ID NO 33
<211> LENGTH: 27
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: Xaa can be any amino acid or absent

<400> SEQUENCE: 33

Xaa Thr Phe Ile Ser Asp Tyr Ser Ile Ala Met Asp Lys Ile His Gln
1               5                   10                  15

Gln Asp Phe Val Asn Trp Leu Leu Ala Gln Lys
            20                  25

<210> SEQ ID NO 34
<211> LENGTH: 27
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(27)
<223> OTHER INFORMATION: GIP4-30

<400> SEQUENCE: 34

Gly Thr Phe Ile Ser Asp Tyr Ser Ile Ala Met Asp Lys Ile His Gln
1               5                   10                  15

Gln Asp Phe Val Asn Trp Leu Leu Ala Gln Lys
            20                  25

<210> SEQ ID NO 35
<211> LENGTH: 26
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(26)
<223> OTHER INFORMATION: GIP5-30

<400> SEQUENCE: 35

Thr Phe Ile Ser Asp Tyr Ser Ile Ala Met Asp Lys Ile His Gln Gln
1               5                   10                  15

Asp Phe Val Asn Trp Leu Leu Ala Gln Lys
            20                  25

<210> SEQ ID NO 36
<211> LENGTH: 25
<212> TYPE: PRT
<213> ORGANISM: Artificial sequence
<220> FEATURE:
```

```
<223> OTHER INFORMATION: peptide
<220> FEATURE:
<221> NAME/KEY: PEPTIDE
<222> LOCATION: (1)..(25)
<223> OTHER INFORMATION: GIP6-30

<400> SEQUENCE: 36

Phe Ile Ser Asp Tyr Ser Ile Ala Met Asp Lys Ile His Gln Gln Asp
1               5                   10                  15

Phe Val Asn Trp Leu Leu Ala Gln Lys
            20                  25

<210> SEQ ID NO 37
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(28)
<223> OTHER INFORMATION: GIP(3-30)

<400> SEQUENCE: 37

Glu Gly Thr Phe Ile Ser Asp Tyr Ser Ile Ala Met Asp Lys Ile His
1               5                   10                  15

Gln Gln Asp Phe Val Asn Trp Leu Leu Ala Gln Lys
            20                  25

<210> SEQ ID NO 38
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(28)
<223> OTHER INFORMATION: GIP(3-30)

<400> SEQUENCE: 38

Glu Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys
            20                  25

<210> SEQ ID NO 39
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(28)
<223> OTHER INFORMATION: GIP(3-30)

<400> SEQUENCE: 39

Ser Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys
            20                  25

<210> SEQ ID NO 40
<211> LENGTH: 28
<212> TYPE: PRT
<213> ORGANISM: Artificial sequence
```

```
<220> FEATURE:
<223> OTHER INFORMATION: peptide
<220> FEATURE:
<221> NAME/KEY: PEPTIDE
<222> LOCATION: (1)..(28)
<223> OTHER INFORMATION: GIP(3-30)

<400> SEQUENCE: 40

Glu Gly Thr Phe Ile Ser Asp Tyr Ser Ile Ala Leu Asp Lys Ile Lys
1               5                   10                  15

Gln Gln Asp Phe Val Asn Trp Leu Leu Glu Gln Lys
            20                  25

<210> SEQ ID NO 41
<211> LENGTH: 36
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(36)
<223> OTHER INFORMATION: GIP(3-30)
<220> FEATURE:
<221> NAME/KEY: MOD_RES
<222> LOCATION: (36)..(36)
<223> OTHER INFORMATION: AMIDATION

<400> SEQUENCE: 41

Glu Gly Thr Phe Ile Ser Asp Tyr Ser Ile Ala Met Asp Lys Ile Lys
1               5                   10                  15

Gln Gln Asp Phe Val Asn Trp Leu Leu Ala Gln Pro Ser Ser Gly Ala
            20                  25                  30

Pro Pro Pro Ser
        35

<210> SEQ ID NO 42
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(28)
<223> OTHER INFORMATION: GIP(3-30)

<400> SEQUENCE: 42

Ser Gly Thr Phe Ile Ser Asp Tyr Ser Ile Ala Met Asp Arg Ile Lys
1               5                   10                  15

Gln Gln Asp Phe Val Asn Trp Leu Leu Ala Gln Arg
            20                  25

<210> SEQ ID NO 43
<211> LENGTH: 28
<212> TYPE: PRT
<213> ORGANISM: Artificial Sequence
<220> FEATURE:
<223> OTHER INFORMATION: Peptide
<220> FEATURE:
<221> NAME/KEY: PEPTIDE
<222> LOCATION: (1)..(28)
<223> OTHER INFORMATION: GIP(3-30)

<400> SEQUENCE: 43

Glu Gly Thr Phe Ile Ser Asp Tyr Lys Ile Ala Met Asp Lys Ile His
1               5                   10                  15
```

Gln Gln Asp Phe Val Asn Trp Leu Leu Ala Gln Lys
            20                  25

<210> SEQ ID NO 44
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(28)
<223> OTHER INFORMATION: GIP(3-30)

<400> SEQUENCE: 44

Glu Gly Thr Phe Ile Ser Asp Tyr Ser Lys Ala Met Asp Lys Ile His
1               5                   10                  15

Gln Gln Asp Phe Val Asn Trp Leu Leu Ala Gln Lys
            20                  25

<210> SEQ ID NO 45
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(28)
<223> OTHER INFORMATION: GIP(3-30)

<400> SEQUENCE: 45

Glu Gly Thr Phe Ile Ser Asp Tyr Ser Ile Ala Met Asp Lys Ile His
1               5                   10                  15

Gln Lys Asp Phe Val Asn Trp Leu Leu Ala Gln Lys
            20                  25

<210> SEQ ID NO 46
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(28)
<223> OTHER INFORMATION: GIP(3-30)

<400> SEQUENCE: 46

Glu Gly Thr Phe Ile Ser Asp Tyr Ser Ile Ala Met Asp Lys Ile His
1               5                   10                  15

Gln Gln Asp Phe Val Lys Trp Leu Leu Ala Gln Lys
            20                  25

<210> SEQ ID NO 47
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(28)
<223> OTHER INFORMATION: GIP(3-30)

<400> SEQUENCE: 47

Glu Gly Thr Phe Ile Ser Asp Tyr Ser Ile Ala Met Asp Lys Lys His
1               5                   10                  15

Gln Gln Asp Phe Val Asn Trp Leu Leu Ala Gln Lys
            20                  25

<210> SEQ ID NO 48
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(28)
<223> OTHER INFORMATION: GIP(3-30)

<400> SEQUENCE: 48

Glu Gly Thr Phe Ile Ser Asp Tyr Ser Ile Ala Met Asp Lys Ile Lys
1               5                   10                  15

Gln Gln Asp Phe Val Asn Trp Leu Leu Ala Gln Gly
            20                  25

<210> SEQ ID NO 49
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(28)
<223> OTHER INFORMATION: GIP(3-30)

<400> SEQUENCE: 49

Glu Gly Thr Phe Ile Ser Asp Tyr Ser Ile Ala Met Asp Lys Ile Lys
1               5                   10                  15

Gln Gln Asp Phe Val Asn Trp Leu Leu Ala Gly Gly
            20                  25

<210> SEQ ID NO 50
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(28)
<223> OTHER INFORMATION: GIP(3-30)

<400> SEQUENCE: 50

Glu Gly Thr Phe Ile Ser Glu Tyr Ser Ile Ala Met Glu Lys Ile Lys
1               5                   10                  15

Gln Gln Glu Phe Val Gln Trp Leu Leu Ala Gln Lys
            20                  25

<210> SEQ ID NO 51
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(28)
<223> OTHER INFORMATION: GIP(3-30)

<400> SEQUENCE: 51

Glu Gly Thr Phe Ile Ser Glu Tyr Ser Ile Ala Met Glu Lys Ile Lys

-continued

```
                1               5                    10                   15
Gln Gln Asp Phe Val Gln Trp Leu Leu Ala Gln Lys
            20                  25

<210> SEQ ID NO 52
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: MOD_RES
<222> LOCATION: (10)..(10)
<223> OTHER INFORMATION: Aib
<220> FEATURE:
<221> NAME/KEY: MOD_RES
<222> LOCATION: (12)..(12)
<223> OTHER INFORMATION: Nle

<400> SEQUENCE: 52

Glu Gly Thr Phe Ile Ser Glu Tyr Ser Ala Ala Leu Glu Lys Ile Lys
1               5                   10                  15

Gln Gln Asp Phe Val Glu Trp Leu Leu Ala Gln Lys
            20                  25

<210> SEQ ID NO 53
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: MOD_RES
<222> LOCATION: (11)..(11)
<223> OTHER INFORMATION: Aib

<400> SEQUENCE: 53

Glu Gly Thr Phe Ile Ser Glu Tyr Ser Ile Ala Met Glu Lys Ile Lys
1               5                   10                  15

Gln Gln Asp Phe Val Glu Trp Leu Leu Ala Gln Lys
            20                  25

<210> SEQ ID NO 54
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(28)
<223> OTHER INFORMATION: GIP(3-30)

<400> SEQUENCE: 54

Glu Gly Thr Phe Ile Ser Asp Tyr Ser Ile Ala Met Asp Lys Ile Lys
1               5                   10                  15

Gln Gln Asp Phe Val Glu Trp Leu Leu Ala Gln Lys
            20                  25

<210> SEQ ID NO 55
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(28)
```

<223> OTHER INFORMATION: GIP(3-30)

<400> SEQUENCE: 55

Glu Gly Thr Phe Ile Ser Asp Tyr Ser Ile Ala Leu Asp Lys Ile Lys
1               5                   10                  15

Gln Gln Asp Phe Val Asn Trp Leu Leu Ala Gln Lys
            20                  25

<210> SEQ ID NO 56
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: MOD_RES
<222> LOCATION: (12)..(12)
<223> OTHER INFORMATION: Nle

<400> SEQUENCE: 56

Glu Gly Thr Phe Ile Ser Asp Tyr Ser Ile Ala Leu Asp Lys Ile Lys
1               5                   10                  15

Gln Gln Asp Phe Val Asn Trp Leu Leu Ala Gln Lys
            20                  25

<210> SEQ ID NO 57
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(28)
<223> OTHER INFORMATION: GIP(3-30)

<400> SEQUENCE: 57

Glu Gly Thr Phe Ile Ser Asp Tyr Ser Ile Ala Glu Asp Lys Ile Lys
1               5                   10                  15

Gln Gln Asp Phe Val Asn Trp Leu Leu Ala Gln Lys
            20                  25

<210> SEQ ID NO 58
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(28)
<223> OTHER INFORMATION: GIP(3-30)

<400> SEQUENCE: 58

Glu Gly Thr Phe Ile Ser Asp Tyr Ser Ile Ala Lys Asp Lys Ile Lys
1               5                   10                  15

Gln Gln Asp Phe Val Asn Trp Leu Leu Ala Gln Lys
            20                  25

<210> SEQ ID NO 59
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: PEPTIDE

```
<222> LOCATION: (1)..(28)
<223> OTHER INFORMATION: GIP(3-30)

<400> SEQUENCE: 59

Glu Gly Thr Phe Ile Ser Asp Tyr Ser Ile Ala Ser Asp Lys Ile Lys
1               5                   10                  15

Gln Gln Asp Phe Val Asn Trp Leu Leu Ala Gln Lys
            20                  25

<210> SEQ ID NO 60
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(28)
<223> OTHER INFORMATION: GIP(3-30)

<400> SEQUENCE: 60

Glu Gly Thr Phe Ile Ser Asp Tyr Ser Ile Ala Met Asp Lys Ile Lys
1               5                   10                  15

Gln Gln Asp Phe Val Glu Trp Leu Leu Ala Gln Ala
            20                  25

<210> SEQ ID NO 61
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(28)
<223> OTHER INFORMATION: GIP(3-30)

<400> SEQUENCE: 61

Glu Gly Thr Phe Ile Ser Asp Tyr Ser Ile Ala Met Asp Lys Ile Lys
1               5                   10                  15

Gln Gln Asp Phe Val Asn Trp Leu Leu Glu Gln Lys
            20                  25

<210> SEQ ID NO 62
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(28)
<223> OTHER INFORMATION: GIP(3-30)

<400> SEQUENCE: 62

Val Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys
            20                  25

<210> SEQ ID NO 63
<211> LENGTH: 28
<212> TYPE: PRT
<213> ORGANISM: Artificial sequence
<220> FEATURE:
<223> OTHER INFORMATION: peptide
<220> FEATURE:
```

```
<221> NAME/KEY: MOD_RES
<222> LOCATION: (1)..(1)
<223> OTHER INFORMATION: Aib

<400> SEQUENCE: 63

Ala Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys
            20                  25

<210> SEQ ID NO 64
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(28)
<223> OTHER INFORMATION: GIP(3-30)

<400> SEQUENCE: 64

Pro Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys
            20                  25

<210> SEQ ID NO 65
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(28)
<223> OTHER INFORMATION: GIP(3-30)

<400> SEQUENCE: 65

Val Glu Thr Phe Ile Ser Asp Tyr Ser Ile Ala Met Asp Lys Ile Lys
1               5                   10                  15

Gln Gln Asp Phe Val Asn Trp Leu Leu Ala Gln Lys
            20                  25

<210> SEQ ID NO 66
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: MOD_RES
<222> LOCATION: (1)..(1)
<223> OTHER INFORMATION: Aib

<400> SEQUENCE: 66

Ala Glu Thr Phe Ile Ser Asp Tyr Ser Ile Ala Met Asp Lys Ile Lys
1               5                   10                  15

Gln Gln Asp Phe Val Asn Trp Leu Leu Ala Gln Lys
            20                  25

<210> SEQ ID NO 67
<211> LENGTH: 28
<212> TYPE: PRT
<213> ORGANISM: Artificial sequence
<220> FEATURE:
<223> OTHER INFORMATION: peptide
```

```
<220> FEATURE:
<221> NAME/KEY: PEPTIDE
<222> LOCATION: (1)..(28)
<223> OTHER INFORMATION: GIP(3-30)

<400> SEQUENCE: 67

Gly Glu Thr Phe Ile Ser Asp Tyr Ser Ile Ala Met Asp Lys Ile Lys
1               5                   10                  15

Gln Gln Asp Phe Val Asn Trp Leu Leu Ala Gln Lys
            20                  25

<210> SEQ ID NO 68
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(28)
<223> OTHER INFORMATION: GIP(3-30)

<400> SEQUENCE: 68

Pro Glu Thr Phe Ile Ser Asp Tyr Ser Ile Ala Met Asp Lys Ile Lys
1               5                   10                  15

Gln Gln Asp Phe Val Asn Trp Leu Leu Ala Gln Lys
            20                  25

<210> SEQ ID NO 69
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(28)
<223> OTHER INFORMATION: GIP(3-30)

<400> SEQUENCE: 69

Asp Thr Thr Phe Ile Ser Asp Tyr Ser Ile Ala Met Asp Lys Ile Lys
1               5                   10                  15

Gln Gln Asp Phe Val Asn Trp Leu Leu Ala Gln Lys
            20                  25

<210> SEQ ID NO 70
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(28)
<223> OTHER INFORMATION: GIP(3-30)

<400> SEQUENCE: 70

Gly Glu Thr Phe Ile Ser Asp Tyr Ala Ile Ala Leu Asp Lys Ile Lys
1               5                   10                  15

Gln Gln Asp Phe Val Glu Trp Leu Leu Ala Gln Gly
            20                  25

<210> SEQ ID NO 71
<211> LENGTH: 28
<212> TYPE: PRT
<213> ORGANISM: Artificial sequence
<220> FEATURE:
```

```
<223> OTHER INFORMATION: peptide
<220> FEATURE:
<221> NAME/KEY: PEPTIDE
<222> LOCATION: (1)..(28)
<223> OTHER INFORMATION: GIP(3-30)

<400> SEQUENCE: 71

Gly Glu Thr Phe Ile Ser Thr Tyr Ser Ile Ala Leu Asp Lys Ile Lys
1               5                   10                  15

Gln Gln Asp Phe Val Glu Trp Leu Leu Ala Gln Gly
            20                  25

<210> SEQ ID NO 72
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(28)
<223> OTHER INFORMATION: GIP(3-30)

<400> SEQUENCE: 72

Glu Gly Thr Phe Ile Ser Thr Tyr Lys Ile Ala Leu Asp Lys Ile His
1               5                   10                  15

Gln Gln Asp Phe Val Glu Trp Leu Leu Ala Gln Lys
            20                  25

<210> SEQ ID NO 73
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: MOD_RES
<222> LOCATION: (11)..(11)
<223> OTHER INFORMATION: Aib

<400> SEQUENCE: 73

Glu Gly Thr Phe Ile Ser Asp Tyr Ser Ile Ala Met Asp Lys Ile Lys
1               5                   10                  15

Gln Gln Asp Phe Val Glu Trp Leu Leu Ala Gln Lys
            20                  25

<210> SEQ ID NO 74
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: MOD_RES
<222> LOCATION: (11)..(11)
<223> OTHER INFORMATION: Aib

<400> SEQUENCE: 74

Glu Gly Thr Phe Ile Ser Asp Tyr Ser Ile Ala Leu Asp Lys Ile Lys
1               5                   10                  15

Gln Gln Asp Phe Val Glu Trp Leu Leu Ala Gln Lys
            20                  25

<210> SEQ ID NO 75
<211> LENGTH: 28
<212> TYPE: PRT
<213> ORGANISM: Artificial sequence
```

```
<220> FEATURE:
<223> OTHER INFORMATION: peptide
<220> FEATURE:
<221> NAME/KEY: MOD_RES
<222> LOCATION: (11)..(11)
<223> OTHER INFORMATION: Aib
<220> FEATURE:
<221> NAME/KEY: MOD_RES
<222> LOCATION: (12)..(12)
<223> OTHER INFORMATION: Nle

<400> SEQUENCE: 75

Glu Gly Thr Phe Ile Ser Asp Tyr Ser Ile Ala Leu Asp Lys Ile Lys
1               5                   10                  15
Gln Gln Asp Phe Val Glu Trp Leu Leu Ala Gln Lys
            20                  25

<210> SEQ ID NO 76
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(28)
<223> OTHER INFORMATION: GIP(3-30)

<400> SEQUENCE: 76

Glu Gly Thr Phe Ile Ser Asp Tyr Ser Ile Ala Leu Asp Lys Ile Lys
1               5                   10                  15
Gln Gln Asp Phe Val Glu Trp Leu Leu Ala Gln Lys
            20                  25

<210> SEQ ID NO 77
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: MOD_RES
<222> LOCATION: (12)..(12)
<223> OTHER INFORMATION: Nle

<400> SEQUENCE: 77

Glu Gly Thr Phe Ile Ser Asp Tyr Ser Ile Ala Leu Asp Lys Ile Lys
1               5                   10                  15
Gln Gln Asp Phe Val Glu Trp Leu Leu Ala Gln Lys
            20                  25

<210> SEQ ID NO 78
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(28)
<223> OTHER INFORMATION: GIP(3-30)

<400> SEQUENCE: 78

Glu Gly Thr Phe Ile Ser Asp Tyr Ser Ile Ala Lys Asp Lys Ile Lys
1               5                   10                  15
Gln Gln Asp Phe Val Glu Trp Leu Leu Ala Gln Lys
            20                  25
```

```
<210> SEQ ID NO 79
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: MOD_RES
<222> LOCATION: (12)..(12)
<223> OTHER INFORMATION: Nle

<400> SEQUENCE: 79

Glu Gly Thr Phe Ile Ser Asp Tyr Ser Ile Ala Leu Asp Lys Ile Lys
1               5                   10                  15

Gln Gln Asp Phe Val Asn Trp Leu Leu Ala Gly Gly
            20                  25

<210> SEQ ID NO 80
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: MOD_RES
<222> LOCATION: (12)..(12)
<223> OTHER INFORMATION: Nle

<400> SEQUENCE: 80

Glu Gly Thr Phe Ile Ser Asp Tyr Ser Ile Ala Leu Asp Lys Ile Lys
1               5                   10                  15

Gln Gln Asp Phe Val Glu Trp Leu Leu Ala Gly Gly
            20                  25

<210> SEQ ID NO 81
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: MOD_RES
<222> LOCATION: (11)..(11)
<223> OTHER INFORMATION: Aib

<400> SEQUENCE: 81

Glu Gly Thr Phe Ile Ser Glu Tyr Ser Ile Ala Leu Glu Lys Ile Lys
1               5                   10                  15

Gln Gln Glu Phe Val Glu Trp Leu Leu Ala Gln Lys
            20                  25

<210> SEQ ID NO 82
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: MOD_RES
<222> LOCATION: (11)..(11)
<223> OTHER INFORMATION: Aib
<220> FEATURE:
<221> NAME/KEY: MOD_RES
<222> LOCATION: (12)..(12)
<223> OTHER INFORMATION: Nle

<400> SEQUENCE: 82

Glu Gly Thr Phe Ile Ser Glu Tyr Ser Ile Ala Leu Glu Lys Ile Lys
```

```
1               5                   10                  15
Gln Gln Glu Phe Val Glu Trp Leu Leu Ala Gln Lys
            20                  25

<210> SEQ ID NO 83
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: gamma-glutamate

<400> SEQUENCE: 83

Glu Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys
            20                  25

<210> SEQ ID NO 84
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: beta-glutamate

<400> SEQUENCE: 84

Glu Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys
            20                  25

<210> SEQ ID NO 85
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: Xaa is Glutaric acid

<400> SEQUENCE: 85

Xaa Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys
            20                  25

<210> SEQ ID NO 86
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(28)
<223> OTHER INFORMATION: GIP(3-30)

<400> SEQUENCE: 86
```

Glu Gly Thr Phe Ile Ser Asp Tyr Ser Ile Ala Leu Asp Lys Ile Lys
1               5                   10                  15

Gln Gln Asp Phe Val Glu Trp Leu Leu Ala Gly Gly
            20                  25

<210> SEQ ID NO 87
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(28)
<223> OTHER INFORMATION: GIP(3-30)

<400> SEQUENCE: 87

Glu Gly Thr Phe Ile Ser Glu Tyr Ser Ile Ala Leu Glu Lys Ile Lys
1               5                   10                  15

Gln Gln Glu Phe Val Glu Trp Leu Leu Ala Gln Lys
            20                  25

<210> SEQ ID NO 88
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: MOD_RES
<222> LOCATION: (12)..(12)
<223> OTHER INFORMATION: Nle

<400> SEQUENCE: 88

Glu Gly Thr Phe Ile Ser Glu Tyr Ser Ile Ala Leu Glu Lys Ile Lys
1               5                   10                  15

Gln Gln Glu Phe Val Glu Trp Leu Leu Ala Gln Lys
            20                  25

<210> SEQ ID NO 89
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: gamma-glutamate
<220> FEATURE:
<221> NAME/KEY: MOD_RES
<222> LOCATION: (12)..(12)
<223> OTHER INFORMATION: Nle

<400> SEQUENCE: 89

Glu Gly Thr Phe Ile Ser Asp Tyr Ser Ile Ala Leu Asp Lys Ile Lys
1               5                   10                  15

Gln Gln Asp Phe Val Glu Trp Leu Leu Ala Gln Lys
            20                  25

<210> SEQ ID NO 90
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: MISC_FEATURE

```
<222> LOCATION: (1)..(1)
<223> OTHER INFORMATION: D-isomer of gamma-glutamate
<220> FEATURE:
<221> NAME/KEY: MOD_RES
<222> LOCATION: (12)..(12)
<223> OTHER INFORMATION: Nle

<400> SEQUENCE: 90

Glu Gly Thr Phe Ile Ser Asp Tyr Ser Ile Ala Leu Asp Lys Ile Lys
1               5                   10                  15
Gln Gln Asp Phe Val Glu Trp Leu Leu Ala Gln Lys
            20                  25

<210> SEQ ID NO 91
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: beta-glutamate
<220> FEATURE:
<221> NAME/KEY: MOD_RES
<222> LOCATION: (12)..(12)
<223> OTHER INFORMATION: Nle

<400> SEQUENCE: 91

Glu Gly Thr Phe Ile Ser Asp Tyr Ser Ile Ala Leu Asp Lys Ile Lys
1               5                   10                  15
Gln Gln Asp Phe Val Glu Trp Leu Leu Ala Gln Lys
            20                  25

<210> SEQ ID NO 92
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: Xaa is Glutaric acid
<220> FEATURE:
<221> NAME/KEY: MOD_RES
<222> LOCATION: (12)..(12)
<223> OTHER INFORMATION: Nle

<400> SEQUENCE: 92

Xaa Gly Thr Phe Ile Ser Asp Tyr Ser Ile Ala Leu Asp Lys Ile Lys
1               5                   10                  15
Gln Gln Asp Phe Val Glu Trp Leu Leu Ala Gln Lys
            20                  25

<210> SEQ ID NO 93
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: beta-glutamate
<220> FEATURE:
<221> NAME/KEY: MOD_RES
<222> LOCATION: (11)..(11)
<223> OTHER INFORMATION: Aib
<220> FEATURE:
```

```
<221> NAME/KEY: MOD_RES
<222> LOCATION: (12)..(12)
<223> OTHER INFORMATION: Nle

<400> SEQUENCE: 93

Glu Gly Thr Phe Ile Ser Asp Tyr Ser Ile Ala Leu Asp Lys Ile Lys
1               5                   10                  15

Gln Gln Asp Phe Val Asn Trp Leu Leu Ala Gln Lys
            20                  25

<210> SEQ ID NO 94
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(28)
<223> OTHER INFORMATION: GIP(3-30)

<400> SEQUENCE: 94

Glu Gly Thr Phe Ile Ser Asp Tyr Ser Ile Ala Leu Asp Lys Ile Lys
1               5                   10                  15

Gln Gln Asp Phe Val Asn Trp Leu Leu Glu Gly Gly
            20                  25

<210> SEQ ID NO 95
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: MOD_RES
<222> LOCATION: (12)..(12)
<223> OTHER INFORMATION: Nle

<400> SEQUENCE: 95

Glu Gly Thr Phe Ile Ser Asp Tyr Ser Ile Ala Leu Asp Lys Ile Lys
1               5                   10                  15

Gln Gln Asp Phe Val Asn Trp Leu Leu Glu Gln Lys
            20                  25

<210> SEQ ID NO 96
<211> LENGTH: 26
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(26)
<223> OTHER INFORMATION: GIP(5-30)

<400> SEQUENCE: 96

Thr Phe Ile Ser Asp Tyr Ser Ile Ala Met Asp Lys Ile His Gln Gln
1               5                   10                  15

Asp Phe Val Asn Trp Leu Leu Ala Gln Lys
            20                  25

<210> SEQ ID NO 97
<211> LENGTH: 26
<212> TYPE: PRT
<213> ORGANISM: Artificial sequence
<220> FEATURE:
<223> OTHER INFORMATION: peptide
```

```
<220> FEATURE:
<221> NAME/KEY: PEPTIDE
<222> LOCATION: (1)..(26)
<223> OTHER INFORMATION: GIP(5-30)

<400> SEQUENCE: 97

Thr Phe Ile Ser Asp Tyr Lys Ile Ala Met Asp Lys Ile His Gln Gln
1               5                   10                  15

Asp Phe Val Asn Trp Leu Leu Ala Gln Lys
            20                  25

<210> SEQ ID NO 98
<211> LENGTH: 38
<212> TYPE: PRT
<213> ORGANISM: Artificial sequence
<220> FEATURE:
<223> OTHER INFORMATION: peptide
<220> FEATURE:
<221> NAME/KEY: MOD_RES
<222> LOCATION: (38)..(38)
<223> OTHER INFORMATION: AMIDATION

<400> SEQUENCE: 98

Glu Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys Pro Ser Ser Gly
            20                  25                  30

Ala Pro Pro Pro Ser Lys
            35

<210> SEQ ID NO 99
<211> LENGTH: 38
<212> TYPE: PRT
<213> ORGANISM: Artificial sequence
<220> FEATURE:
<223> OTHER INFORMATION: peptide
<220> FEATURE:
<221> NAME/KEY: MOD_RES
<222> LOCATION: (38)..(38)
<223> OTHER INFORMATION: AMIDATION

<400> SEQUENCE: 99

Pro Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys Pro Ser Ser Gly
            20                  25                  30

Ala Pro Pro Pro Ser Lys
            35

<210> SEQ ID NO 100
<211> LENGTH: 26
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(26)
<223> OTHER INFORMATION: GIP(5-30)

<400> SEQUENCE: 100

Thr Phe Ile Ser Asp Tyr Ser Ile Ala Met Asp Lys Ile Lys Gln Gln
1               5                   10                  15

Asp Phe Val Asn Trp Leu Leu Ala Gln Lys
            20                  25
```

```
<210> SEQ ID NO 101
<211> LENGTH: 26
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(26)
<223> OTHER INFORMATION: GIP(5-30)

<400> SEQUENCE: 101

Thr Phe Ile Ser Asp Tyr Lys Ile Ala Met Asp Arg Ile His Gln Gln
1               5                   10                  15

Asp Phe Val Asn Trp Leu Leu Ala Gln Arg
            20                  25

<210> SEQ ID NO 102
<211> LENGTH: 26
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(26)
<223> OTHER INFORMATION: GIP(5-30)

<400> SEQUENCE: 102

Thr Phe Ile Ser Asp Tyr Ser Lys Ala Met Asp Lys Ile His Gln Gln
1               5                   10                  15

Asp Phe Val Asn Trp Leu Leu Ala Gln Lys
            20                  25

<210> SEQ ID NO 103
<211> LENGTH: 26
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(26)
<223> OTHER INFORMATION: GIP(5-30)

<400> SEQUENCE: 103

Thr Phe Ile Ser Asp Tyr Ser Ile Ala Met Asp Lys Ile His Gln Lys
1               5                   10                  15

Asp Phe Val Asn Trp Leu Leu Ala Gln Lys
            20                  25

<210> SEQ ID NO 104
<211> LENGTH: 26
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(26)
<223> OTHER INFORMATION: GIP(5-30)

<400> SEQUENCE: 104

Thr Phe Ile Ser Asp Tyr Ser Ile Ala Met Asp Lys Ile His Gln Gln
1               5                   10                  15

Asp Phe Val Lys Trp Leu Leu Ala Gln Lys
            20                  25
```

<210> SEQ ID NO 105
<211> LENGTH: 25
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(25)
<223> OTHER INFORMATION: GIP(6-30)

<400> SEQUENCE: 105

Phe Ile Ser Asp Tyr Ser Ile Ala Met Asp Lys Ile Lys Gln Gln Asp
1               5                   10                  15

Phe Val Asn Trp Leu Leu Ala Gln Lys
            20                  25

<210> SEQ ID NO 106
<211> LENGTH: 34
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(34)
<223> OTHER INFORMATION: GIP(3-36)

<400> SEQUENCE: 106

Glu Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys Gly Lys Lys Asn
            20                  25                  30

Asp Trp

<210> SEQ ID NO 107
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(37)
<223> OTHER INFORMATION: GIP(3-30+CEX31-39)

<400> SEQUENCE: 107

Glu Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys Pro Ser Ser Gly
            20                  25                  30

Ala Pro Pro Pro Ser
        35

<210> SEQ ID NO 108
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(37)
<223> OTHER INFORMATION: GIP(3-30+CEX31-39)
<220> FEATURE:
<221> NAME/KEY: MOD_RES -continued

```
<222> LOCATION: (37)..(37)
<223> OTHER INFORMATION: AMIDATION

<400> SEQUENCE: 108

Glu Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys Pro Ser Ser Gly
            20                  25                  30

Ala Pro Pro Pro Ser
        35

<210> SEQ ID NO 109
<211> LENGTH: 38
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(38)
<223> OTHER INFORMATION: GIP(3-30+CEX)

<400> SEQUENCE: 109

Glu Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys Gly Pro Ser Ser
            20                  25                  30

Gly Ala Pro Pro Pro Ser
        35

<210> SEQ ID NO 110
<211> LENGTH: 38
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(38)
<223> OTHER INFORMATION: GIP(3-30+CEX)
<220> FEATURE:
<221> NAME/KEY: MOD_RES
<222> LOCATION: (38)..(38)
<223> OTHER INFORMATION: AMIDATION

<400> SEQUENCE: 110

Glu Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys Gly Pro Ser Ser
            20                  25                  30

Gly Ala Pro Pro Pro Ser
        35

<210> SEQ ID NO 111
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(37)
<223> OTHER INFORMATION: GIP(3-30+CEX)

<400> SEQUENCE: 111

Glu Gly Thr Phe Ile Ser Asp Tyr Ser Ile Ala Met Asp Lys Ile Lys
```

```
                1               5                  10                  15
Gln Gln Asp Phe Val Asn Trp Leu Leu Ala Gln Lys Gly Pro Ser Ser
                20                  25                  30

Gly Ala Pro Pro Pro
            35

<210> SEQ ID NO 112
<211> LENGTH: 36
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(36)
<223> OTHER INFORMATION: GIP(3-30+CEX)

<400> SEQUENCE: 112

Glu Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys Gly Pro Ser Ser
                20                  25                  30

Gly Ala Pro Pro
            35

<210> SEQ ID NO 113
<211> LENGTH: 35
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(35)
<223> OTHER INFORMATION: GIP(3-30+CEX)

<400> SEQUENCE: 113

Glu Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys Gly Pro Ser Ser
                20                  25                  30

Gly Ala Pro
        35

<210> SEQ ID NO 114
<211> LENGTH: 34
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(34)
<223> OTHER INFORMATION: GIP(3-30+CEX)

<400> SEQUENCE: 114

Glu Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys Gly Pro Ser Ser
                20                  25                  30

Gly Ala

<210> SEQ ID NO 115
<211> LENGTH: 33
```

```
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(33)
<223> OTHER INFORMATION: GIP(3-30+CEX)

<400> SEQUENCE: 115

Glu Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys Gly Pro Ser Ser
            20                  25                  30

Gly

<210> SEQ ID NO 116
<211> LENGTH: 32
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(32)
<223> OTHER INFORMATION: GIP(3-30+CEX)

<400> SEQUENCE: 116

Glu Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys Gly Pro Ser Ser
            20                  25                  30

<210> SEQ ID NO 117
<211> LENGTH: 31
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(31)
<223> OTHER INFORMATION: GIP(3-30+CEX)

<400> SEQUENCE: 117

Glu Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys Gly Pro Ser
            20                  25                  30

<210> SEQ ID NO 118
<211> LENGTH: 30
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(30)
<223> OTHER INFORMATION: GIP(3-30+CEX)

<400> SEQUENCE: 118

Glu Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys Gly Pro
            20                  25                  30
```

<210> SEQ ID NO 119
<211> LENGTH: 29
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(29)
<223> OTHER INFORMATION: GIP(3-31)

<400> SEQUENCE: 119

Glu Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys Gly
            20                  25

<210> SEQ ID NO 120
<211> LENGTH: 30
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(30)
<223> OTHER INFORMATION: GIP(3-32)

<400> SEQUENCE: 120

Glu Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys Gly Lys
            20                  25                  30

<210> SEQ ID NO 121
<211> LENGTH: 31
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(31)
<223> OTHER INFORMATION: GIP(3-33)

<400> SEQUENCE: 121

Glu Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys Gly Lys Lys
            20                  25                  30

<210> SEQ ID NO 122
<211> LENGTH: 32
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(32)
<223> OTHER INFORMATION: GIP(3-34)

<400> SEQUENCE: 122

Glu Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys Gly Lys Lys Asn
            20                  25                  30

<210> SEQ ID NO 123
<211> LENGTH: 33
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(33)
<223> OTHER INFORMATION: GIP(3-35)

<400> SEQUENCE: 123

Glu Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys Gly Lys Lys Asn
            20                  25                  30

Asp

<210> SEQ ID NO 124
<211> LENGTH: 35
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(35)
<223> OTHER INFORMATION: GIP(3-37)

<400> SEQUENCE: 124

Glu Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys Gly Lys Lys Asn
            20                  25                  30

Asp Trp Lys
        35

<210> SEQ ID NO 125
<211> LENGTH: 36
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(36)
<223> OTHER INFORMATION: GIP(3-38)

<400> SEQUENCE: 125

Glu Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys Gly Lys Lys Asn
            20                  25                  30

Asp Trp Lys His
        35

<210> SEQ ID NO 126
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(37)

<223> OTHER INFORMATION: GIP(3-39)

<400> SEQUENCE: 126

Glu Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys Gly Lys Lys Asn
            20                  25                  30

Asp Trp Lys His Asn
        35

<210> SEQ ID NO 127
<211> LENGTH: 38
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(38)
<223> OTHER INFORMATION: GIP(3-40)

<400> SEQUENCE: 127

Glu Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys Gly Lys Lys Asn
            20                  25                  30

Asp Trp Lys His Asn Ile
        35

<210> SEQ ID NO 128
<211> LENGTH: 39
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(39)
<223> OTHER INFORMATION: GIP(3-41)

<400> SEQUENCE: 128

Glu Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys Gly Lys Lys Asn
            20                  25                  30

Asp Trp Lys His Asn Ile Thr
        35

<210> SEQ ID NO 129
<211> LENGTH: 40
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(40)
<223> OTHER INFORMATION: GIP(3-42)

<400> SEQUENCE: 129

Glu Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys Gly Lys Lys Asn
            20                  25                  30

```
Asp Trp Lys His Asn Ile Thr Gln
        35                  40

<210> SEQ ID NO 130
<211> LENGTH: 34
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(34)
<223> OTHER INFORMATION: GIP(3-30)

<400> SEQUENCE: 130

Ser Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys Gly Lys Lys Asn
            20                  25                  30

Asp Trp

<210> SEQ ID NO 131
<211> LENGTH: 38
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(38)
<223> OTHER INFORMATION: GIP(3-30)

<400> SEQUENCE: 131

Ser Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys Gly Pro Ser Ser
            20                  25                  30

Gly Ala Pro Pro Pro Ser
        35

<210> SEQ ID NO 132
<211> LENGTH: 34
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(34)
<223> OTHER INFORMATION: GIP(3-30)

<400> SEQUENCE: 132

Ser Gly Thr Phe Ile Ser Asp Tyr Ser Ile Ala Met Asp Arg Ile Lys
1               5                   10                  15

Gln Gln Asp Phe Val Asn Trp Leu Leu Ala Gln Arg Gly Arg Arg Asn
            20                  25                  30

Asp Trp

<210> SEQ ID NO 133
<211> LENGTH: 38
<212> TYPE: PRT
<213> ORGANISM: Artificial sequence
<220> FEATURE:
<223> OTHER INFORMATION: peptide
<220> FEATURE:
<221> NAME/KEY: PEPTIDE
```

```
<222> LOCATION: (1)..(38)
<223> OTHER INFORMATION: GIP(3-30)

<400> SEQUENCE: 133

Ser Gly Thr Phe Ile Ser Asp Tyr Ser Ile Ala Met Asp Arg Ile Lys
1               5                   10                  15

Gln Gln Asp Phe Val Asn Trp Leu Leu Ala Gln Arg Gly Pro Ser Ser
            20                  25                  30

Gly Ala Pro Pro Pro Ser
        35

<210> SEQ ID NO 134
<211> LENGTH: 34
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(34)
<223> OTHER INFORMATION: GIP(3-30)

<400> SEQUENCE: 134

Glu Gly Thr Phe Ile Ser Asp Tyr Lys Ile Ala Met Asp Lys Ile His
1               5                   10                  15

Gln Gln Asp Phe Val Asn Trp Leu Leu Ala Gln Lys Gly Lys Lys Asn
            20                  25                  30

Asp Trp

<210> SEQ ID NO 135
<211> LENGTH: 34
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(34)
<223> OTHER INFORMATION: GIP(3-30)

<400> SEQUENCE: 135

Glu Gly Thr Phe Ile Ser Asp Tyr Ser Lys Ala Met Asp Lys Ile His
1               5                   10                  15

Gln Gln Asp Phe Val Asn Trp Leu Leu Ala Gln Lys Gly Lys Lys Asn
            20                  25                  30

Asp Trp

<210> SEQ ID NO 136
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: MOD_RES
<222> LOCATION: (37)..(37)
<223> OTHER INFORMATION: AMIDATION

<400> SEQUENCE: 136

Glu Gly Thr Phe Ile Ser Asp Tyr Ser Ile Ala Met Asp Lys Ile His
1               5                   10                  15

Gln Lys Asp Phe Val Asn Trp Leu Leu Ala Gln Lys Pro Ser Ser Gly
            20                  25                  30

Ala Pro Pro Pro Ser
```

<210> SEQ ID NO 137
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: MOD_RES
<222> LOCATION: (37)..(37)
<223> OTHER INFORMATION: AMIDATION

<400> SEQUENCE: 137

Glu Gly Thr Phe Ile Ser Asp Tyr Ser Ile Ala Met Asp Lys Lys His
1               5                   10                  15

Gln Gln Asp Phe Val Asn Trp Leu Leu Ala Gln Lys Pro Ser Ser Gly
            20                  25                  30

Ala Pro Pro Pro Ser
            35

<210> SEQ ID NO 138
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: MOD_RES
<222> LOCATION: (37)..(37)
<223> OTHER INFORMATION: AMIDATION

<400> SEQUENCE: 138

Glu Gly Thr Phe Ile Ser Asp Tyr Ser Ile Ala Met Asp Lys Ile Lys
1               5                   10                  15

Gln Gln Asp Phe Val Asn Trp Leu Leu Ala Gln Gly Pro Ser Ser Gly
            20                  25                  30

Ala Pro Pro Pro Ser
            35

<210> SEQ ID NO 139
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: MOD_RES
<222> LOCATION: (37)..(37)
<223> OTHER INFORMATION: AMIDATION

<400> SEQUENCE: 139

Glu Gly Thr Phe Ile Ser Asp Tyr Ser Ile Ala Met Asp Lys Ile Lys
1               5                   10                  15

Gln Gln Asp Phe Val Asn Trp Leu Leu Ala Gly Gly Pro Ser Ser Gly
            20                  25                  30

Ala Pro Pro Pro Ser
            35

<210> SEQ ID NO 140
<211> LENGTH: 37
<212> TYPE: PRT
<213> ORGANISM: Artificial sequence
<220> FEATURE:
<223> OTHER INFORMATION: peptide
<220> FEATURE:

```
<221> NAME/KEY: PEPTIDE
<222> LOCATION: (1)..(37)
<223> OTHER INFORMATION: GIP(3-30)

<400> SEQUENCE: 140

Glu Gly Thr Phe Ile Ser Asp Tyr Ser Ile Ala Met Asp Lys Ile Lys
1               5                   10                  15

Gln Gln Asp Phe Val Asn Trp Leu Leu Ala Gly Gly Pro Ser Ser Gly
            20                  25                  30

Ala Pro Pro Pro Ser
            35

<210> SEQ ID NO 141
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(37)
<223> OTHER INFORMATION: GIP(3-30)

<400> SEQUENCE: 141

Glu Gly Thr Phe Ile Ser Glu Tyr Ser Ile Ala Met Glu Lys Ile Lys
1               5                   10                  15

Gln Gln Glu Phe Val Gln Trp Leu Leu Ala Gly Lys Pro Ser Ser Gly
            20                  25                  30

Ala Pro Pro Pro Ser
            35

<210> SEQ ID NO 142
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(37)
<223> OTHER INFORMATION: GIP(3-30)

<400> SEQUENCE: 142

Glu Gly Thr Phe Ile Ser Glu Tyr Ser Ile Ala Met Glu Lys Ile Lys
1               5                   10                  15

Gln Gln Asp Phe Val Glu Trp Leu Leu Ala Gln Lys Pro Ser Ser Gly
            20                  25                  30

Ala Pro Pro Pro Ser
            35

<210> SEQ ID NO 143
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: MOD_RES
<222> LOCATION: (10)..(10)
<223> OTHER INFORMATION: Aib
<220> FEATURE:
<221> NAME/KEY: MOD_RES
<222> LOCATION: (12)..(12)
<223> OTHER INFORMATION: Nle

<400> SEQUENCE: 143
```

```
Glu Gly Thr Phe Ile Ser Glu Tyr Ser Ala Ala Leu Glu Lys Ile Lys
1               5                   10                  15

Gln Gln Asp Phe Val Glu Trp Leu Leu Ala Gln Lys Pro Ser Ser Gly
            20                  25                  30

Ala Pro Pro Pro Ser
        35

<210> SEQ ID NO 144
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: MOD_RES
<222> LOCATION: (11)..(11)
<223> OTHER INFORMATION: Aib

<400> SEQUENCE: 144

Glu Gly Thr Phe Ile Ser Glu Tyr Ser Ile Ala Met Glu Lys Ile Lys
1               5                   10                  15

Gln Gln Asp Phe Val Glu Trp Leu Leu Ala Gln Lys Pro Ser Ser Gly
            20                  25                  30

Ala Pro Pro Pro Ser
        35

<210> SEQ ID NO 145
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(37)
<223> OTHER INFORMATION: GIP(3-30)

<400> SEQUENCE: 145

Glu Gly Thr Phe Ile Ser Asp Tyr Ser Ile Ala Met Asp Lys Ile Lys
1               5                   10                  15

Gln Gln Asp Phe Val Glu Trp Leu Leu Ala Gln Lys Pro Ser Ser Gly
            20                  25                  30

Ala Pro Pro Pro Ser
        35

<210> SEQ ID NO 146
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(37)
<223> OTHER INFORMATION: GIP(3-30)

<400> SEQUENCE: 146

Glu Gly Thr Phe Ile Ser Asp Tyr Ser Ile Ala Leu Asp Lys Ile Lys
1               5                   10                  15

Gln Gln Asp Phe Val Asn Trp Leu Leu Ala Gln Lys Pro Ser Ser Gly
            20                  25                  30

Ala Pro Pro Pro Ser
        35
```

```
<210> SEQ ID NO 147
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: MOD_RES
<222> LOCATION: (12)..(12)
<223> OTHER INFORMATION: Nle

<400> SEQUENCE: 147

Glu Gly Thr Phe Ile Ser Asp Tyr Ser Ile Ala Leu Asp Lys Ile Lys
1               5                   10                  15

Gln Gln Asp Phe Val Asn Trp Leu Leu Ala Gln Lys Pro Ser Ser Gly
            20                  25                  30

Ala Pro Pro Pro Ser
        35

<210> SEQ ID NO 148
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(37)
<223> OTHER INFORMATION: GIP(3-30)

<400> SEQUENCE: 148

Glu Gly Thr Phe Ile Ser Asp Tyr Ser Ile Ala Glu Asp Lys Ile Lys
1               5                   10                  15

Gln Gln Asp Phe Val Asn Trp Leu Leu Ala Gln Lys Pro Ser Ser Gly
            20                  25                  30

Ala Pro Pro Pro Ser
        35

<210> SEQ ID NO 149
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(37)
<223> OTHER INFORMATION: GIP(3-30)

<400> SEQUENCE: 149

Glu Gly Thr Phe Ile Ser Asp Tyr Ser Ile Ala Lys Asp Lys Ile Lys
1               5                   10                  15

Gln Gln Asp Phe Val Asn Trp Leu Leu Ala Gln Lys Pro Ser Ser Gly
            20                  25                  30

Ala Pro Pro Pro Ser
        35

<210> SEQ ID NO 150
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(37)
<223> OTHER INFORMATION: GIP(3-30)
```

```
<400> SEQUENCE: 150

Glu Gly Thr Phe Ile Ser Asp Tyr Ser Ile Ala Ser Asp Lys Ile Lys
1               5                   10                  15

Gln Gln Asp Phe Val Asn Trp Leu Leu Ala Gln Lys Pro Ser Ser Gly
            20                  25                  30

Ala Pro Pro Pro Ser
        35

<210> SEQ ID NO 151
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(37)
<223> OTHER INFORMATION: GIP(3-30)

<400> SEQUENCE: 151

Glu Gly Thr Phe Ile Ser Asp Tyr Ser Ile Ala Met Asp Lys Ile Lys
1               5                   10                  15

Gln Gln Asp Phe Val Glu Trp Leu Leu Ala Gln Ala Pro Ser Ser Gly
            20                  25                  30

Ala Pro Pro Pro Ser
        35

<210> SEQ ID NO 152
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(37)
<223> OTHER INFORMATION: GIP(3-30)

<400> SEQUENCE: 152

Glu Gly Thr Phe Ile Ser Asp Tyr Ser Ile Ala Met Asp Lys Ile Lys
1               5                   10                  15

Gln Gln Asp Phe Val Asn Trp Leu Glu Ala Gln Lys Pro Ser Ser Gly
            20                  25                  30

Ala Pro Pro Pro Ser
        35

<210> SEQ ID NO 153
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(37)
<223> OTHER INFORMATION: GIP(3-30)

<400> SEQUENCE: 153

Glu Gly Thr Phe Ile Ser Asp Tyr Ser Ile Ala Met Asp Lys Ile Lys
1               5                   10                  15

Gln Gln Asp Phe Val Asn Trp Leu Leu Glu Gln Lys Pro Ser Ser Gly
            20                  25                  30

Ala Pro Pro Pro Ser
```

<210> SEQ ID NO 154
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(37)
<223> OTHER INFORMATION: GIP(3-30)

<400> SEQUENCE: 154

Val Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys Pro Ser Ser Gly
            20                  25                  30

Ala Pro Pro Pro Ser
        35

<210> SEQ ID NO 155
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: MOD_RES
<222> LOCATION: (1)..(1)
<223> OTHER INFORMATION: Aib

<400> SEQUENCE: 155

Ala Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys Pro Ser Ser Gly
            20                  25                  30

Ala Pro Pro Pro Ser
        35

<210> SEQ ID NO 156
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(37)
<223> OTHER INFORMATION: GIP(3-30)

<400> SEQUENCE: 156

Pro Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys Pro Ser Ser Gly
            20                  25                  30

Ala Pro Pro Pro Ser
        35

<210> SEQ ID NO 157
<211> LENGTH: 37
<212> TYPE: PRT
<213> ORGANISM: Artificial sequence
<220> FEATURE:
<223> OTHER INFORMATION: peptide
<220> FEATURE:

```
<221> NAME/KEY: PEPTIDE
<222> LOCATION: (1)..(37)
<223> OTHER INFORMATION: GIP(3-30)

<400> SEQUENCE: 157

Val Glu Thr Phe Ile Ser Asp Tyr Ser Ile Ala Met Asp Lys Ile Lys
1               5                   10                  15

Gln Gln Asp Phe Val Asn Trp Leu Leu Ala Gln Lys Pro Ser Ser Gly
            20                  25                  30

Ala Pro Pro Pro Ser
        35

<210> SEQ ID NO 158
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: MOD_RES
<222> LOCATION: (1)..(1)
<223> OTHER INFORMATION: Aib

<400> SEQUENCE: 158

Ala Glu Thr Phe Ile Ser Asp Tyr Ser Ile Ala Met Asp Lys Ile Lys
1               5                   10                  15

Gln Gln Asp Phe Val Asn Trp Leu Leu Ala Gln Lys Pro Ser Ser Gly
            20                  25                  30

Ala Pro Pro Pro Ser
        35

<210> SEQ ID NO 159
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(37)
<223> OTHER INFORMATION: GIP(3-30)

<400> SEQUENCE: 159

Gly Glu Thr Phe Ile Ser Asp Tyr Ser Ile Ala Met Asp Lys Ile Lys
1               5                   10                  15

Gln Gln Asp Phe Val Asn Trp Leu Leu Ala Gln Lys Pro Ser Ser Gly
            20                  25                  30

Ala Pro Pro Pro Ser
        35

<210> SEQ ID NO 160
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(37)
<223> OTHER INFORMATION: GIP(3-30)

<400> SEQUENCE: 160

Pro Glu Thr Phe Ile Ser Asp Tyr Ser Ile Ala Met Asp Lys Ile Lys
1               5                   10                  15

Gln Gln Asp Phe Val Asn Trp Leu Leu Ala Gln Lys Pro Ser Ser Gly
```

```
                20                  25                  30

Ala Pro Pro Ser
        35

<210> SEQ ID NO 161
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(37)
<223> OTHER INFORMATION: GIP(3-30)

<400> SEQUENCE: 161

Asp Thr Thr Phe Ile Ser Asp Tyr Ser Ile Ala Met Asp Lys Ile Lys
1               5                   10                  15

Gln Gln Asp Phe Val Asn Trp Leu Leu Ala Gln Lys Pro Ser Ser Gly
            20                  25                  30

Ala Pro Pro Ser
        35

<210> SEQ ID NO 162
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(37)
<223> OTHER INFORMATION: GIP(3-30)

<400> SEQUENCE: 162

Gly Glu Thr Phe Ile Ser Asp Tyr Ala Ile Ala Leu Asp Lys Ile Lys
1               5                   10                  15

Gln Gln Asp Phe Val Glu Trp Leu Leu Ala Gln Gly Pro Ser Ser Gly
            20                  25                  30

Ala Pro Pro Ser
        35

<210> SEQ ID NO 163
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(37)
<223> OTHER INFORMATION: GIP(3-30)

<400> SEQUENCE: 163

Gly Glu Thr Phe Ile Ser Thr Tyr Ser Ile Ala Leu Asp Lys Ile Lys
1               5                   10                  15

Gln Gln Asp Phe Val Glu Trp Leu Leu Ala Gln Lys Pro Ser Ser Gly
            20                  25                  30

Ala Pro Pro Ser
        35

<210> SEQ ID NO 164
<211> LENGTH: 37
<212> TYPE: PRT
<213> ORGANISM: Artificial sequence
```

```
<220> FEATURE:
<223> OTHER INFORMATION: peptide
<220> FEATURE:
<221> NAME/KEY: PEPTIDE
<222> LOCATION: (1)..(37)
<223> OTHER INFORMATION: GIP(3-30)

<400> SEQUENCE: 164

Glu Gly Thr Phe Ile Ser Thr Tyr Lys Ile Ala Leu Asp Lys Ile His
1               5                   10                  15

Gln Gln Asp Phe Val Glu Trp Leu Leu Ala Gln Lys Pro Ser Ser Gly
            20                  25                  30

Ala Pro Pro Pro Ser
            35

<210> SEQ ID NO 165
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: MOD_RES
<222> LOCATION: (37)..(37)
<223> OTHER INFORMATION: AMIDATION

<400> SEQUENCE: 165

Glu Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys Pro Ser Ser Gly
            20                  25                  30

Ala Pro Pro Pro Ser
            35

<210> SEQ ID NO 166
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: MOD_RES
<222> LOCATION: (11)..(11)
<223> OTHER INFORMATION: Aib

<400> SEQUENCE: 166

Glu Gly Thr Phe Ile Ser Asp Tyr Ser Ile Ala Met Asp Lys Ile Lys
1               5                   10                  15

Gln Gln Asp Phe Val Glu Trp Leu Leu Ala Gln Lys Pro Ser Ser Gly
            20                  25                  30

Ala Pro Pro Pro Ser
            35

<210> SEQ ID NO 167
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: MOD_RES
<222> LOCATION: (11)..(11)
<223> OTHER INFORMATION: Aib

<400> SEQUENCE: 167

Glu Gly Thr Phe Ile Ser Asp Tyr Ser Ile Ala Leu Asp Lys Ile Lys
```

```
1               5                   10                  15
Gln Gln Asp Phe Val Glu Trp Leu Leu Ala Gln Lys Pro Ser Ser Gly
            20                  25                  30

Ala Pro Pro Pro Ser
        35
```

<210> SEQ ID NO 168
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: MOD_RES
<222> LOCATION: (11)..(11)
<223> OTHER INFORMATION: Aib
<220> FEATURE:
<221> NAME/KEY: MOD_RES
<222> LOCATION: (12)..(12)
<223> OTHER INFORMATION: Nle

<400> SEQUENCE: 168

```
Glu Gly Thr Phe Ile Ser Asp Tyr Ser Ile Ala Leu Asp Lys Ile Lys
1               5                   10                  15

Gln Gln Asp Phe Val Glu Trp Leu Leu Ala Gln Lys Pro Ser Ser Gly
            20                  25                  30

Ala Pro Pro Pro Ser
        35
```

<210> SEQ ID NO 169
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(37)
<223> OTHER INFORMATION: GIP(3-30)

<400> SEQUENCE: 169

```
Glu Gly Thr Phe Ile Ser Asp Tyr Ser Ile Ala Leu Asp Lys Ile Lys
1               5                   10                  15

Gln Gln Asp Phe Val Glu Trp Leu Leu Ala Gln Lys Pro Ser Ser Gly
            20                  25                  30

Ala Pro Pro Pro Ser
        35
```

<210> SEQ ID NO 170
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: MOD_RES
<222> LOCATION: (12)..(12)
<223> OTHER INFORMATION: Nle

<400> SEQUENCE: 170

```
Glu Gly Thr Phe Ile Ser Asp Tyr Ser Ile Ala Leu Asp Lys Ile Lys
1               5                   10                  15

Gln Gln Asp Phe Val Glu Trp Leu Leu Ala Gln Lys Pro Ser Ser Gly
            20                  25                  30

Ala Pro Pro Pro Ser
```

<210> SEQ ID NO 171
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(37)
<223> OTHER INFORMATION: GIP(3-30)

<400> SEQUENCE: 171

Glu Gly Thr Phe Ile Ser Asp Tyr Ser Ile Ala Lys Asp Lys Ile Lys
1               5                   10                  15

Gln Gln Asp Phe Val Glu Trp Leu Leu Ala Gln Lys Pro Ser Ser Gly
            20                  25                  30

Ala Pro Pro Pro Ser
        35

<210> SEQ ID NO 172
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: MOD_RES
<222> LOCATION: (12)..(12)
<223> OTHER INFORMATION: Nle

<400> SEQUENCE: 172

Glu Gly Thr Phe Ile Ser Asp Tyr Ser Ile Ala Leu Asp Lys Ile Lys
1               5                   10                  15

Gln Gln Asp Phe Val Asn Trp Leu Leu Ala Gly Gly Pro Ser Ser Gly
            20                  25                  30

Ala Pro Pro Pro Ser
        35

<210> SEQ ID NO 173
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: MOD_RES
<222> LOCATION: (12)..(12)
<223> OTHER INFORMATION: Nle

<400> SEQUENCE: 173

Glu Gly Thr Phe Ile Ser Asp Tyr Ser Ile Ala Leu Asp Lys Ile Lys
1               5                   10                  15

Gln Gln Asp Phe Val Glu Trp Leu Leu Ala Gly Gly Pro Ser Ser Gly
            20                  25                  30

Ala Pro Pro Pro Ser
        35

<210> SEQ ID NO 174
<211> LENGTH: 37
<212> TYPE: PRT
<213> ORGANISM: Artificial sequence
<220> FEATURE:
<223> OTHER INFORMATION: peptide
<220> FEATURE:

```
<221> NAME/KEY: MOD_RES
<222> LOCATION: (11)..(11)
<223> OTHER INFORMATION: Aib

<400> SEQUENCE: 174

Glu Gly Thr Phe Ile Ser Glu Tyr Ser Ile Ala Leu Glu Lys Ile Lys
1               5                   10                  15

Gln Gln Glu Phe Val Glu Trp Leu Leu Ala Gln Lys Pro Ser Ser Gly
            20                  25                  30

Ala Pro Pro Pro Ser
        35

<210> SEQ ID NO 175
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: MOD_RES
<222> LOCATION: (11)..(11)
<223> OTHER INFORMATION: Aib
<220> FEATURE:
<221> NAME/KEY: MOD_RES
<222> LOCATION: (12)..(12)
<223> OTHER INFORMATION: Nle

<400> SEQUENCE: 175

Glu Gly Thr Phe Ile Ser Glu Tyr Ser Ile Ala Leu Glu Lys Ile Lys
1               5                   10                  15

Gln Gln Glu Phe Val Glu Trp Leu Leu Ala Gln Lys Pro Ser Ser Gly
            20                  25                  30

Ala Pro Pro Pro Ser
        35

<210> SEQ ID NO 176
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: gamma-glutamate

<400> SEQUENCE: 176

Glu Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys Pro Ser Ser Gly
            20                  25                  30

Ala Pro Pro Pro Ser
        35

<210> SEQ ID NO 177
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: beta-glutamate

<400> SEQUENCE: 177
```

Glu Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys Pro Ser Ser Gly
            20                  25                  30

Ala Pro Pro Pro Ser
        35

<210> SEQ ID NO 178
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: Xaa is Glutaric acid

<400> SEQUENCE: 178

Xaa Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys Pro Ser Ser Gly
            20                  25                  30

Ala Pro Pro Pro Ser
        35

<210> SEQ ID NO 179
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(37)
<223> OTHER INFORMATION: GIP(3-30)

<400> SEQUENCE: 179

Glu Gly Thr Phe Ile Ser Asp Tyr Ser Ile Ala Leu Asp Lys Ile Lys
1               5                   10                  15

Gln Gln Asp Phe Val Glu Trp Leu Leu Ala Gly Gly Pro Ser Ser Gly
            20                  25                  30

Ala Pro Pro Pro Ser
        35

<210> SEQ ID NO 180
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(37)
<223> OTHER INFORMATION: GIP(3-30)

<400> SEQUENCE: 180

Glu Gly Thr Phe Ile Ser Glu Tyr Ser Ile Ala Leu Glu Lys Ile Lys
1               5                   10                  15

Gln Gln Glu Phe Val Glu Trp Leu Leu Ala Gln Lys Pro Ser Ser Gly
            20                  25                  30

Ala Pro Pro Pro Ser
        35

```
<210> SEQ ID NO 181
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: MOD_RES
<222> LOCATION: (12)..(12)
<223> OTHER INFORMATION: Nle

<400> SEQUENCE: 181

Glu Gly Thr Phe Ile Ser Glu Tyr Ser Ile Ala Leu Glu Lys Ile Lys
1               5                   10                  15

Gln Gln Glu Phe Val Glu Trp Leu Leu Ala Gln Lys Pro Ser Ser Gly
            20                  25                  30

Ala Pro Pro Pro Ser
            35

<210> SEQ ID NO 182
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: gamma-glutamate
<220> FEATURE:
<221> NAME/KEY: MOD_RES
<222> LOCATION: (12)..(12)
<223> OTHER INFORMATION: Nle

<400> SEQUENCE: 182

Glu Gly Thr Phe Ile Ser Asp Tyr Ser Ile Ala Leu Asp Lys Ile Lys
1               5                   10                  15

Gln Gln Asp Phe Val Glu Trp Leu Leu Ala Gln Lys Pro Ser Ser Gly
            20                  25                  30

Ala Pro Pro Pro Ser
            35

<210> SEQ ID NO 183
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: gamma-glutamate
<220> FEATURE:
<221> NAME/KEY: MOD_RES
<222> LOCATION: (12)..(12)
<223> OTHER INFORMATION: Nle

<400> SEQUENCE: 183

Glu Gly Thr Phe Ile Ser Asp Tyr Ser Ile Ala Leu Asp Lys Ile Lys
1               5                   10                  15

Gln Gln Asp Phe Val Glu Trp Leu Leu Ala Gln Lys Pro Ser Ser Gly
            20                  25                  30

Ala Pro Pro Pro Ser
            35

<210> SEQ ID NO 184
<211> LENGTH: 37
```

<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: beta-glutamate
<220> FEATURE:
<221> NAME/KEY: MOD_RES
<222> LOCATION: (12)..(12)
<223> OTHER INFORMATION: Nle

<400> SEQUENCE: 184

Glu Gly Thr Phe Ile Ser Asp Tyr Ser Ile Ala Leu Asp Lys Ile Lys
1               5                   10                  15

Gln Gln Asp Phe Val Glu Trp Leu Leu Ala Gln Lys Pro Ser Ser Gly
            20                  25                  30

Ala Pro Pro Pro Ser
        35

<210> SEQ ID NO 185
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: Xaa is glutaric acid
<220> FEATURE:
<221> NAME/KEY: MOD_RES
<222> LOCATION: (12)..(12)
<223> OTHER INFORMATION: Nle

<400> SEQUENCE: 185

Xaa Gly Thr Phe Ile Ser Asp Tyr Ser Ile Ala Leu Asp Lys Ile Lys
1               5                   10                  15

Gln Gln Asp Phe Val Glu Trp Leu Leu Ala Gln Lys Pro Ser Ser Gly
            20                  25                  30

Ala Pro Pro Pro Ser
        35

<210> SEQ ID NO 186
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: beta-glutamate
<220> FEATURE:
<221> NAME/KEY: MOD_RES
<222> LOCATION: (11)..(11)
<223> OTHER INFORMATION: Aib
<220> FEATURE:
<221> NAME/KEY: MOD_RES
<222> LOCATION: (12)..(12)
<223> OTHER INFORMATION: Nle

<400> SEQUENCE: 186

Glu Gly Thr Phe Ile Ser Asp Tyr Ser Ile Ala Leu Asp Lys Ile Lys
1               5                   10                  15

Gln Gln Asp Phe Val Asn Trp Leu Leu Ala Gln Lys Pro Ser Ser Gly
            20                  25                  30

Ala Pro Pro Pro Ser
            35

<210> SEQ ID NO 187
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: MOD_RES
<222> LOCATION: (1)..(1)
<223> OTHER INFORMATION: ACETYLATION

<400> SEQUENCE: 187

Glu Gly Thr Phe Ile Ser Asp Tyr Ser Ile Ala Met Asp Lys Ile Lys
1               5                   10                  15

Gln Gln Asp Phe Val Asn Trp Leu Leu Ala Gln Lys Pro Ser Ser Gly
            20                  25                  30

Ala Pro Pro Pro Ser
            35

<210> SEQ ID NO 188
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: MOD_RES
<222> LOCATION: (1)..(1)
<223> OTHER INFORMATION: ACETYLATION

<400> SEQUENCE: 188

Glu Gly Thr Phe Ile Ser Glu Tyr Ser Ile Ala Met Glu Lys Ile Lys
1               5                   10                  15

Gln Gln Asp Phe Val Asn Trp Leu Leu Ala Gln Lys Pro Ser Ser Gly
            20                  25                  30

Ala Pro Pro Pro Ser
            35

<210> SEQ ID NO 189
<211> LENGTH: 29
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(29)
<223> OTHER INFORMATION: GIP(5-30)

<400> SEQUENCE: 189

Thr Phe Ile Ser Asp Tyr Lys Ile Ala Met Asp Lys Ile His Gln Gln
1               5                   10                  15

Asp Phe Val Asn Trp Leu Leu Ala Gln Lys Gly Lys Lys
            20                  25

<210> SEQ ID NO 190
<211> LENGTH: 32
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(32)

<223> OTHER INFORMATION: GIP(5-30)

<400> SEQUENCE: 190

Thr Phe Ile Ser Asp Tyr Lys Ile Ala Met Asp Lys Ile His Gln Gln
1               5                   10                  15

Asp Phe Val Asn Trp Leu Leu Ala Gln Lys Gly Lys Lys Asn Asp Trp
            20                  25                  30

<210> SEQ ID NO 191
<211> LENGTH: 32
<212> TYPE: PRT
<213> ORGANISM: Artificial sequence
<220> FEATURE:
<223> OTHER INFORMATION: peptide
<220> FEATURE:
<221> NAME/KEY: MOD_RES
<222> LOCATION: (32)..(32)
<223> OTHER INFORMATION: AMIDATION

<400> SEQUENCE: 191

Thr Phe Ile Ser Asp Tyr Lys Ile Ala Met Asp Lys Ile His Gln Gln
1               5                   10                  15

Asp Phe Val Asn Trp Leu Leu Ala Gln Lys Gly Lys Lys Asn Asp Trp
            20                  25                  30

<210> SEQ ID NO 192
<211> LENGTH: 32
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(32)
<223> OTHER INFORMATION: GIP(5-30)

<400> SEQUENCE: 192

Thr Phe Ile Ser Asp Tyr Ser Lys Ala Met Asp Lys Ile His Gln Gln
1               5                   10                  15

Asp Phe Val Asn Trp Leu Leu Ala Gln Lys Gly Lys Lys Asn Asp Trp
            20                  25                  30

<210> SEQ ID NO 193
<211> LENGTH: 35
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(35)
<223> OTHER INFORMATION: GIP(5-30)

<400> SEQUENCE: 193

Thr Phe Ile Ser Asp Tyr Lys Ile Ala Met Asp Lys Ile His Gln Gln
1               5                   10                  15

Asp Phe Val Asn Trp Leu Leu Ala Gln Lys Gly Lys Lys Asn Asp Trp
            20                  25                  30

Lys His Asn
        35

<210> SEQ ID NO 194
<211> LENGTH: 38
<212> TYPE: PRT
<213> ORGANISM: Artificial sequence
<220> FEATURE:

<223> OTHER INFORMATION: peptide
<220> FEATURE:
<221> NAME/KEY: PEPTIDE
<222> LOCATION: (1)..(38)
<223> OTHER INFORMATION: GIP(5-30)

<400> SEQUENCE: 194

Thr Phe Ile Ser Asp Tyr Lys Ile Ala Met Asp Lys Ile His Gln Gln
1               5                   10                  15

Asp Phe Val Asn Trp Leu Leu Ala Gln Lys Gly Lys Lys Asn Asp Trp
            20                  25                  30

Lys His Asn Ile Thr Gln
        35

<210> SEQ ID NO 195
<211> LENGTH: 27
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(27)
<223> OTHER INFORMATION: GIP(5-30)

<400> SEQUENCE: 195

Thr Phe Ile Ser Asp Tyr Lys Ile Ala Met Asp Lys Ile His Gln Gln
1               5                   10                  15

Asp Phe Val Asn Trp Leu Leu Ala Gln Lys Gly
            20                  25

<210> SEQ ID NO 196
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(28)
<223> OTHER INFORMATION: GIP(5-30)

<400> SEQUENCE: 196

Thr Phe Ile Ser Asp Tyr Lys Ile Ala Met Asp Lys Ile His Gln Gln
1               5                   10                  15

Asp Phe Val Asn Trp Leu Leu Ala Gln Lys Gly Lys
            20                  25

<210> SEQ ID NO 197
<211> LENGTH: 30
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(30)
<223> OTHER INFORMATION: GIP(5-30)

<400> SEQUENCE: 197

Thr Phe Ile Ser Asp Tyr Lys Ile Ala Met Asp Lys Ile His Gln Gln
1               5                   10                  15

Asp Phe Val Asn Trp Leu Leu Ala Gln Lys Gly Lys Lys Asn
            20                  25                  30

<210> SEQ ID NO 198

```
<211> LENGTH: 31
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(31)
<223> OTHER INFORMATION: GIP(5-30)

<400> SEQUENCE: 198

Thr Phe Ile Ser Asp Tyr Lys Ile Ala Met Asp Lys Ile His Gln Gln
1               5                  10                  15

Asp Phe Val Asn Trp Leu Leu Ala Gln Lys Gly Lys Lys Asn Asp
            20                  25                  30

<210> SEQ ID NO 199
<211> LENGTH: 33
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(33)
<223> OTHER INFORMATION: GIP(5-30)

<400> SEQUENCE: 199

Thr Phe Ile Ser Asp Tyr Lys Ile Ala Met Asp Lys Ile His Gln Gln
1               5                  10                  15

Asp Phe Val Asn Trp Leu Leu Ala Gln Lys Gly Lys Lys Asn Asp Trp
            20                  25                  30

Lys

<210> SEQ ID NO 200
<211> LENGTH: 34
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(34)
<223> OTHER INFORMATION: GIP(5-30)

<400> SEQUENCE: 200

Thr Phe Ile Ser Asp Tyr Lys Ile Ala Met Asp Lys Ile His Gln Gln
1               5                  10                  15

Asp Phe Val Asn Trp Leu Leu Ala Gln Lys Gly Lys Lys Asn Asp Trp
            20                  25                  30

Lys His

<210> SEQ ID NO 201
<211> LENGTH: 36
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(36)
<223> OTHER INFORMATION: GIP(5-30)

<400> SEQUENCE: 201

Thr Phe Ile Ser Asp Tyr Lys Ile Ala Met Asp Lys Ile His Gln Gln
1               5                  10                  15
```

Asp Phe Val Asn Trp Leu Leu Ala Gln Lys Gly Lys Lys Asn Asp Trp
            20                  25                  30

Lys His Asn Ile
        35

<210> SEQ ID NO 202
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(37)
<223> OTHER INFORMATION: GIP(5-30)

<400> SEQUENCE: 202

Thr Phe Ile Ser Asp Tyr Lys Ile Ala Met Asp Lys Ile His Gln Gln
1               5                   10                  15

Asp Phe Val Asn Trp Leu Leu Ala Gln Lys Gly Lys Lys Asn Asp Trp
            20                  25                  30

Lys His Asn Ile Thr
        35

<210> SEQ ID NO 203
<211> LENGTH: 35
<212> TYPE: PRT
<213> ORGANISM: Artificial sequence
<220> FEATURE:
<223> OTHER INFORMATION: peptide
<220> FEATURE:
<221> NAME/KEY: MOD_RES
<222> LOCATION: (35)..(35)
<223> OTHER INFORMATION: AMIDATION

<400> SEQUENCE: 203

Thr Phe Ile Ser Asp Tyr Lys Ile Ala Met Asp Lys Ile His Gln Gln
1               5                   10                  15

Asp Phe Val Asn Trp Leu Leu Ala Gln Lys Pro Ser Ser Gly Ala Pro
            20                  25                  30

Pro Pro Ser
        35

<210> SEQ ID NO 204
<211> LENGTH: 32
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(32)
<223> OTHER INFORMATION: GIP(5-30)

<400> SEQUENCE: 204

Thr Phe Ile Ser Asp Tyr Lys Ile Ala Met Asp Arg Ile His Gln Gln
1               5                   10                  15

Asp Phe Val Asn Trp Leu Leu Ala Gln Arg Gly Arg Arg Asn Asp Trp
            20                  25                  30

<210> SEQ ID NO 205
<211> LENGTH: 36
<212> TYPE: PRT
<213> ORGANISM: Artificial sequence
<220> FEATURE:
<223> OTHER INFORMATION: peptide

```
<220> FEATURE:
<221> NAME/KEY: PEPTIDE
<222> LOCATION: (1)..(36)
<223> OTHER INFORMATION: GIP(5-30)

<400> SEQUENCE: 205

Thr Phe Ile Ser Asp Tyr Lys Ile Ala Met Asp Arg Ile His Gln Gln
1               5                   10                  15

Asp Phe Val Asn Trp Leu Leu Ala Gln Arg Gly Pro Ser Ser Gly Ala
            20                  25                  30

Pro Pro Pro Ser
            35

<210> SEQ ID NO 206
<211> LENGTH: 32
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(32)
<223> OTHER INFORMATION: GIP(5-30)

<400> SEQUENCE: 206

Thr Phe Ile Ser Asp Tyr Ser Ile Ala Met Asp Lys Ile Lys Gln Gln
1               5                   10                  15

Asp Phe Val Asn Trp Leu Leu Ala Gln Lys Gly Lys Lys Asn Asp Trp
            20                  25                  30

<210> SEQ ID NO 207
<211> LENGTH: 36
<212> TYPE: PRT
<213> ORGANISM: Artificial sequence
<220> FEATURE:
<223> OTHER INFORMATION: peptide
<220> FEATURE:
<221> NAME/KEY: MOD_RES
<222> LOCATION: (36)..(36)
<223> OTHER INFORMATION: AMIDATION

<400> SEQUENCE: 207

Thr Phe Ile Ser Asp Tyr Lys Ile Ala Met Asp Lys Ile His Gln Gln
1               5                   10                  15

Asp Phe Val Asn Trp Leu Leu Ala Gln Lys Gly Pro Ser Ser Gly Ala
            20                  25                  30

Pro Pro Pro Ser
            35

<210> SEQ ID NO 208
<211> LENGTH: 35
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(35)
<223> OTHER INFORMATION: GIP(5-30)

<400> SEQUENCE: 208

Thr Phe Ile Ser Asp Tyr Lys Ile Ala Met Asp Lys Ile His Gln Gln
1               5                   10                  15

Asp Phe Val Asn Trp Leu Leu Ala Gln Lys Pro Ser Ser Gly Ala Pro
            20                  25                  30
```

```
Pro Pro Ser
        35
```

<210> SEQ ID NO 209
<211> LENGTH: 32
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(32)
<223> OTHER INFORMATION: GIP(5-30)

<400> SEQUENCE: 209

```
Thr Phe Ile Ser Asp Tyr Ser Ile Ala Met Asp Lys Ile His Gln Lys
1               5                   10                  15

Asp Phe Val Asn Trp Leu Leu Ala Gln Lys Gly Lys Lys Asn Asp Trp
            20                  25                  30
```

<210> SEQ ID NO 210
<211> LENGTH: 32
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(32)
<223> OTHER INFORMATION: GIP(5-30)

<400> SEQUENCE: 210

```
Thr Phe Ile Ser Asp Tyr Ser Ile Ala Met Asp Lys Ile His Gln Gln
1               5                   10                  15

Asp Phe Val Lys Trp Leu Leu Ala Gln Lys Gly Lys Lys Asn Asp Trp
            20                  25                  30
```

<210> SEQ ID NO 211
<211> LENGTH: 28
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(28)
<223> OTHER INFORMATION: GIP(5-30)

<400> SEQUENCE: 211

```
Phe Ile Ser Asp Tyr Ser Ile Ala Met Asp Lys Ile Lys Gln Gln Asp
1               5                   10                  15

Phe Val Asn Trp Leu Leu Ala Gln Lys Gly Lys Lys
            20                  25
```

<210> SEQ ID NO 212
<211> LENGTH: 31
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(31)
<223> OTHER INFORMATION: GIP(5-30)

<400> SEQUENCE: 212

```
Phe Ile Ser Asp Tyr Ser Ile Ala Met Asp Lys Ile Lys Gln Gln Asp
1               5                   10                  15
```

Phe Val Asn Trp Leu Leu Ala Gln Lys Gly Lys Lys Asn Asp Trp
            20                  25                  30

<210> SEQ ID NO 213
<211> LENGTH: 34
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(34)
<223> OTHER INFORMATION: GIP(5-30)

<400> SEQUENCE: 213

Phe Ile Ser Asp Tyr Ser Ile Ala Met Asp Lys Ile Lys Gln Gln Asp
1               5                   10                  15

Phe Val Asn Trp Leu Leu Ala Gln Lys Gly Lys Lys Asn Asp Trp Lys
            20                  25                  30

His Asn

<210> SEQ ID NO 214
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(37)
<223> OTHER INFORMATION: GIP(5-30)

<400> SEQUENCE: 214

Phe Ile Ser Asp Tyr Ser Ile Ala Met Asp Lys Ile Lys Gln Gln Asp
1               5                   10                  15

Phe Val Asn Trp Leu Leu Ala Gln Lys Gly Lys Lys Asn Asp Trp Lys
            20                  25                  30

His Asn Ile Thr Gln
        35

<210> SEQ ID NO 215
<211> LENGTH: 35
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(35)
<223> OTHER INFORMATION: GIP(5-30)

<400> SEQUENCE: 215

Phe Ile Ser Asp Tyr Ser Ile Ala Met Asp Lys Ile Lys Gln Gln Asp
1               5                   10                  15

Phe Val Asn Trp Leu Leu Ala Gln Lys Gly Pro Ser Ser Gly Ala Pro
            20                  25                  30

Pro Pro Ser
        35

<210> SEQ ID NO 216
<211> LENGTH: 35
<212> TYPE: PRT
<213> ORGANISM: Artificial sequence
<220> FEATURE:
<223> OTHER INFORMATION: peptide

```
<220> FEATURE:
<221> NAME/KEY: MOD_RES
<222> LOCATION: (35)..(35)
<223> OTHER INFORMATION: AMIDATION

<400> SEQUENCE: 216

Thr Phe Ile Ser Asp Tyr Lys Ile Ala Met Asp Lys Ile His Gln Gln
1               5                   10                  15

Asp Phe Val Asn Trp Leu Leu Ala Gly Gly Pro Ser Ser Gly Ala Pro
            20                  25                  30

Pro Pro Ser
        35

<210> SEQ ID NO 217
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(37)
<223> OTHER INFORMATION: GIP(3-30)

<400> SEQUENCE: 217

Glu Gly Thr Phe Ile Ser Asp Tyr Ser Ile Ala Leu Asp Lys Ile Lys
1               5                   10                  15

Gln Gln Asp Phe Val Asn Trp Leu Leu Glu Gln Lys Pro Ser Ser Gly
            20                  25                  30

Ala Pro Pro Pro Ser
        35

<210> SEQ ID NO 218
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: MOD_RES
<222> LOCATION: (12)..(12)
<223> OTHER INFORMATION: Nle

<400> SEQUENCE: 218

Glu Gly Thr Phe Ile Ser Asp Tyr Ser Ile Ala Leu Asp Lys Ile Lys
1               5                   10                  15

Gln Gln Asp Phe Val Asn Trp Leu Leu Glu Gln Lys Pro Ser Ser Gly
            20                  25                  30

Ala Pro Pro Pro Ser
        35

<210> SEQ ID NO 219
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(37)
<223> OTHER INFORMATION: GIP(3-30)

<400> SEQUENCE: 219

Glu Gly Thr Phe Ile Ser Asp Tyr Ser Ile Ala Leu Asp Lys Ile Lys
1               5                   10                  15
```

-continued

Gln Gln Asp Phe Val Asn Trp Leu Leu Glu Gly Gly Pro Ser Ser Gly
            20                  25                  30

Ala Pro Pro Ser
        35

<210> SEQ ID NO 220
<211> LENGTH: 37
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(37)
<223> OTHER INFORMATION: GIP(3-30)

<400> SEQUENCE: 220

Glu Gly Thr Phe Ile Ser Asp Tyr Ser Ile Ala Met Asp Lys Ile Lys
1               5                   10                  15

Gln Gln Asp Phe Val Asn Trp Leu Leu Glu Gly Gly Pro Ser Ser Gly
            20                  25                  30

Ala Pro Pro Ser
        35

<210> SEQ ID NO 221
<211> LENGTH: 35
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(35)
<223> OTHER INFORMATION: GIP(5-30)

<400> SEQUENCE: 221

Thr Phe Ile Ser Asp Tyr Ser Ile Ala Met Asp Lys Ile Lys Gln Gln
1               5                   10                  15

Asp Phe Val Asn Trp Leu Leu Ala Gln Lys Pro Ser Ser Gly Ala Pro
            20                  25                  30

Pro Pro Ser
        35

<210> SEQ ID NO 222
<211> LENGTH: 35
<212> TYPE: PRT
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(35)
<223> OTHER INFORMATION: GIP(5-30)

<400> SEQUENCE: 222

Thr Phe Ile Ser Asp Tyr Ser Ile Ala Met Asp Lys Ile Lys Gln Gln
1               5                   10                  15

Asp Phe Val Asn Trp Leu Leu Ala Gln Lys Pro Ser Ser Gly Ala Pro
            20                  25                  30

Pro Pro Ser
        35

<210> SEQ ID NO 223
<211> LENGTH: 32
<212> TYPE: PRT

```
<213> ORGANISM: Artificial sequence
<220> FEATURE:
<223> OTHER INFORMATION: peptide
<220> FEATURE:
<221> NAME/KEY: PEPTIDE
<222> LOCATION: (1)..(32)
<223> OTHER INFORMATION: GIP(5-30)

<400> SEQUENCE: 223

Thr Phe Ile Ser Asp Tyr Ser Ile Ala Met Asp Lys Ile His Gln Lys
1               5                   10                  15

Asp Phe Val Asn Trp Leu Leu Ala Gln Lys Gly Lys Lys Asn Asp Trp
            20                  25                  30
```